United States Patent
Kiyomoto et al.

[11] Patent Number: 5,844,682
[45] Date of Patent: *Dec. 1, 1998

[54] OPTICAL SENSOR DEVICE

[75] Inventors: Hironobu Kiyomoto, Nara; Naru Yasuda, Uji; Kouichi Ekawa, Takatsuki; Hayami Hosokawa, Yawata, all of Japan

[73] Assignee: Omron Corporation

[*] Notice: This patent issued on a continued prosecution application filed under 37 CFR 1.53(d), and is subject to the twenty year patent term provisions of 35 U.S.C. 154(a)(2).

[21] Appl. No.: 406,540

[22] Filed: Mar. 20, 1995

[30] Foreign Application Priority Data

Mar. 25, 1994 [JP] Japan .................................. 6-055426
Dec. 8, 1994 [JP] Japan .................................. 6-331155

[51] Int. Cl.⁶ ...................................................... G01J 4/00
[52] U.S. Cl. .......................... 356/369; 356/356; 356/355; 356/73.1; 356/237
[58] Field of Search ................................... 356/356, 369, 356/385, 73.1, 237

[56] References Cited

U.S. PATENT DOCUMENTS

| | | |
|---|---|---|
| 3,603,458 | 9/1971 | Bliss . |
| 4,318,003 | 3/1982 | Ono et al. . |
| 4,919,534 | 4/1990 | Reed . |
| 5,139,339 | 8/1992 | Courtney et al. . |
| 5,197,105 | 3/1993 | Uemura et al. ............................ 356/237 |
| 5,198,575 | 3/1993 | Bazin et al. ............................... 356/369 |
| 5,554,262 | 9/1996 | Turner ..................................... 356/385 |
| 5,570,217 | 10/1996 | Fleuren ..................................... 356/73.1 |

FOREIGN PATENT DOCUMENTS

| | | |
|---|---|---|
| 18505 | 11/1980 | European Pat. Off. . |
| 72236 | 2/1983 | European Pat. Off. . |
| 532344 | 3/1993 | European Pat. Off. . |
| 63-19246 | 2/1988 | Japan . |
| 2-189408 | 7/1990 | Japan . |

OTHER PUBLICATIONS

"Thin–Film Optical Filters," H.A. Macleod (Japanese translation).
"Optical Thin Films", S. Fujiwara.

*Primary Examiner*—Frank G. Font
*Assistant Examiner*—Reginald A. Ratliff
*Attorney, Agent, or Firm*—Dickstein Shapiro Morin & Oshinsky LLP

[57] ABSTRACT

Whether or not an object is present, the surface state of the object, the material constituting the object and the presence of scattering bodies are discriminated through a simple arrangement which includes a light-emitting element for projecting light upon an object to be sensed, and a polarization beam splitter upon which light reflected from the object (or light transmitted through or scattered from the object) impinges. Reflected light from the polarization beam splitter is received by a first light-receiving element, and transmitted light from the polarization beam splitter is received by a second light-receiving element. The aforesaid discrimination is performed on the basis of the value of S/P, S–P, S–kP or (S–P)/(S+P), where S and P represent light-reception signals from the first and second light-receiving elements, and k is a constant.

74 Claims, 139 Drawing Sheets

Fig.21

POLARIZATION BEAM SPLITTER G

| Value | Type | |
|---|---|---|
| 1.199 | H | |
| 1.870 | L | |
| 2.420 | H | |
| 1.195 | L | PERIODIC LAYERS |
| 0.987 | H | |
| 1.195 | L | |
| 0.987 | H | |
| 1.195 | L | |
| 0.987 | H | |
| 1.195 | L | |
| 0.987 | H | |
| 1.141 | L | |
| 1.122 | H | |
| 1.148 | L | |
| 0.983 | H | |
| 1.102 | L | |
| 0.911 | H | |
| 1.196 | L | |
| 1.054 | H | PERIODIC LAYERS |
| 1.028 | L | |
| 1.054 | H | |
| 1.028 | L | |
| 1.054 | H | |
| 1.028 | L | |
| 1.054 | H | |
| 1.028 | L | |
| 1.078 | H | |
| 1.009 | L | |
| 0.885 | H | |
| 1.089 | L | |
| 0.907 | H | |
| 0.980 | L | |
| 0.522 | H | |

SUBSTRATE

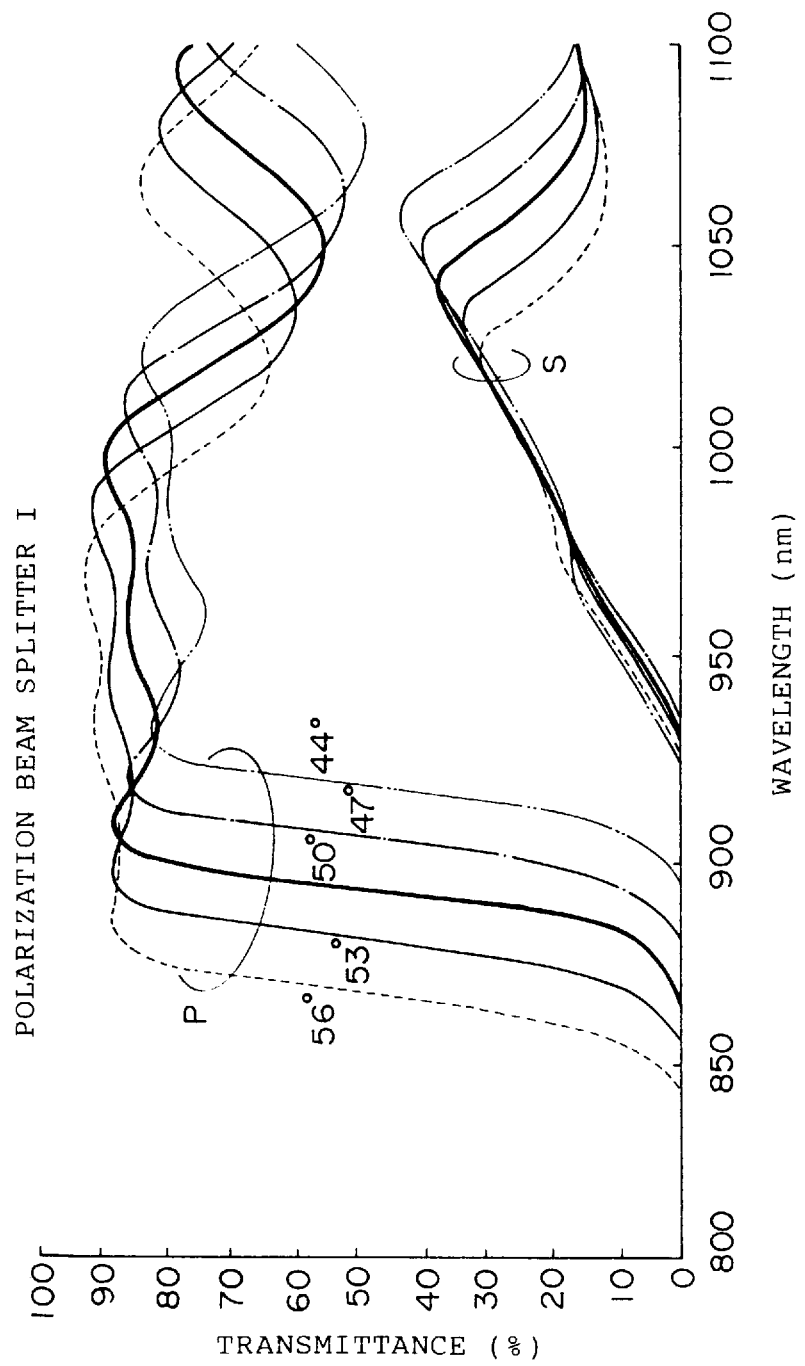

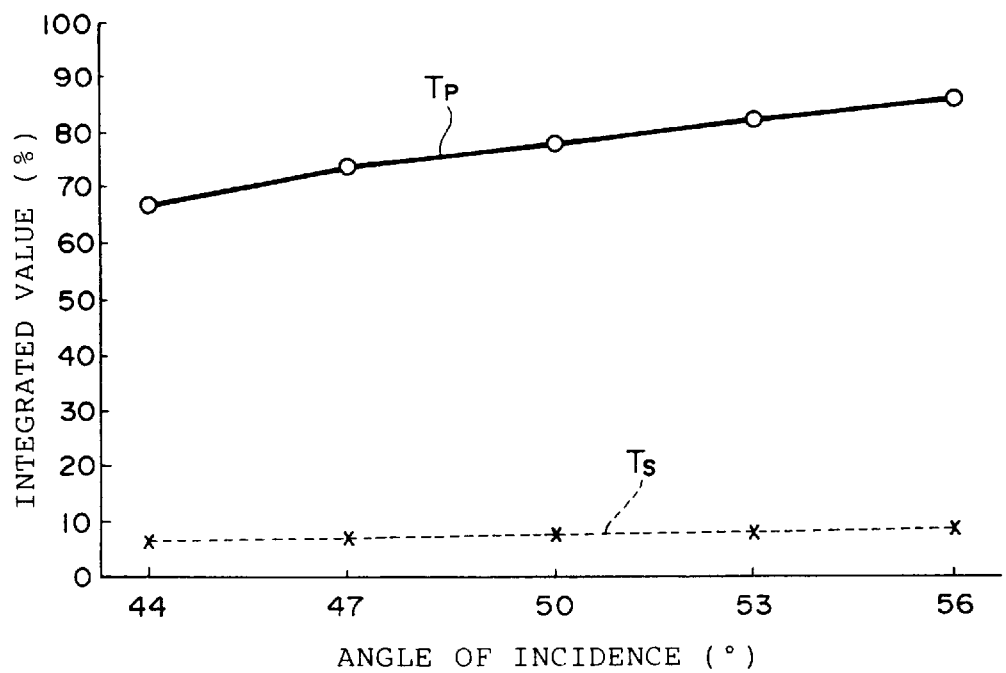

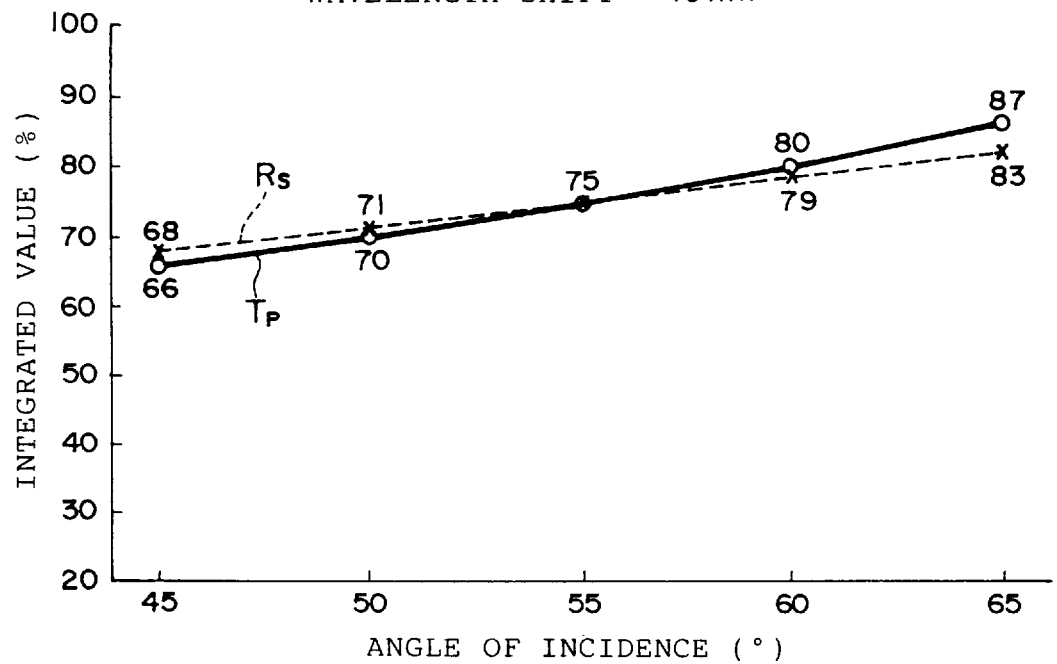
Fig. 30a  POLARIZATION BEAM SPLITTER A
WAVELENGTH SHIFT: −10 nm
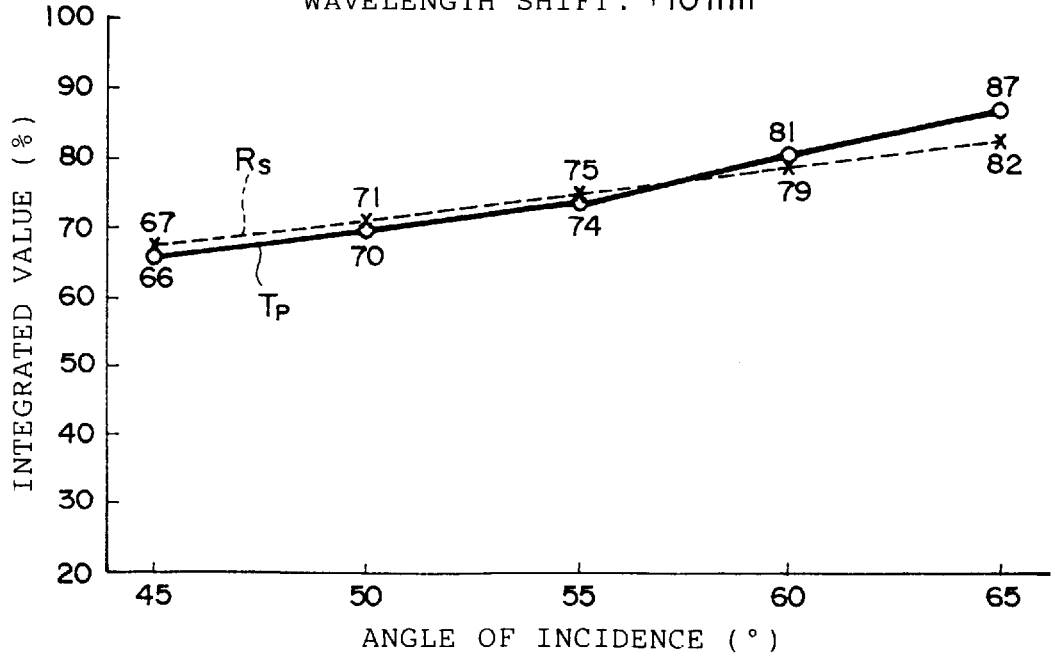
Fig. 30b  POLARIZATION BEAM SPLITTER A
WAVELENGTH SHIFT: +10 nm

Fig. 35

| AMOUNT OF CENTRAL WAVELENGTH SHIFT | -10nm | 0nm | +10nm |
|---|---|---|---|
| ΔRs/Tp (%) IN POLARIZATION BEAM SPLITTER A | 8 | 6 | 8 |
| ΔRs (%) IN POLARIZATION BEAM SPLITTER B | 2 | 2 | 3 |
| ΔRs (%) IN POLARIZATION BEAM SPLITTER C | 1 | 3 | 3 |
| ΔRs (%) IN POLARIZATION BEAM SPLITTER D | 5 | 3 | 3 |
| ΔRs (%) IN POLARIZATION BEAM SPLITTER E | 2 | 2 | 1 |

Fig. 38

| AMOUNT OF CENTRAL WAVELENGTH SHIFT | -10nm | 0nm | +10nm |
|---|---|---|---|
| ΔRs/Tp (%) IN POLARIZATION BEAM SPLITTER F | 17 | 17 | 18 |
| ΔRs (%) IN POLARIZATION BEAM SPLITTER G | 6 | 9 | 8 |

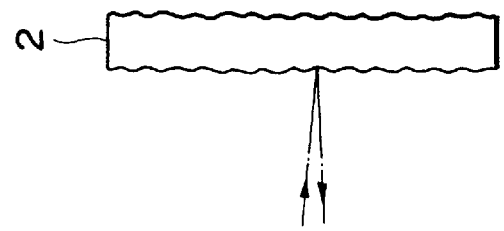
Fig. 41
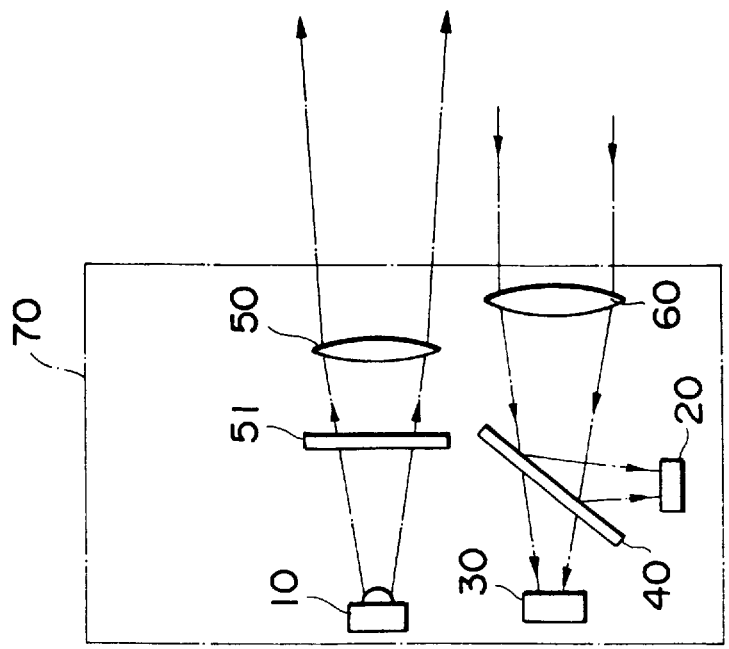

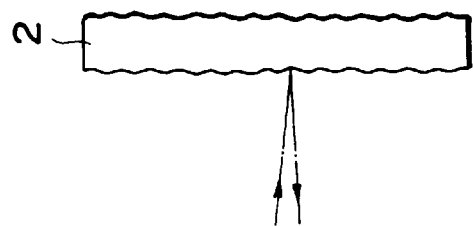
Fig. 43
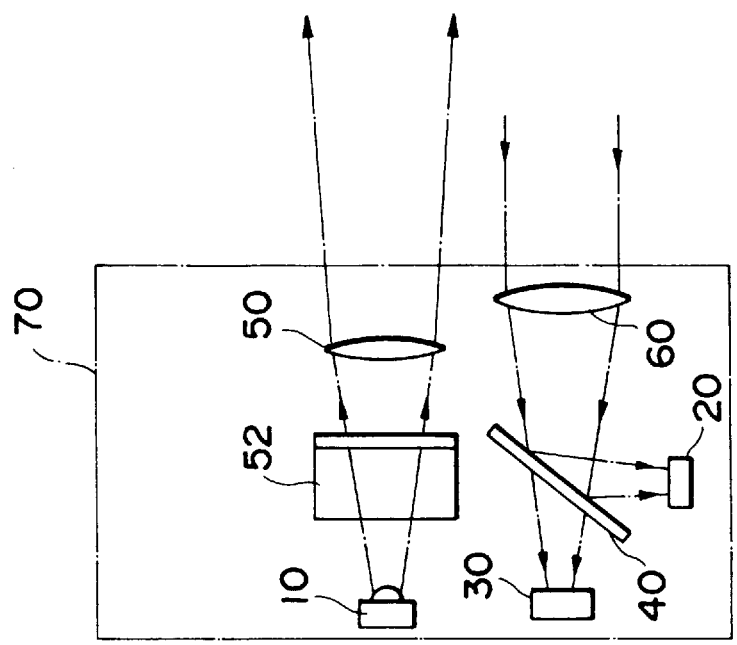

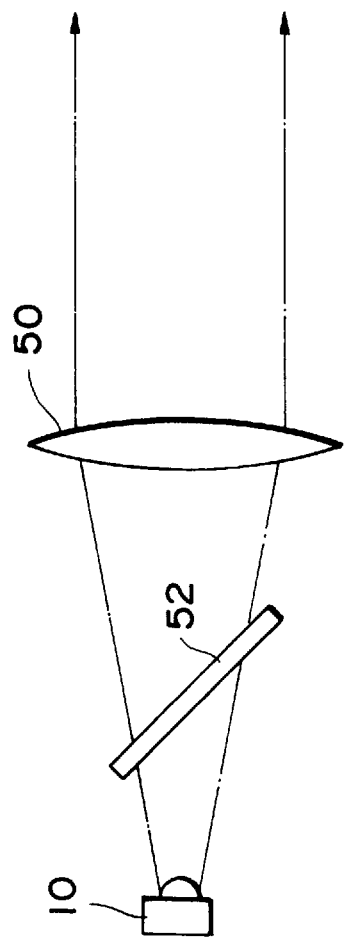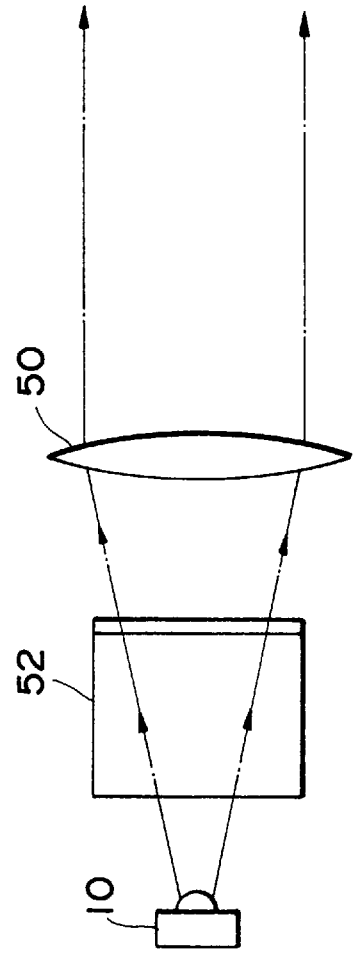

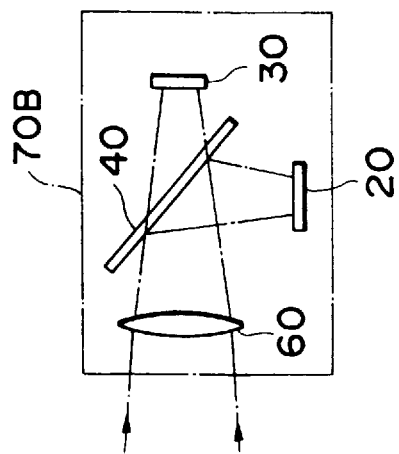
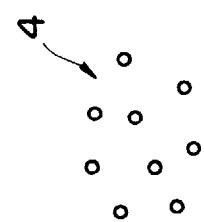
Fig. 82
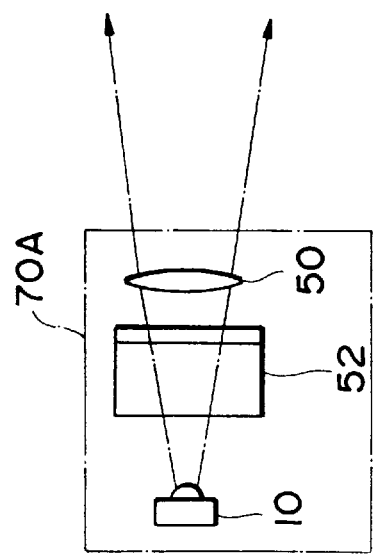

Fig. 89a
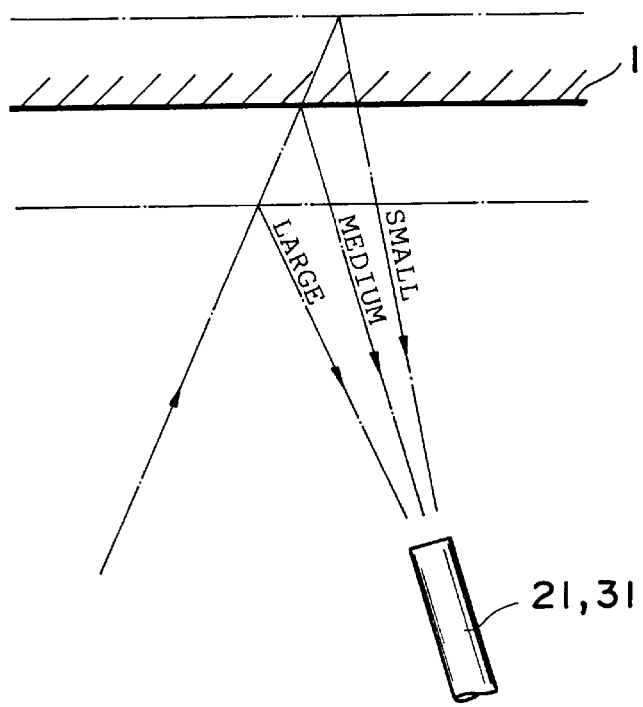
Fig. 89b
Fig. 89c
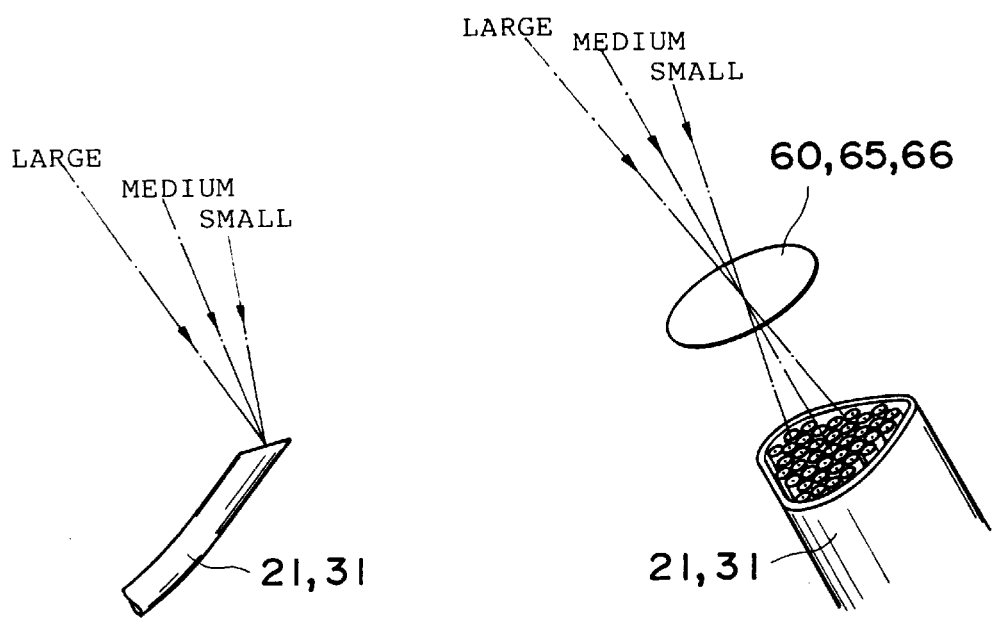

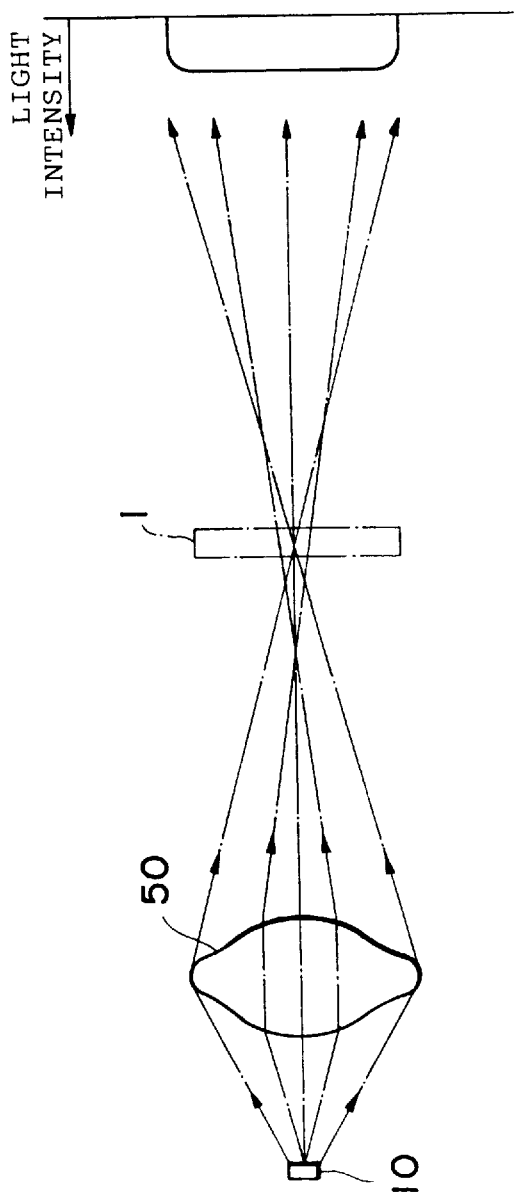

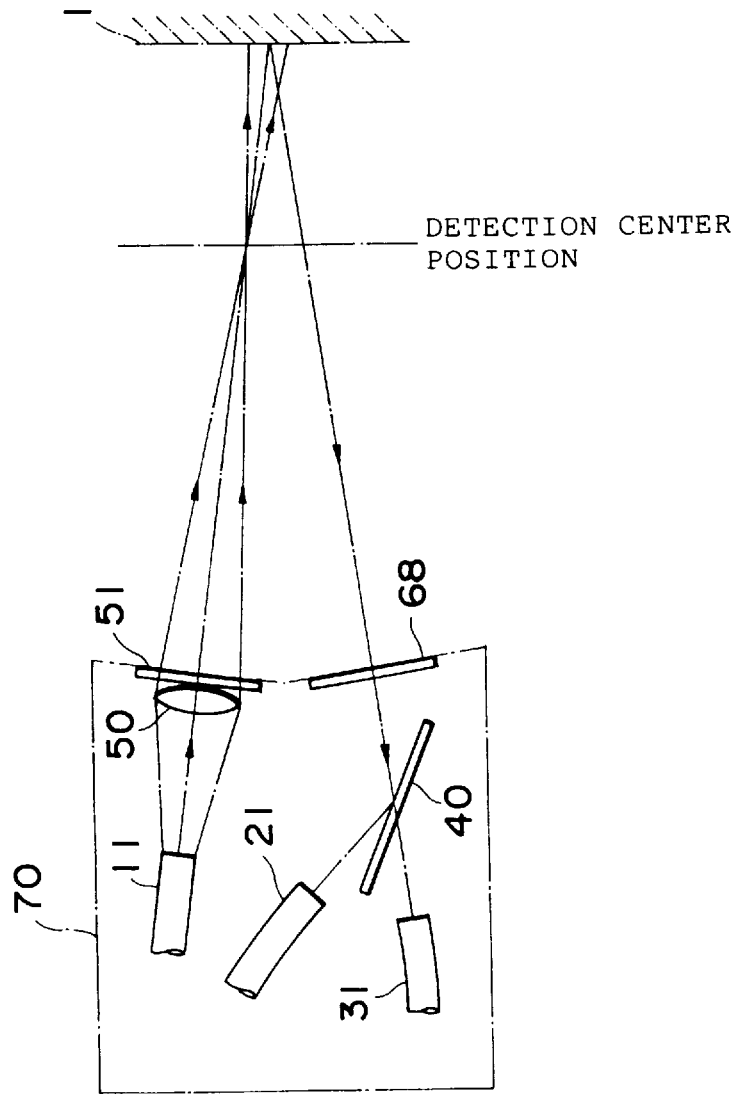

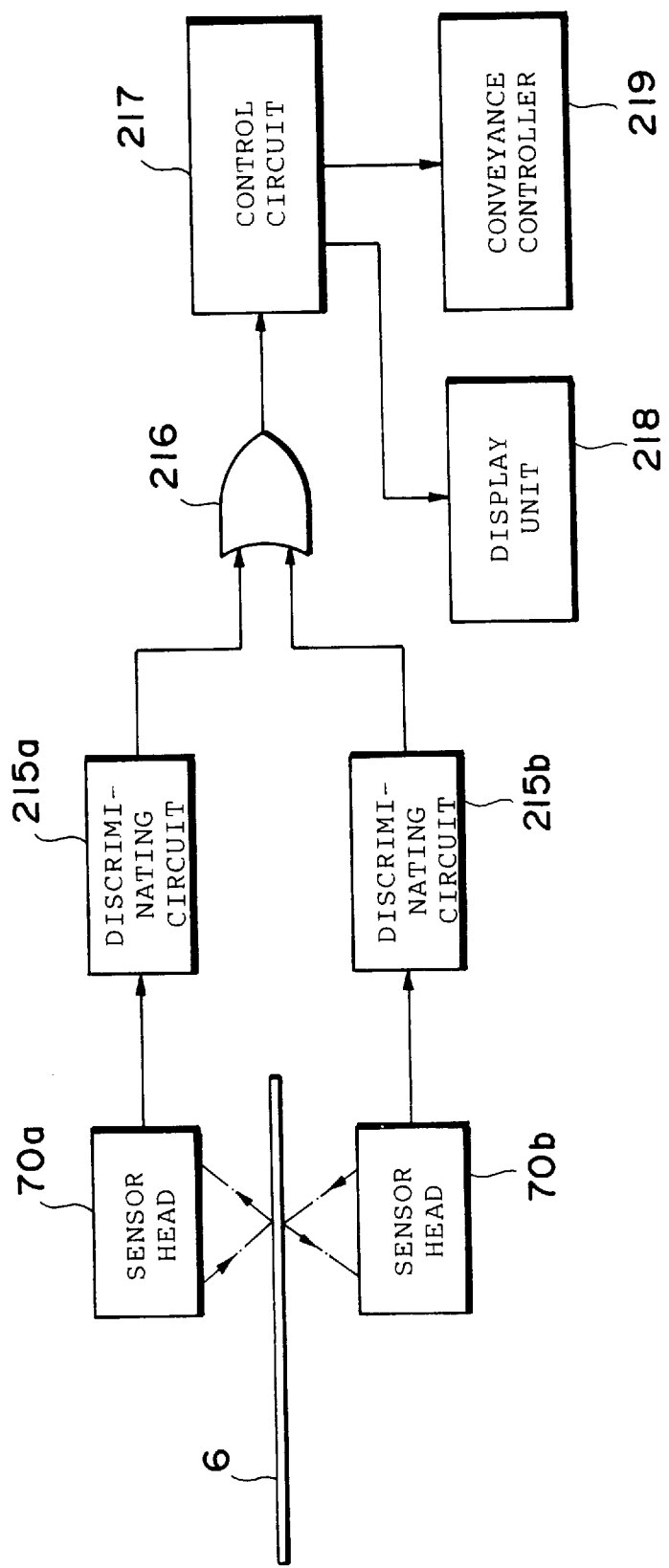

OPTICAL SENSOR DEVICE

BACKGROUND OF THE INVENTION

1. Field of the Invention

This invention relates to an optical sensor device.

2. Description of the Related Art

It is known that when light is make to impinge upon an object, the state of polarization of the light reflected from or transmitted through the object is influenced by the surface state of the object, the material constituting the object, etc.

An apparatus which utilizes this principle to evaluate the surface properties of an object is described in the specification of Japanese Utility Model Application Laid-Open (KOKAI) No. 63-19246. This apparatus irradiates the surface of the object with light and senses the reflected light through a polarization filter. Only a specific polarized component of the reflected light can be extracted by passing the light through the polarization filter.

In an adhesive-tape detecting apparatus described in Japanese Patent Application Laid-Open (KOKAI) No. 2-189408, light reflected from the surface of paper to which an adhesive tape has been affixed is received through a polarizing element (variable polarizer). The variable polarizer is obtained by sealing liquid crystal inside a thin cell made of glass and forming transparent electrodes on both surfaces of the cell.

In both the above-described polarization filter and variable polarizer, only a light component having a single direction of polarization can be extracted. In order to extract two polarized components in mutually perpendicular directions, the polarization filter in Japanese Utility Model Application Laid-Open No. 63-19246 is rotated 90° in the plane thereof. In this arrangement, a mechanism for rotating the polarization filter is necessary and measurement takes time. This document also describes an arrangement in which two polarization filters in mutually perpendicular directions are disposed side by side. Part of the luminous flux of the light reflected from the surface of an object passes through one polarization filter and the other part of the luminous flux passes through the other polarization filter. Since the light reflected from the surface of the object is such that the constitution of the polarized components changes depending upon the particular portion of the luminous flux, the properties of the surface of the object cannot be detected accurately.

The variable polarizer is such that the direction of polarization is changed by changing the voltage impressed upon the transparent electrodes. Application of voltage is necessary and, hence, a circuit for generating a variable voltage is required. In addition, measurement must be performed while varying the applied voltage.

SUMMARY OF THE INVENTION

Accordingly, an object of the present invention is to solve all of the aforesaid problems and provide an optical sensor device which, through a comparatively simple construction, simultaneously extracts polarized light components in two mutually perpendicular directions from an identical luminous flux, measures the intensities of these components and can perform an accurate discrimination concerning an object.

Another object of the present invention is to provide an optical sensor device applicable broadly to detection of absence/presence of an object, surface state of an object, material constituting the object and absence/presence of light-scattering bodies temporarily attaching to an object or suspended in a medium such as air.

A further object of the present invention is to provide an optical sensor device which performs stable operation without being adversely affected by the divergence angle or convergence angle of projected light, a variance in angle of incidence of light incident upon the sensor device or a fluctuation in the angle of incidence of light incident upon the sensor device, wherein the fluctuation is caused by a change in the position of the object undergoing sensing.

Still another object of the present invention is to assure stable operation of the sensor device without such operation being adversely affected by the light-emission wavelength distribution of a light source such as a light-emitting diode and a variance in light-emission wavelength caused by a variance in the light source itself.

An optical sensor device according to the present invention includes a light-projecting optical system for projecting light toward an object to be sensed and a light-receiving optical system upon which reflected light, transmitted light or scattered light from the object to be sensed impinges. The light-projecting optical system includes at least a light-emitting element for outputting projected light. The light-receiving optical system includes a polarization beam splitter for separating the reflected light, transmitted light or scattered light from the object into a first luminous flux which is mainly an s-polarized component with regard to the plane of incidence and a second luminous flux which is mainly a p-polarized component with regard to the plane of incidence, a first light-receiving element for receiving the first luminous flux, and a second light-receiving element for receiving the second luminous flux.

The optical sensor device is further provided with discriminating means for outputting a signal relating to absence/presence of an object to be sensed, surface property of the object or material constituting the object on the basis of outputs from the first and second light-receiving elements.

In order to implement the operation for the discrimination based upon the outputs from the first and second light-receiving elements, it will suffice to employ an means conforming to the material and surface state, etc., of the object to be discriminated.

In accordance with this invention, a polarization beam splitter is used in the light-receiving optical system. By virtue of the polarization beam splitter, therefore, light can be separated (splitted) into a first luminous flux containing mainly an s-polarized component and a second luminous flux containing mainly a p-polarized component, wherein the s- and p-polarized components, defined using the plane of incidence as a reference, are mutually perpendicular. The two luminous fluxes thus separated from light are received by respective ones of the light-receiving elements, and information relating to absence/presence of an object to be sensed, surface property of the object or material of the object is obtained on the basis of output signals from the light-receiving elements.

Since all of the light incident upon the light-receiving optical system is treated as a single luminous flux and the incident light is divided into two mutually perpendicular polarized light components contained in this single luminous flux, information regarding the material of the object and the surface state thereof can be reflected in the light-reception signal without this information being divided up into parts. This makes accurate discrimination possible. In addition, there is no need for the rotating mechanism or variable applied-voltage generating circuit mentioned in the documents cited above. The result is a simpler construction.

In a preferred embodiment of the invention, use is made of a polarization beam splitter for separating the reflected light, transmitted light or scattered light from the object to be sensed into a first luminous flux which is mainly an s-polarized component with regard to the plane of incidence and a second luminous flux which is mainly a p-polarized component with regard to the plane of incidence, the beam splitter having a light separating characteristic that is substantially constant within a range of angles of incidence used.

More preferably, the polarization beam splitter is such that the aforementioned light separating characteristic, which is substantially constant within a range of angles of incidence used, is held constant within the range of wavelength spread exhibited by the projected light from light-emitting element.

In another preferred embodiment, use is made of a polarization beam splitter for separating the reflected light, transmitted light or scattered light from the object to be sensed into a first luminous flux which is mainly an s-polarized component with regard to the plane of incidence and a second luminous flux which is mainly a p-polarized component with regard to the plane of incidence, the beam splitter having a light separating characteristic which is substantially constant within a range of wavelength spread exhibited by the projected light from light-emitting element.

The light separating characteristic is represented by a first proportion expressed by the ratio of the quantity of light of the s-polarized component contained in the first luminous flux to the quantity of light of the s-polarized component incident upon the polarization beam splitter, a second proportion expressed by the ratio of the quantity of light of the p-polarized component contained in the second luminous flux to the quantity of light of the p-polarized component incident upon the polarization beam splitter, or the ratio of the first proportion to the second proportion. At least one of the first proportion and second proportion or the ratio between them is held substantially constant.

The first proportion, second proportion and the ratio are represented by values obtained by multiplying the light-emission spectrum of the light-emitting element and the spectral sensitivity characteristic of the light-receiving element and integrating the result with regard to wavelength.

The projected light from the light-projecting optical system is not limited to collimated light and may be diverging light or converging light. Accordingly, the direction of reflected light from the object to be sensed possesses a certain angular range. If the light is scattered light, then light having a wider angular range impinges upon the light-receiving optical system. The result is that light having a wide variety of directions impinged upon the polarization beam splitter.

In a case where the light-receiving optical system includes a light-receiving lens, the polarization beam splitter is placed in the optical path of the light converged by the light-receiving lens. In this case, the result is that the angle of incidence of the light incident upon the polarization beam splitter also has a value within a certain range.

Furthermore, in a case where the distance between the object to be sensed and the sensor device fluctuates, the angle of incidence of the light incident upon the polarization beam splitter changes.

Since the light separating characteristic of the polarization beam splitter is held substantially constant in this range of spread of angles of incidence under the conditions in which the optical sensor device is used, stable and accurate discrimination of an object is possible.

Though a light-emitting diode or semiconductor laser is used as the light-emitting element of the light-projecting optical system, use of the light-emitting diode is desirable from various points of view. A light-emitting diode has a wider light-emission spectrum than that of a semiconductor laser. In addition, a light-emitting diode is such that the central wavelengths of the light-emission spectrum are not fixed owing to a variance in the diode caused by the manufacturing process. The central wavelengths of the light emission shift owing to a change in temperature or with the passage of time.

By holding the light separating characteristic of the polarization beam splitter substantially constant with the range of fluctuation or spread of the light-emission wavelengths of the light-emitting element, stabilized, accurate discrimination becomes possible.

The optical sensor device may be of the reflecting type or transmitting type. In the reflecting type, the light-projecting optical system is so arranged that the projected light is projected obliquely or substantially perpendicularly to the surface of the object to be sensed, and the light-receiving optical system is so arranged that the reflected light or scattered light from the surface of the object impinges obliquely or substantially perpendicularly. In the transmitting type of optical sensor device, the light-projecting optical system and light-receiving optical system are spaced apart and arranged to oppose each other.

The invention includes a variety of embodiments.

In one embodiment, a projecting lens is provided and the projected light is projected upon being converged, diverged or collimated by the projecting lens.

In a second embodiment, polarizing means is further provided for converting projected light composed of randomly polarized light to projected light composed of linearly polarized light. Since linearly polarized light is projected, the action of the object of interest upon the state of polarization of the light appears is conspicuous fashion. As a result, more accurate sensing becomes possible depending upon the object to be sensed.

In a third embodiment, light which has emerged from the light-emitting element is introduced to a projecting optical fiber and light which has emerged from an end face of the optical fiber is projected. The construction of the head of the optical sensor device is thus simplified.

In a fourth embodiment, a light-receiving lens is further provided for converging light incident upon the light-receiving optical system. In this case, the polarization beam splitter is placed in the optical path of the light converged by the light-receiving lens.

In a fifth embodiment, the first and second luminous fluxes are introduced to first and second light-receiving elements by respective light-receiving optical fibers. This is intended to reduce the size of the sensor head.

In a sixth embodiment, the device is provided with at least one of first analyzing means provided in front of the first light-receiving element for allowing transmission of s-polarized light and second analyzing means provided in front of the second light-receiving element for allowing transmission of p-polarized light. As a result, only s-polarized light impinges upon the first light-receiving element, and only p-polarized light impinges upon the second light-receiving element. This makes much more accurate discrimination possible. In addition, even a polarization beam splitter incapable of completely separating light into the s- and p-polarized components can be used satisfactorily.

In a seventh embodiment, a reflector is provided to face the polarization beam splitter on the side from which the first or second luminous flux emerges. As a result, the first and second light-receiving elements can be arranged on the same side of the polarization beam splitter.

In an eighth embodiment, an opening for limiting incident light is formed in front of the light-receiving optical system. Regular reflected light from the object to be sensed can be made to impinge upon the light-receiving optical system by the opening. Further, incidence of scattered light can be excluded. Depending upon the angle of incidence, there is the possibility that scattered light will enter the light-receiving elements directly without impinging upon the polarization beam splitter. This situation can be prevented.

The present invention provides many apparatus and methods that make use of the above-described optical sensor device. Typical examples thereof will be illustrated.

One example is an object identification apparatus in which the above-described optical sensor device is placed on an object conveyance path and objects conveyed are identified on the basis of an output signal from the optical sensor device.

Another example is a printing apparatus in which the above-described optical sensor device is placed on a conveyance path of a printing medium and an edge or positional offset of the printing medium is sensed on the basis of an output signal from the optical sensor device.

Another example is a printing apparatus in which the above-described optical sensor device is held so as to move together with a printing head.

Another example is a printing apparatus comprising the above-described optical sensor device, discriminating means for discriminating the type of a printing medium on the basis of an output signal from the optical sensor device, and control means for controlling printing conditions on the basis of results of discrimination performed by the discriminating means.

Another example is an air conditioning apparatus comprising the above-described optical sensor device so arranged as to discriminate the surface state of a condensation medium or frost medium, and control means for controlling air-conditioning running conditions on the basis of an output signal from the optical sensor device.

Another example is a humidity control apparatus comprising a heat exchanger, the above-described optical sensor device for discriminating the surface state of the heat exchanger, and a control unit for controlling running conditions on the basis of an output signal from the optical sensor device.

Another example is a vehicle comprising the above-described optical sensor device so arranged as to discriminate the surface state on the inner side of a window glass of the vehicle, means for eliminating fogging of the window glass, and control means for controlling the fog eliminating means on the basis of an output signal from the optical sensor device.

Another example is a vehicle comprising the above-described optical sensor device so arranged as to discriminate the surface state on the outer side of a window glass of the vehicle, a window wiper device for cleaning the surface on the outer side of the window glass, and control means for controlling the operation of the window wiper device on the basis of an output signal from the optical sensor device.

Another example is a vehicle comprising the above-described optical sensor device so arranged as to discriminate the state of a road surface, operating-state detecting means for detecting the state in which the vehicle is being operated, and control means for controlling drive of an actuator, which is related to the state in which the vehicle is being run, on the basis of results of discriminating the road surface by the optical sensor device and results of detecting the operating state by the operating-state detecting means.

Another example is a vehicle comprising the above-described optical sensor device so arranged and constructed as to sense a mark or the like represented on a road surface, warning means for warning an individual driving the vehicle, and control means for controlling the warning means on the basis of an output signal from the optical sensor device.

Another example is a traveling body comprising the above-described optical sensor device for sensing deviation from a guide provided along a path of travel, and means for performing steering on the basis of a detection signal from the optical sensor device.

Another example is a bank note handling apparatus comprising the above-described optical sensor device for sensing the surface of a bank note, and control means for controlling operation of the apparatus on the basis of an output from the sensor device.

Another example is an offset printing apparatus comprising a printing roller for fixing a printing original sheet, wetting-water supply means for supplying the printing original sheet with wetting water, the above-described optical sensor device for sensing the surface of the printing original sheet, and control means for controlling the wetting-water supply means on the basis of an output from the optical sensor device.

Another example is an inspection apparatus comprising the above-described optical sensor device so arranged as to discriminate the surface state of an article conveyed on a conveyance path, direction changing means for changing conveyance direction of the conveyed article, and means for controlling the direction changing means on the basis of results of discrimination by the optical sensor device.

Another example is an inspection method for discriminating the surface state of an article, conveyed on a conveyance path, by the above-described optical sensor device, and controlling the conveyance direction of the article on the basis of the results of discrimination.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 21 illustrates the structure of a polarization beam splitter G;

FIG. 28 is a graph showing the transmittance characteristic of the polarization beam splitter I;

FIG. 29 is a graph showing the dependency of reflectivity of an s-polarized light component and transmittance of a p-polarized light component on angle of incidence of the polarization beam splitter I;

FIGS. 30a, 30b are graphs showing dependency on angle of incidence in the polarization beam splitter A when the central wavelength of a light emission from a light-emitting diode has shifted by −10 nm and +10 nm, respectively;

FIG. 35 collectively illustrates $\Delta R_s/T_p$ and $\Delta R_s$ with regard to the polarization beam splitters A, B, C, D and E;

FIG. 38 collectively illustrates $\Delta R_s/T_p$ and $\Delta R_s$ with regard to the polarization beam splitters F and G;

FIG. 41 shows another example of an arrangement of a sensor head in a reflecting-type optical sensor device;

FIG. 43 shows yet another example of an arrangement of a sensor head;

FIGS. 44a, 44b are a plan view and side view, respectively, illustrating the light-projecting optical system of the sensor head of FIG. 43;

FIG. 82 shows an example of the arrangement of a transmissive sensor head;

FIGS. 89a, 89b and 89c illustrate examples of arrangements in which the quantity of incident light is held constant irrespective of a fluctuation in the distance of an object to be sensed;

FIG. 91 illustrates an example of an arrangement in which the quantity of incident light is held constant irrespective of a fluctuation in the distance of an object to be sensed

FIG. 93 illustrates an example of an arrangement in which the quantity of incident light is held constant irrespective of a fluctuation in the distance of an object to be sensed;

FIGS. 107a, 197b, 107care perspective views showing the disposition of a sensor head;

FIG. 121 is a block diagram showing a wiper control circuit;

FIG. 122 is a perspective view showing application to a brake control system and illustrating the front part of an automobile;

FIG. 123 is a block diagram showing the configuration of the brake control system;

FIG. 124 is a flowchart showing a processing procedure for brake control;

FIG. 125 is a block diagram showing a brake control circuit;

FIG. 126 is a block diagram showing a system for sensing that a driver is dozing at the wheel;

FIG. 127 is a flowchart showing a processing procedure for sensing that a driver is dozing at the wheel;

FIG. 128 is a block diagram showing a circuit for sensing that a driver is dozing at the wheel;

FIG. 129 is a block diagram showing a system for controlling the travel of an unmanned vehicle;

FIG. 130 illustrates a white line and a projected light spot;

FIG. 131 is a flowchart illustrating a processing procedure for controlling an unmanned vehicle;

FIG. 132 is a block diagram showing a tape sensing system;

Figure 133A:
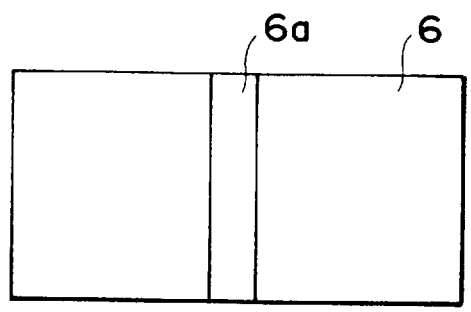
Figure 133B:
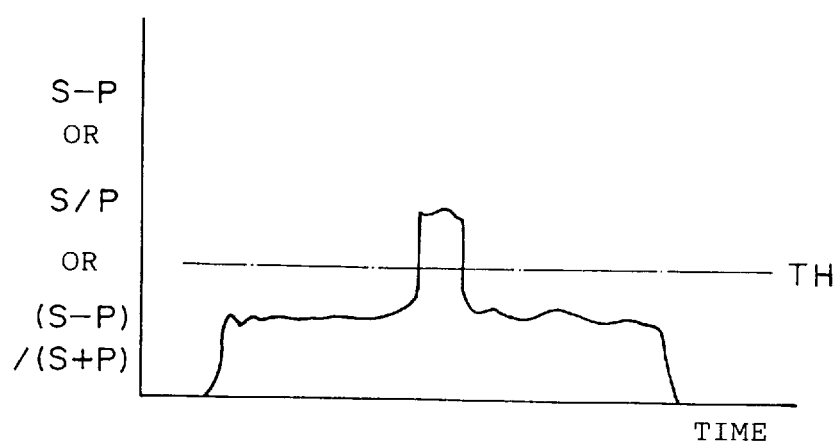
Figure 134:
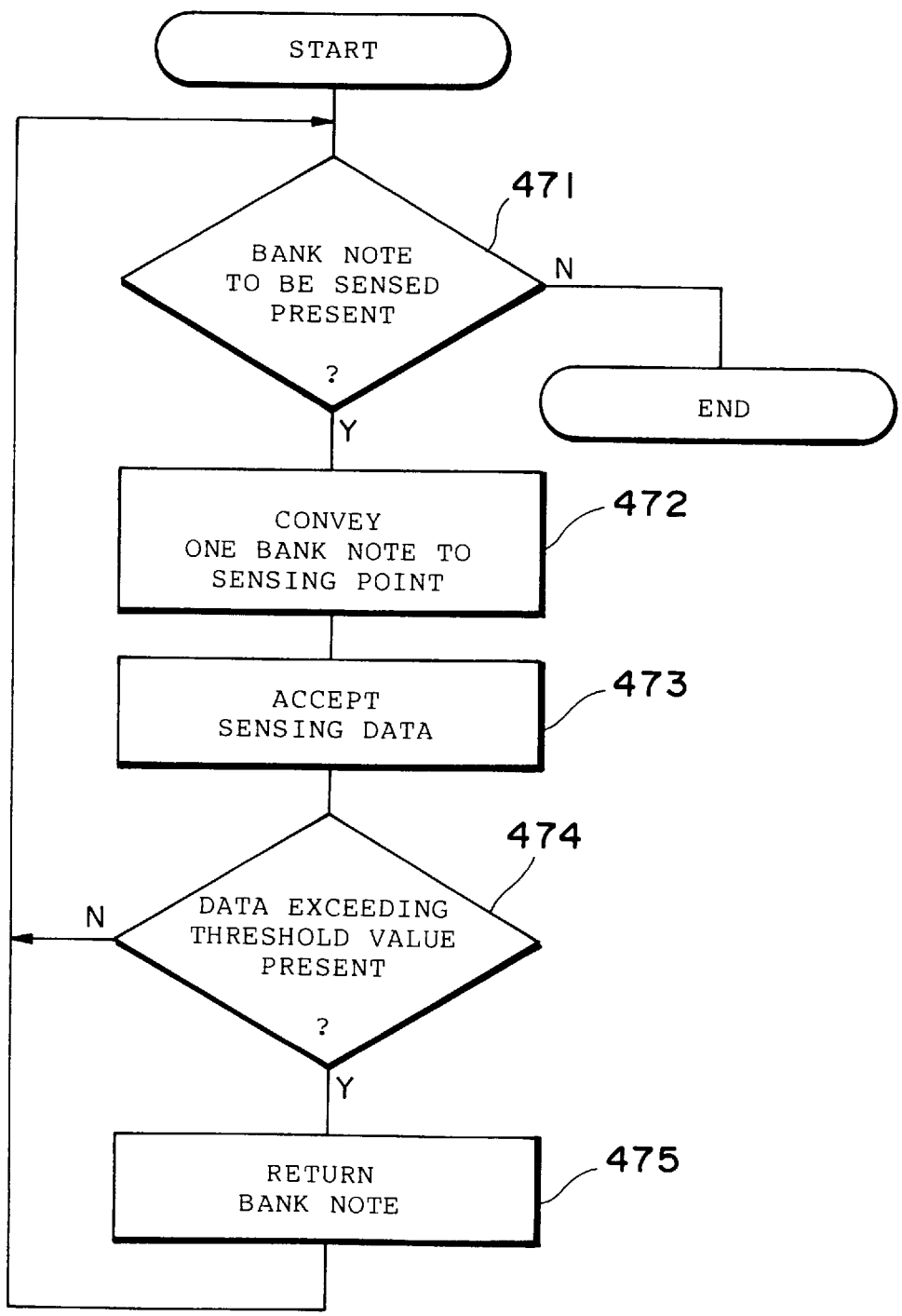
Figure 135:
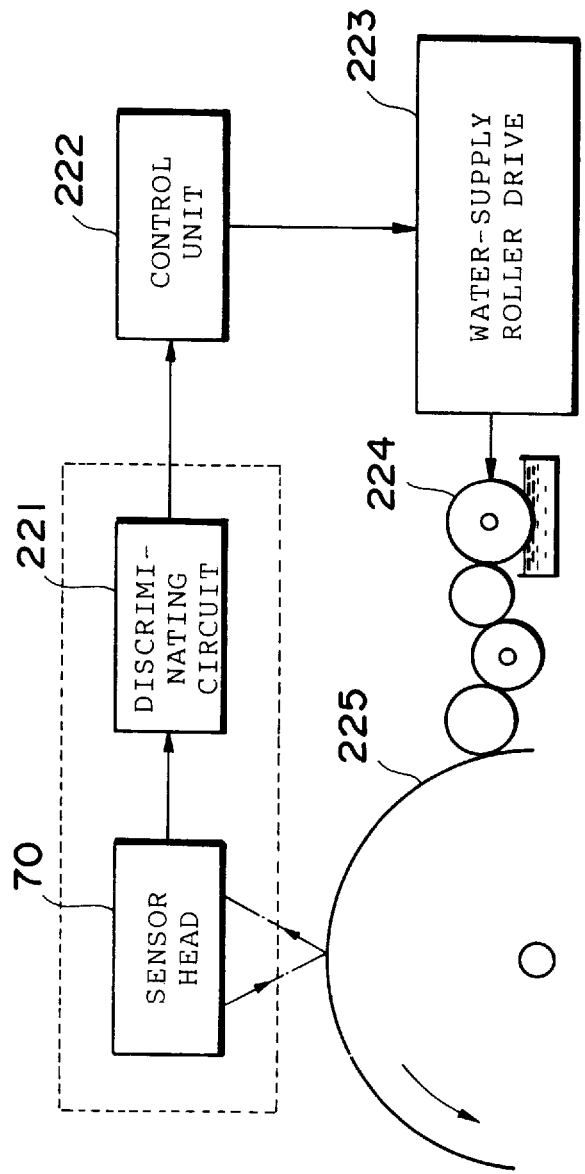
Figure 136:
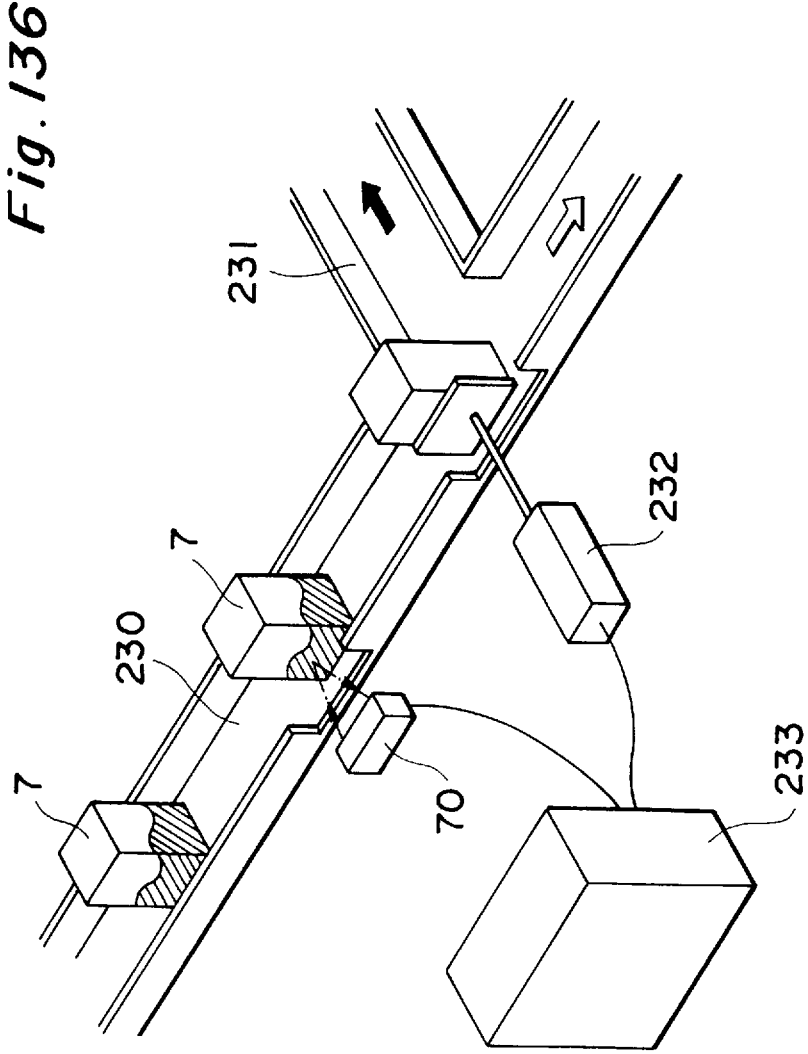
Figure 137:
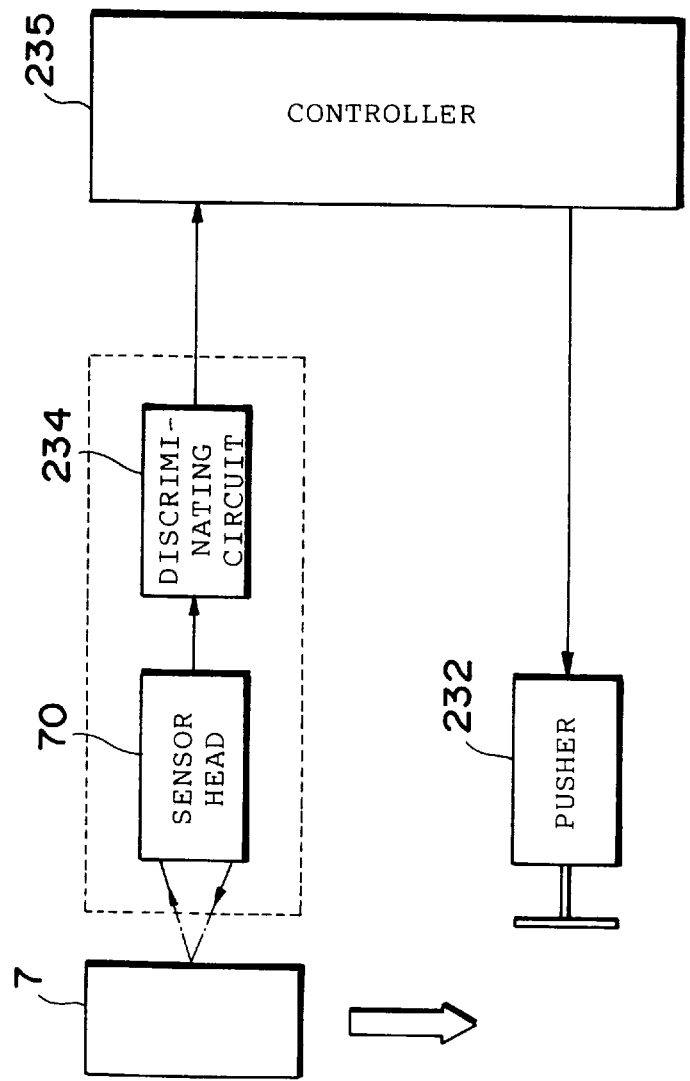
Figure 138:
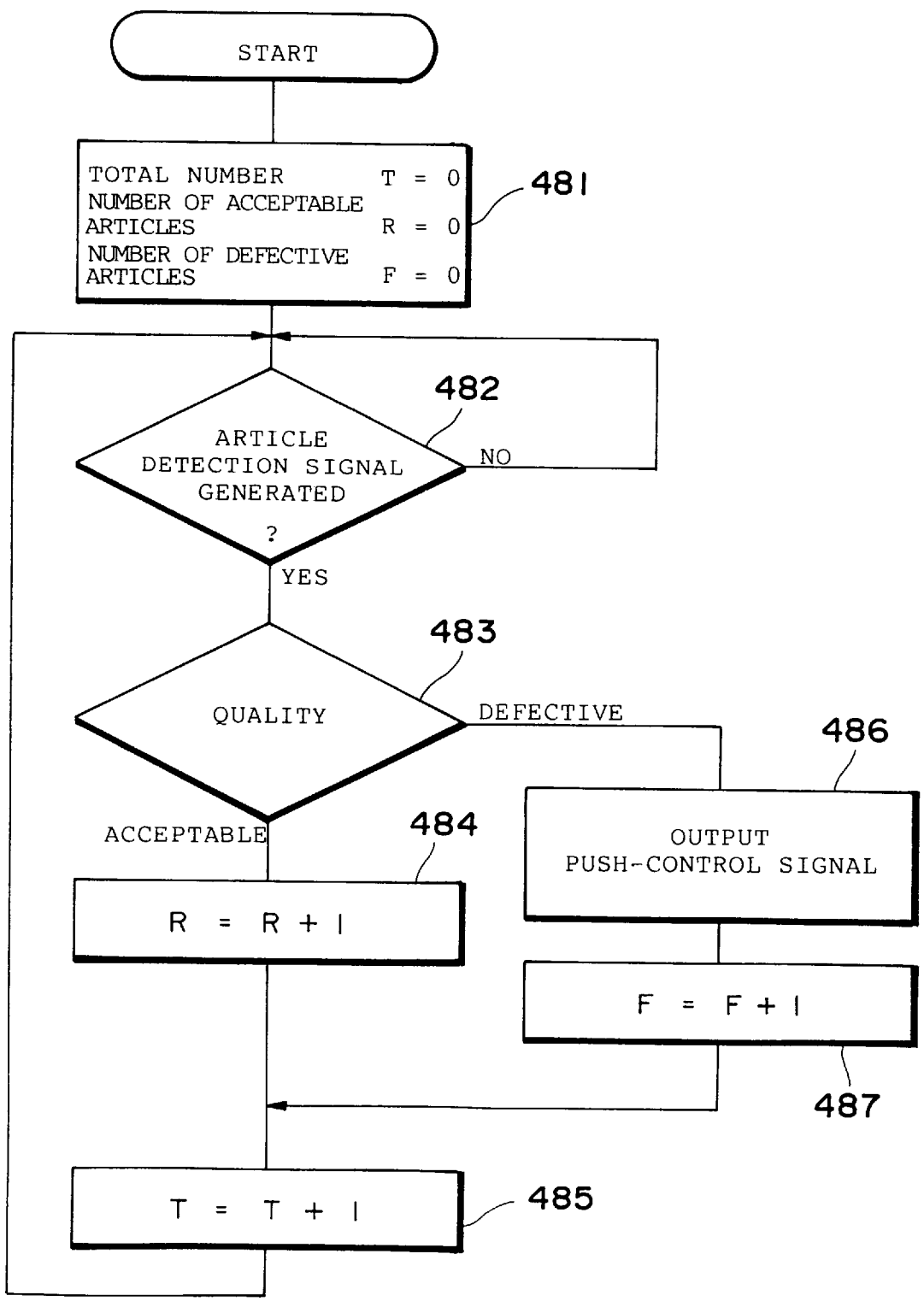
Figure 139:
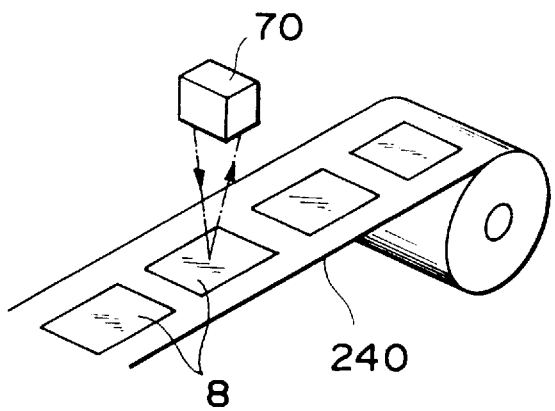

FIG. 133a illustrates a bank note to which tape has been adhered, and FIG. 133b shows a sensed signal;

FIG. 134 is a flowchart showing a processing procedure for sensing tape;

FIG. 135 illustrates part of an offset printing apparatus;

FIG. 136 is a perspective view illustrating an inspection apparatus in a manufacturing line;

FIG. 137 is a block diagram showing an inspection apparatus in a manufacturing line;

FIG. 138 is a flowchart showing a processing procedure for inspection in a manufacturing line; and FIG. 139 shows another example of a manufacturing line.

DESCRIPTION OF THE PREFERRED EMBODIMENTS (1) Construction and characteristics of polarization beam splitter A polarization beam splitter used in the optical sensor device of this invention basically is formed by building up multiple layers of thin films of a dielectric or metal on a substrate, in which thin films of a comparatively high index of refraction are alternated with thin films of a comparatively low index of refraction.

The polarization beam splitter separates an incident light beam (with the exception of light incident on the plane of incidence of the polarization beam splitter at right angles) into a light beam mainly containing a p-polarized light component and a light beam mainly containing an s-polarized light component. As will be set forth later, light transmitted through the polarization beam splitter mainly contains the p-polarized light component and light reflected by the polarization beam splitter (regular reflected light) mainly contains the s-polarized light.

Here p-polarized light refers to linearly polarized light in which the vibrating direction of the electric vector of light impinging upon the surface of a specimen is contained in the plane of incidence [a plane containing the normal to the specimen surface and the normal to the wave surface (the direction in which the light propagates)], and s-polarized light refers to linearly polarized light in which the vibration direction of the electric vector of light impinging upon the surface of a specimen is perpendicular to the plane of incidence (see the "Dictionary on Light", edited by Ryuichi Hioki, published by Ohmsha K.K., 1989).

The specimen surface in a polarization beam splitter refers to one surface thereof (either one of the surfaces). As will be described later, p-polarized light and s-polarized light are defined also in an object to be sensed (an object to sensed by the optical sensor device). In this case, the specimen surface is the surface of the object to be sensed (the surface upon which light projected from the optical sensor device impinges).

Methods of computing the characteristics of a given structure of multilayered films [the material (index of refraction) of each layer, the thickness of each layer, the number of layers, etc.] are described, for example, in "Thin-Film Optical Filters" by H. A. Macleod, translated by Shigetaro Ogura, Yuji Nakajima, Takashi Yabe and Kunio Yoshida, published by Nikkan Kogyo Shimbun-sha, 1989, and "Optical Thin Films" by Kozo Ishiguro, Hideo Ikeda and Hideshi Yokota, edited by Shiro Fujiwara, Second Edition, published by Kyoritsu Shuppan K.K., 1986. The desired characteristics can be obtained by using a computer to repeat the operation of giving a structure, computing the characteristics thereof and correcting the structure upon observing the results of computation.

One feature of a polarization beam splitter used in an optical sensor device is that the light separating (splitting) characteristic within a range of incidence angles decided by the structure of the optical sensor device and the conditions under which it is used is substantially constant (the dependency of the light separating characteristic upon the angle of incidence is small within a predetermined range of angles of incidence).

The angle at which light impinges upon a polarization beam splitter is influenced by the fact that projected light from a light source (a light-emitting element) possesses angular spread, the fact that the polarization beam splitter is placed in light that converges, and the fact that the distance between the object to be sensed and the sensor device fluctuates. Consequently, the angle of incidence of the light that impinges upon the polarization beam splitter possesses spread. This is the range of angles of incident of light decided by the structure of the optical sensor device and the conditions under which the device is used.

The light separating characteristic in a polarization beam splitter is represented by the p-polarized light component or s-polarized light component, the ratio between them, the difference between them or by some other operation between them (the details of which will be described later). The light-emission characteristic of the light source (light-emitting element) or the light-receiving sensitivity characteristic of a light-receiving element also is taken into consideration as necessary.

The fact that the light separating characteristic is substantially constant means that a given detection sensitivity (or detection capability) is obtained for the optical sensor device (a specific example will be described later).

One other feature of a polarization beam splitter is that the light separating (splitting) characteristic is held substantially constant within a range of wavelength spread exhibited by the light generated by the light source of the optical sensor device.

The spread of the wavelength of light from a light source signifies a spread resulting from one or both of the wavelength region decided by the light-emission spectrum of the light from the light source and a fluctuation in the light-emission wavelength caused by a variance in manufacture of the light source, a change in temperature or a change with the passage of time.

Ideally, the polarization beam splitter should have both of the features mentioned above. Specifically, a polarization beam splitter should be such that the dependency of the light separating characteristic on the angle of incidence is small over a given range of angles of incidence within the range of wavelength spread exhibited by the light generated by the light source of the optical sensor device.

Of course, it is sufficient in actual practice if the polarization beam splitter possesses at least one of the above-mentioned two features. In such case, it is preferred that other components of the optical sensor device be so arranged as to have a specific structure. For example, in a case where the range of incident angles within which the light separating characteristic is held substantially constant is narrow, parallel light is used. In a case where the range of wavelength within which the light separating characteristics is held substantially constant is narrow, a semiconductor laser having a narrow light-emission spectrum is used as the light source.

A specific example of a polarization beam splitter having the above-mentioned light separating characteristic will now be described.

A polarization beam splitter (PBS) having the optimum characteristic will be illustrated first.

Figure 1:
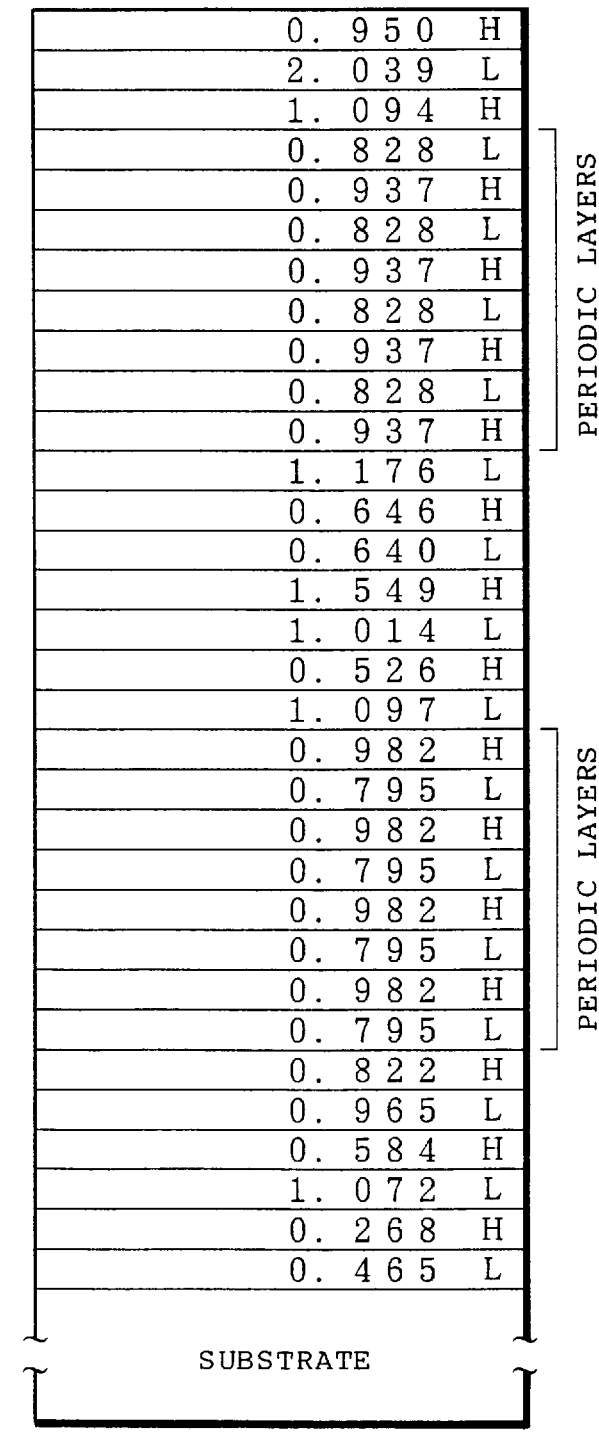
FIG. 1 illustrates the structure of a polarization beam splitter A.

FIG. 1 illustrates the structure of a first polarization beam splitter (referred to as "polarization beam splitter A"). The beam splitter is obtained by forming dielectric films in multiple layers on substrate comprising a flat plate of glass or the like.

This construction is expressed as follows: glass substrate (refractive index n=1.51)/0.465 L, 0.268 H, 1.072 L, 0.584 H, 0.965 L, 0.822 H, (0.795 L, 0.982 H) 4, 1.097 L,0.526 H, 1.014 L, 1.549 H, 0.640 L, 0.646 H, 1.176 L, (0.937 H, 0.828 L) 4, 1.094 H, 2.039 L, 0.950 H/air (n=1).

The H and L in the foregoing representation signify thin films having relatively high and low indices of refraction, respectively. The thin films having the high index of refraction are made of $TiO_2$ whose index of refraction is 2.26, and the thin films having the low index of refraction are made of $SiO_2$ whose index of refraction is 1.46.

The numerical values preceding H and L represent the optical film thickness of the thin film, where this is expressed taking $\lambda/4$ at the time of $\lambda$=610 nm as being 1.000.

Further, (0.795 L, 0.982 H) 4 indicates that the combination of the 0.795 L layer and 0.982 H layer is repeated four times. The same is true for (0.937 H, 0.828 L) 4. These repeated layers are referred to as "periodic layers".

Figure 2:
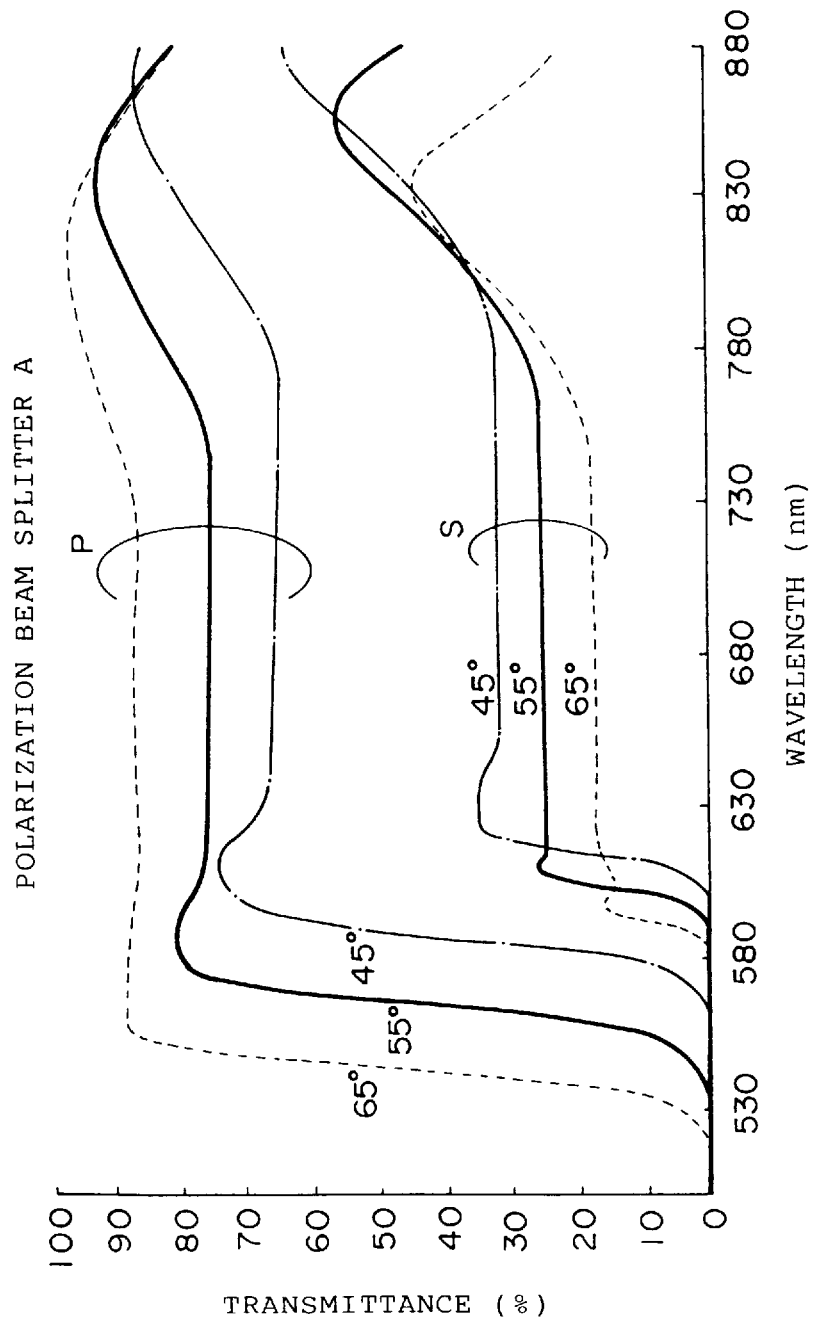
FIG. 2 is a graph showing the transmittance characteristic of the polarization beam splitter A.

FIG. 2 illustrates the transmittance characteristic of the polarization beam splitter A having the structure shown in FIG. 1. This characteristic is obtained by computation (simulation) based upon the methods described in the literature cited above. The same is true for polarization beam splitters having other structures described below in succession.

In FIG. 2, wavelength is plotted along the horizontal axis and transmittance along the vertical axis. Also shown in FIG. 2 are the p-polarized light component (indicated at P in FIG. 2) and s-polarized light component (indicated at S in FIG. 2) of the light incident upon the polarization beam splitter A. The transmittance characteristic is shown for each of three difference angles of incidence (45°, 55° and 65°). Reflectivity is a value obtained by subtracting transmittance from 1.

At each angle of incidence there is a range of wavelengths (on the order of 600~750 nm) within which the transmittance (reflectivity) is held substantially constant for both the p- and s-polarized light components. This range of wavelengths is 150 nm or more. The transmittance (separation characteristic) has almost no wavelength dependence within this range of wavelengths.

The transmittance of the p-polarized light component is considerably larger than that of the s-polarized light component in this range of wavelengths. It will be understood that the polarization beam splitter A possesses a separation (a beam split) characteristic which transmits the p-polarized light component and reflects the s-polarized light component. In other words, the transmitted light from the polarization beam splitter A mainly contains the p-polarized light components while the reflected light contains many s-polarized light components.

All of the other polarization beam splitters illustrated below exhibit light separating characteristics which transmit mainly the p-polarized light components and reflect mainly the s-polarized light component.

When the angle of incidence in the graph of FIG. 2 differs, the transmittance (reflectivity) also differs for both the p-polarized light component and s-polarized light component. If solely the p-polarized light component or s-polarized light component is observed, it is seen that the light separating characteristic of the polarization beam splitter A is dependent upon the angle of incidence.

However, when the light separating characteristic of the polarization beam splitter A is represented by the ratio of the reflectivity $R_s$ of the s-polarized light component to the transmittance $T_p$ of the p-polarized light component (hereinafter written simply as $R_s/T_p$), there is almost no dependency upon the angle of incidence.

Figure 3:
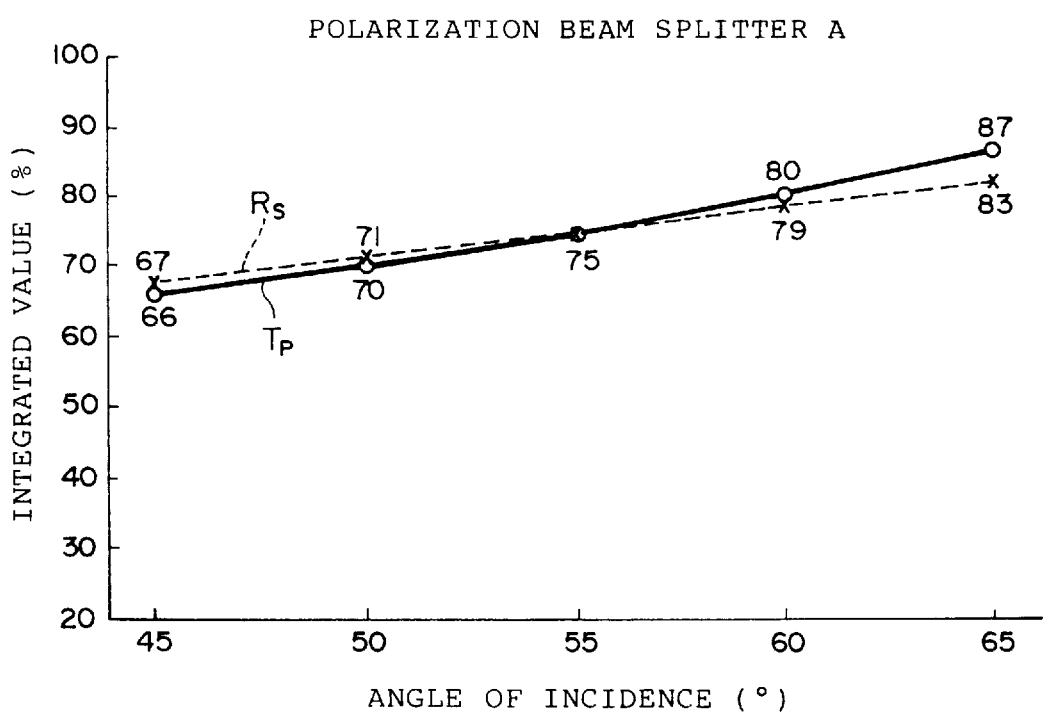
FIG. 3 is a graph showing the dependency of reflectivity of an s-polarized light component and transmittance of a p-polarized light component on angle of incidence of the polarization beam splitter A.

FIG. 3 is a graph showing the dependency of reflectivity $R_s$ of the s-polarized light component and transmittance $T_p$ of the p-polarized light component on angle of incidence of the polarization beam splitter A. The angle of incidence of light on the polarization beam splitter A is plotted along the horizontal axis of the graph. An integrated value is plotted along the vertical axis (this will be described later in detail).

In the graph of FIG. 3, reflectivity $R_s$ and transmittance $T_p$ (both of which are integrated values) vary substantially linearly as the angle of incidence of light varies. However, the rate of change in reflectivity $R_s$ (with respect to the change in the angle of incidence) and the rate of change in transmittance $T_p$ are approximately the same. In other words, $R_s/T_p$ is held substantially constant (over the range of 45° to 65°) irrespective of the change in angle of incidence.

It will be understood that the polarization beam splitter A has almost no dependency on the angle of incidence (i.e., that $R_s/T_p$ is held substantially constant) within a certain range of angles of incidence to the extent that the separation characteristic can be ascertained from the viewpoint of $R_s/T_p$ (the same holds for $T_p/R_s$) The polarization beam splitter A is so designed that the light separating characteristic thereof represented by Rs/Tp possesses almost no dependency on wavelength in the range of wavelengths used (FIG. 2) and almost no dependency on angle of incidence in the range of angles of incidence used.

In an optical sensor device using this polarization beam splitter A, the reflected light (the s-polarized light component) and the transmitted light (the p-polarized light component) of the polarization beam splitter are sensed by respective ones of light-receiving elements. Let S(R) represent the quantity of reflected light and P(T) the quantity of transmitted light of the polarization beam splitter. Since S(R)/P(T) is held substantially constant in the range of wavelengths used and in the range of angles of incidence used, highly accurate sensing of an object of interest is possible using the value of S(R)/P(T). In order to sense the object, it is possible to use not only the value of S(R)/P(T) but also the value of S(R)–P(T), [S(R)–P(T)]/[S(R)+P(T)] or S(R)–kP(T) (where k is a constant). This holds true for all of the other polarization beam splitter described later.

As will be set forth later, the optical sensor device is equipped with a light source (light-emitting element) from which light is projected toward an object to be sensed. Reflected light (in case of a reflective-type device) from the object to be sensed or transmitted or scattered light (in case of a transmissive-type device) from the object to be sensed is received. Two light-receiving elements are provided (inclusive of a light-receiving element divided into two portions). Reflected light or transmitted light from the object to be sensed is split by the polarization beam splitter and is then received by respective ones of the two light-receiving elements.

Figure 4:
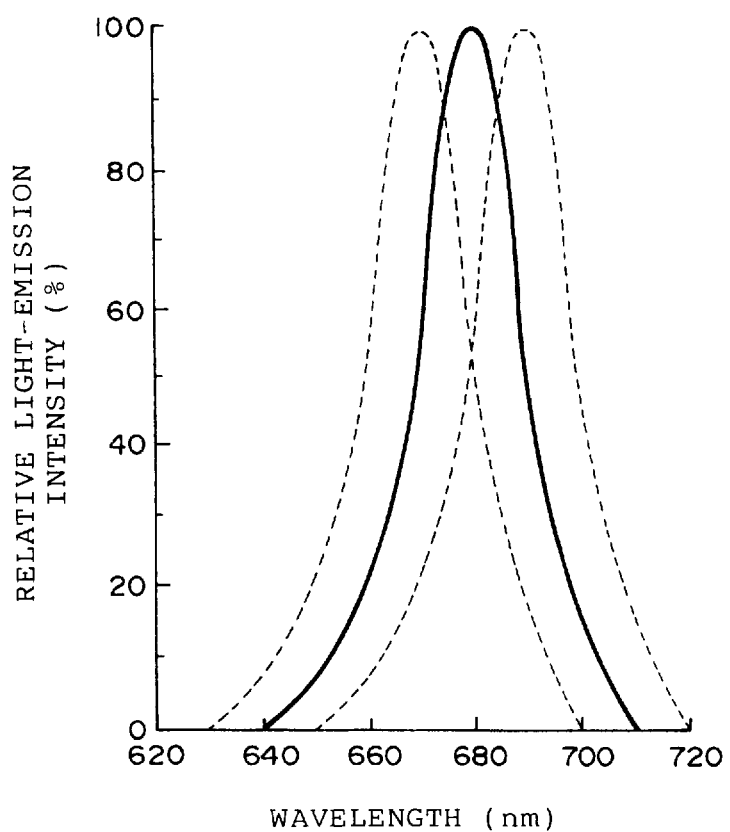
FIG. 4 illustrates a light-emission spectrum of a GaAlAs light-emitting diode.

FIG. 4 illustrates the light-emission spectrum of a GaAlAs light-emitting diode serving as one example of a light-emitting element. The light-emission spectrum has a peak at a position of a wavelength of about 680 nm and a half-width of about 20 nm. This light-emission spectrum extends over a wider wavelength range in comparison with the semiconductor laser.

In a case where use is made of a light-emitting element in which the light-emission wavelength band is comparatively wide, the polarization beam splitter is required to have a light separating characteristic free of wavelength dependency with regard to a range of wavelengths over almost the entire region of the light-emission wavelength band.

A light-emitting element such as a light-emitting diode exhibits a comparatively large variance in characteristics stemming from the manufacturing process. In terms of the light-emission spectrum, the wavelength indicating the peak of the light-emission intensity has a variance on the order of ±10~±20 nm. The light-emission spectrum which results when the light-emission wavelength is shifted by +10 nm and–10 nm is indicated by the dashed line in FIG. 4.

The polarization beam splitter used in the optical sensor device is required to have a light separating characteristic capable of covering this range of variance in the light-emission wavelength of the light-emitting element (i.e., the characteristic should be held constant even over the wavelength range of variance).

The polarization beam splitter having the structure shown in FIG. 1 possesses the most desirable characteristic, namely one in which the light separating characteristic (the value of $R_s$ or $T_p$ or the value of $R_s/T_p$ or $T_p/R_s$) is held substantially constant over the range of spread of the light-emission wavelength of the light-emitting diode and over the range of variance thereof (compare FIGS. 2 and 4).

In an optical sensor device using a polarization beam splitter having such a light separating characteristic, an advantage is that a light-emitting diode can be used instead of a semiconductor laser. This is because the laser beam of a semiconductor laser possesses a high light energy density, by reason of which danger to the human body must be taken into account. In addition, a semiconductor laser is costly and great care in handling is necessary at the time of assembly.

Figure 5:
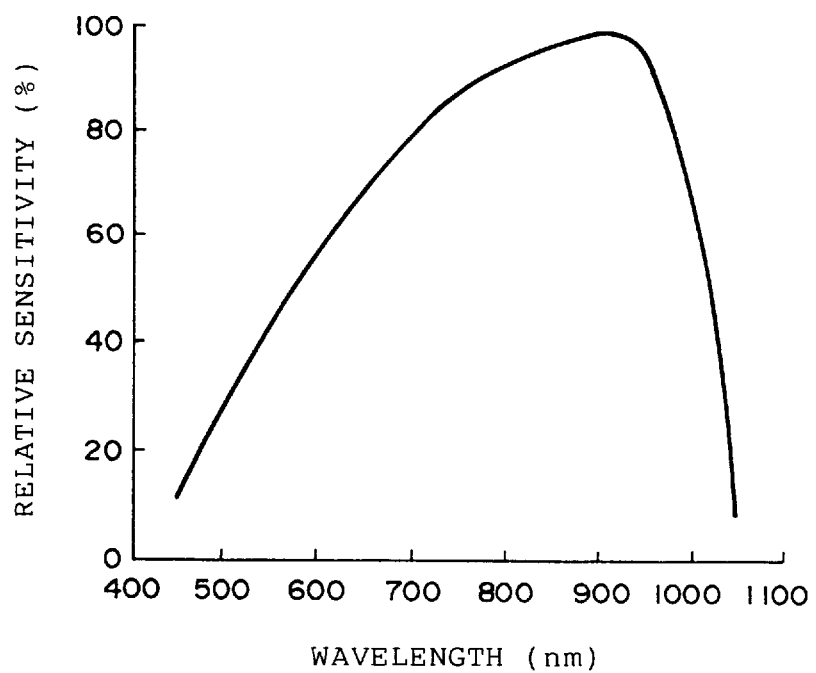
FIG. 5 illustrates a spectral sensitivity characteristic of an Si pin photodiode.

FIG. 5 illustrates a spectral sensitivity characteristic of an Si pin photodiode serving as one example of a light-receiving element. It will be appreciated that the sensitivity of this light-receiving element differs depending upon the wavelength of the incident light.

The optical sensor device performs signal processing (arithmetic operations, etc.) based upon the light-reception signals (output signals) of the light-receiving elements and eventually outputs sensing information regarding the object to be sensed. Light incident upon the light-receiving element is converted to an electric signal in accordance with the spectral sensitivity characteristic of the light-receiving element. The light-reception signals outputted by the light-receiving elements represent the total sum of values obtained by photoelectrically converting the quantity of incident light in accordance with the spectral sensitivity characteristic with regard to all wavelengths possessed by the incident light. The incident light has a light-emission spectrum of the kind depicted in FIG. 4. Accordingly, when taking into account the light separating characteristic of the polarization beam splitter, it is desirable to give consideration to the light-emission spectrum of the light-emitting element and to the spectral sensitivity of the light-receiving elements.

In this sense, the integrated values shown in FIG. 3 indicate values obtained by integrating the light-emission spectrum of FIG. 4, the transmittance (reflectivity) shown in FIG. 2 and the spectral sensitivity shown in FIG. 5 over the entire wavelength band (which ultimately is decided by the wavelength band of the light-emission spectrum).

Other examples of polarization beam splitters will now be described. Four types of polarization beam splitters designated by B, C, D and E will be described. These polarization beam splitters have been so designed as to particularly eliminate the dependency of the reflectivity $R_s$ of the s-polarized light component on the angle of incidence (i.e., in such a manner that $R_s$ maintains a substantially constant value irrespective of a change in the angle of incidence).

Figure 6:
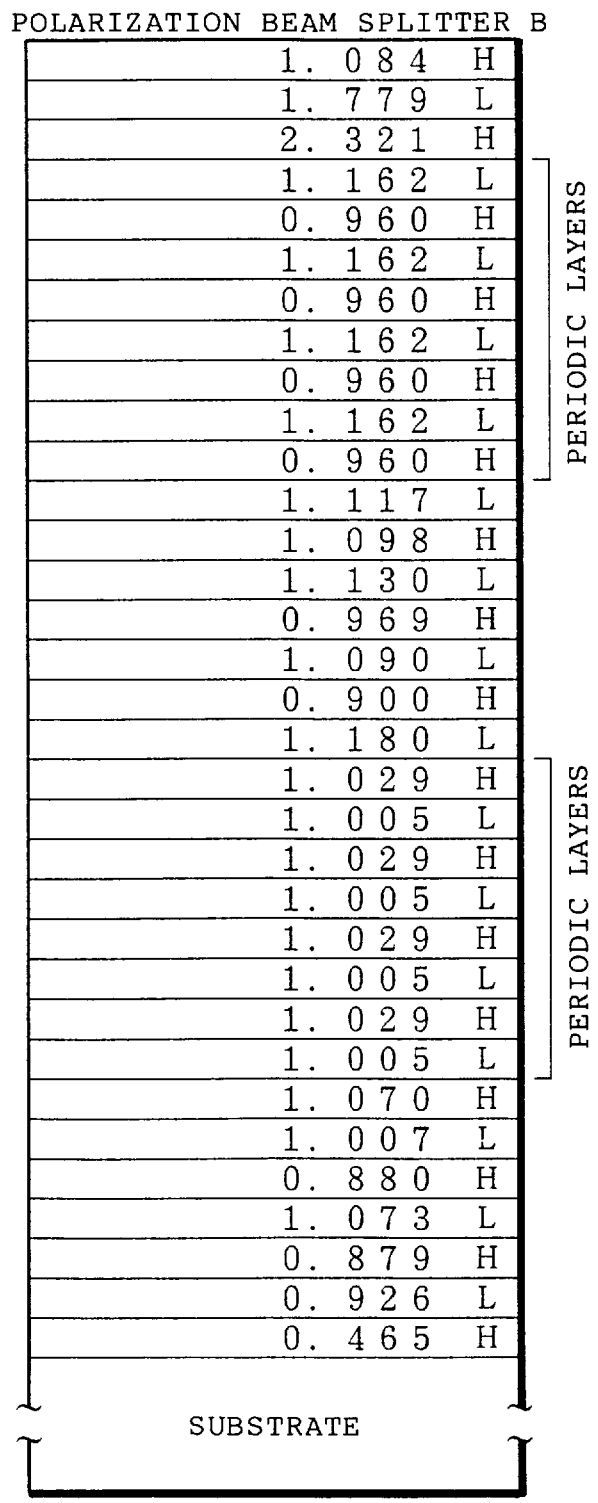
FIG. 6 illustrates the structure of a polarization beam splitter B.

FIG. 6 illustrates the structure of a polarization beam splitter B. In FIG. 6, the optical thin film thickness is expressed taking λ/4 at the time of λ=590 nm as being 1.000.

Figure 7:
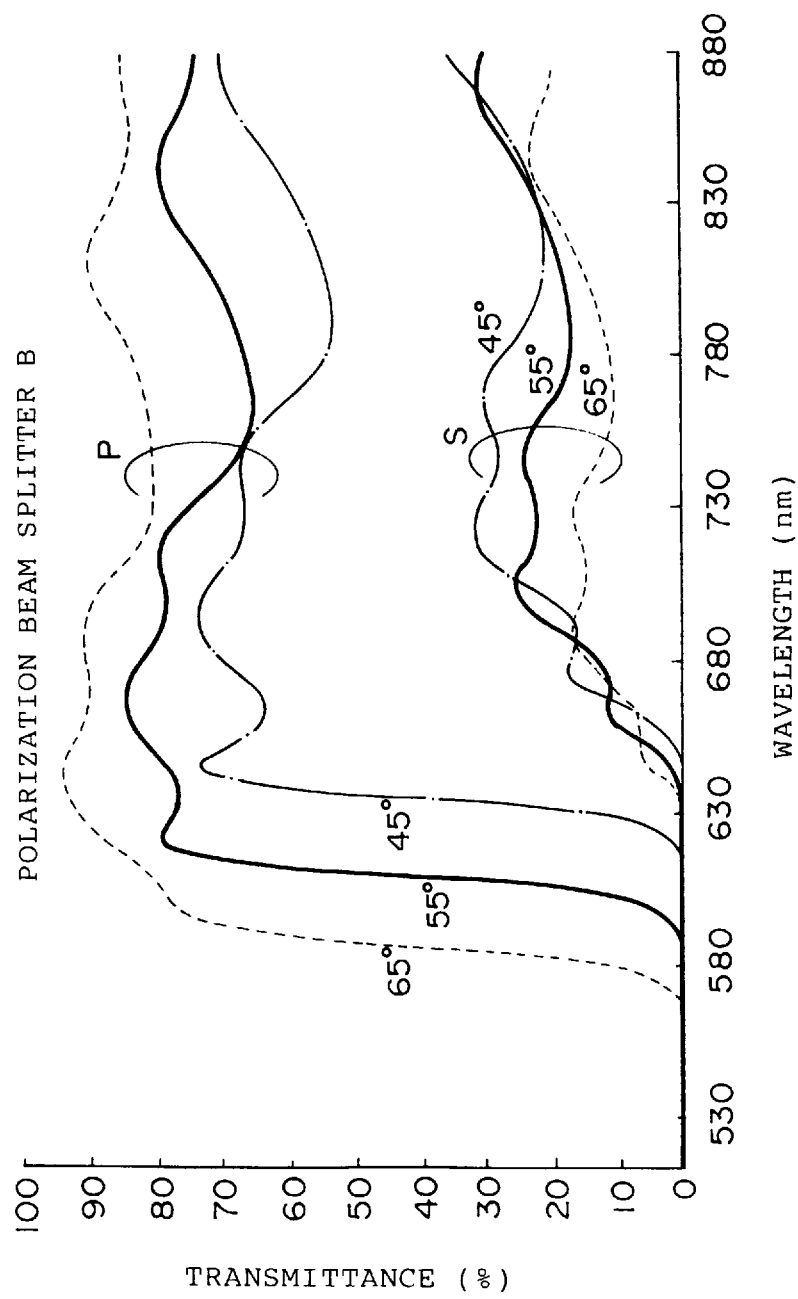
FIG. 7 is a graph showing the transmittance characteristic of the polarization beam splitter B.

FIG. 7 shows the transmittance characteristic of the polarization beam splitter B with regard to the p-polarized light component and s-polarized light component, with angle of incidence serving as a parameter. In the graph of FIG. 7, the transmittances of the p- and s-polarized light components undulate with respect to a change in wavelength. In the integrated values shown in FIG. 8, however, the light-emission spectrum of the light-emitting element and the spectral sensitivity of the light-receiving elements are integrated, as a result of which the effects of this undulating change are almost entirely eliminated.

Figure 8:
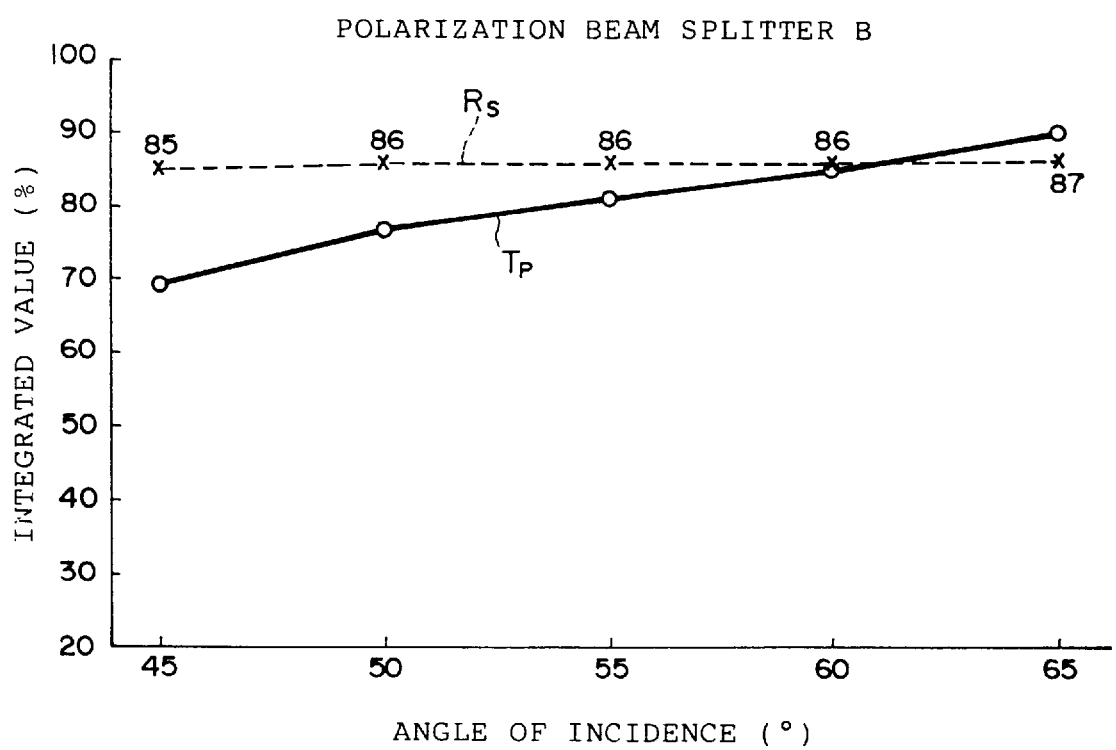
FIG. 8 is a graph showing the dependency of reflectivity of an s-polarized light component and transmittance of a p-polarized light component on angle of incidence of the polarization beam splitter B.

FIG. 8 is a graph showing the dependency of reflectivity Rs of the s-polarized light component and transmittance Tp of the p-polarized light component on angle of incidence in the polarization beam splitter B. It will be appreciated that the reflectivity $R_s$ (integrated value) of the s-polarized light is held substantially constant over the range of angles of incidence of 45° to 65°.

Figure 9:
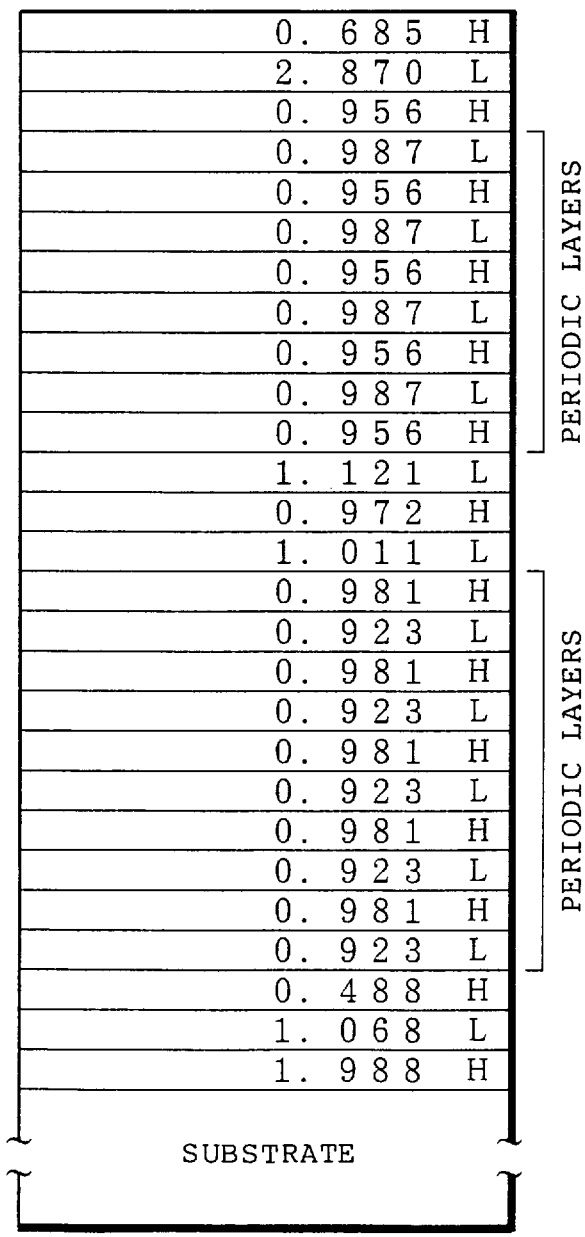
FIG. 9 illustrates the structure of a polarization beam splitter C.
Figure 10:
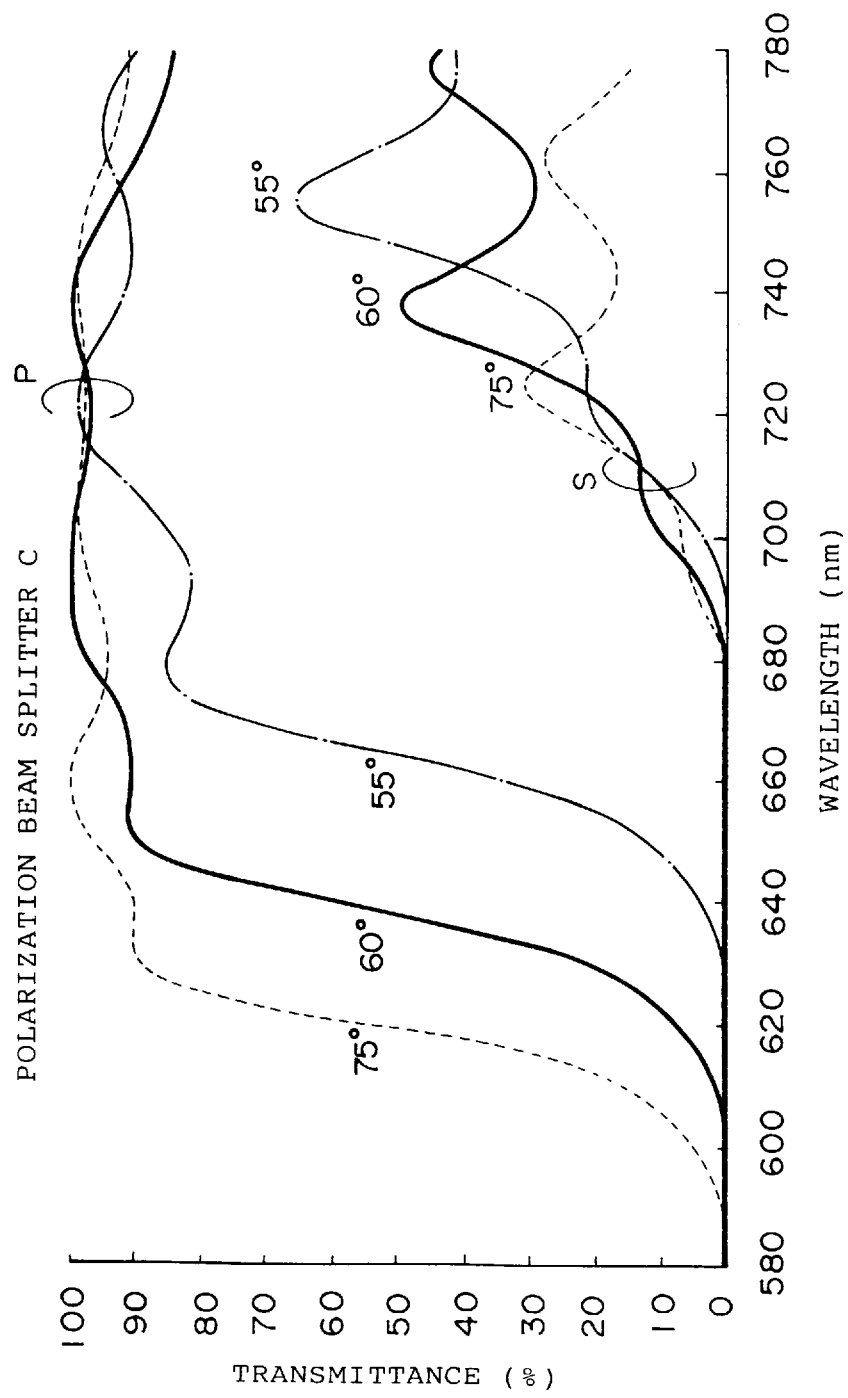
FIG. 10 is a graph showing the transmittance characteristic of the polarization beam splitter C.
Figure 11:
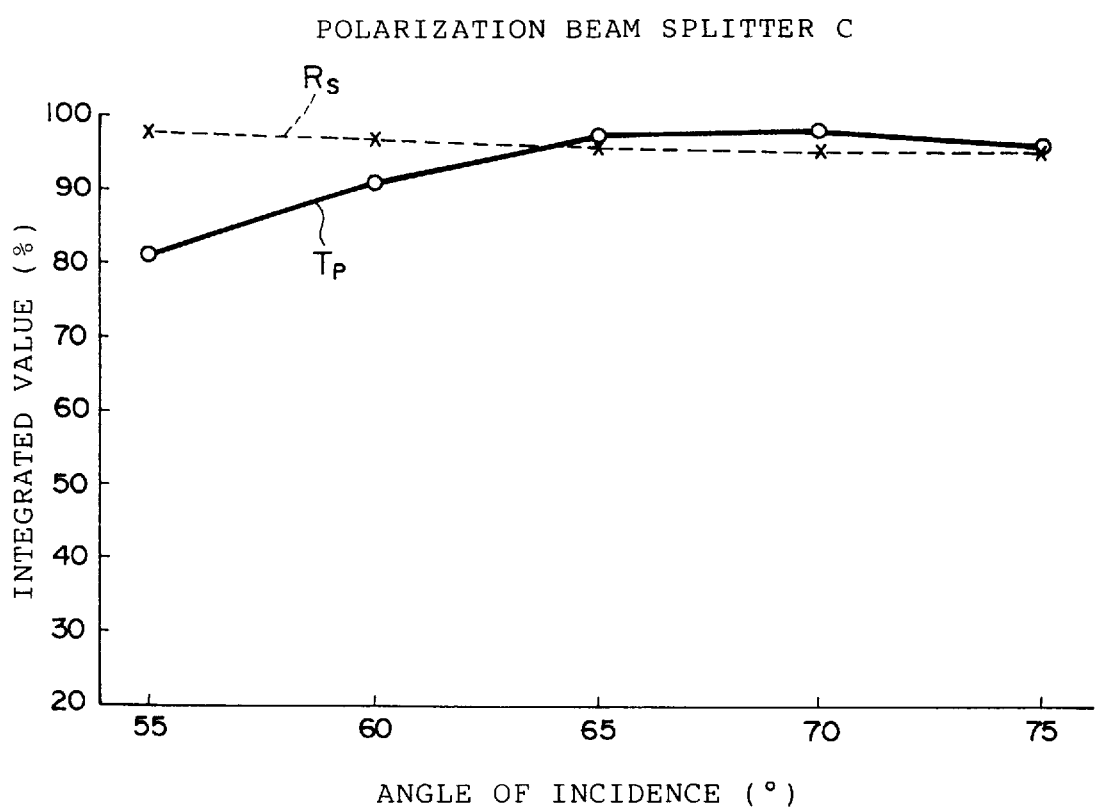
FIG. 11 is a graph showing the dependency of reflectivity of an s-polarized light component and transmittance of a p-polarized light component on angle of incidence of the polarization beam splitter C.

The structure of the polarization beam splitter C is shown in FIG. 9, the transmittance characteristic thereof in FIG. 10 and a graph illustrating the dependency on angle of incidence in FIG. 11. The optical thin film thickness is expressed taking $\lambda/4$ at the time of $\lambda=680$ nm as being 1.000. The central angle of incidence is set at 65°, and the reflectivity $R_s$ and transmittance $T_p$ are maintain very high values. It will be appreciated that the reflectivity $R_s$ of the s-polarized light component is held substantially constant over the range of angles of incidence of 55° to 75°.

Figure 12:
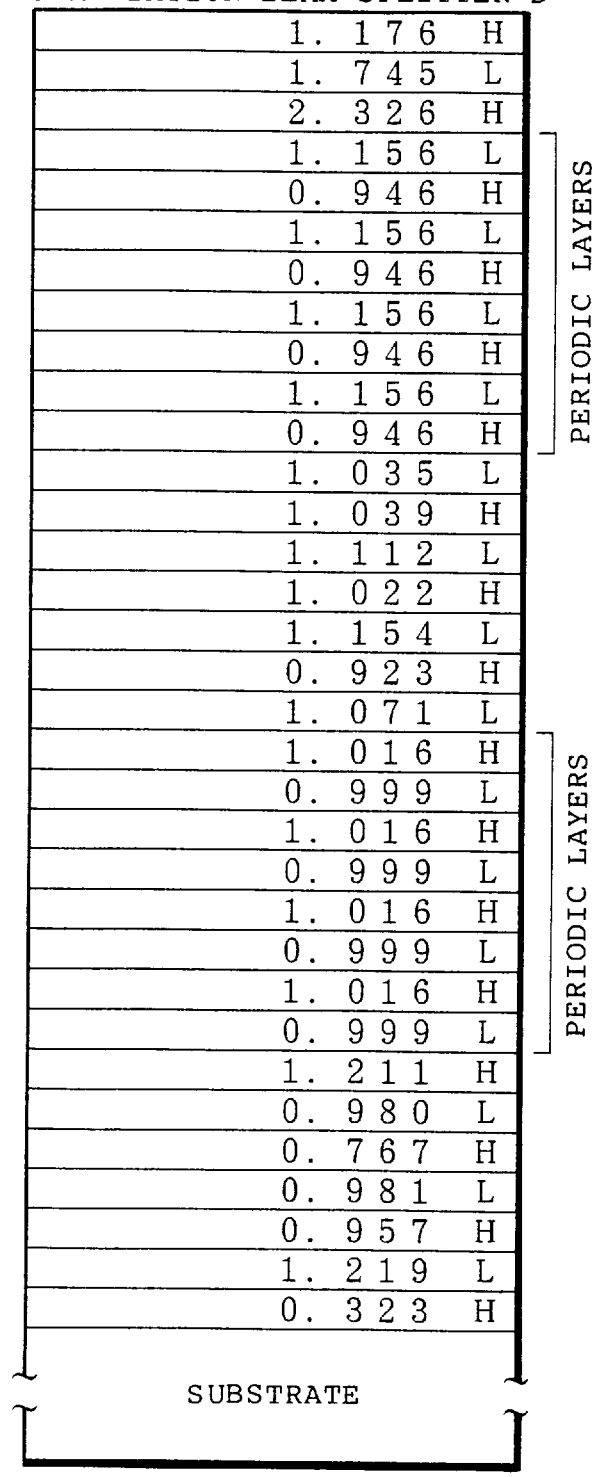
FIG. 12 illustrates the structure of a polarization beam splitter D.
Figure 13:
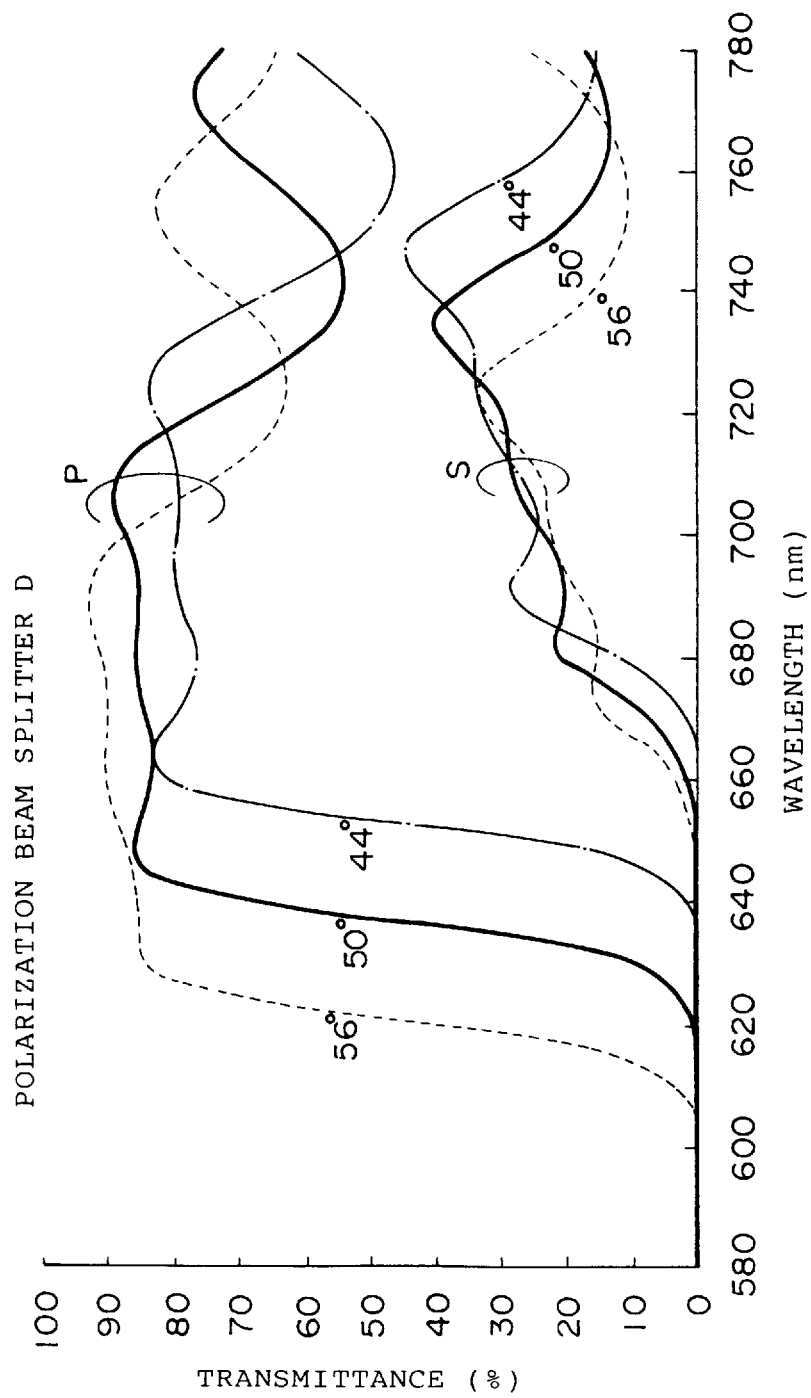
FIG. 13 is a graph showing the transmittance characteristic of the polarization beam splitter D.
Figure 14:
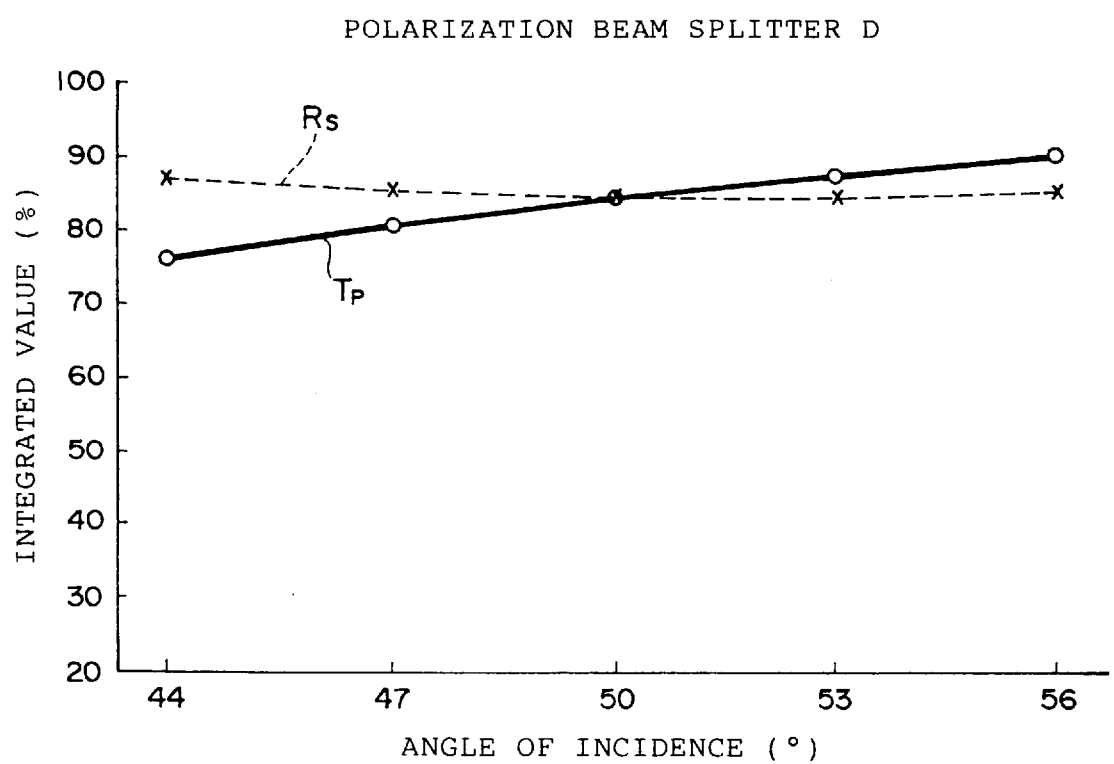
FIG. 14 is a graph showing the dependency of reflectivity of an s-polarized light component and transmittance of a p-polarized light component on angle of incidence of the polarization beam splitter D.

The structure of the polarization beam splitter D is shown in FIG. 12, the transmittance characteristic thereof in FIG. 13 and a graph illustrating the dependency on angle of incidence in FIG. 14.

Figure 15:
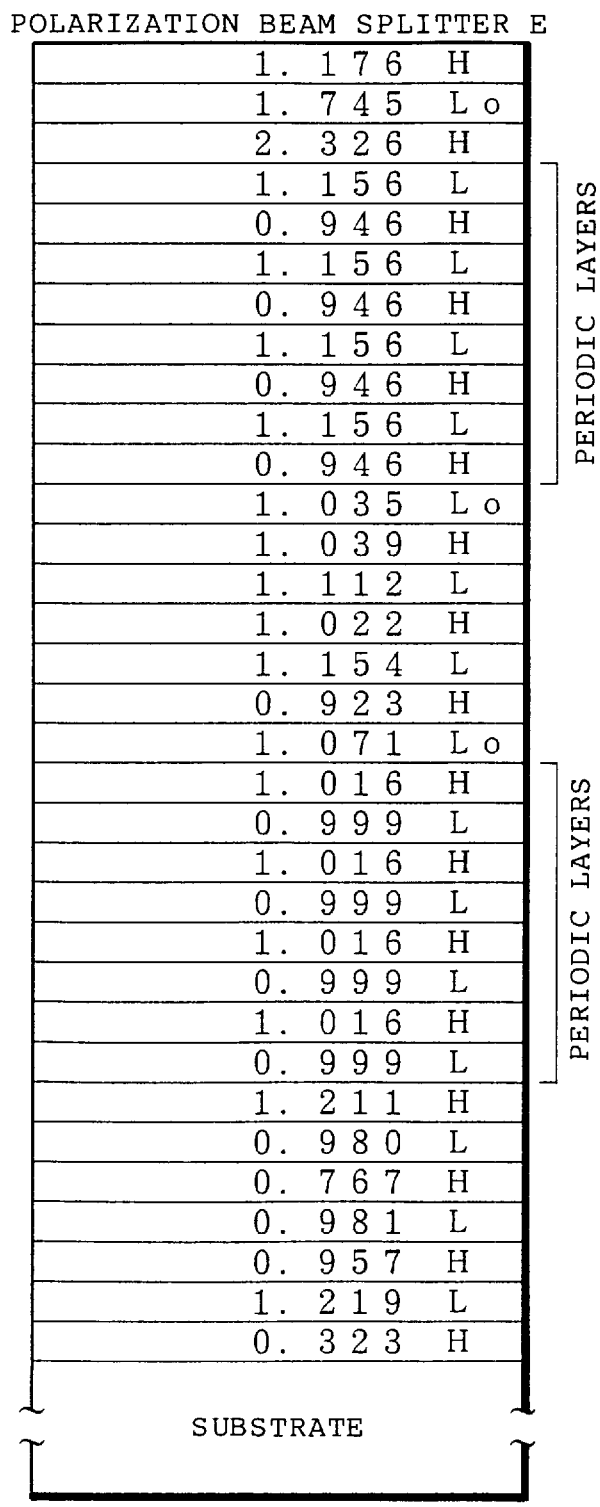
FIG. 15 illustrates the structure of a polarization beam splitter E.
Figure 16:
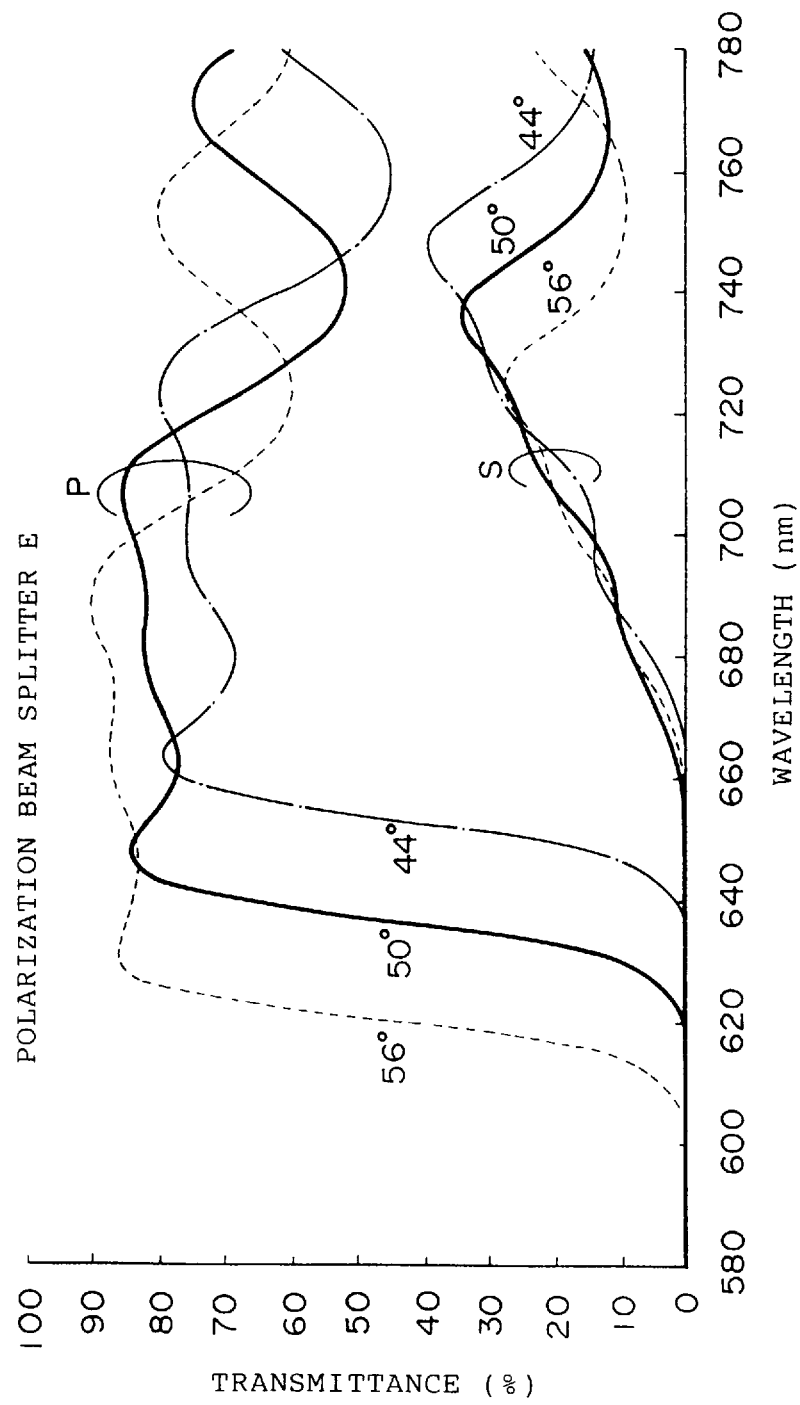
FIG. 16 is a graph showing the transmittance characteristic of the polarization beam splitter E.
Figure 17:
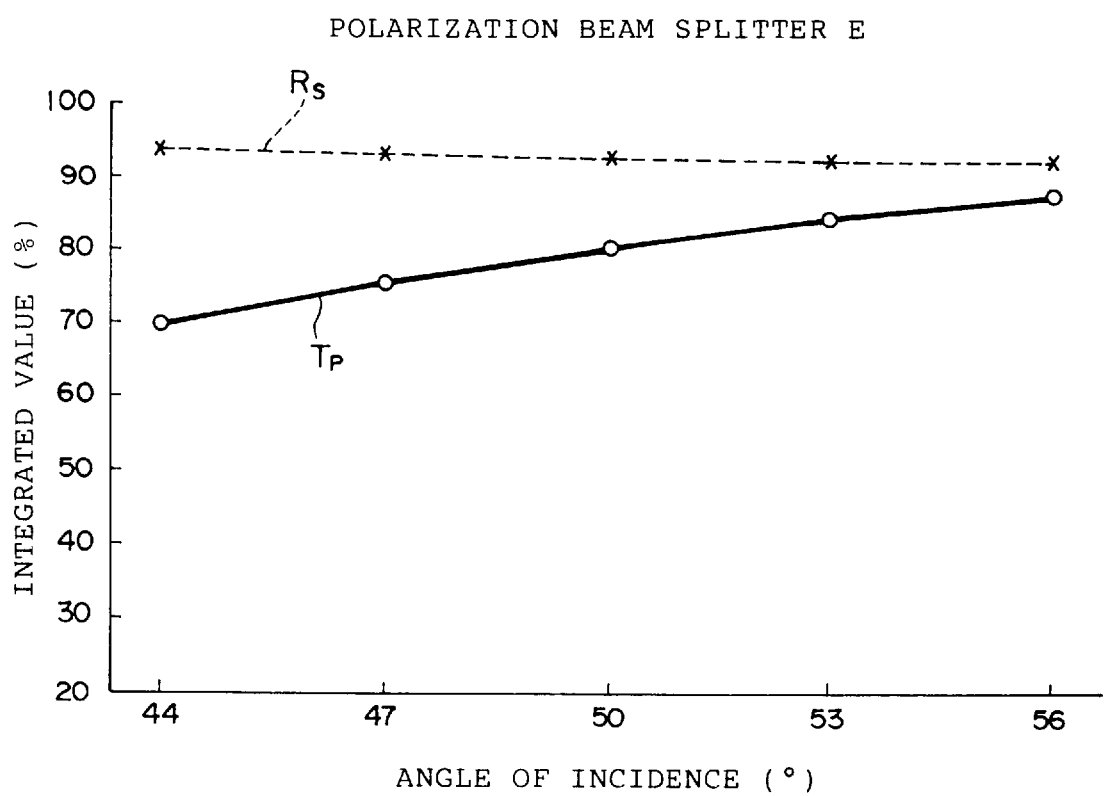
FIG. 17 is a graph showing the dependency of reflectivity of an s-polarized light component and transmittance of a p-polarized light component on angle of incidence of the polarization beam splitter E.

The structure of the polarization beam splitter E is shown in FIG. 15, the transmittance characteristic thereof in FIG. 16 and a graph illustrating the dependency on angle of incidence in FIG. 17.

In the polarization beam splitters D and E, the optical thin film thickness is expressed taking $\lambda/4$ at the time of $\lambda=610$ nm as being 1.000. The central angle of incidence is 50° and allowance for a change of 6° is set on either side.

In the structure of the polarization beam splitter E shown in FIG. 15, two types of thin films of low index of refraction are used in comparison with the structure of the polarization beam splitter D shown in FIG. 12. One is $SiO_2$ indicated by L, and the other is $MgF_2$ (refractive index n=1.38) indicated by $L_0$. It will be appreciated that the reflectivity $R_s$ of the s-polarized light component is raised by using the thin film $MgF_2$ having the much lower index of refraction (compare FIGS. 14 and 17).

In these polarization beam splitters D and E also the reflectivity $R_s$ of the s-polarized light component is held substantially constant within the range of angles of incidence of 45° to 56°.

Polarization beam splitters F and G corresponding to the foregoing polarization beam splitters A and B but being slightly inferior in terms of dependency upon angle of incidence will now be described. These polarization beam splitters F and G can of course be used satisfactorily in the optical sensor device, as will be described later.

Figure 18:
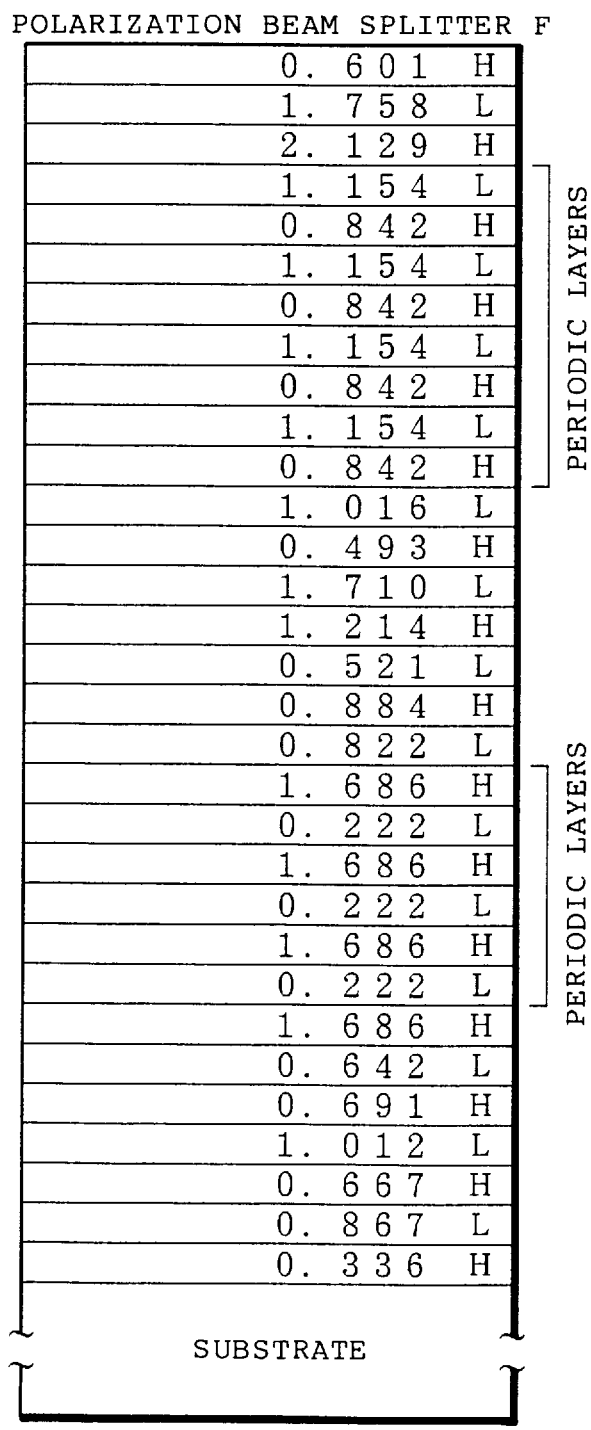
FIG. 18 illustrates the structure of a polarization beam splitter F.
Figure 19:
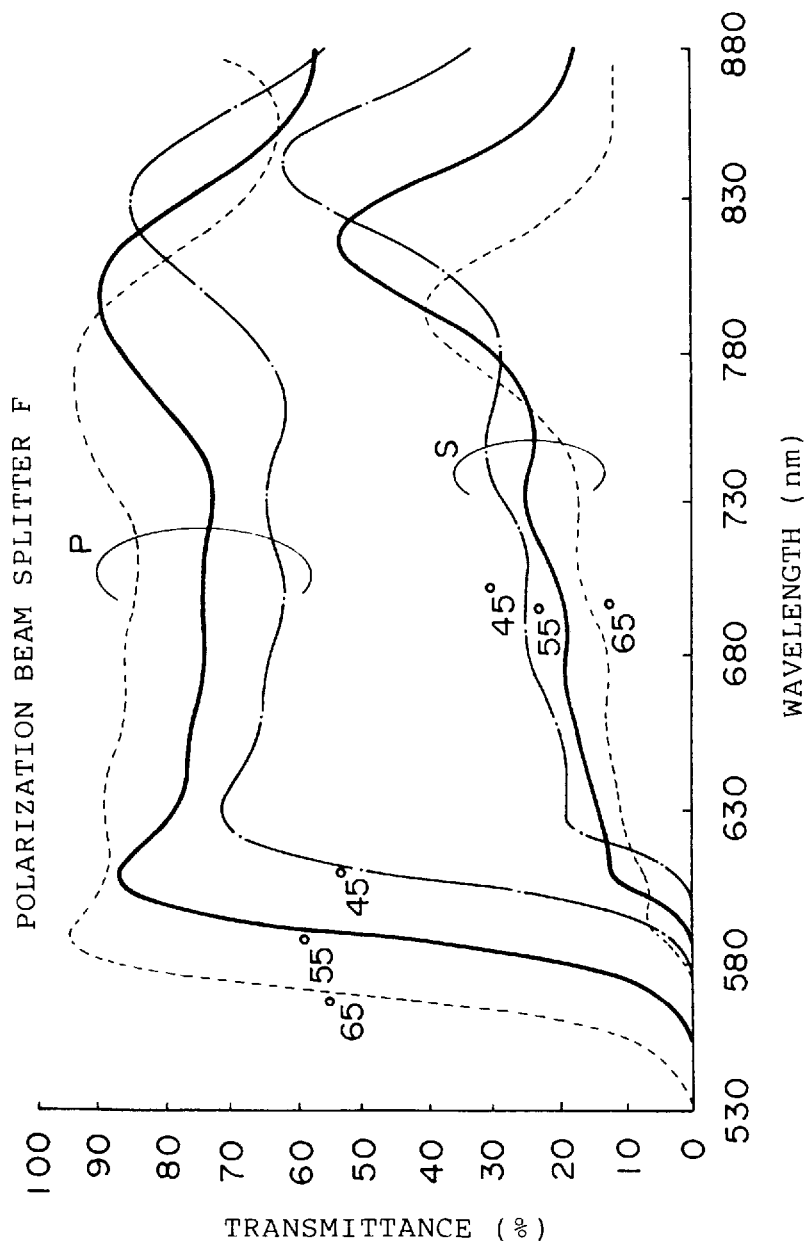
FIG. 19 is a graph showing the transmittance characteristic of the polarization beam splitter F.
Figure 20:
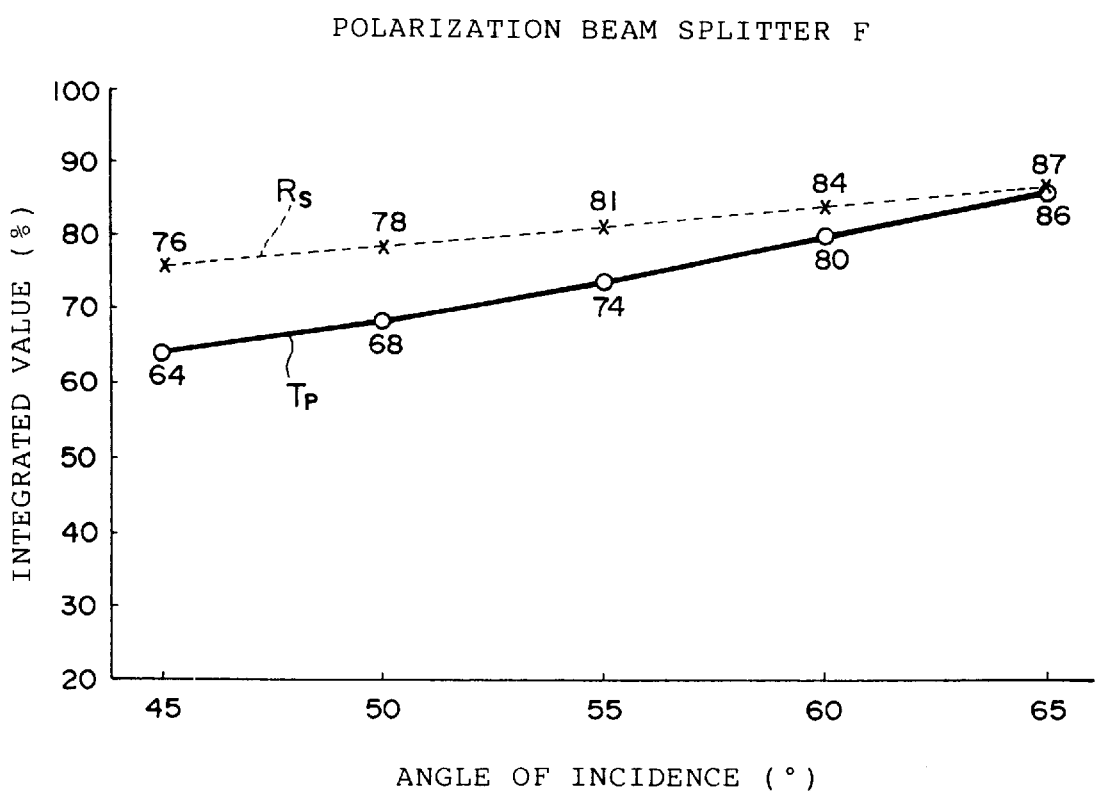
FIG. 20 is a graph showing the dependency of reflectivity of an s-polarized light component and transmittance of a p-polarized light component on angle of incidence of the polarization beam splitter F.

The structure of the polarization beam splitter F is shown in FIG. 18, the transmittance characteristic thereof in FIG. 19 and a graph illustrating the dependency on angle of incidence in FIG. 20.

Figure 22:
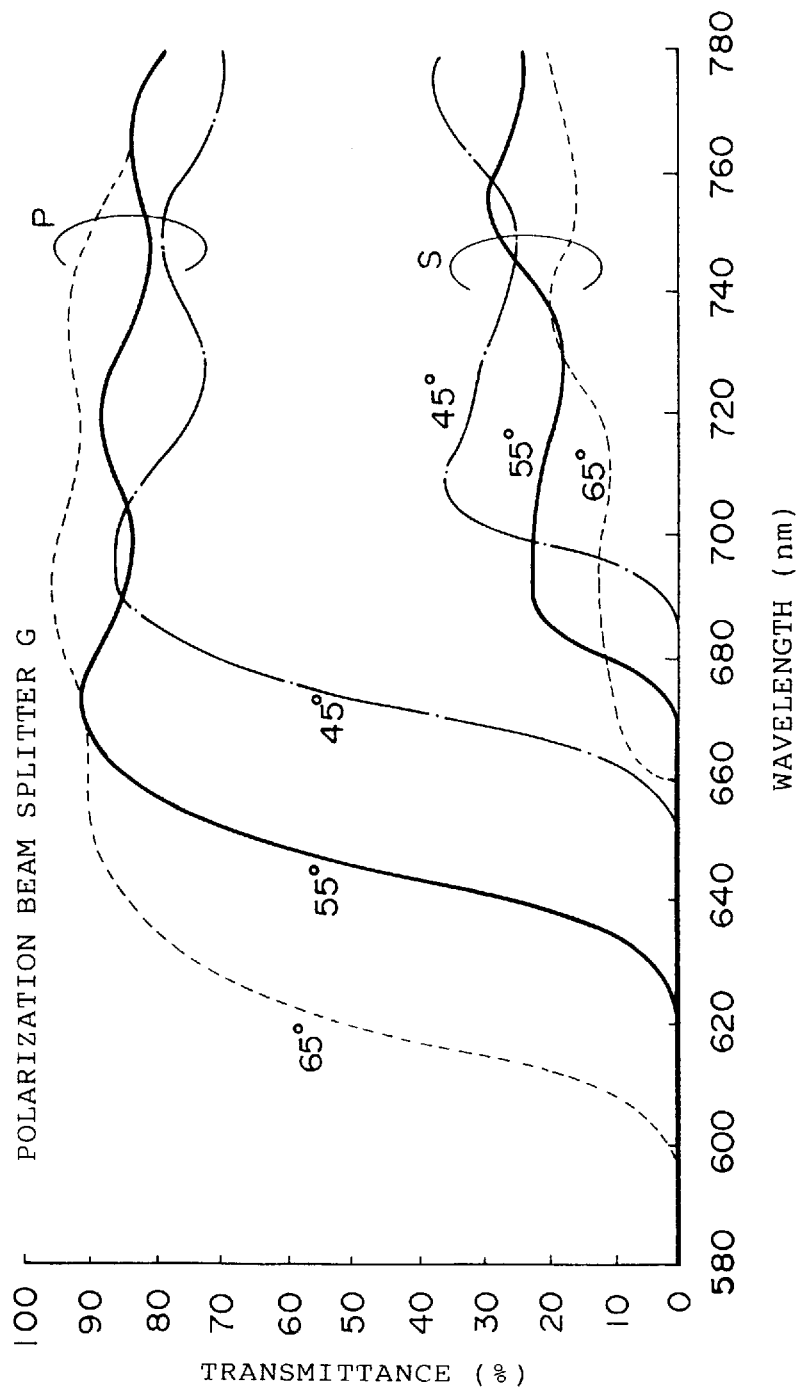
FIG. 22 is a graph showing the transmittance characteristic of the polarization beam splitter G.
Figure 23:
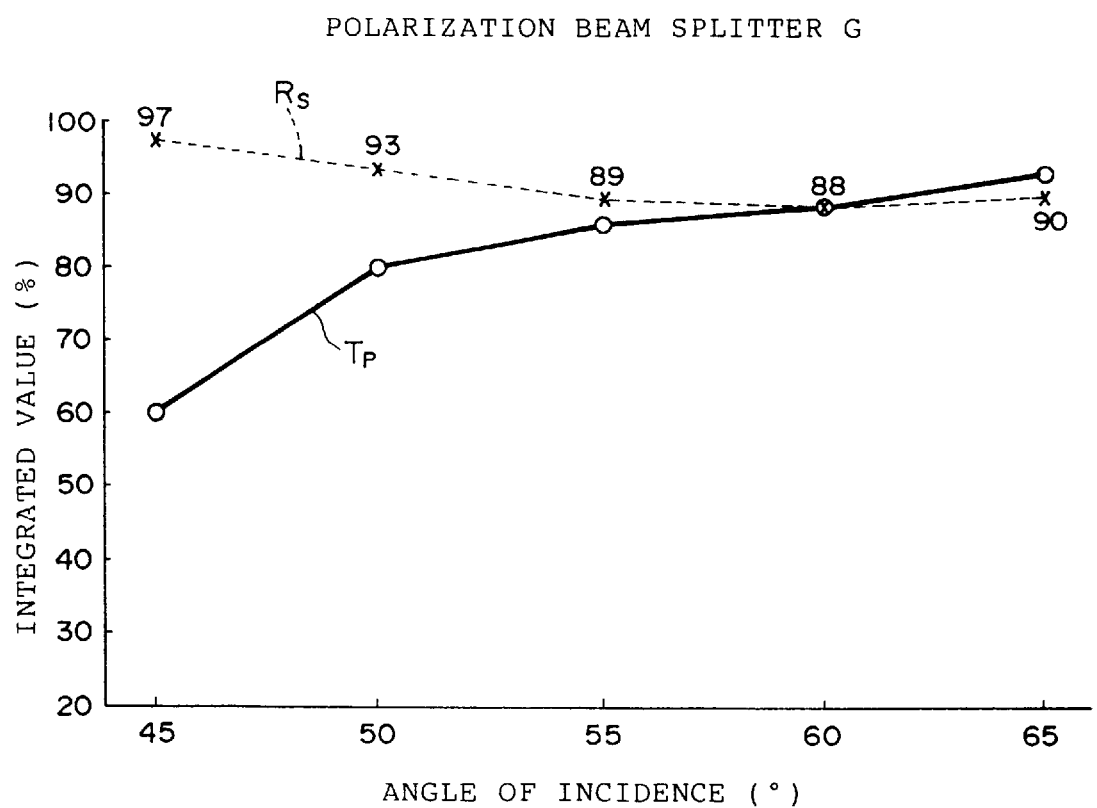
FIG. 23 is a graph showing the dependency of reflectivity of an s-polarized light component and transmittance of a p-polarized light component on angle of incidence of the polarization beam splitter G.

The structure of the polarization beam splitter G is shown in FIG. 21, the transmittance characteristic thereof in FIG. 22 and a graph illustrating the dependency on angle of incidence in FIG. 23.

In FIGS. 18 and 21, the optical thin film thickness is expressed taking $\lambda/4$ at the time of $\lambda=610$ nm as being 1.000.

Even though the light separating characteristic expressed by $R_s/T_p$ in the polarization beam splitter F shown in FIG. 20 is slightly inferior in comparison with the characteristic (FIG. 3) of the polarization beam splitter A, this change is comparatively small within the range of angles of incidence of 45° to 65°. Similarly, even though the light separating characteristic expressed by $R_s$ in the polarization beam splitter G shown in FIG. 23 is slightly inferior in comparison with the characteristic (FIG. 8) of the polarization beam splitter B, this change is comparatively small within the range of angles of incidence of 45° to 65°. The polarization beam splitters having these degrees of dependency on angle of incidence are satisfactory for practical use.

Figure 24:
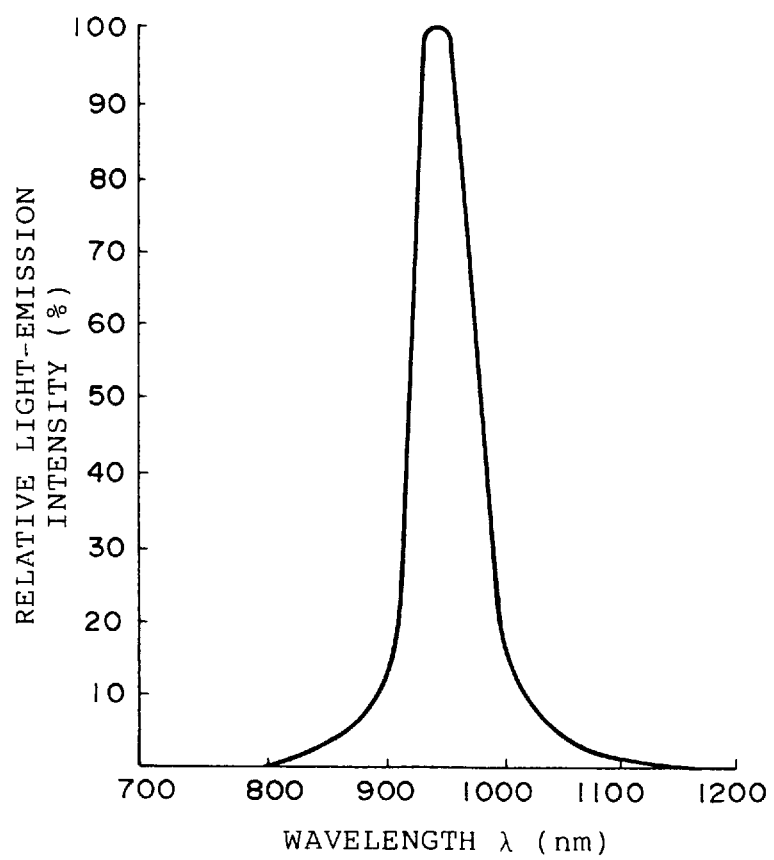
FIG. 24 illustrates a light-emission spectrum of a GaAs light-emitting diode.

FIG. 24 illustrates a light-emission spectrum of a GaAs light-emitting diode which emits light in the vicinity of 900~1000 nm. A polarization beam splitter ideal for use in an optical sensor device in which a light-emitting diode having this light-emission spectrum is employed as the light source (light-emitting element) will be described.

Figure 25:
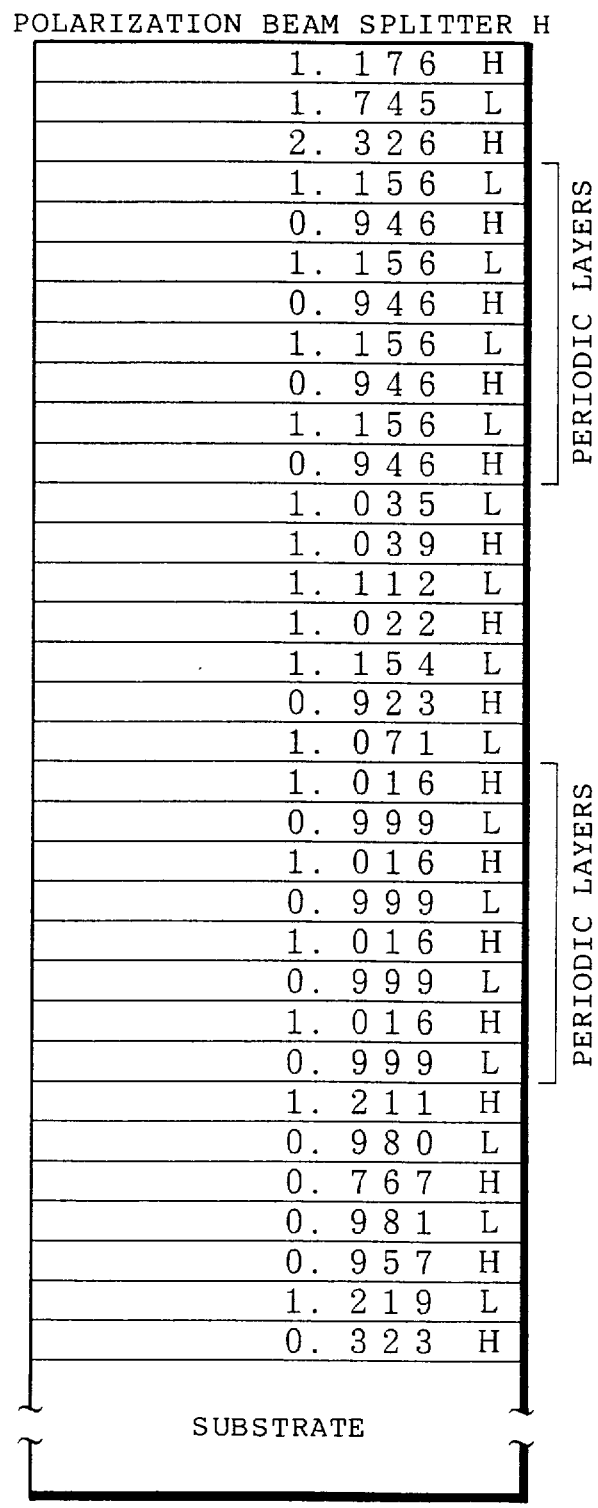
FIG. 25 illustrates the structure of a polarization beam splitter H.
Figure 26:
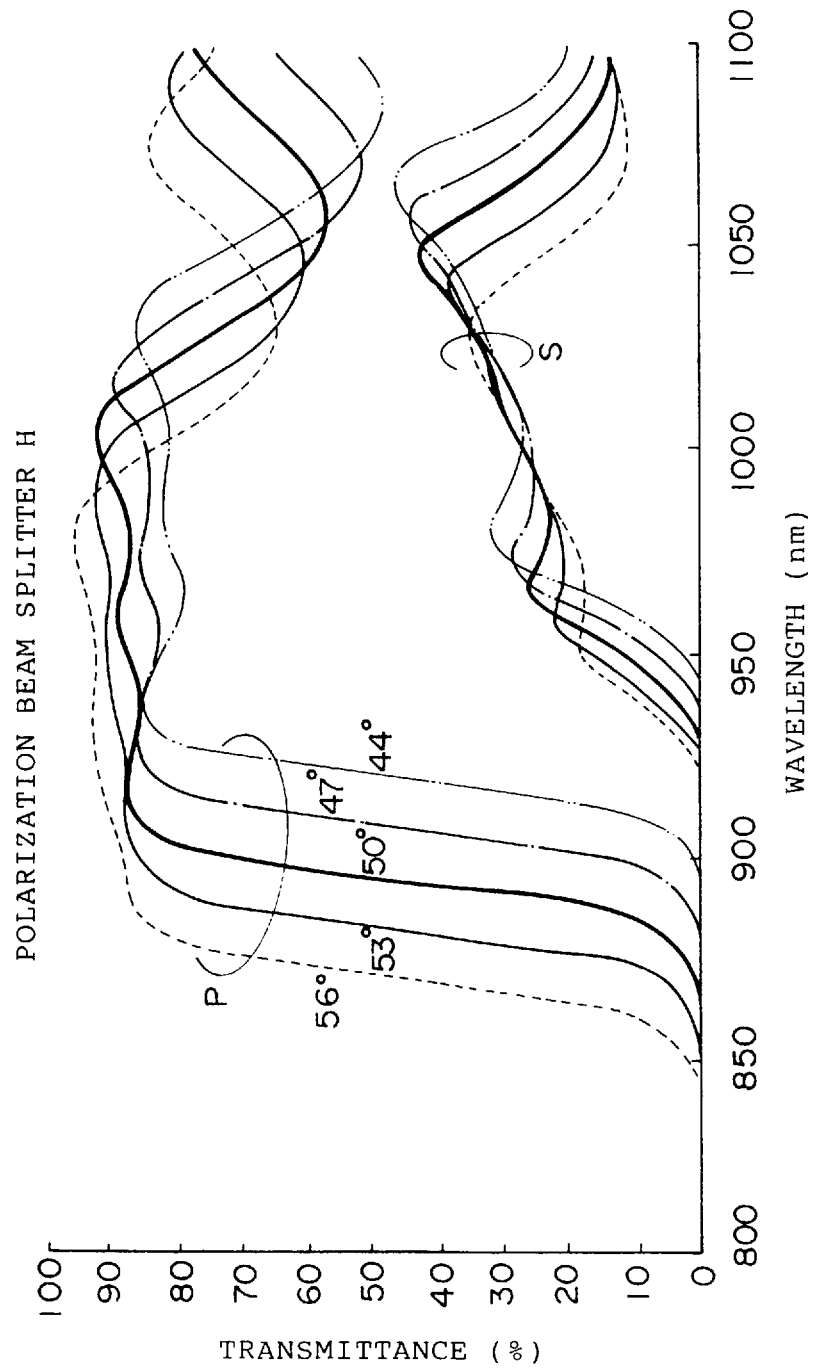
FIG. 26 is a graph showing the transmittance characteristic of the polarization beam splitter H.

FIG. 25 illustrates the structure of a polarization beam splitter H, and FIG. 26 shows the transmittance characteristic of this polarization beam splitter.

Figure 27:
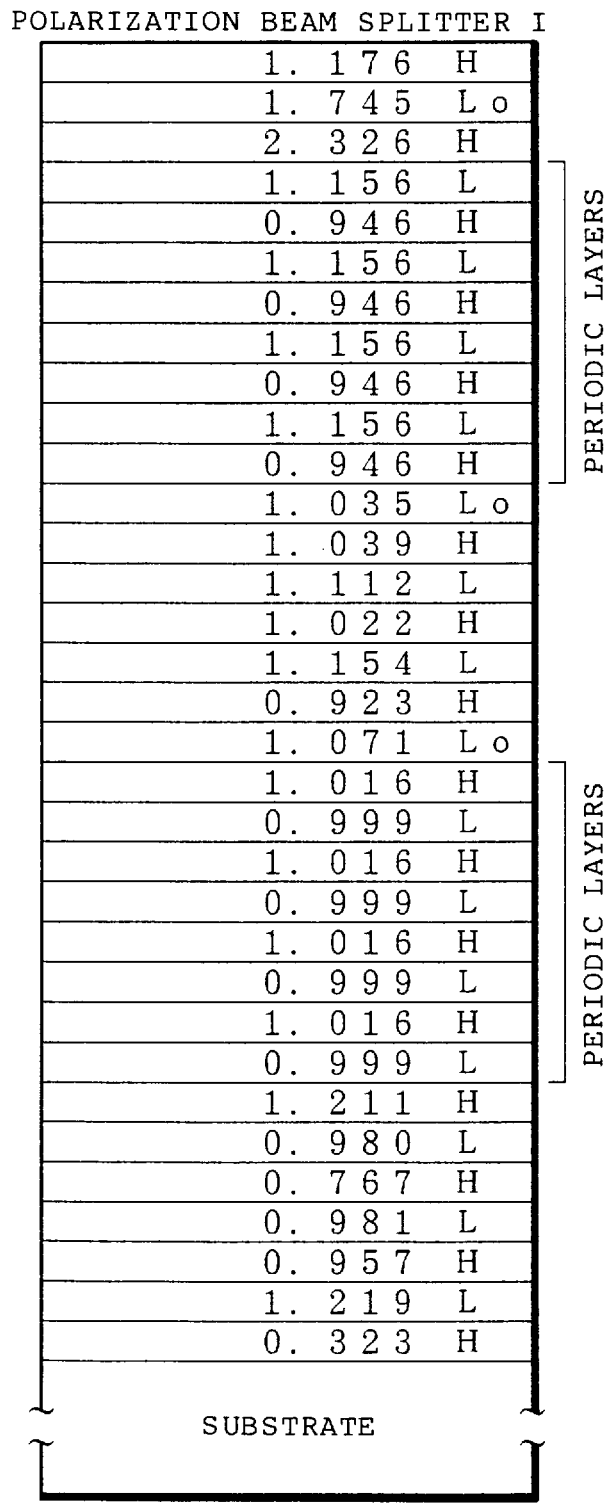
FIG. 27 illustrates the structure of a polarization beam splitter I.

FIG. 27 illustrates the structure of a polarization beam splitter I, and FIG. 28 shows the transmittance characteristic of this polarization beam splitter.

Superficially, these polarization beam splitters H and I have structures identical with those of the foregoing polarization beam splitters D and E, respectively (compare FIGS. 25 and 12 as well as FIGS. 27 and 15). However, the optical thin film thickness is represented taking $\lambda/4$ at the time of $\lambda=610$ nm as being 1.000 in FIGS. 12 and 15, while the optical thin film thickness is represented taking $\lambda/4$ at the time of $\lambda=860$ nm as being 1.000 in FIGS. 25 and 27. In actuality, therefore, the thicknesses of these thin films are different.

FIG. 29 shows the transmittance $T_s$ (reflectivity $R_s=1-T_s$) of the s-polarized light component and the transmittance $T_p$ of the p-polarized light component calculated using the light-emission spectrum shown in FIG. 24 in the polarization beam splitter having the structure depicted in FIG. 27. The transmittance $T_s$ (reflectivity $R_s$) of the s-polarized light component in particular is held substantially constant over the range of angles of incidence used.

As mentioned above, the light-emitting diode serving as the light source has a light-emission spectrum which fluctuates owing to a variance in manufacture, a change in environment (inclusive of a change in temperature) and a change with the passage of time. The variance in the light-emission spectrum caused by a variance in manufacture is the most prominent and is on the order of ±10~±20 nm. Accordingly, it is desired that the aforementioned light separating characteristic of the polarization beam splitter (namely that $R_s$ or $R_s/T_p$ is held substantially constant even if the angle of incidence changes) be maintained even when the central wavelength of the light emission from the light-emitting diode changes (experiences variance).

The fact that dependency upon angle of incidence is almost unchanged when the central wavelength of the light-emission spectrum shown in FIG. 4 is shifted by −10 nm and by +10 nm will be described quantitatively with regard to the above-mentioned polarization beam splitters A, B, C, D, E and F, G.

The polarization beam splitter A is so designed that $R_s/T_p$ is held at a substantially constant value irrespective of a change in the angle of incidence in the range (45°~65°) of angles of incidence used.

In the graph of dependence upon angle of incidence shown in FIG. 3, values of $R_s/T_p$ at angles of incidence of 45°, 50°, 55°, 60° and 65° are 67/66, 71/70, 75/75, 79/80 and 83/87, respectively. Among these, the maximum value is 67/66 (angle of incidence of 450) and the minimum value is 83/87 (angle of incidence of 65°). [maximum value]/[minimum value]=1.064 or 6%. This is referred to as $\Delta R_s/T_p$ (%).

FIGS. 30a, 30b are graphs showing dependency on angle of incidence in the polarization beam splitter A when the central wavelength of a light emission from the light-emitting diode has shifted by −10 nm and +10 nm, respectively. When $\Delta R_s/T_p$ (%) is obtained in these graphs, in a manner similar to that set forth above, the result is approximately 8%.

The polarization beam splitter B is so designed that $R_s$ is held at a substantially constant value in the range of angles of incidence used irrespective of the change in the angle of incidence.

In the graph of FIG. 8 showing degree of dependence upon angle of incidence, the difference between the maximum value (87: angle of incidence of 65°) of $R_s$ and the minimum value (85: angle of incidence of 45°) of $R_s$ is 2. This is referred to $\Delta R_s$ (%).

Figure 31A:
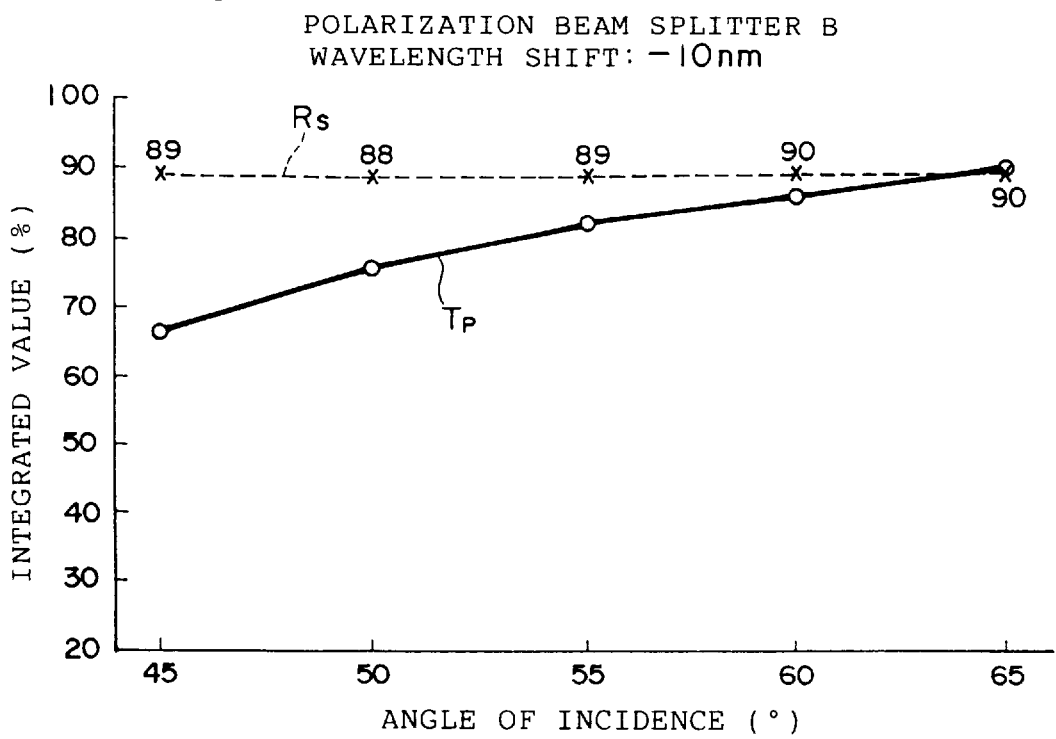
FIGS. 31a, 31b are graphs showing dependency on angle of incidence in the polarization beam splitter B when the central wavelength of a light emission from a light-emitting diode has shifted by −10 nm and +10 nm, respectively.
Figure 31B:
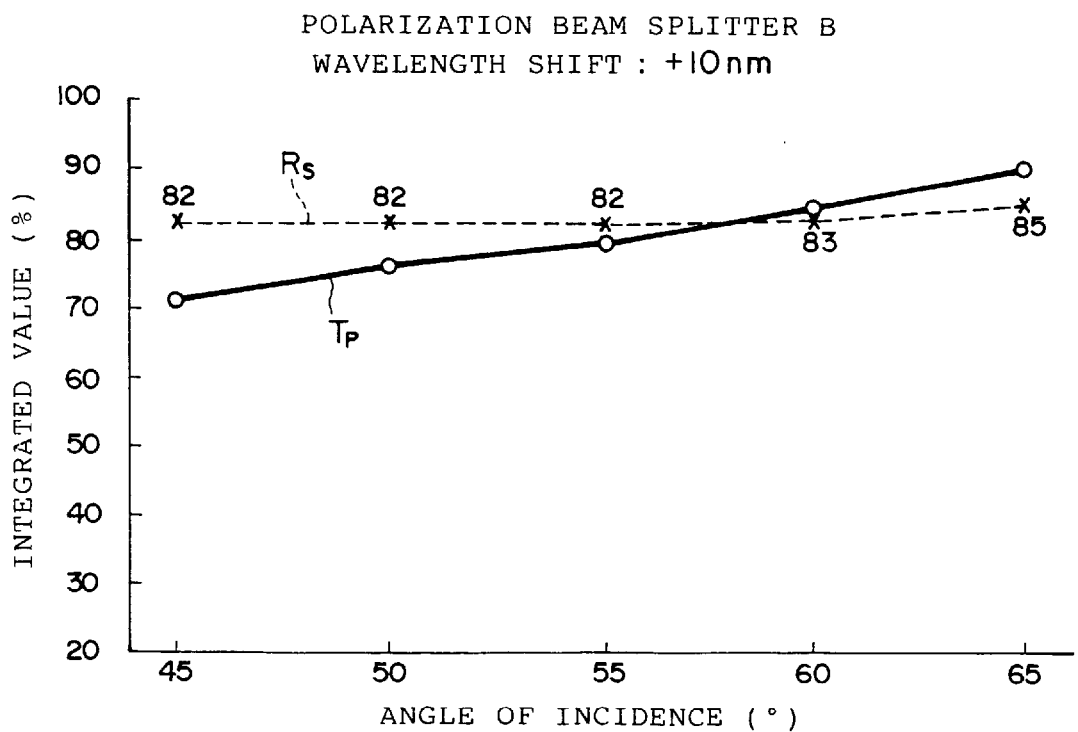

FIGS. 31a, 31b are graphs showing dependency on angle of incidence in the polarization beam splitter B when the central wavelength of a light emission from the light-emitting diode has shifted by −10 nm and +10 nm, respectively. In FIGS. 31a, 31b, $\Delta R_s/T_p$ (%) is 2 and 3, respectively.

Figure 32A:
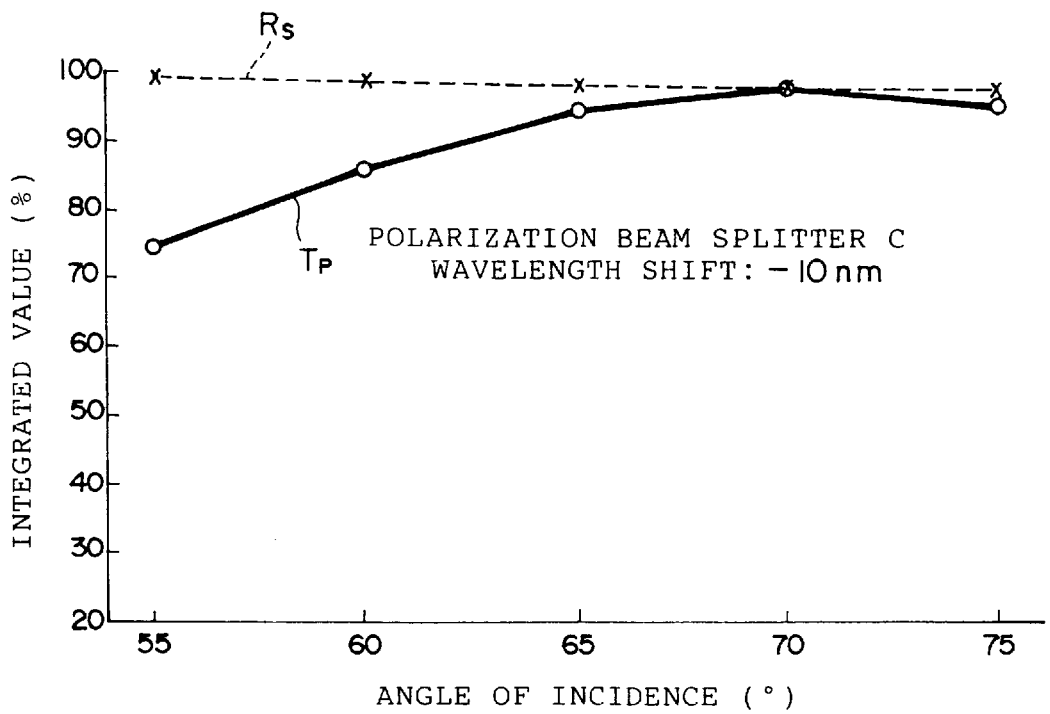
FIGS. 32a, 32b are graphs showing dependency on angle of incidence in the polarization beam splitter C when the central wavelength of a light emission from a light-emitting diode has shifted by −10 nm and +10 nm, respectively.
Figure 32B:
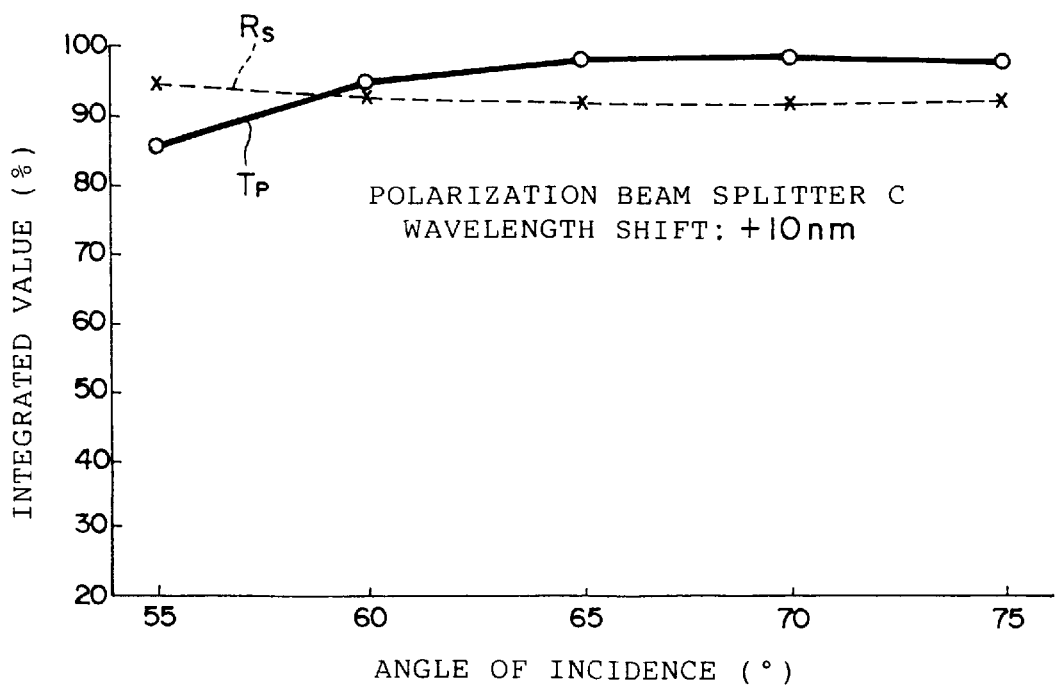
Figure 33A:
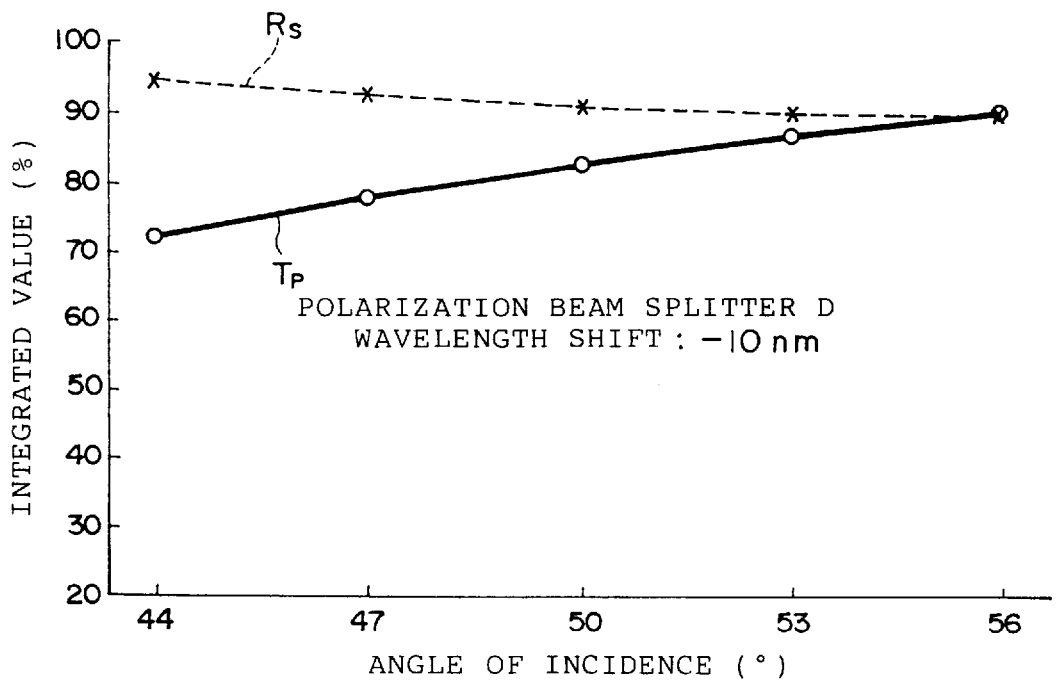
FIGS. 33a, 33b are graphs showing dependency on angle of incidence in the polarization beam splitter D when the central wavelength of a light emission from a light-emitting diode has shifted by −10 nm and +10 nm, respectively.
Figure 33B:
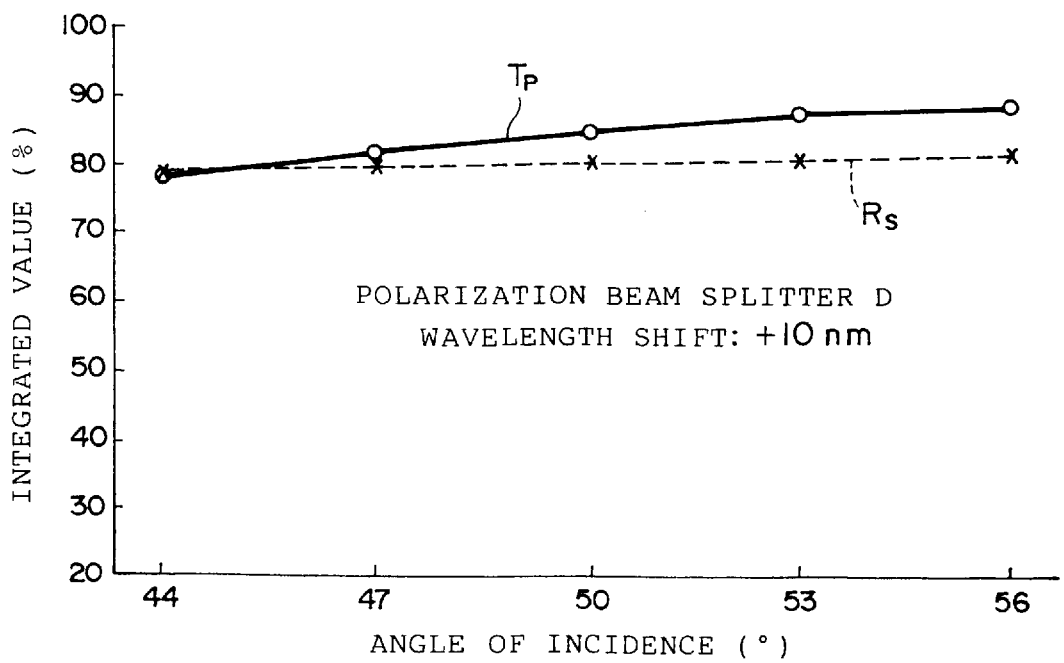
Figure 34A:
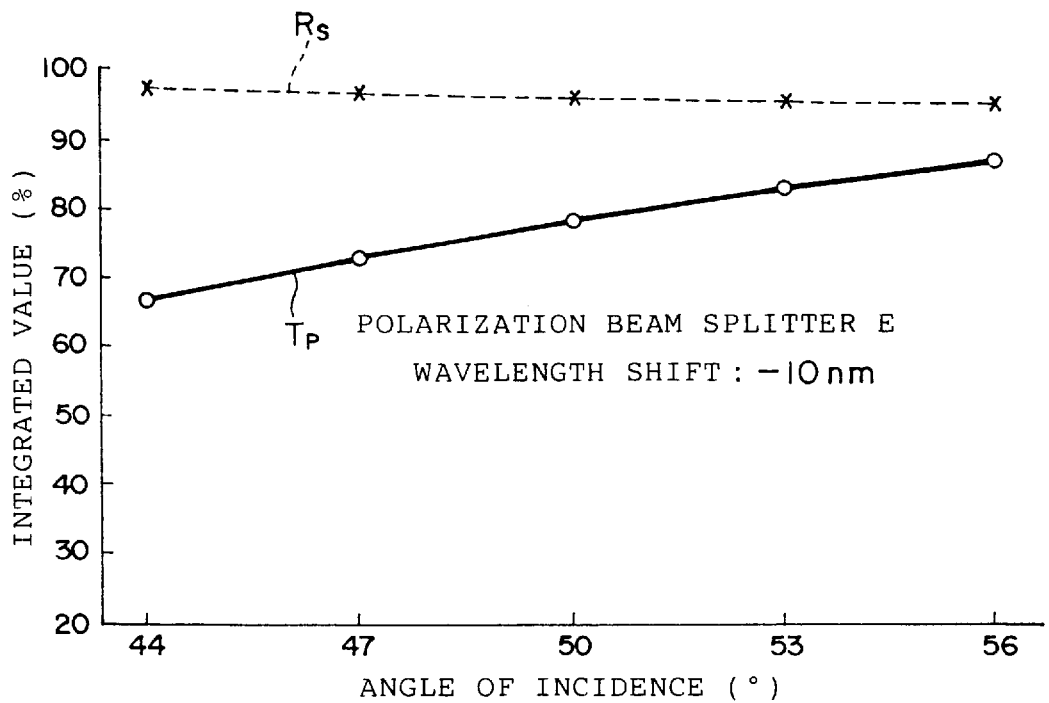
FIGS. 34a, 34b are graphs showing dependency on angle of incidence in the polarization beam splitter E when the central wavelength of a light emission from a light-emitting diode has shifted by −10 nm and +10 nm, respectively.
Figure 34B:
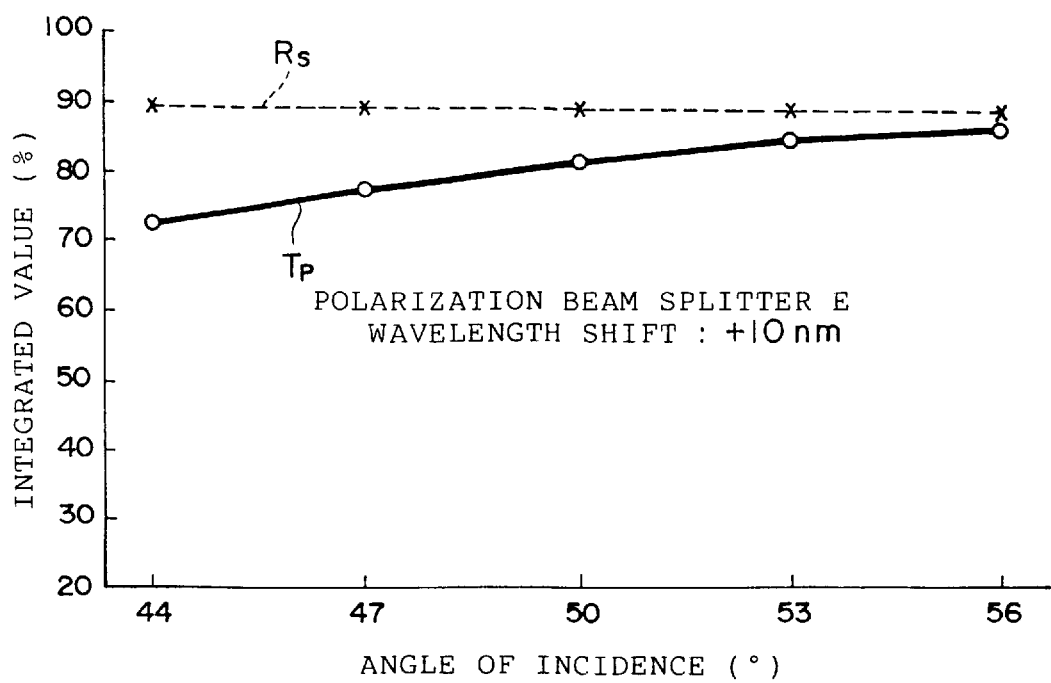
Figure 36A:
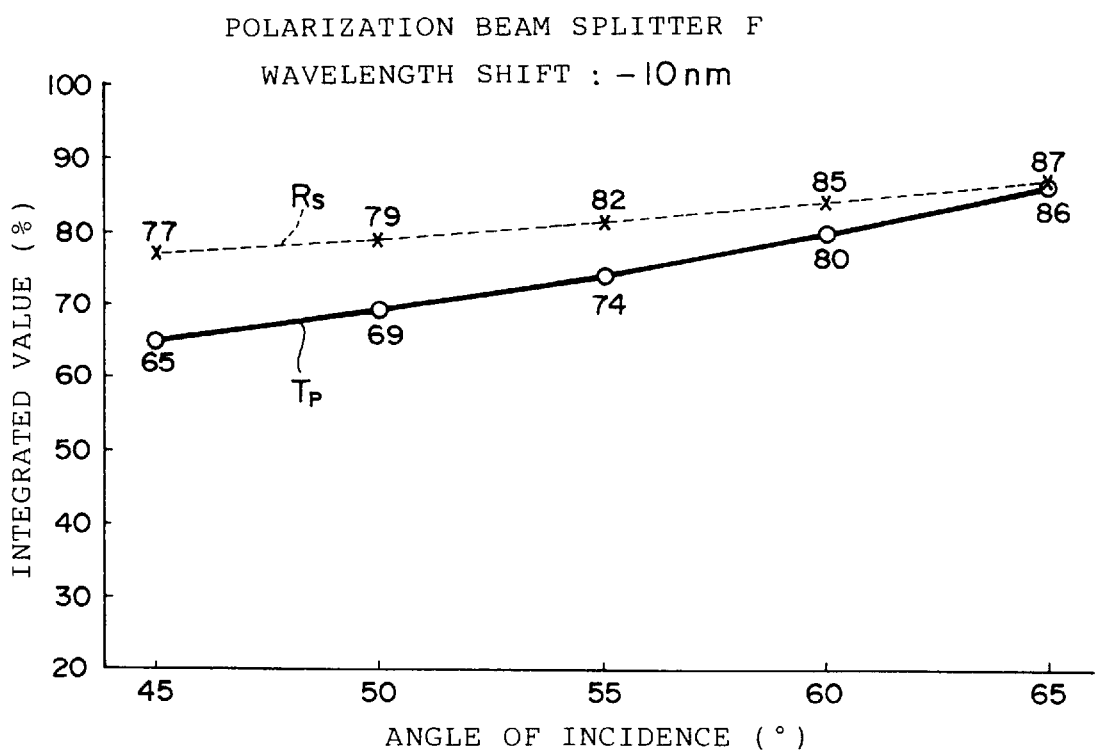
FIGS. 36a, 36b are graphs showing dependency on angle of incidence in the polarization beam splitter F when the central wavelength of a light emission from a light-emitting diode has shifted by −10 nm and +10 nm, respectively.
Figure 36B:
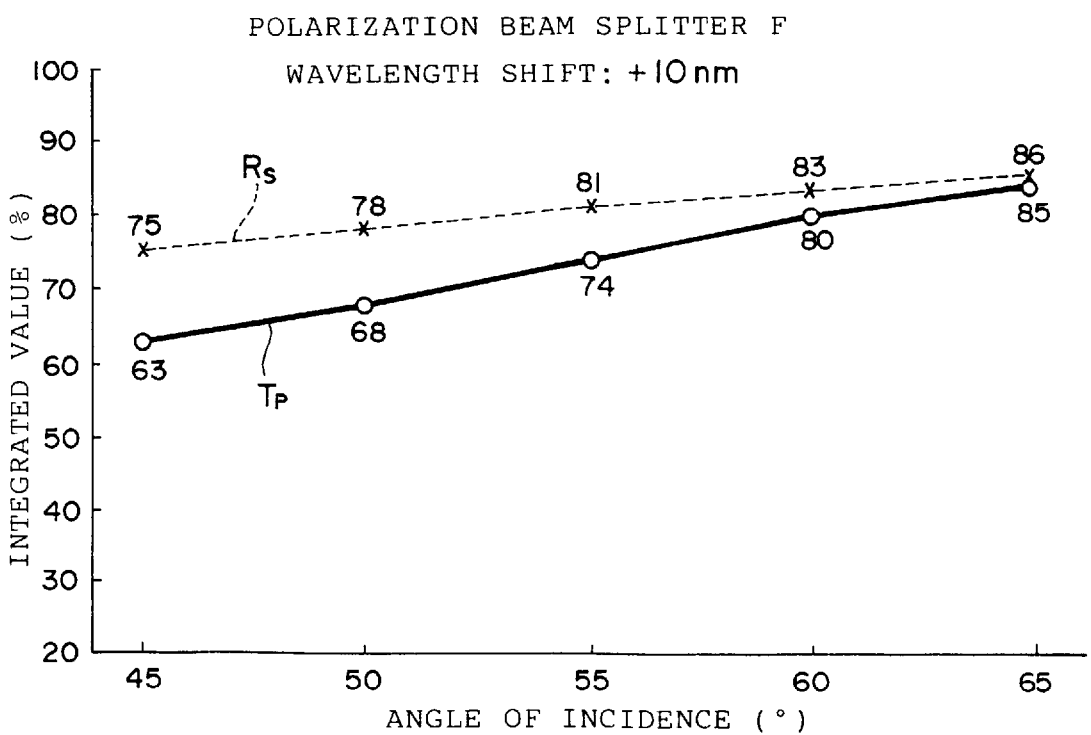
Figure 37A:
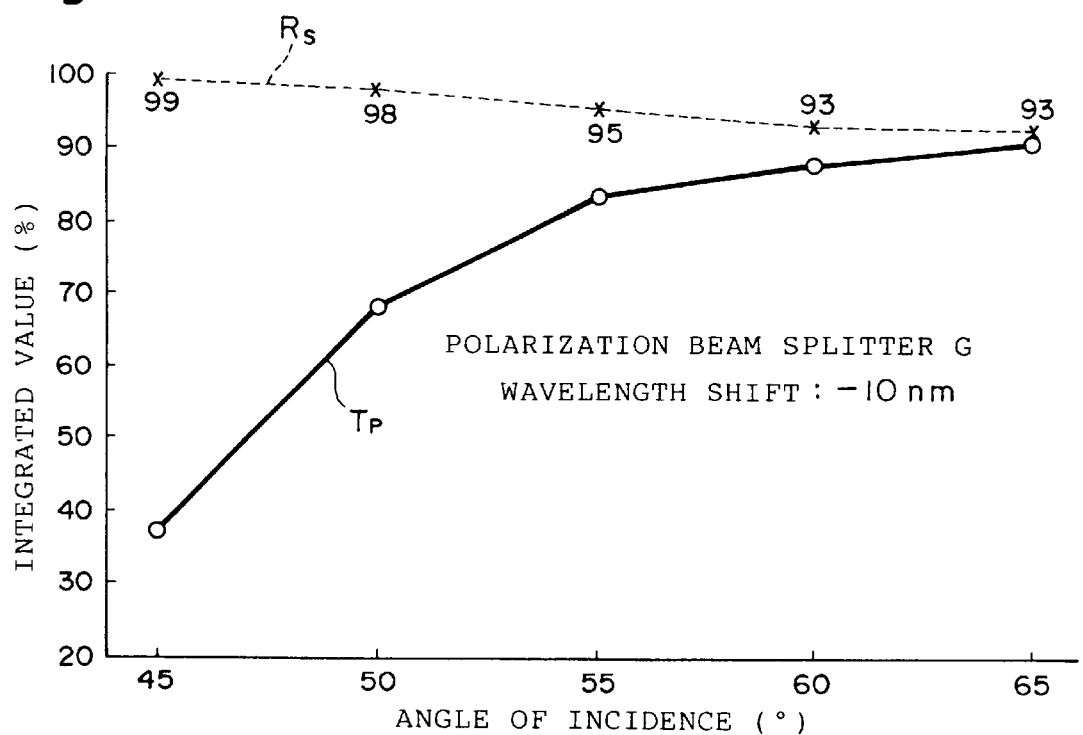
FIGS. 37a, 37b are graphs showing dependency on angle of incidence in the polarization beam splitter G when the central wavelength of a light emission from a light-emitting diode has shifted by −10 nm and +10 nm, respectively.
Figure 37B:
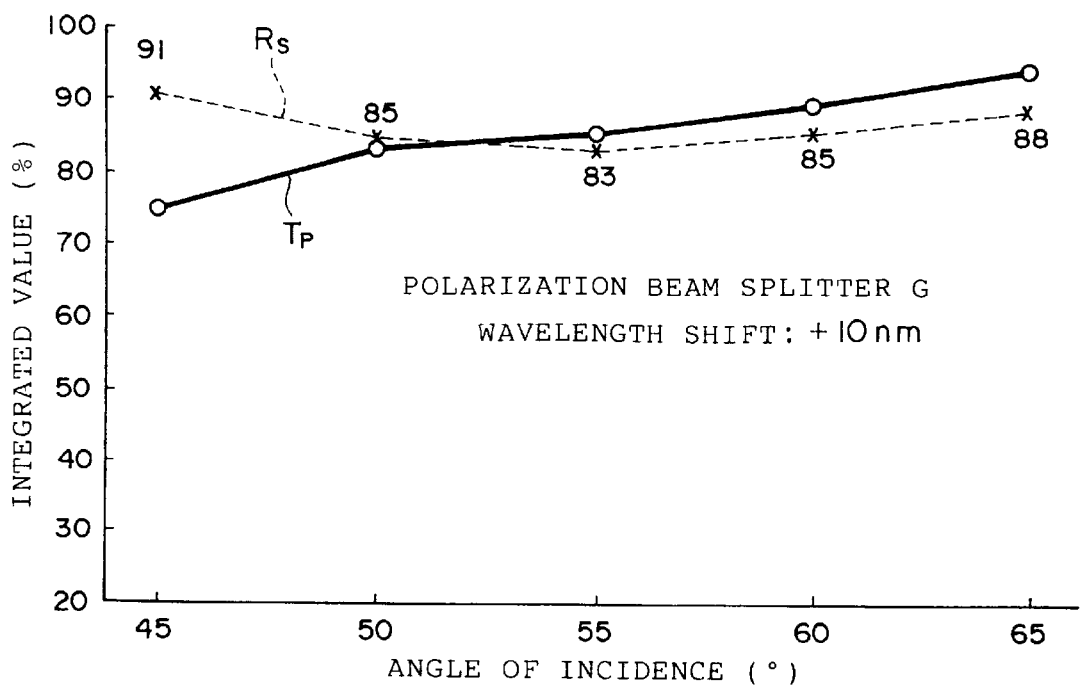

FIGS. 32a, 32b; 33a, 33b; and 34a, 34b are graphs showing dependency on angle of incidence in the polarization beam splitters C, D and E, respectively, when the central wavelength of a light emission has shifted by −10 nm and +10 nm, respectively.

These polarization beam splitters C, D and E are so designed that $R_s$ is held at a substantially constant value irrespective of a change in angle of incidence. Here $\Delta R_s$ (%) can be obtained for each of the polarization beam splitters C, D and E from FIGS. 11, 14 and 17 and FIGS. 32a, 32b, 33a, 33b, 34a and 34b.

FIG. 35 collectively illustrates the results thus obtained.

In the range of angles of incidence used in the polarization beam splitter A, $\Delta R_s/T_p$ is less than about 8% even when a shift in the light-emission wavelength of the light-emitting element is taken into account. In the polarization beam splitters B, C, D and E, $\Delta R_s$ is less than 5%. If $\Delta R_s/T_p$ is less than 10% or $\Delta R_s$ is less than 5%, it can be said that these polarization beam splitters possess a very good light separating characteristic with respect to a change in angle of incidence and with respect to a shift in wavelength.

The polarization beam splitters F and G correspond to the polarization beam splitters A and B, respectively, but the design is such that these are slightly inferior in terms of dependency on angle of incidence.

FIGS. 36a, 36b and 37a, 37b are graphs showing dependency on angle of incidence in the polarization beam splitters F and G, respectively, when the central wavelength of a light emission has shifted by −10 nm and +10 nm, respectively.

FIG. 38 collectively illustrates the results of obtaining $\Delta R_s/T_p$ with regard to the polarization beam splitter F and $\Delta R_s$ with regard to the polarization beam splitter G, wherein reference is made to FIGS. 20, 23 and FIGS. 36a, 36b and 37a, 37b.

In the range of angles of incidence used in the polarization beam splitter F, $\Delta R_s/T_p$ is less than about 18% even when a shift in the light-emission wavelength of the light-emitting element is taken into account. In the polarization beam splitter G, $\Delta R_s$ is less than 9%. If $\Delta R_s/T_p$ is less than 20% or $\Delta R_s$ is less than 10%, it can be said that these polarization beam splitters are capable of being used satisfactorily in an optical sensor device even if there is a change in angle of incidence and a shift in wavelength.

(2) Basic construction and basic operation of optical sensor device

When light is made to impinge upon an object, the state of polarization of the light reflected from or transmitted through the object is influenced by the surface state of the object, the material of the object, etc. Important forms of this phenomenon are as set forth below.

If the surface of the object is specular, the state of polarization of the incident light is preserved in the reflected light.

As mentioned above, p-polarized light and s-polarized light can be defined on the surface of an object using the plane of incidence of the incident light as a reference. If light incident upon a specular (mirror) surface is p-polarized light, then the reflected light also will be p-polarized light. If the incident light is s-polarized light, the light reflected from the specular surface will be s-polarized light.

If the surface of the object is rough (a surface of diffuse reflection), the reflected light will be randomly polarized (unpolarized) or in a state approaching it irrespective of the state of polarization of the incident light (whether circularly polarized or linearly polarized).

In the case of the surface of a transparent object (in which the surface is glossy), the reflectivity of the s-polarized light is greater than that of the p-polarized light. Therefore, when light is obliquely incident upon the surface of a transparent object, the light reflected from the object contains more s-polarized light components than p-polarized light components. Light transmitted through the transparent object contains more p-polarized light components than s-polarized light components.

In particular, the reflectivity of the p-polarized light component becomes zero (and the transmittance becomes 1 or 100%) at the Brewster angle. At this angle only the s-polarized light component of the incident light is reflected.

The proportions of the reflected (or transmitted) s-polarized light components and p-polarized light components differs depending upon the glossiness of the surface of the transparent object.

When linearly polarized light is made to impinge upon a transparent object possessing a birefringence characteristic, a component having a direction perpendicular to the direction of polarization of the incident light will appear as the incident light passes through the object if the direction of polarization of the incident light differs from the direction of birefringence.

When particles, water drops or frost which scatter light are present in the optical path regardless of whether this is inside the object, on the surface of the object or in the air, almost all of the reflected light or transmitted light becomes randomly polarized light irrespective of the kind of polarization possessed by the incident light (i.e., irrespective of whether the incident light is linearly, circularly or elliptically polarized light).

The optical sensor device described below utilizes this property relating to the polarization of light to sense whether an object (especially a transparent object) is present or not, the surface state of the object, the material constituting the object, the presence of particles, water drops or frost, etc., attached to the object surface temporarily or permanently, and whether light scattering objects are suspended in the air.

A reflecting-type optical sensor device will be taken as an example and the construction and operation thereof will be described.

Figure 39:
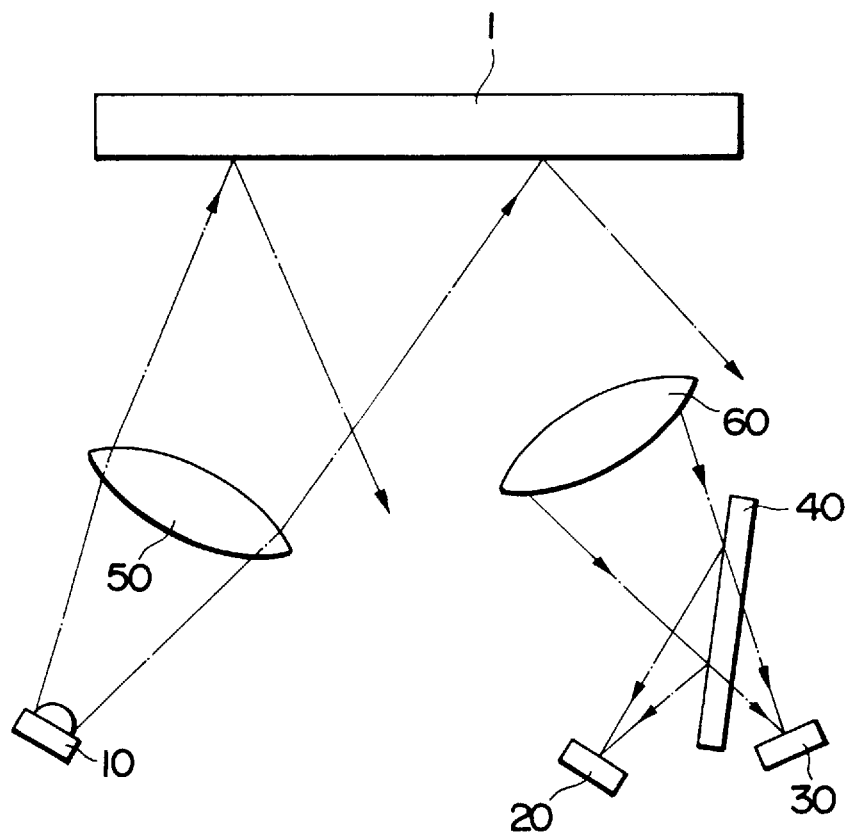
FIG. 39 illustrates the optical arrangement of a sensor head in a reflecting-type optical sensor device.

FIG. 39 illustrates the optical arrangement of a sensor head in a reflecting-type optical sensor device. The sensor head comprises a light-projecting optical system composed of a light-emitting element 10 and a projecting lens 50, and a light-receiving optical system composed of a light-receiving lens 60, a polarization beam splitter 40 and two light-receiving elements 20, 30.

Here the light-emitting element 10 is a light-emitting diode (which has the light-emission spectrum of FIG. 4 or FIG. 24, by way of example) that emits randomly polarized light. The projecting lens 50 converts the light exiting from the light-emitting element 10 to a slightly diverging luminous flux, a parallel luminous flux or a converging luminous flux, depending upon the particular application. The projecting lens 50 projects the converted light upon the surface of an object of interest 1 at an oblique angle. It should be noted, however, that the projecting lens 50 need not always be provided.

A polarization filter (or polarization beam splitter) may be placed between the light-emitting element 10 and lens 50 or in front of the lens 50 to project linearly polarized light having a specific direction of polarization. A light-emitting diode equipped with a lens can be used as well. A semiconductor laser can also be used as the light-emitting element, as will be illustrated below.

In dependence upon the light-emission spectrum of the light-emitting element 10 and the particular application, any of the above-described polarization beam splitters A~I, or a polarization beam splitter having different characteristics, may be used in the light-receiving optical system. Some of the light projected by the light projecting optical system is reflected by the object 1 of interest. This reflected light (inclusive of regular reflected light) is converged by the light-receiving lens 60. The polarization beam splitter is placed in the optical path of the converged light at an oblique angle with respect to the principal axis (i.e., at an angle in the vicinity of the central angle in the range of angles of incidence used as mentioned above). The light-receiving elements 20, 30 are arranged in such a manner that the light reflected by the polarization beam splitter 40 is received by the light-receiving element 20 and the light transmitted through the polarization beam splitter 40 is received by the light-receiving element 30. The light receiving lens 60 need not always be provided.

In order to raise the detection sensitivity, polarization filters are provided in front of respective ones of the light-receiving elements 20 and 30. These filters pass the s-polarized reflected light and p-polarized transmitted light from the polarization beam splitter. If necessary, an optical filter which blocks stray external light is provided in front of the light-receiving lens 60. For example, in a case where infrared projection light is used, the optical filter would block visible light and pass infrared light. A light-receiving element having a lens integrally molded on its front surface can also be used.

In a case where the object 1 to be sensed is a transparent body, the reflected light contains more s-polarized light components than p-polarized light components, as mentioned above. In a case where the object 1 is an opaque body, the surface thereof is a diffuse reflection surface or the surface has water drops or frost attached to it, the reflected light is randomly polarized light.

On the other hand, the polarization beam splitter 40 separates incident light into reflected light mainly containing the s-polarized light component and the transmitted light mainly containing the p-polarized light component, as described earlier.

In the arrangement depicted in FIG. 39, the directions of the s- and p-polarized light defined in the object 1 coincide with the directions of the s- and p-polarized light defined in the polarization beam splitter 40, respectively.

Accordingly, by calculating the values of S/P, (S−P)/(S+P), S−P or S−kP [where S represents the level of the output signal from the light-receiving element 20 and P the level of the output signal from the light-receiving element 30 (the symbols S and P are used for the sake of simplicity)] and discriminating the results of calculation using an appropriate threshold value, it can be determined whether the object to be sensed is a transparent body, a diffuse reflection surface or a surface to which water drops or the like are attached. In other words, the above-mentioned results of calculation exhibit large values in the case of a transparent body and relatively low values in the case of an opaque body.

In a case where the polarization beam splitter 40 is placed in the optical path of the converging light, as illustrated in FIG. 39, the angle of incidence of the incident light differs depending upon the location. The angle of incidence upon the polarization beam splitter 40 changes when the distance between the object 1 to be sensed and the sensor head fluctuates. In the above-described polarization beam splitters A~I, the light separating characteristic ($R_s/T_p$ or $R_s$) is held substantially constant in the range of angles of incidence used. Accordingly, detection accuracy is improved since the danger of erroneous detection owing to dependence of the detected results on spread or change of the angle of incidence is eliminated. Since $R_s/T_p$ is held substantially constant especially in the polarization beam splitters A and F, stability of detection is improved in an arrangement in which S/P is calculated.

In the polarization beam splitters A~I described above, dependency of the light separating characteristic on angle of incidence is small even if spread of the light-emission spectrum of the light-emitting diode is taken into account and even if a shift in the wavelength of the spectrum is considered. This means that it is possible to use the light-emitting diode as the light-emitting element.

Figure 40:
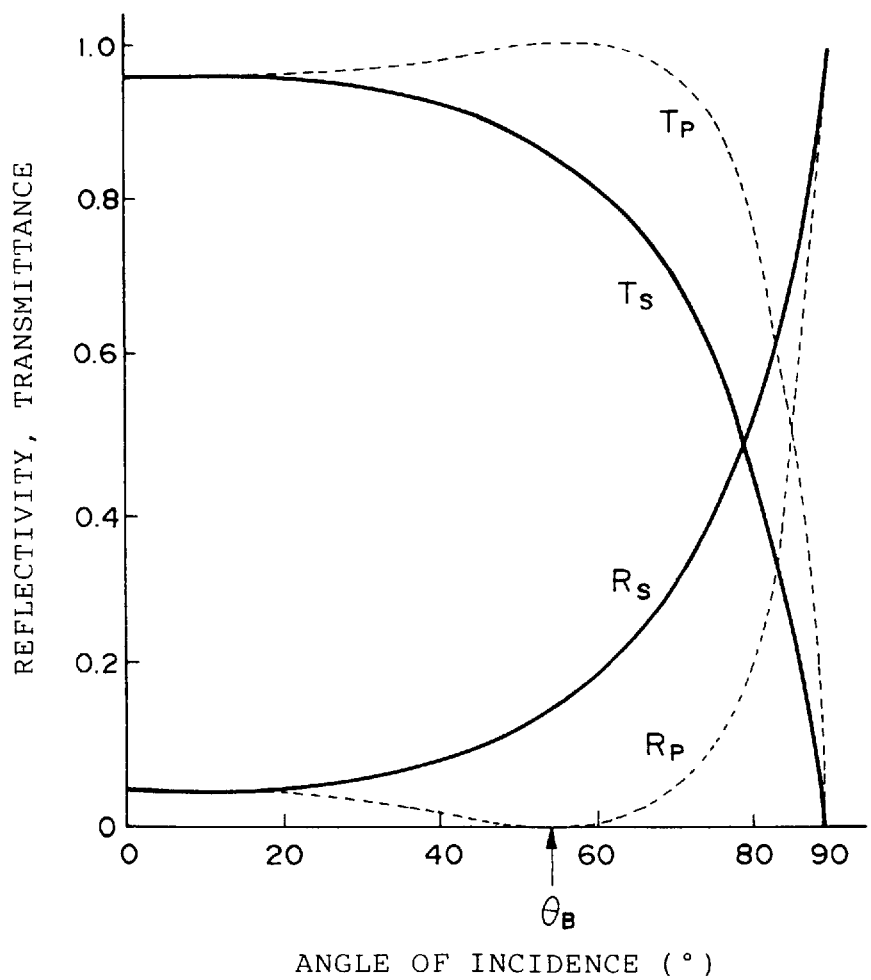
FIG. 40 shows the dependency of reflectivity and transmittance on angle of incidence in a transparent body.

FIG. 40 shows the dependency of reflectivity and transmittance on angle of incidence in a transparent body such as glass (refractive index n=1.5). Here $R_s$, $R_p$ represent the reflectivities of the s- and p-polarized light components, respectively, and $T_s$, $T_p$ represent the transmittances of the s- and p-polarized light components, respectively.

If the angle of incidence is enlarged, the reflectivity increases. The reflectivity $R_s$ of the s-polarized light component becomes larger than the reflectivity $R_p$ of the p-polarized light component, and the ratio $R_s/R_p$ becomes largest in the vicinity of an angle of incidence of from 50° to 60°.

In particular, when the angle of incidence of light with respect to a glass surface is 56.3°, the reflectivity $R_p$ of the p-polarized light component becomes zero. This angle of incidence is referred to as the Brewster angle $\theta_B$.

By adopting an arrangement in which the projected light from the sensor head is projected upon the object of interest in such a manner that the angle of incidence attains a value in the vicinity of 40° to 65°, the reflected light of the s-polarized light component increases and detection accuracy can be improved in a case where the object of interest is a transparent body. If an arrangement is adopted in which the angle of incidence approaches the Brewster angle, the incident light can be separated into the s- and p-polarized light components effectively even in a polarization beam splitter constructed by forming multiple-layer thin films on a glass substrate or the like.

FIG. 41 shows another example of an arrangement of a sensor head in a reflecting-type optical sensor device. In the sensor head illustrated in FIG. 39, an arrangement is adopted in which the projected light is projected upon the object of interest at an oblique angle and obliquely reflected light is received. By contrast, the sensor head 70 shown in FIG. 41 is so arranged that light is projected upon the surface of the object of interest substantially perpendicularly, and the light which returns upon being reflected substantially perpendicularly is received.

A polarization filter 51 is provided between the light-emitting element (light-emitting diode) 10 and the projecting lens 50. The polarization filter 51 passes s-polarized light defined in the polarization beam splitter 40 of the light-receiving optical system. The other structural elements are the same as those shown in FIG. 39.

The sensor head 70 is used ideally to identify an object having a specular surface and an object having a rough surface (a light diffusing surface). As mentioned above, a specular surface preserves the state of polarization of the incident light. Accordingly, when s-polarized light impinges upon a mirror surface, the resulting regular reflected light is almost all s-polarized light. By contrast, since a rough surface causes random polarization, light reflected from this surface contains s-polarized light components and p-polarized light components in substantially equal proportions even s-polarized light impinges upon the surface.

Accordingly, if reflected light from an object 2 of interest is separated into light mainly containing the s-polarized light component and light mainly containing the p-polarized light component by means of the polarization beam splitter 40 of the light-receiving optical system, these light beams are received by the light-receiving elements 20, 30, respectively, S–P, S–kP, (S–P)/(S+P), S/P, etc., are calculated and the results of calculation are compared with a threshold value, then it can be determined whether the object 2 has a specular (mirror) surface or a rough surface. It should be noted that the p-polarized light may be adopted as the projected light if desired.

Figure 42:
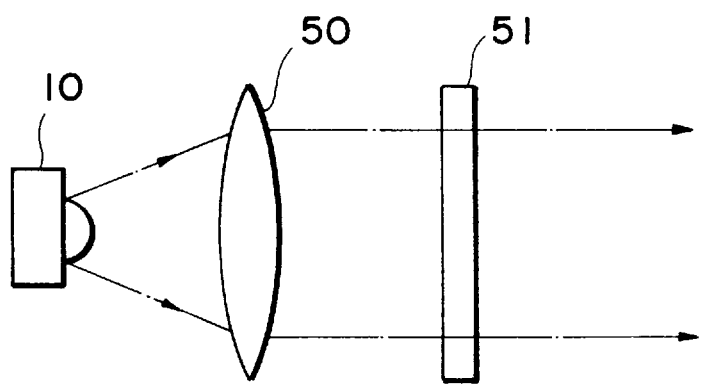
FIG. 42 shows another example of light-projecting optical system.

In a case where the lens 50 of the light-projecting optical system is a special plastic lens possessing birefringence, it is better to place the polarization filter 51 on the optical path of the projected light rendered parallel by the projecting lens 50, as illustrated in FIG. 42.

In FIG. 43, a polarization beam splitter 52 is used in the light-projecting optical system in place of the polarization filter. The polarization beam splitter 52 is placed in the optical path of the diverging light projected from the light-emitting element 10 and is arranged obliquely with respect to the optic axis thereof. FIG. 44a is a plan view of the light-projecting optical system, and FIG. 44b is a side view thereof. It will be appreciated from these diagrams that the polarization beam splitter 52 of the light-projecting optical system and the polarization beam splitter 40 of the light-receiving optical system are arranged so as to approximately perpendicularly intersect each other.

In a case where a light-emitting diode having a light-emission spectrum (of the kind shown in FIG. 24) in the infrared region is used as the light-emitting element 10 in the arrangement of FIG. 41, a polarization filter in the infrared region must be used. Since an infrared polarization filter is costly, it is preferred that the polarization beam splitter 52 be used, as depicted in FIG. 43.

As mentioned above, projected light can be made s-polarized light or p-polarized light using a polarization filter or polarization beam splitter even in the sensor head shown in FIG. 39.

The foregoing may be summarized as follows: The arrangement shown in FIG. 39 is referred to one as an oblique incidence type, and the arrangement shown in FIG. 41 is referred to one as a vertical incidence type.

In the oblique incidence type, randomly polarized light or s-polarized light can be used as the projected light. When randomly polarized projected light is used, it is possible to distinguish between a transparent body and an opaque body. When s-polarized projected light is employed, it is possible to distinguish between not only a transparent body and an opaque body but also between a specular surface and a rough surface.

In the vertical incidence type, s-polarized light or p-polarized light can be used as the projected light, and it is possible to distinguish between a specular surface and a rough surface in either case.

Examples of circuits for identifying or discriminating an object of interest on the basis of output signals from the two light-receiving elements 20, 30 will now be described with reference to FIGS. 45 through 48.

Figure 45:
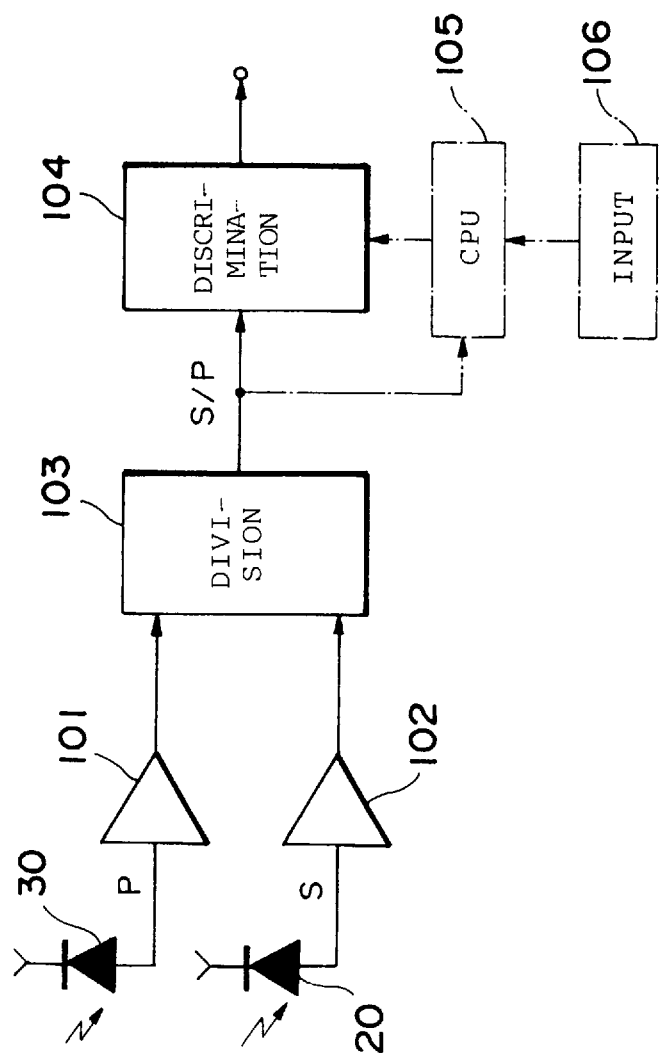
FIG. 45 is a block diagram illustrating an example of a discriminating circuit in an optical sensor device.

FIG. 45 illustrates a circuit for calculating S/P and performing a discriminating operation on the basis of the value calculated. Light-reception signals P, S from the light-receiving elements 30, 20 are amplified by amplifiers 101, 102, respectively, and the amplified signals enter a dividing circuit 103. The latter performs the operation S/P and applies the results of the operation to a discriminating circuit 104. In its simplest form, the discriminating circuit 104 is constituted by a comparator. The value of S/P resulting from the division operation is compared with one threshold value or with a plurality of different threshold values set in the discriminating circuit 104 in advance. The discriminating circuit 104 outputs the result of the comparison as is or in the form of value obtained by decoding the result of the comparison. It is preferred that the threshold value or values be variable.

An arrangement may be adopted in which values of S/P resulting from the division operation performed with regard to various samples are applied to a CPU 105, which may then decide or revise the threshold values. An arrangement may be adopted in which threshold values are entered or revised by the user from an input unit 106 by way of the CPU 105.

The circuit shown in FIG. 45 is particularly suited to an object of interest which produces a large difference between the signals P and S. In such case, an error will not be produced in the results of discrimination even if the light incident upon the light-receiving element experiences some fluctuation in quantity of light caused by a fluctuation in the output of the light-emitting element or a fluctuation in the position of the object of interest.

Figure 46:
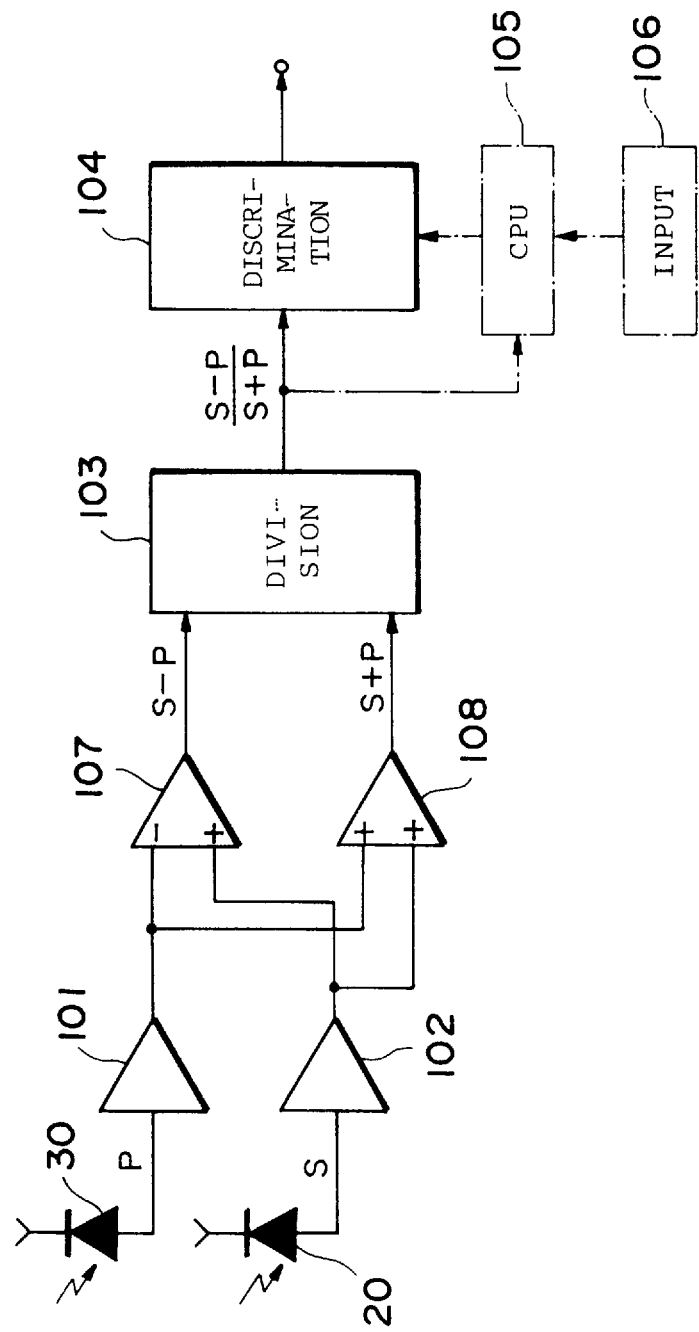
FIG. 46 is a block diagram illustrating an example of a discriminating circuit in an optical sensor device.

FIG. 46 illustrates a circuit for calculating (S–P)/(S+P) and performing a discriminating operation on the basis of the value calculated. The operations S-P and S+P are performed by a subtractor 107 and an adder 108, respectively, and the results are applied to the dividing circuit 103.

The value of S+P represents to total quantity of incident light. Since the difference S–P is susceptible to the effects of a fluctuation in quantity of light, this difference is normalized by the total quantity of light, thereby rendering the difference strongly resistant to fluctuations in quantity of light.

Figure 47:
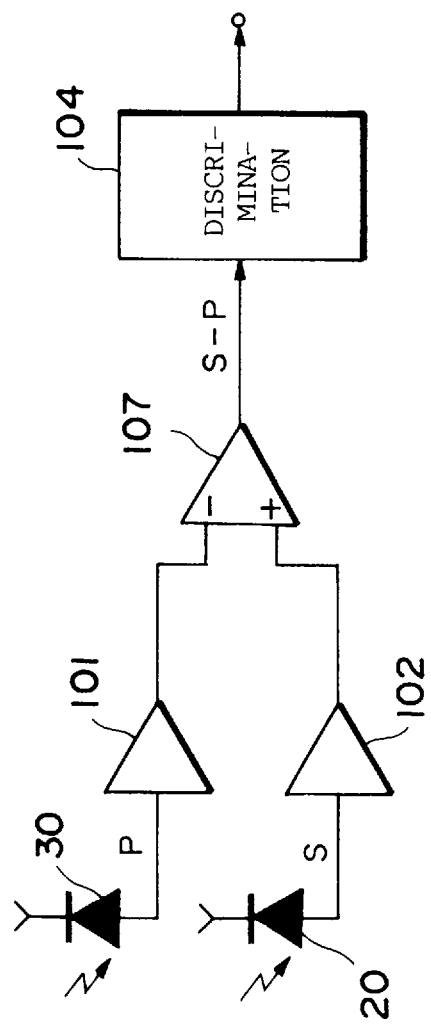
FIG. 47 is a block diagram illustrating an example of a discriminating circuit in an optical sensor device.

FIG. 47 illustrates a circuit for calculating S–P and performing a discriminating operation on the basis of the value calculated. This circuit is suited to the arrangements of FIGS. 41 and 43 (in which s-polarized light is used as the projected light).

In this arrangement, the s-polarized light component of the regularly reflected light and the s-polarized light component of the diffusely reflected light from the object to be sensed mainly impinge upon the light-receiving element 20. The p-polarized light component of the diffusely reflected light from the object to be sensed mainly impinges upon the light-receiving element 30. What is desired to be sensed is the regularly reflected light component. The s-polarized light component and p-polarized light component of the diffusely reflected light are substantially equal. Accordingly, it will suffice to perform the operation S−P. This operation is carried out by the subtracting circuit 107, and the result of the operation is fed into the discriminating circuit 104.

The amplification-factor of the amplifier 102 may be made k times the amplification-factor of the amplifier 101 (where k is an arbitrary constant). In such case the operation S−kP will be performed by the subtracting circuit 107. This correction is useful when a polarization filter is placed on the front side of a light-receiving element or when the reflectivity of the s-polarized light and the transmittance of the p-polarized light of the polarization beam splitter differ.

Figure 48:
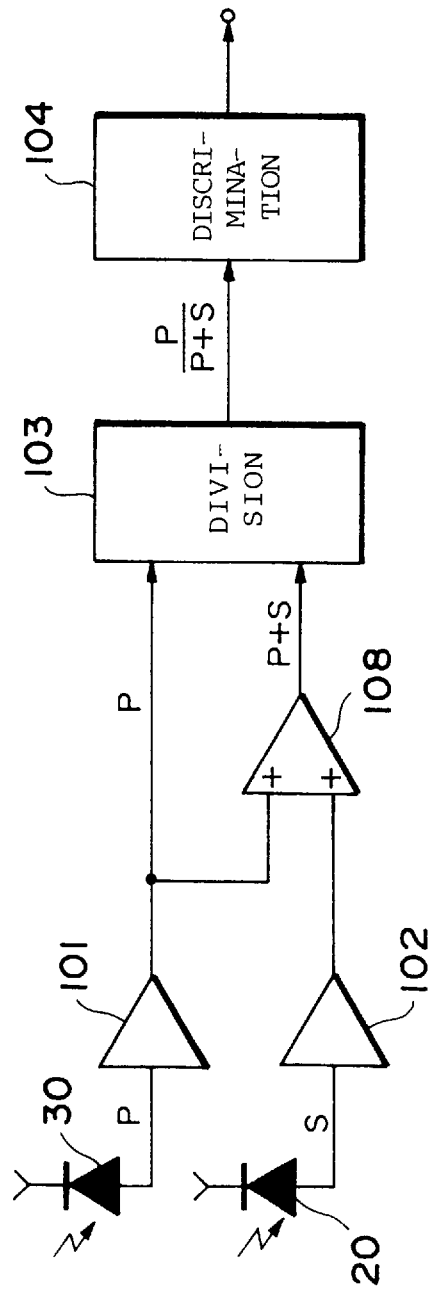
FIG. 48 is a block diagram illustrating an example of a discriminating circuit in an optical sensor device.

The circuit of FIG. 48 is for identifying or discriminating an object of interest by sensing the proportion of the p-polarized light components in an arrangement in which s-polarized light is projected upon the object. More specifically, the degree of glossiness of the surface of the object is sensed by calculating the proportion of diffuse reflection components obtained from the object of interest.

The adder 108 performs the operation P+S, and P/(P+S) is calculated by the dividing circuit 103. The result is applied to the discriminating circuit 104. Since normalization by the total light quantity P+S is performed, there is little susceptibility to the effects of a fluctuation in quantity of light.

By combining the results of discrimination performed by the above-described circuits, final results of discrimination can also be obtained. For example, in a case where S/P is calculated in the circuit of FIG. 45 but a judgment cannot be made on the basis of this value (the difference between values of S/P is small with regard to a plurality of different objects), discrimination is attempted by calculating S−P using the circuit illustrated in FIG. 47. It is also possible to adopt an arrangement in which the result of discrimination from one circuit is checked on the basis of the result of discrimination performed by another circuit.

The sensing operation performed by the optical sensing device will now be described with regard to a concrete example.

Figure 49:
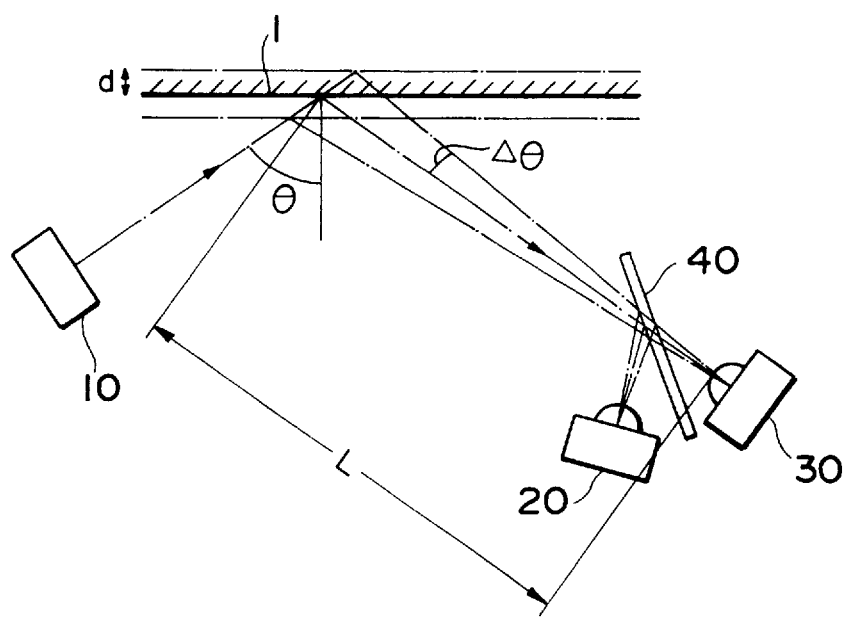
FIG. 49 illustrates a sensor head of the oblique incidence type.

FIG. 49 illustrates a sensor head of the oblique incidence type. Components identical with those of the arrangement shown in FIG. 39 are designated by like reference characters and need not be described again. A projecting lens and a light-receiving lens are not provided. The light-receiving element illustrated is one equipped with a lens. The light-emitting element 10 is a light-emitting diode.

The above-described polarization beam splitter A is used as the polarization beam splitter 40.

There are three types objects 1 to be sensed, namely plain paper, coated paper (fine-quality paper) and glossy paper. Glossy paper is paper which is more glossy than coated paper and is used in printing photographs, by way of example.

An angle θ of incident light projected by the light-emitting 10 so as to impinge upon the object 1 is a standard angle of 55°, which is very close to the Brewster angle. Since plain paper may be considered to be an object from which light is diffusely reflected, the reflected light is randomly polarized light and the ratio of s-polarized light components to p-polarized light components is 1:1. Since the surface of coated paper is provided with a coating material (dielectric), the regularly reflected light is s-polarized light. Though the reflected light from the coated paper naturally contains scattered (diffused) light, there are also p-polarized light components but the s-polarized light components are greater in quantity. The proportion of s-polarized light components in reflected light from glossy paper is larger than in the case of the coated paper.

Let the ratio of s-polarized light components to p-polarized light components be represented by S/P, and let S/P=1 hold for plain paper, S/P=1.5 for coated paper and S/P=2 for glossy paper.

Assume that the distance between the object 1 and the sensor head fluctuates by ±d. The angle of incidence of regularly reflected light from the object 1 to the light-receiving system of the sensor head (the angle of incidence on the polarization beam splitter 40) in this case fluctuates by ±Δθ.

Letting L represent the distance along the optical axis between the object 1 at a standard position and the light-receiving element 20 or 30, Δθ is determined geometrically in FIG. 49 by the following equation:

$$\Delta\theta = \theta - \tan^{-1}\left\{ \frac{L \cdot \sin\theta - d \cdot \tan\theta}{L \cdot \cos\theta + d} \right\} \quad \text{Eq. (1)}$$

If L=15 mm, d=±1 mm and θ=55° hold, then Δθ will be about ±4°. If the beam diameter is taken into account, then we will have Δθ=±5°.

Assume that the aforesaid three types of objects of interest are identified on the basis of the operational result S/P using the circuit shown in FIG. 45. Here S/P is (quantity of light received by the light-receiving element 20)/(quantity of light received by the light-receiving element 30). This shall be referred to as a "received-light quantity ratio".

The received-light quantity ratio can be obtained in accordance with the following equation:

receiving-light quantity ratio =

$$\frac{\text{quantity of light received by light-receiving element 20}}{\text{quantity of light received by light-receiving element 30}} = \frac{R_p + h \cdot R_s}{T_p + h \cdot T_s} \quad \text{Eq. (2)}$$

Here $R_s$ represents the reflectivity of the s-polarized light component in the polarization beam splitter 40, $T_s$ the transmittance (1-$R_s$) of the s-polarized light component, $R_p$ the reflectivity (1-$T_p$) of the p-polarized light component and $T_p$ the transmittance of the p-polarized light component. Further, h represents the values (i.e., h=1, 1.5 and 2) of S/P of the objects of interest.

Figure 50:
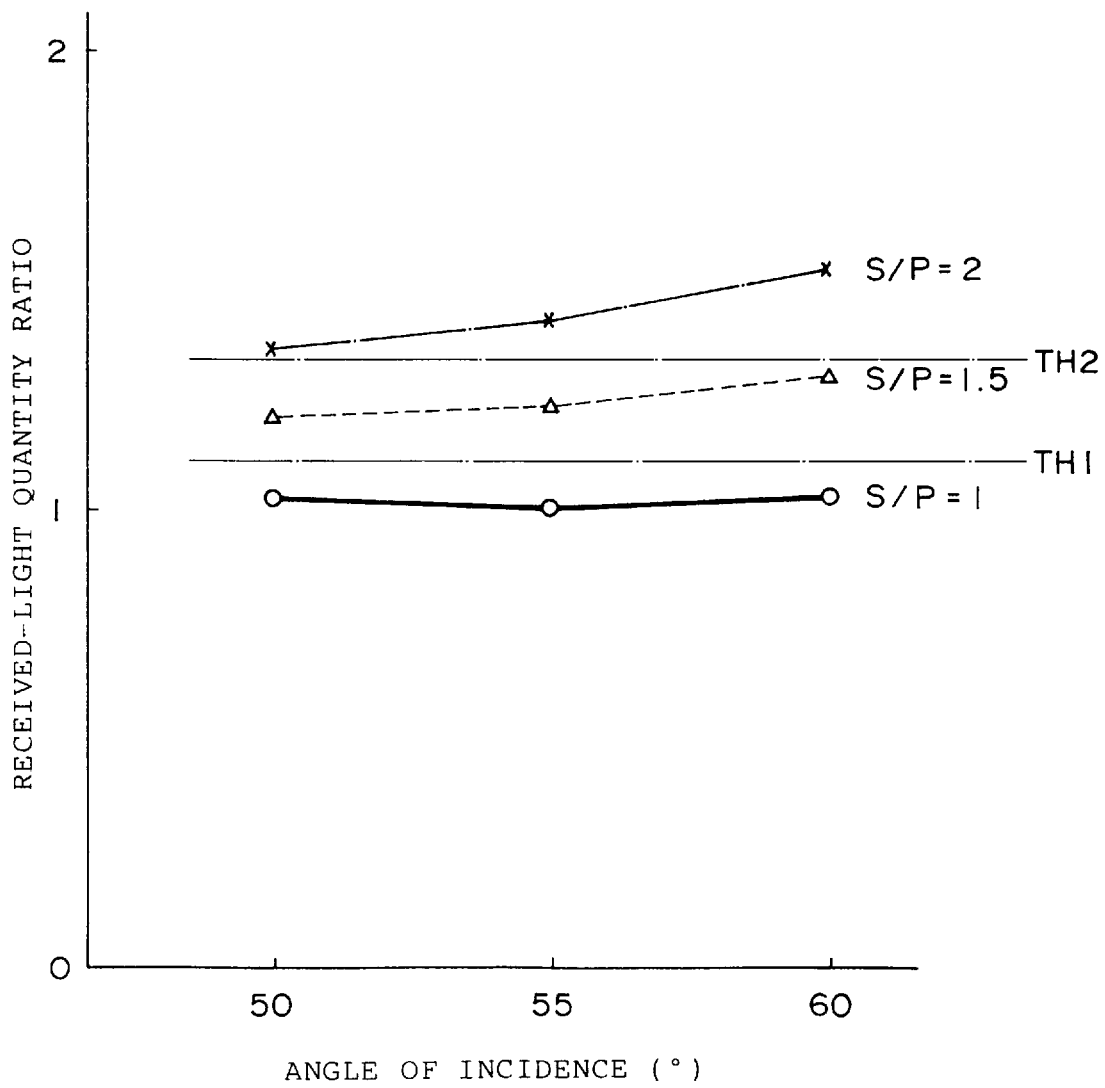
FIG. 50 is a graph showing a received-light quantity ratio when angle of incidence fluctuates.

FIG. 50 shows the received-light quantity ratio, for each of the three types of objects of interest, when angle of incidence upon the polarization beam splitter 40 fluctuates by ±5° attendant upon a fluctuation of ±d=±1 mm with regard to the object of interest.

Figure 51:
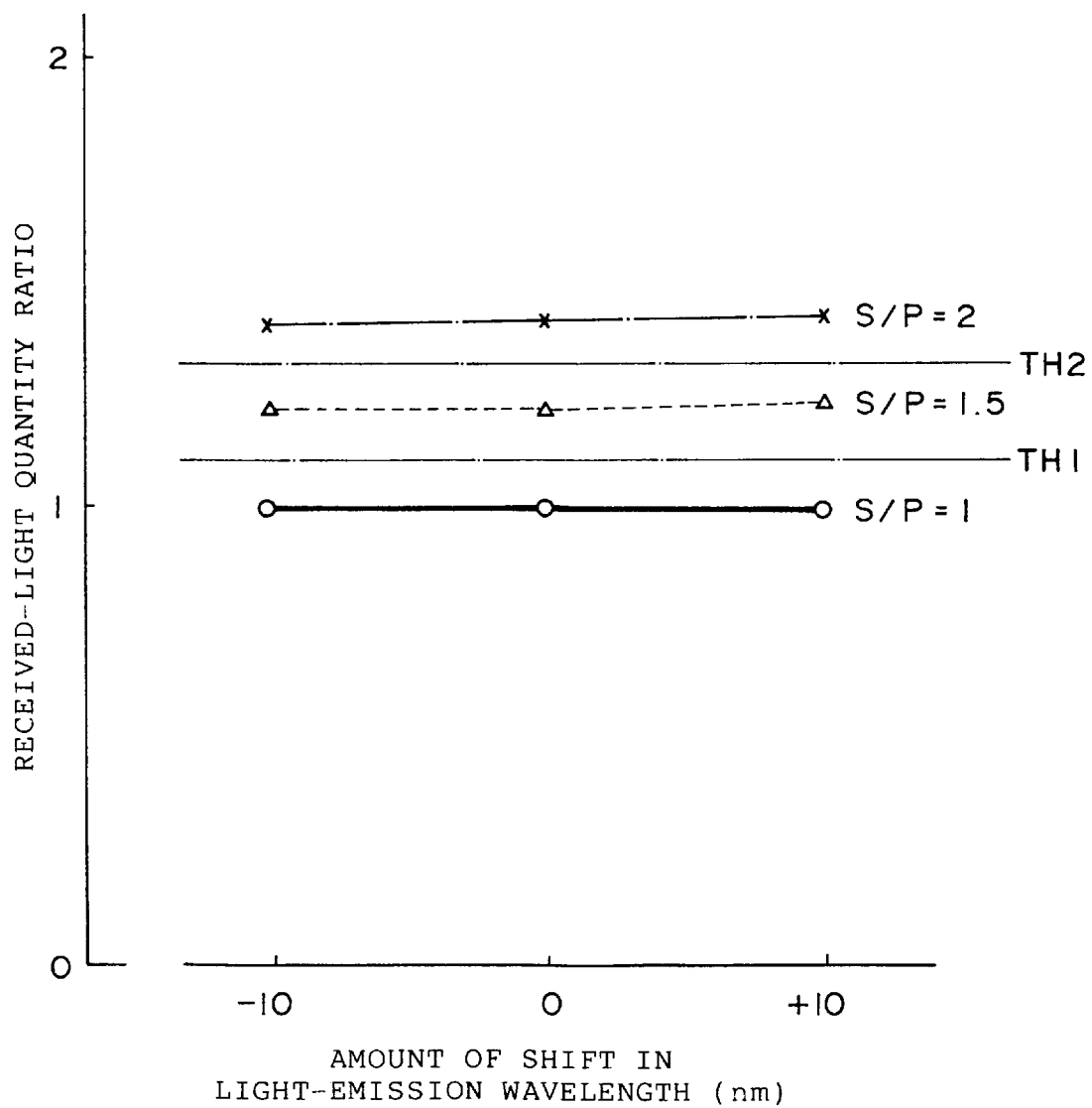
FIG. 51 is a graph showing a received-light quantity ratio when the central wavelength of a light emission from a light-emitting diode shifts by ±10 nm.

FIG. 51 shows the received-light quantity ratio, for each of the three types of objects of interest, when the central wavelength of the light emission from the light-emitting diode 10 shifts by ±10 nm in the standard state (the state in which there is no fluctuation in the object of interest).

Figure 52:
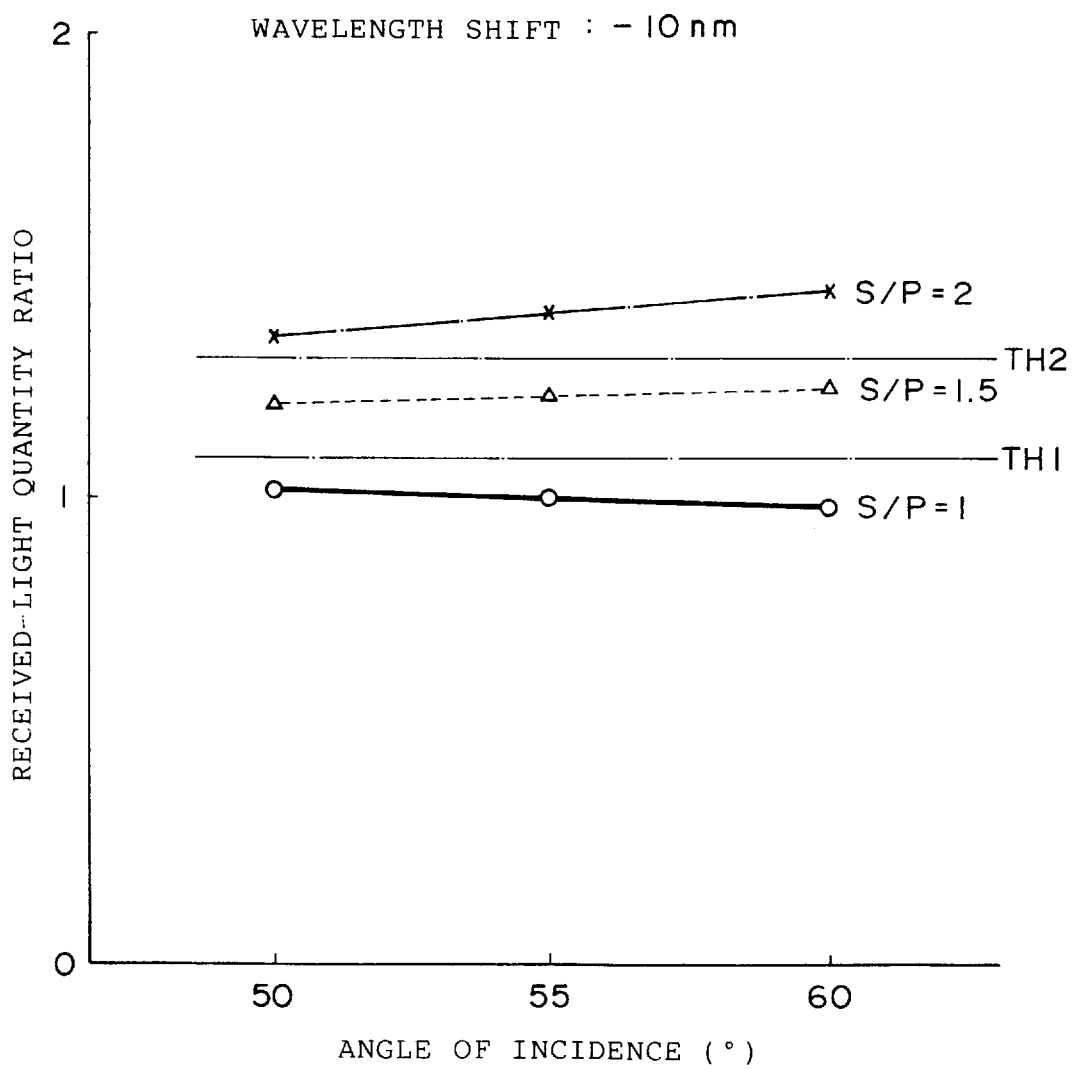
FIG. 52 is a graph showing the manner in which the received-light quantity ratio changes with a fluctuation in angle of incidence when the central wavelength of a light emission from a light-emitting diode shifts by −10 nm.

FIG. 52 shows the manner in which the receiving light quantity ratio varies with a fluctuation in angle of incidence when the central wavelength of the light emission from the light-emitting diode 10 shifts by −10 nm.

Figure 53:
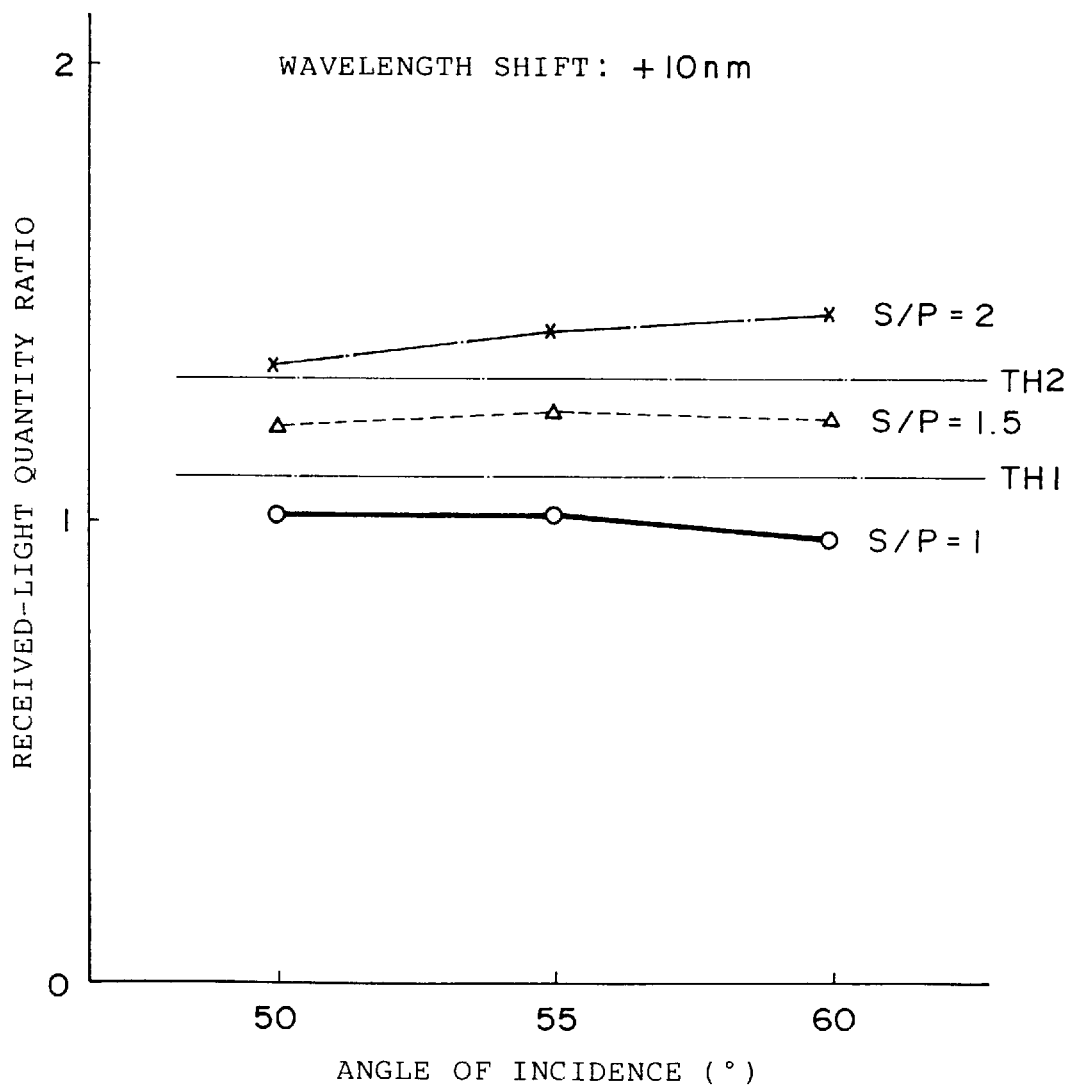
FIG. 53 is a graph showing the manner in which the received-light quantity ratio changes with a fluctuation in angle of incidence when the central wavelength of a light emission from a light-emitting diode shifts by +10 nm.

FIG. 53 shows the manner in which the receiving-light quantity ratio varies with a fluctuation in angle of incidence when the central wavelength of the light emission from the light-emitting diode 10 shifts by +10 nm.

It will be understood from these graphs if two threshold values TH1=1.10, TH2=1.31 set, the three types of objects of interest can be identified based upon S/P in all cases.

More specifically, it is possible distinguish among plain paper, coated paper and glossy paper regardless of a fluctuation in angle of incidence upon the polarization beam splitter caused by a fluctuation in the distance between the object of interest and the sensor head and regardless of a fluctuation in light-emission wavelength due to a variance in the light-emitting diode.

The same results are obtained also in a case where a light-receiving lens is provided in the light-receiving optical system and a polarization beam splitter is disposed in the optical path of the convergent light.

Another concrete example will now be described.

Figure 54:
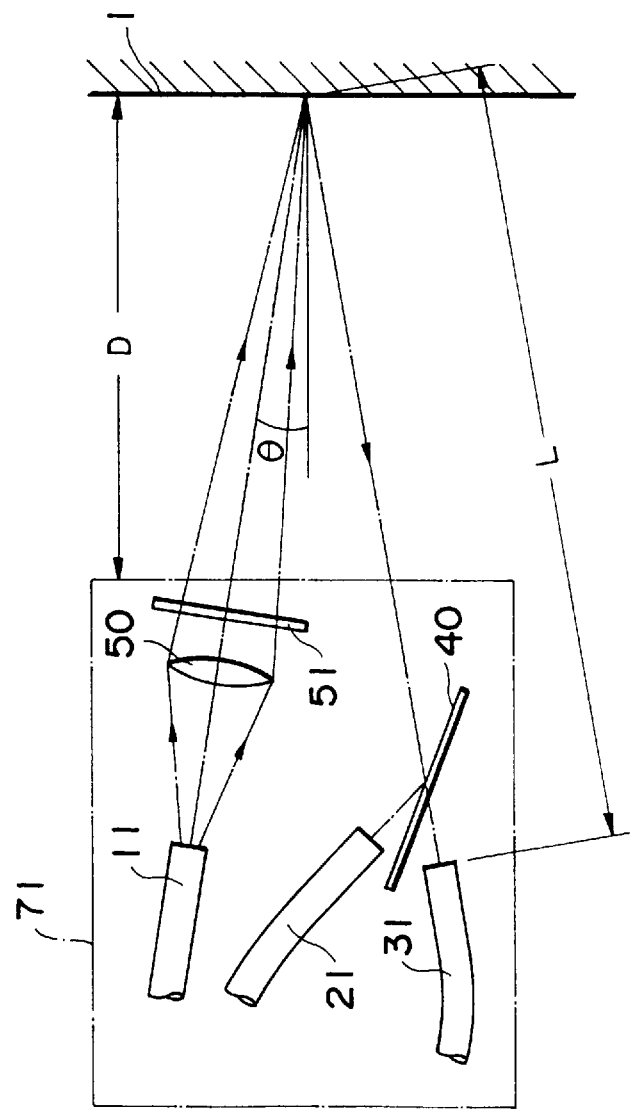
FIG. 54 illustrates an example of the construction of a sensor head.

FIG. 54 illustrates a sensor head which utilizes an optical fiber. In this sensor head, light from the light-emitting element is guided by a projecting optical fiber 11 and exits from the end face of the fiber. The exiting light is converged by the projecting lens 50. The polarization filter 51, which passes only the s-polarized light component, is provided in the optical path of the convergent light. Regular reflected light from the object 1 to be sensed impinges upon the polarization beam splitter 40. The reflected light enters a light-receiving optical fiber there 21 from the end face thereof and is introduced to a light-receiving element (which corresponds to the light-receiving 20). The light transmitted through the polarization beam splitter 40 enters a light-receiving optical fiber 31 from the end face thereof and is introduced to a light-receiving element (which corresponds to the light-receiving 30).

The object 1 of interest is a package or box wrapped in film. The surface of the package also is glossy. Since the wrapping film is a transparent body, the s-polarized light components contained in the regular reflected light in a case where the package is wrapped in the film are greater than in a case where there is no film wrapping.

In a case where the projected light from the projecting lens 50 is incident upon the object 1 at an angle of incidence θ of 20°, the ratio S/P of s-polarized light components to p-polarized light components in the reflected light is 3 for a package with a glossy surface (no film wrapping) and 7 when there is a film wrapping.

The sensor head shown in FIG. 54 senses the absence/presence of film wrapping on the package.

Assume that the specifications of the sensor head are such that detection distance D is 10 mm±3 mm and the angular offset of the object 1 is ±3'. These specifications are for the purpose of performing an inspection to determine whether a package, which is the object 1 of interest, is wrapped in film or not. The inspection is carried out in the course of conveying the packages along a conveyance path. The object 1 shifts in position and oscillates in the course of conveyance.

To give some allowance the design values are assumed to be as follows: detection distance D=10 mm ±4 mm, angular offset =±4°.

Figure 55:
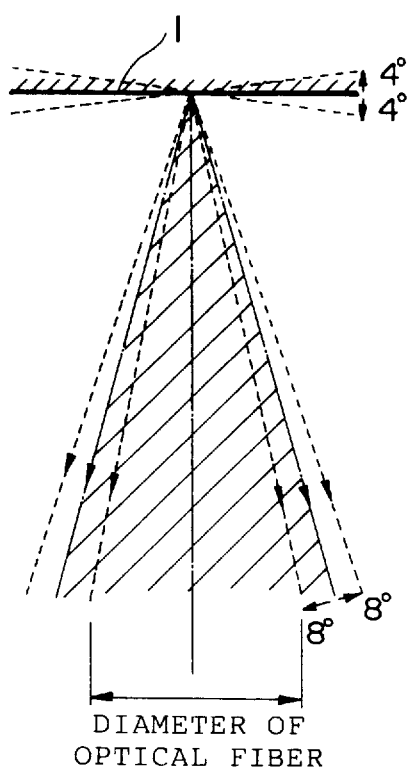
FIG. 55 illustrates a range over which reflected light fluctuates when an object to be sensed is tilted.

When the object tilts by ±4°, the optic axis of the reflected light tilts by ±8°, as shown in FIG. 55. It is necessary that the optical fibers 21 and 31 be placed at positions at which the reflected light will impinge upon these optical fibers in spite of such tilt.

When the detection distance D is 10 mm±4 mm and the diameter of the optical fibers is 1.25 mm, the distance L between the object 1 and the light-receiving end faces of the optical fibers 21, 31 becomes about 25 mm on the optic axis.

If we let L=25 mm, d=±4 mm and θ=20° hold in Equation (1), Δθ becomes +5.5 ~−6.5°. Since it is necessary to take the optical beam diameter and the like into account in actual practice, it is considered that Δθ=±7.5°.

The discriminating circuit used is that shown in FIG. 45. Accordingly, the received-light quantity ratio is compared with a threshold value.

Figure 56:
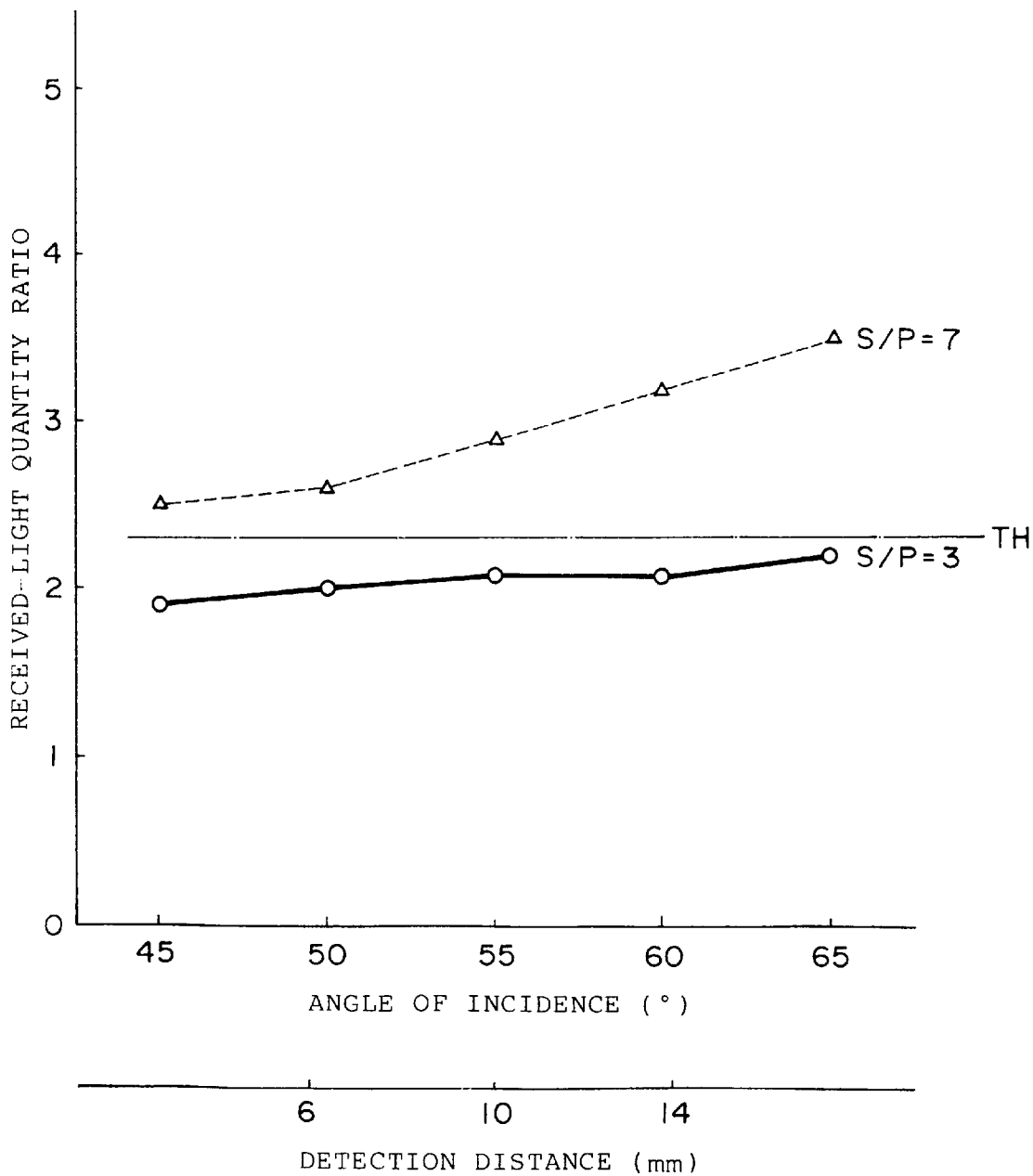
FIG. 56 is a graph showing a received-light quantity ratio when angle of incidence fluctuates.

FIG. 56 illustrates the received-light quantity ratio in a case where the above-mentioned polarization beam splitter F of somewhat inferior characteristics is used as the polarization beam splitter 40. The angle of incidence of light impinging upon the polarization beam splitter is plotted along the horizontal axis.

Figure 57:
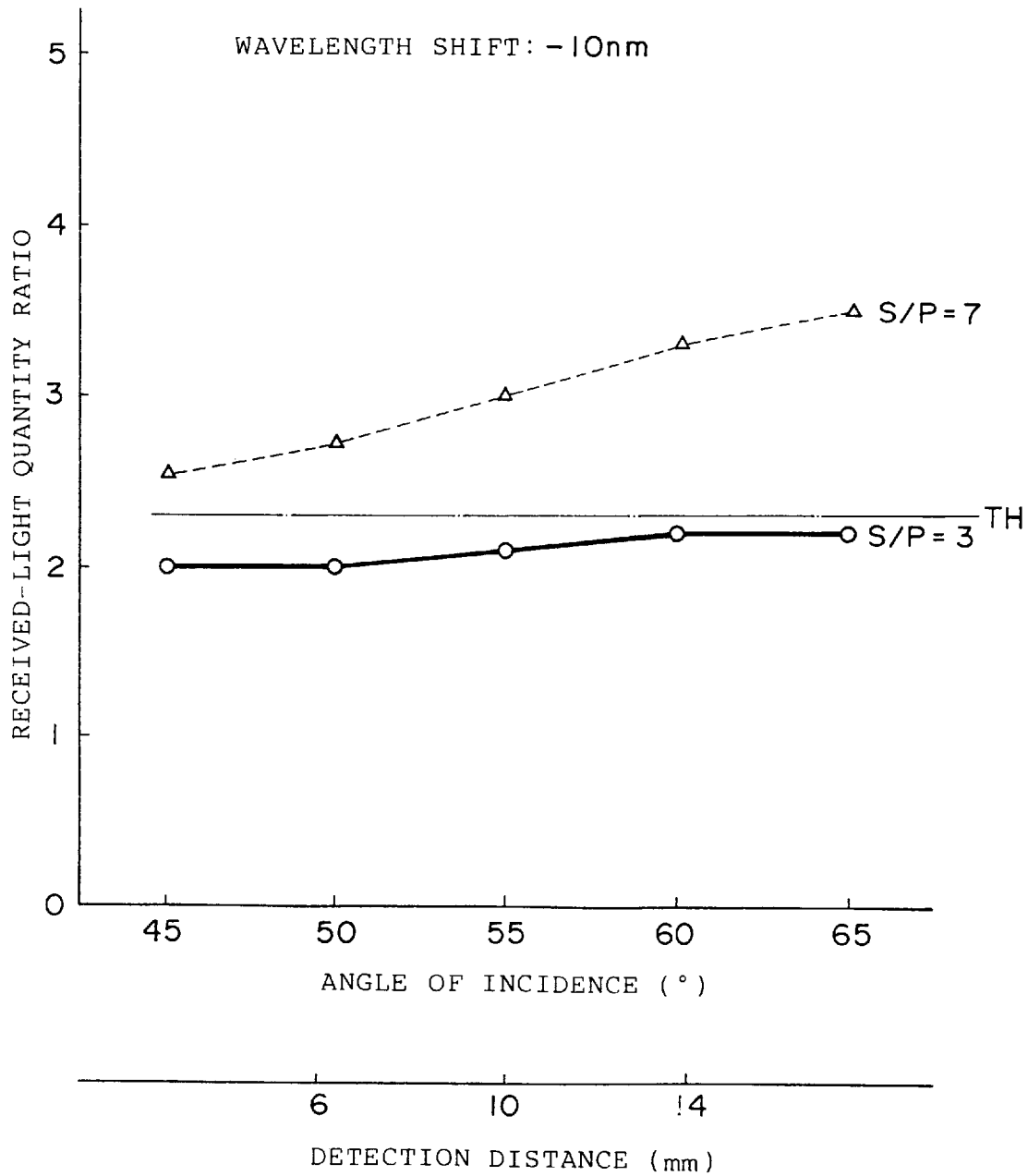
FIG. 57 is a graph showing the manner in which a received-light quantity ratio changes with a fluctuation in angle of incidence when the central wavelength of a light emission from a light-emitting diode shifts by −10 nm.
Figure 58:
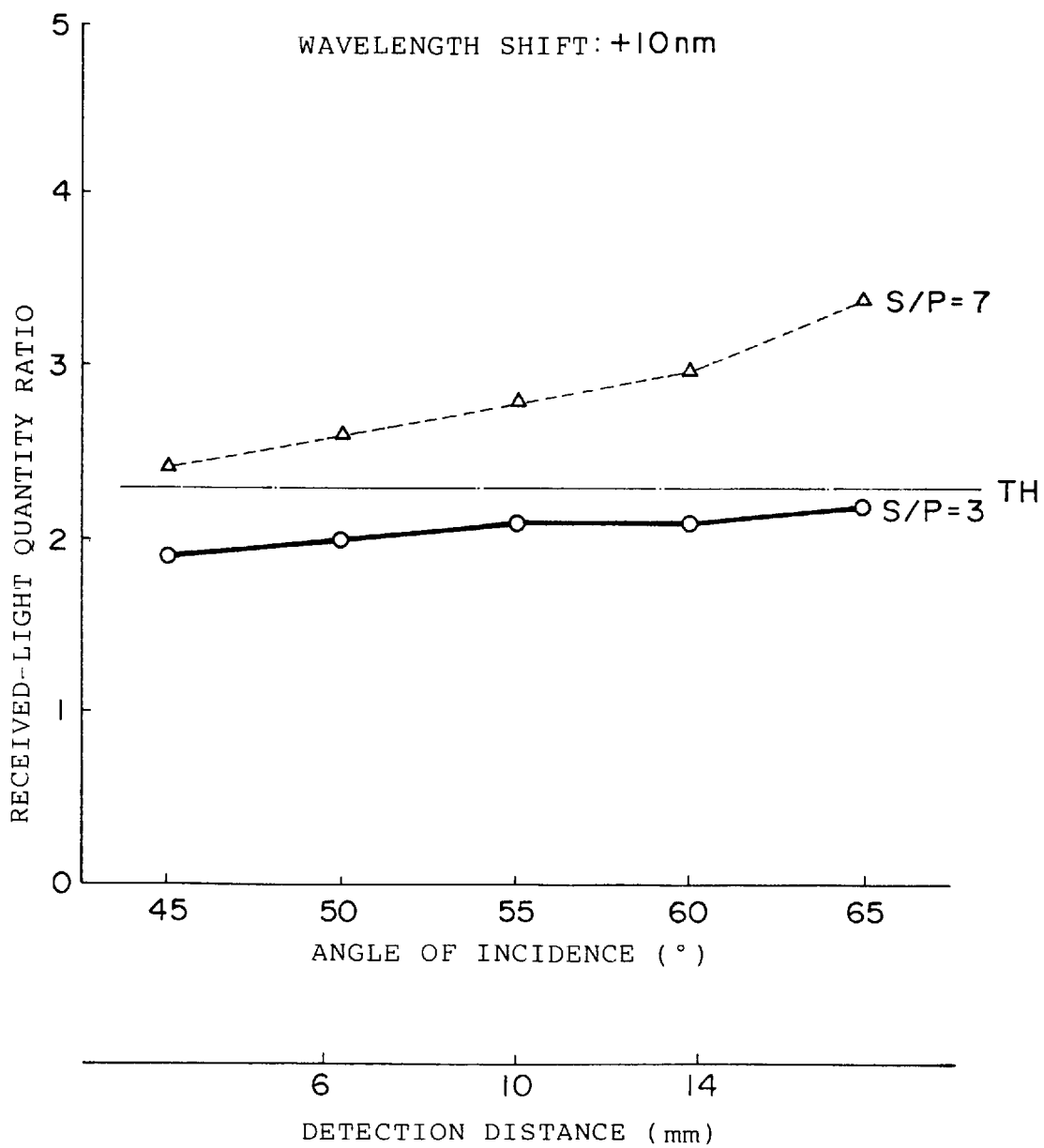
FIG. 58 is a graph showing the manner in which a received-light quantity ratio changes with a fluctuation in angle of incidence when the central wavelength of a light emission from the light-emitting diode shifts by +10 nm.

FIGS. 57 and 58 show received-light quantity ratios when the light-emission wavelength of the light-emitting diode shifts by −10 nm and +10 nm, respectively, with angle of incidence (or detection distance) being plotted along the horizontal axis.

It will be appreciated from these graphs that even if there is a ±10 nm wavelength shift in the light-emission wavelength of the light-emitting element, the absence or presence of film wrapping can be discriminated over a range of angles of incidence of 55 ±10°. The threshold value TH for discriminating the received-light quantity ratio is set to, say, 2.3.

Figure 59:
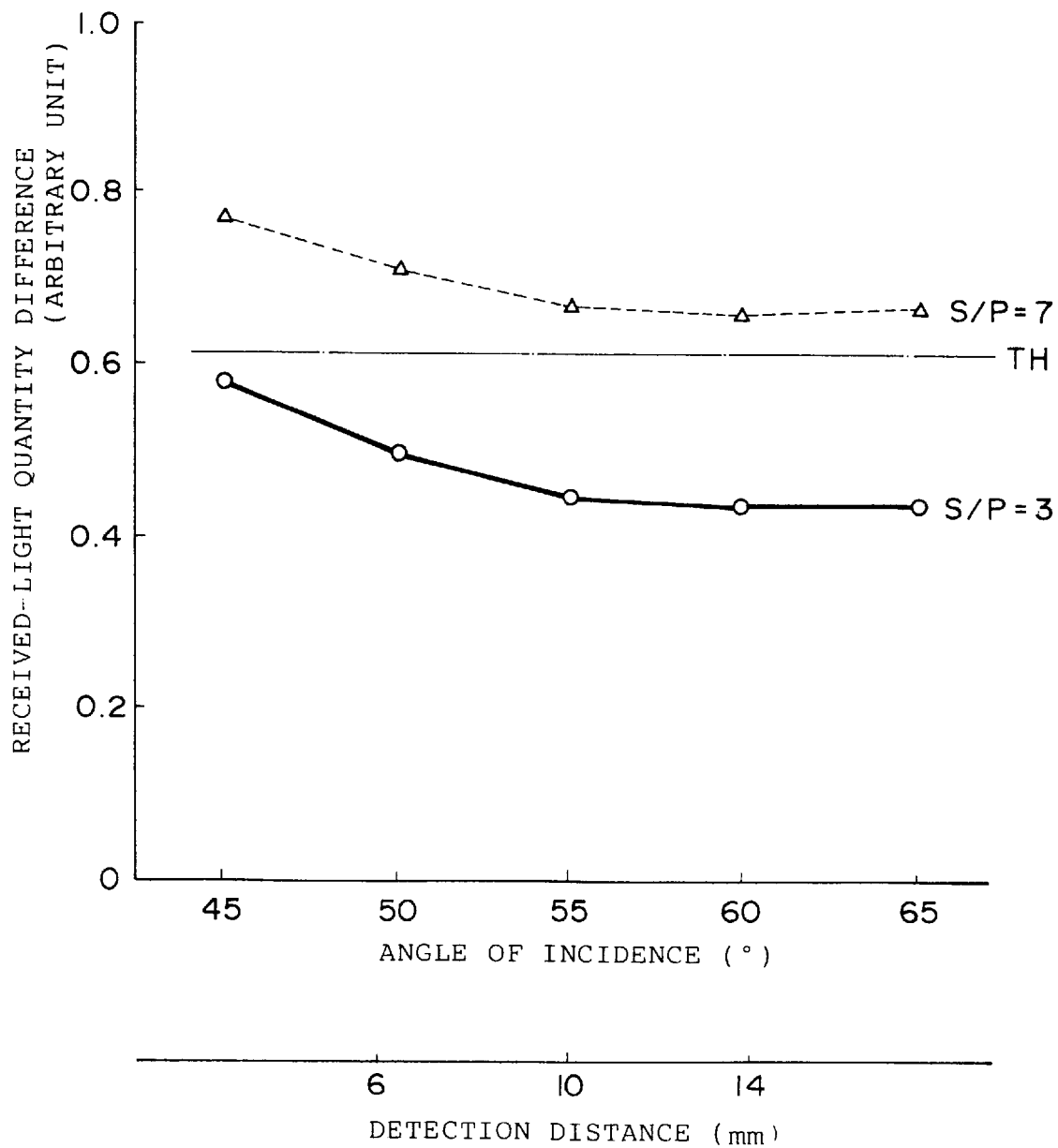
FIG. 59 is a graph showing a difference between received-light quantities when angle of incidence fluctuates.

FIG. 59 illustrates a characteristic in a case where the above-described polarization beam splitter G is used as the polarization beam splitter. The arrangement adopted here is one in which polarization filters are placed in front of the light-receiving elements of the light-receiving optical system in order to raise the polarized-light separation ratio. An s-polarized light filter is provided in front of the light-receiving element (corresponding to the light-receiving element 20) which receives the reflected light from the polarization beam splitter, and a p-polarized light filter is provided in front of the light-receiving element (corresponding to the light-receiving element 30) which receives the transmitted light through the polarization beam splitter The circuit shown in FIG. 47 is used. That is, a value (referred to as a "received-light quantity difference", for which an arbitrary unit is used) obtained by subtracting the received-light quantity (proportional to $T_p$) of p-polarized transmitted light from the received-light quantity (proportional to $R_s$) of s-polarized reflected light from the polarization beam splitter is compared with a threshold value.

Figure 60:
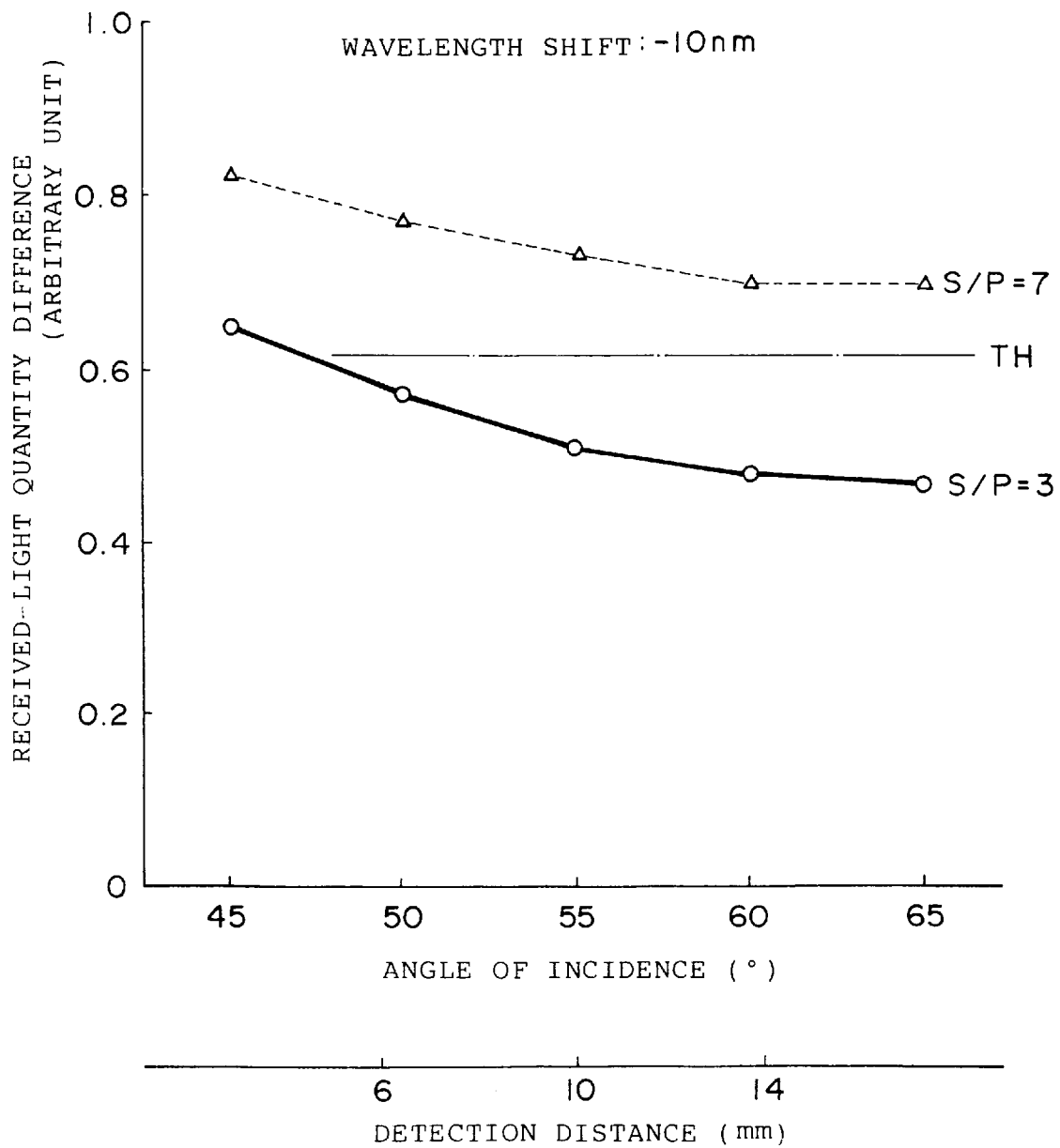
FIG. 60 is a graph showing the manner in which a received-light quantity difference changes with a fluctuation in angle of incidence when the central wavelength of a light emission from a light-emitting diode shifts by −10 nm.
Figure 61:
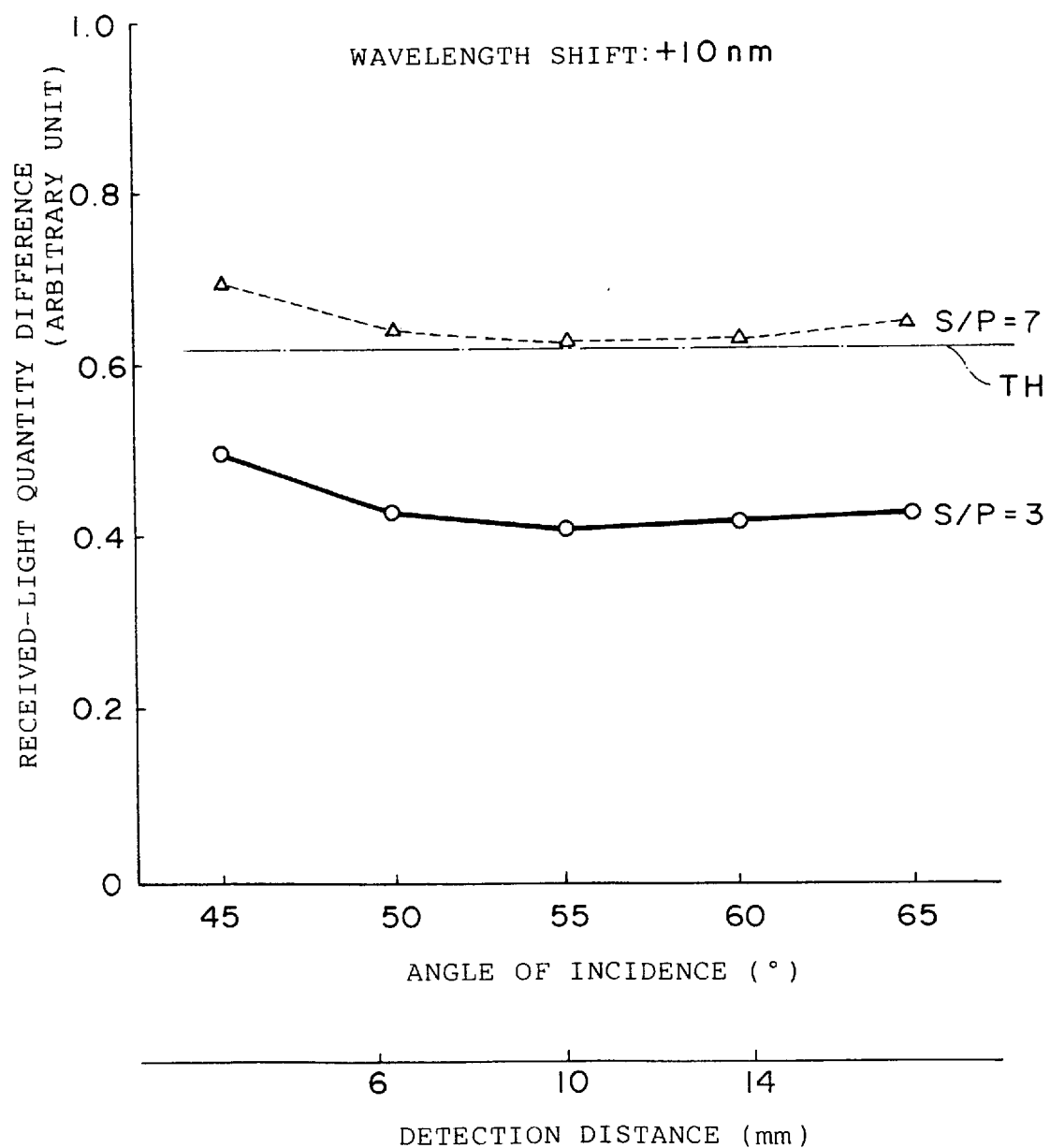
FIG. 61 is a graph showing the manner in which a received-light quantity difference changes with a fluctuation in angle of incidence when the central wavelength of a light emission from the light-emitting diode shifts by +10 nm.

FIGS. 60 and 61 shows received-light quantity differences when the light-emission wavelength of the light-emitting element shifts by −10 nm and +10 nm, respectively. In FIGS. 59 to 61, the angle of incidence of light impinging upon the polarization beam splitter 40 (or the detection distance) is plotted along the horizontal axis.

It will be understood from these graphs that by setting the threshold value TH to 0.615, discrimination of the absence/presence of film wrapping is possible in a range of angles of incidence of at least 55±7.5° even if the light-emission wavelength of the light-emitting element fluctuates by ±10 nm.

It will be appreciated that optical sensing devices using the polarization beam splitters A, F and G possess a satisfactory polarized-light separation capability and, as a result, are capable of sensing an object accurately irrespective of a variance in the light-emission wavelength of the light-emitting element and the spread of the angle of incidence.

(3) Sensor head variations

Examples of sensor heads having various constructions will now be described.

A variation on the reflective sensor head of oblique incidence type will be described first.

Figure 62:
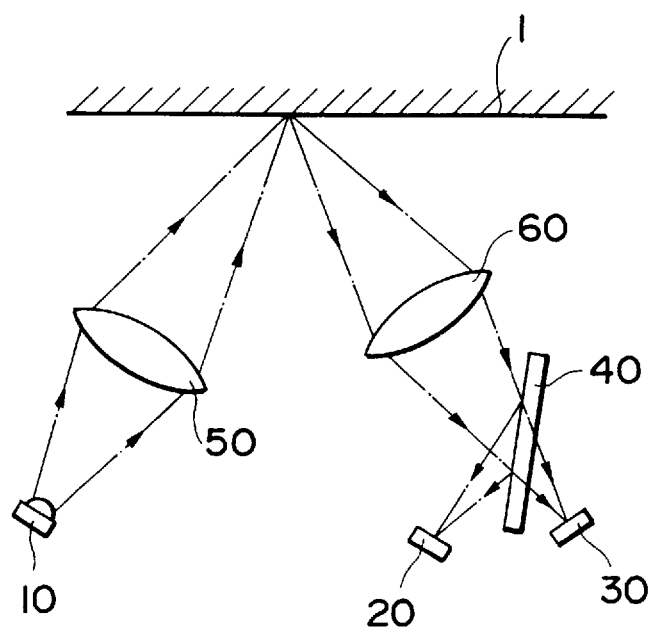
FIG. 62 shows an example of the arrangement of a reflective sensor head of oblique incidence type.

The sensor head shown in FIG. 62 has a construction basically the same as that of the sensor head shown in FIG. 39. The difference is that the projecting lens 50 converges the projected light before the light is projected upon the object 1 to be sensed. The light-receiving lens 60 converges the reflected light from the object 1.

In accordance with this arrangement, the spot of projected light is readily visible to the eye. In addition, the projection efficiency is high. The sensing of very small spacings (such as the seams in transparent labels) is possible.

Figure 63:
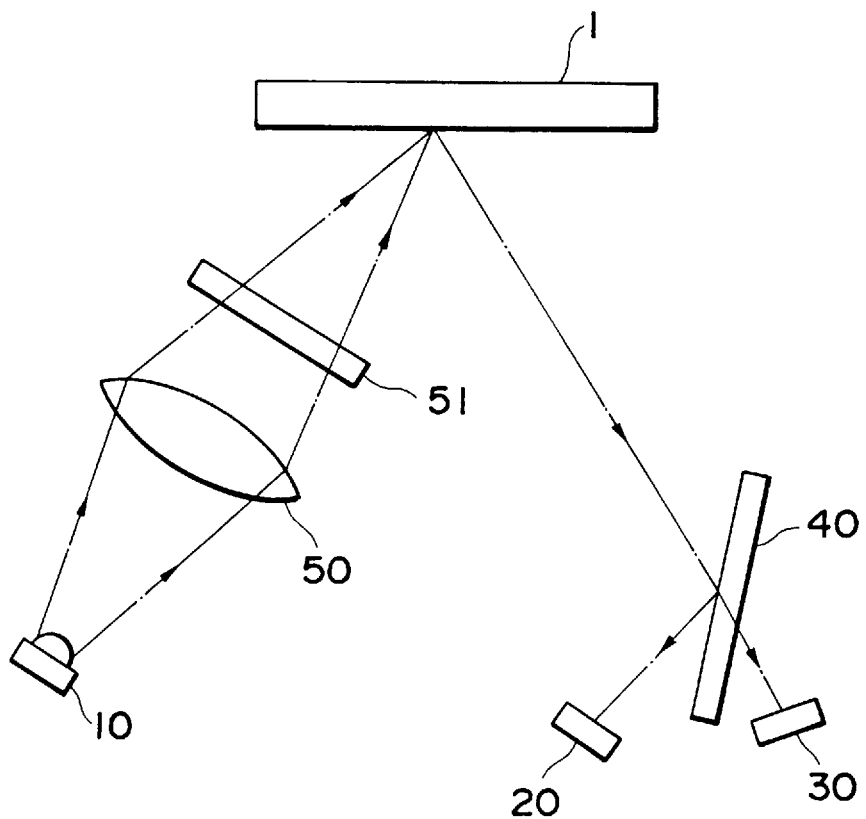
FIG. 63 shows an example of the arrangement of a reflective sensor head of oblique incidence type.

In the sensor head shown in FIG. 63, the polarization filter 51 is provided in front of the projecting lens 50. This polarization filter 51 passes p-polarized light.

In a case where the object 1 to be sensed is a transparent body (with the exception of a substance exhibiting birefringence) or one having a specular surface, regular reflected light does not contained any s-polarized light. If the object 1 is a substance exhibiting birefringence, an s-polarized light component is generated if the directions of birefringence and p-polarized light differ, and the generated s-polarized light is received by the light-receiving element 20 of the light-receiving optical system. Accordingly, the sensor head of FIG. 63 is capable of sensing a substance possessing birefringence.

Figure 64:
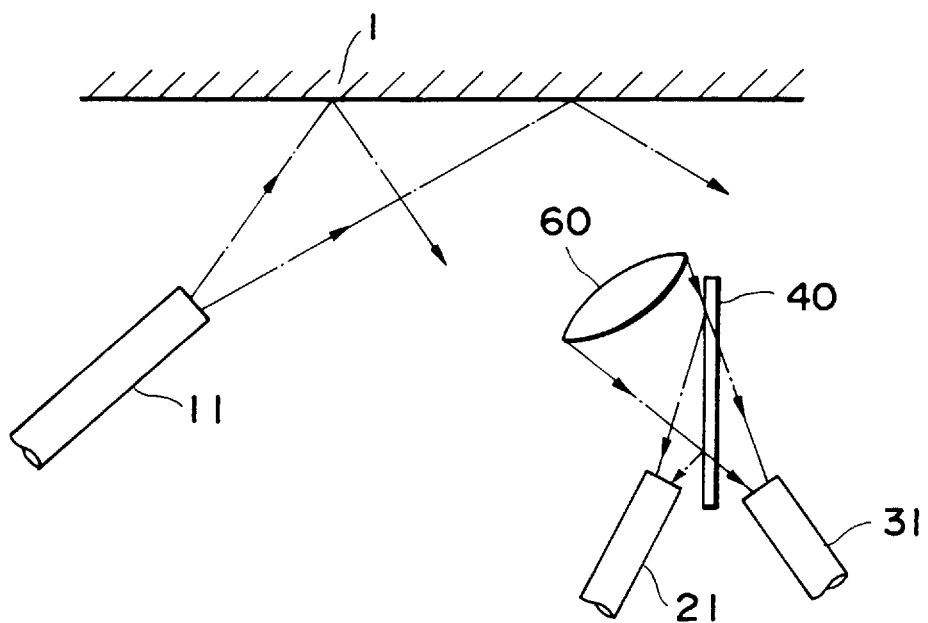
FIG. 64 shows an example of the arrangement of a reflective sensor head of oblique incidence type.

In the sensor head shown in FIG. 64, projected light emerges from the projecting optical filter 11 and is projected obliquely upon the object 1. The reflected light and transmitted light from the polarization beam splitter 40 is led to light-receiving elements via the optical fibers 21, 31 in the light-receiving optical system. This sensor head can be made more compact. A projecting lens may be provided to converge the projected light.

Figure 65:
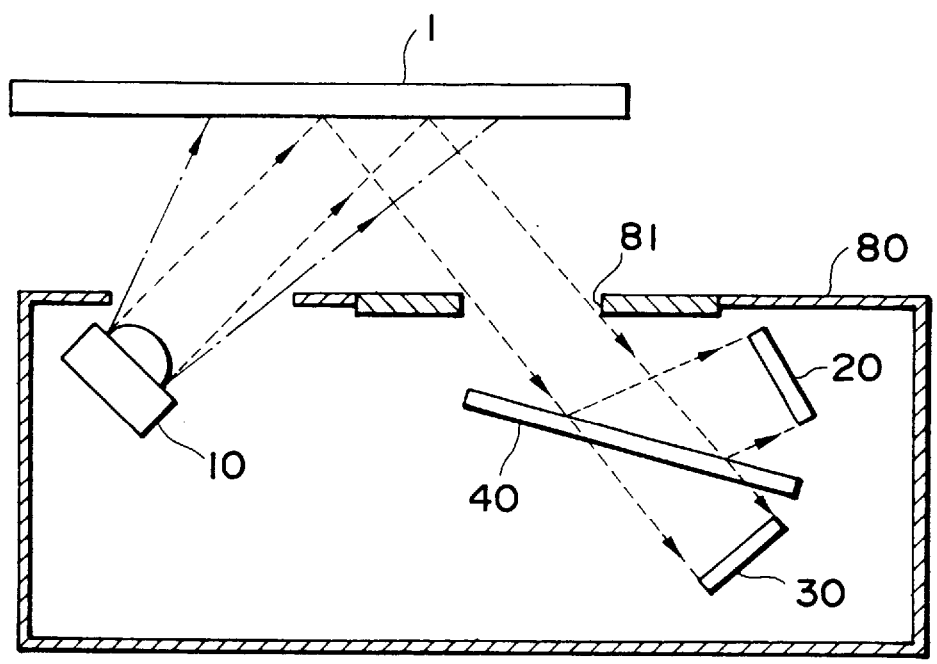
FIG. 65 shows an example of the arrangement of a reflective sensor head of oblique incidence type.

In FIG. 65, an opening 81 for limiting reflected light from the object 1 of interest is provided in a case 80 of the sensor head housing the light-projecting and light-receiving optical systems. The opening 81 is formed at a position and at a size which limits the incidence of scattered light and the like from the object 1 and causes regular reflected light to impinge mainly upon the polarization beam splitter 40 when the object is placed at the standard position. Further, the opening prevents some of the reflected light from the object 1 from impinging upon the light-receiving element 20 without being reflected by the polarization beam splitter 40 and prevents some of the reflected light from the object 1 from impinging upon the light-receiving 30 without passing through the polarization beam splitter 40. Discriminating among the above-mentioned plain paper, coated paper and glossy paper is very delicate. By virtue of the opening 81, regular reflected light from the object 1 can be introduced to the light-receiving elements efficiently via the polarization beam splitter and accurate discrimination can be carried out.

Figure 66:
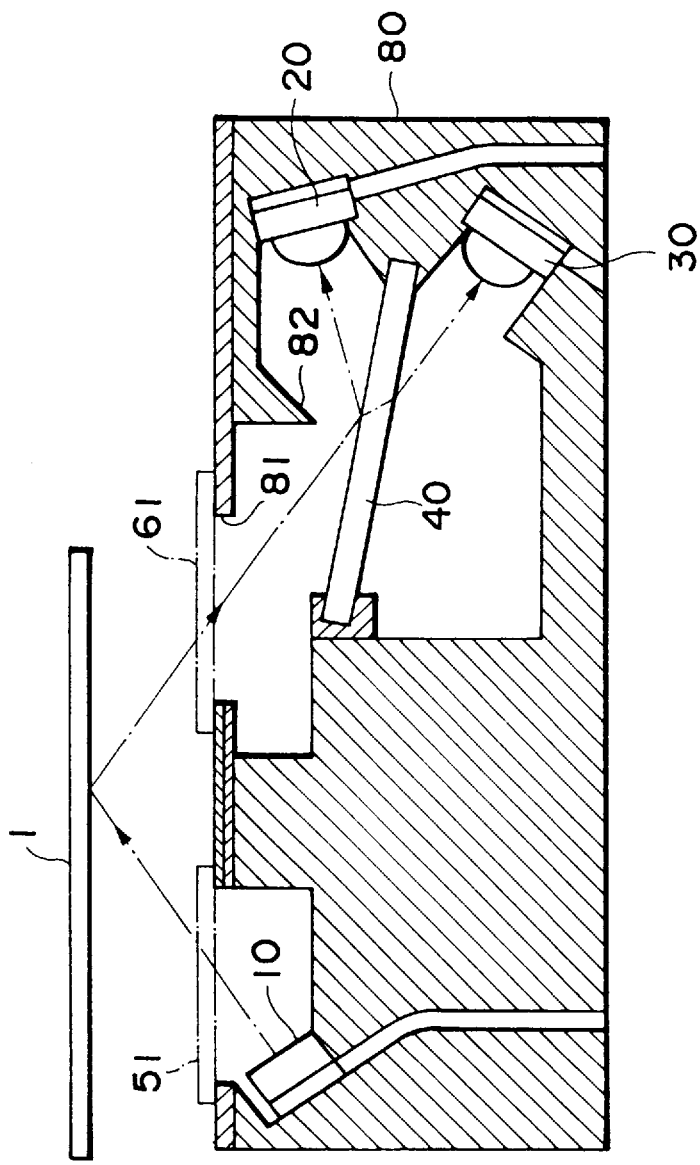
FIG. 66 shows an example of the arrangement of a reflective sensor head of oblique incidence type.

FIG. 66 illustrates the specific construction of the case 80. The case is provided not only with the opening 81 but also with a projection 82 for limiting the incidence of scattered light, etc.

If necessary, the polarization filter 51 is provided in front of the light-emitting diode 10. Further, an optical filter 61 which blocks visible light is attached to the opening 81 (in a case where the light-emitting diode 10 is one which emits infrared light).

As shown in FIGS. 65 and 66, the sensor head can be made small in size by placing the light-receiving element 20, which receives the reflected light from the polarization beam splitter 40, at a position at which it is closer to the opening 81 than is the other light-receiving element 30.

Figure 67A:
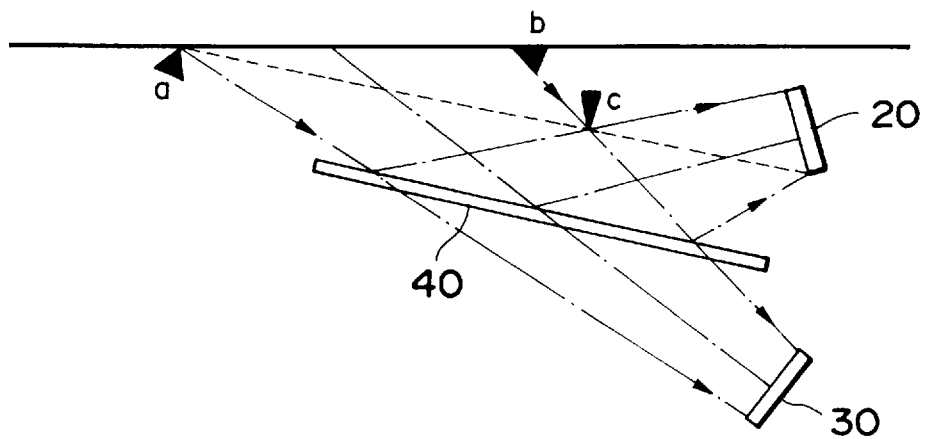
FIG. 67a illustrates the arrangement shown in FIG. 66.
Figure 67B:
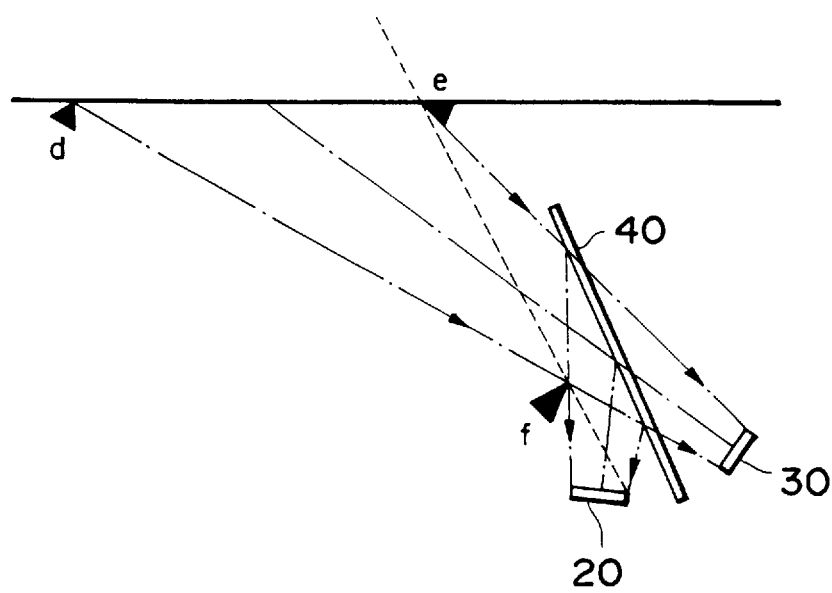
FIG. 67b illustrates an arrangement in which the positions of the light-receiving elements are reversed.

FIG. 67a illustrates the arrangement described above, and FIG. 67b shows an arrangement in which the positions of the light-receiving elements 20 and 30 are reversed. In order to introduce all of the regular reflected light and diffused light from the object of interest to the polarization beam splitter, it will suffice if the edge of the opening or part of the wall (the projection) of the case is situated at the positions a, b and c in FIG. 67a. In FIG. 67b, however, these positions must be the positions d, e and f. In a case where the visual fields of the light-receiving elements are identical in FIGS. 67a and 67b, an increase in the size of the case is unavoidable with the arrangement of FIG. 67b. In addition, there is a decline in utilization efficiency of light because the optical path is lengthened.

Figure 68A:
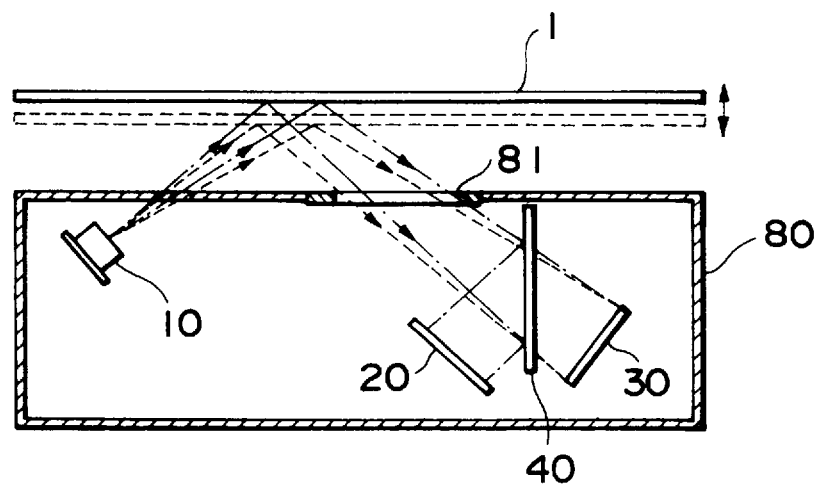
FIG. 68a illustrates the arrangement of a sensor head.
Figure 68B:
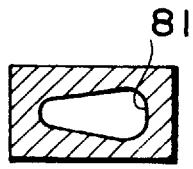
FIGS. 68b, 68c show the shapes of an opening.
Figure 68C:
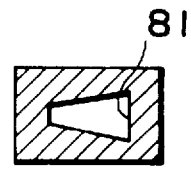

FIG. 68a illustrates the case 80 of the sensor head having the opening 81, and FIGS. 68b, 68c show shapes of the opening 81. More regular reflected light can be introduced by making the shape of the opening 81 substantially agree with the cross section of the beam of light regularly reflected by the object 1. Since the cross section of the regular reflected light is small when the object 1 draws near the sensor head (as indicated by the dashed line in FIG. 68a), the opening 81 should be made to conform to the smaller cross section.

Figure 69A:
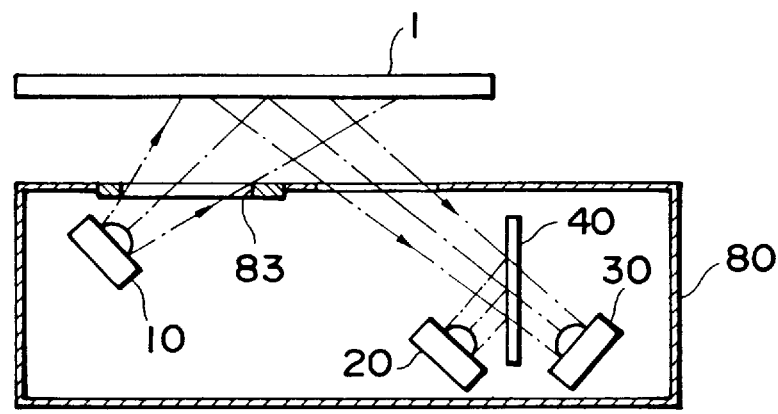
FIG. 69a illustrates the arrangement of a sensor head.
Figure 69B:
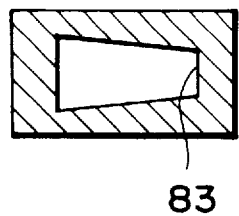
FIGS. 69b, 69c show the shapes of an opening.
Figure 69C:
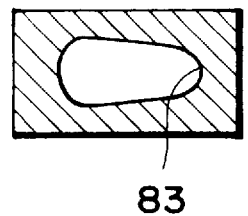

FIG. 69a illustrates the case 80 having an opening 83 of a specific shape at the exit of the projected light, and FIGS. 69b, 69c show shapes of the opening 83. Since the projected light is projected obliquely upward, the greater the distance from the light-emitting element 10, the more the light spreads. Accordingly, in order for the irradiation width of the light on the surface of the object 1 to be made substantially constant, the width of the opening 83 is reduced in proportion to the distance of the particular part of the opening from the light-emitting element 10.

Figure 70:
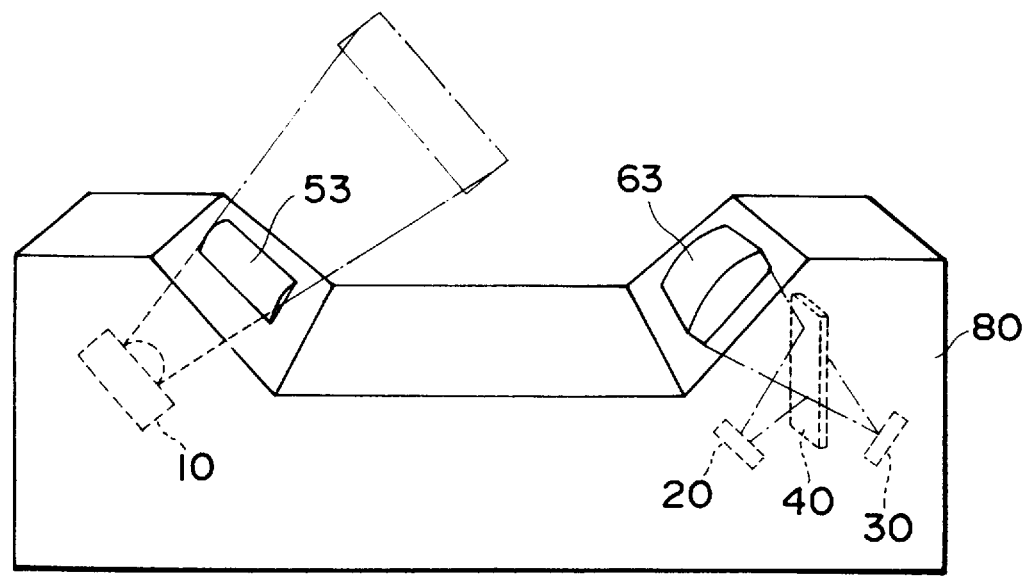
FIG. 70 shows an example of the arrangement of a reflective sensor head of oblique incidence type.

FIG. 70 illustrates the case 80 in which the exit for the projected light is provided with a cylindrical lens 53 that limits the width of the projected light, and in which a light-receiving port is provided with a cylindrical lens 63 that converges reflected light in the longitudinal direction in which the light has diverged.

Variations on the sensor head of vertical incidence type or of a type approximating it will be described next.

Figure 71:
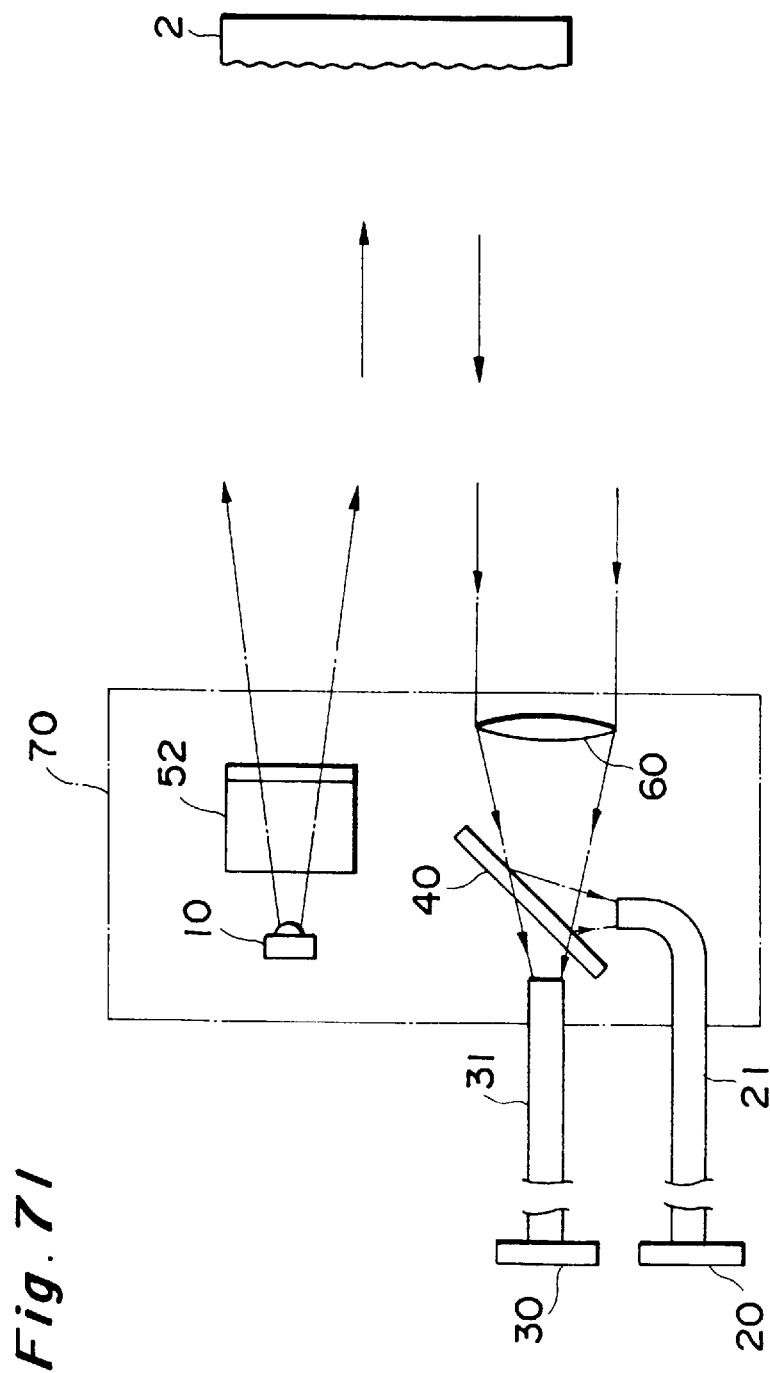
FIG. 71 shows an example of the arrangement of a reflective sensor head of vertical incidence type.

A sensor head 70 illustrated in FIG. 71 differs from the arrangement of FIG. 43 in that reflected light and transmitted light from the polarization beam splitter 40 is received by the optical fibers 21, 31, respectively, and introduced to the light-receiving elements 20, 30, respectively, in the light-receiving optical system. It is possible to make the sensor head 70 small in size. The light-emitting element 10 is equipped with a lens.

Figure 72:
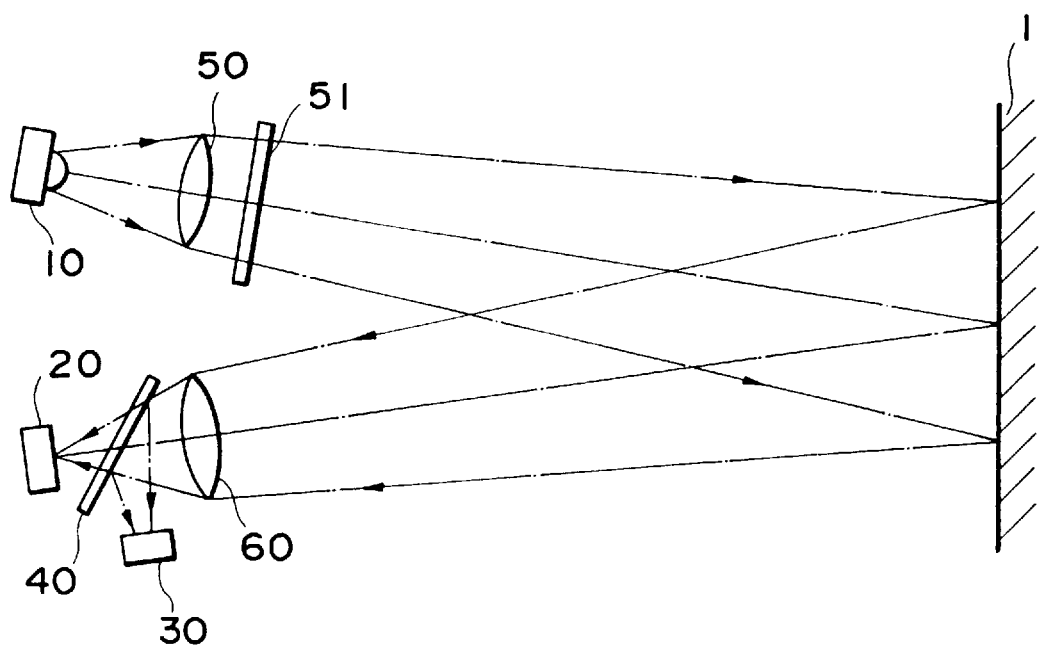
FIG. 72 shows an example of the arrangement of a reflective sensor head of vertical incidence type.

FIG. 72 illustrates an optical system constructed in such a manner that a greater amount of regular reflected light is received. The projected light spreads somewhat owing to the lens 50 and is projected upon the object 1 at an angle close to the vertical. The regular reflected light from the object 1 is converged by the light-receiving lens 60. The polarization filter 51 which passes the s-polarized light components is provided in front of the projecting lens 50. The degree of glossiness of the surface of object 1 is sensed on the basis of the quantity of s-polarized light components contained in the regular reflected light from the object 1.

Figure 73:
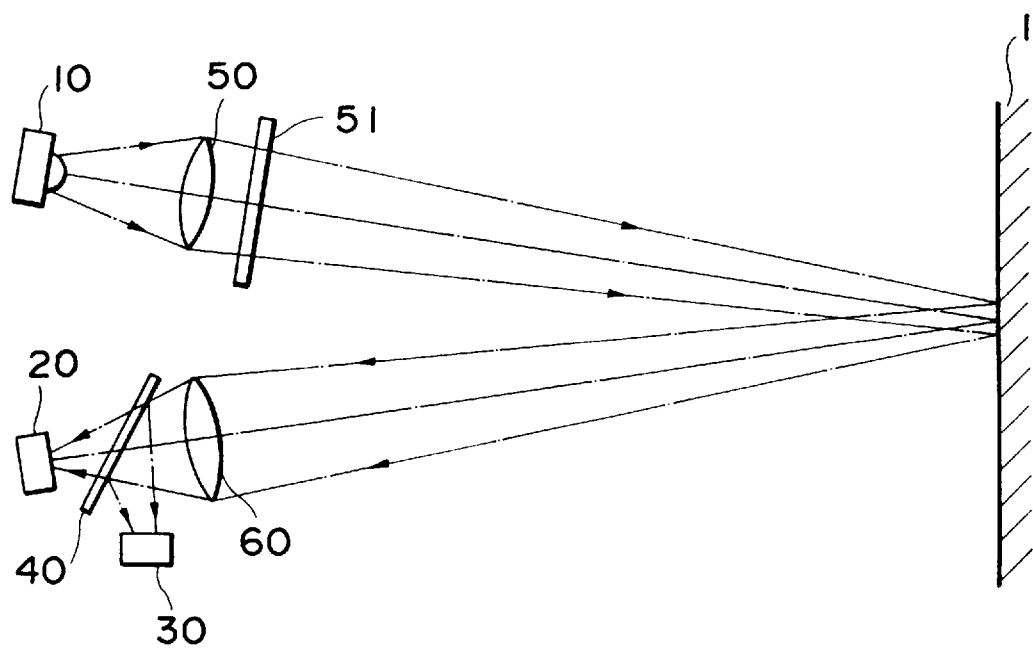
FIG. 73 shows an example of the arrangement of a reflective sensor head of vertical incidence type.

FIG. 73 illustrates an optical system in which projected light is converged by the projecting lens 50 before being projected upon the object 1.

Figure 74:
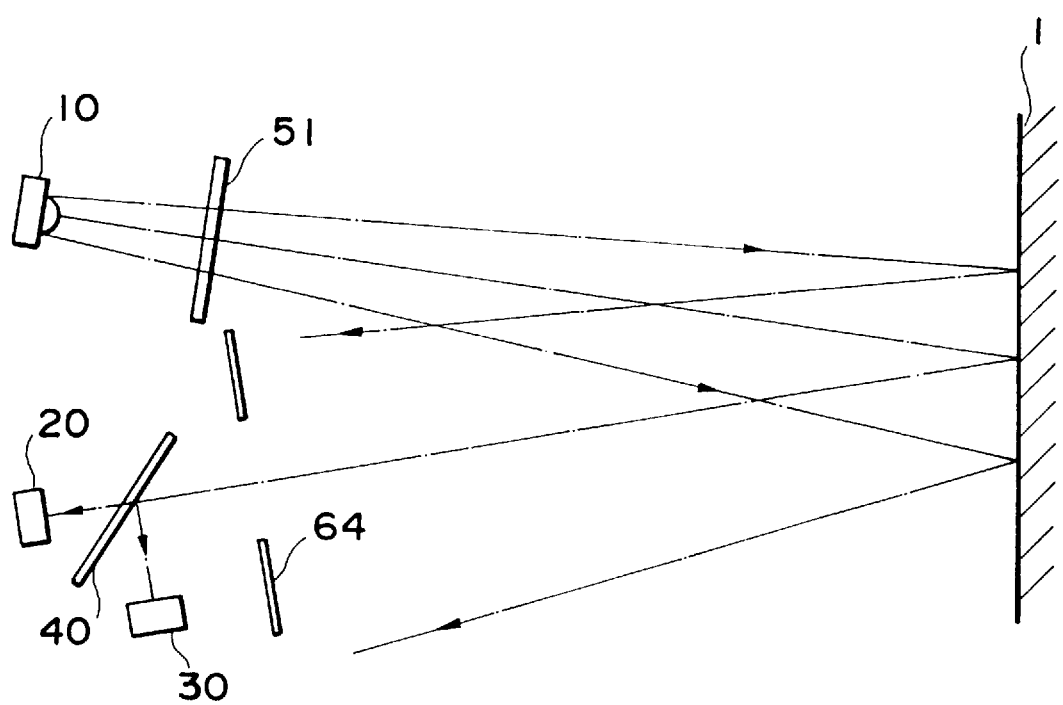
FIG. 74 shows an example of the arrangement of a reflective sensor head of vertical incidence type.

In FIG. 74, the projecting lens is not provided. The light-receiving optical system is provided with an aperture plate or slit 64 for introducing regular reflected light from the object 1. The regular reflected light that has passed through the aperture impinges upon the polarization beam splitter 40. A light-receiving lens also is not provided.

Figure 75:
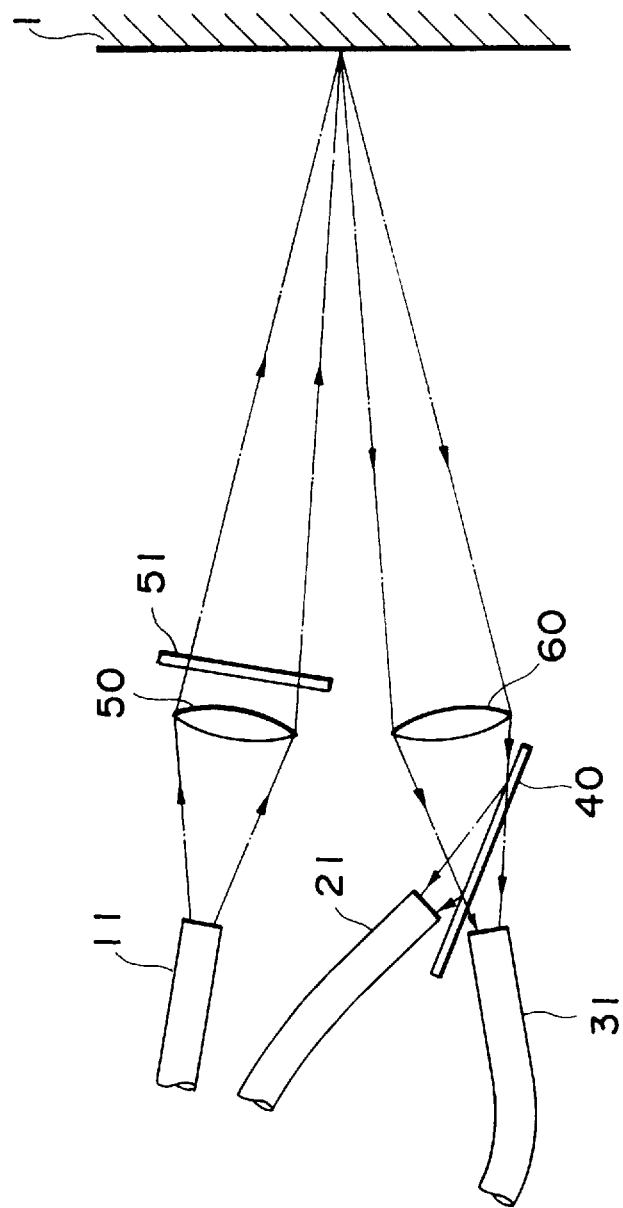
FIG. 75 shows an example of the arrangement of a reflective sensor head of vertical incidence type.

FIG. 75 illustrates an optical system using the optical fibers 11, 21 and 31. The projected light is converged by the projecting lens 50. The light-receiving lens 60 also is provided.

Figure 76:
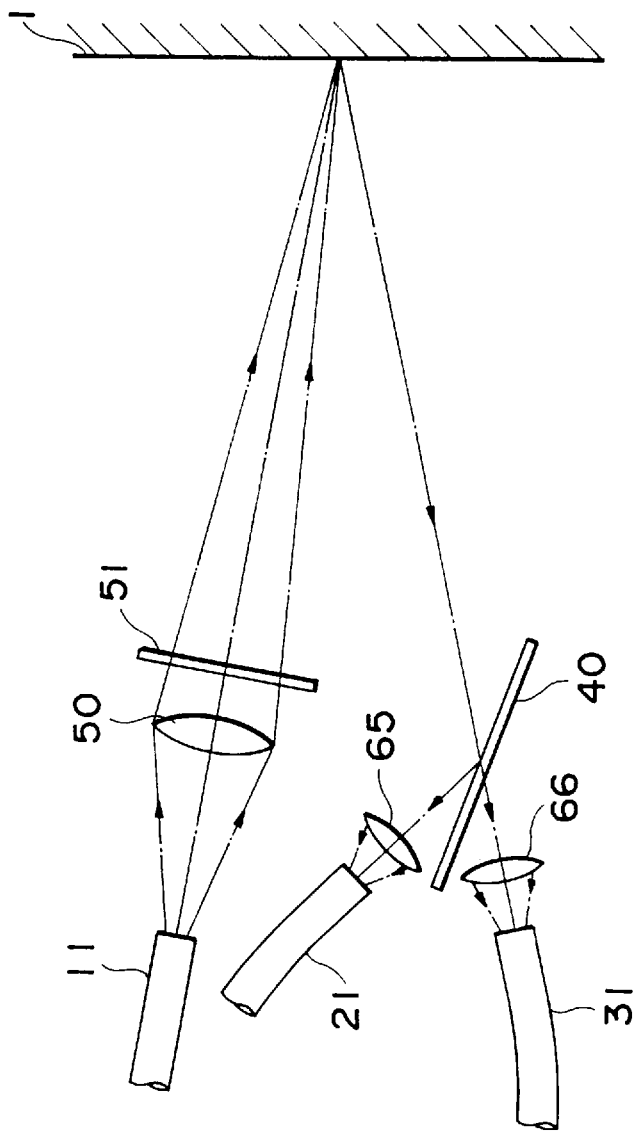
FIG. 76 shows an example of the arrangement of a reflective sensor head of vertical incidence type.

FIG. 76 illustrates an arrangement in which light-receiving lenses 65, 66 are provided with regard to the light-receiving optical fibers 21 and 31, respectively. Reflected light and transmitted light from the polarization beam splitter 40 impinges upon the optical fibers 21, 31 through the light-receiving lenses 65, 66, respectively.

Figure 77:
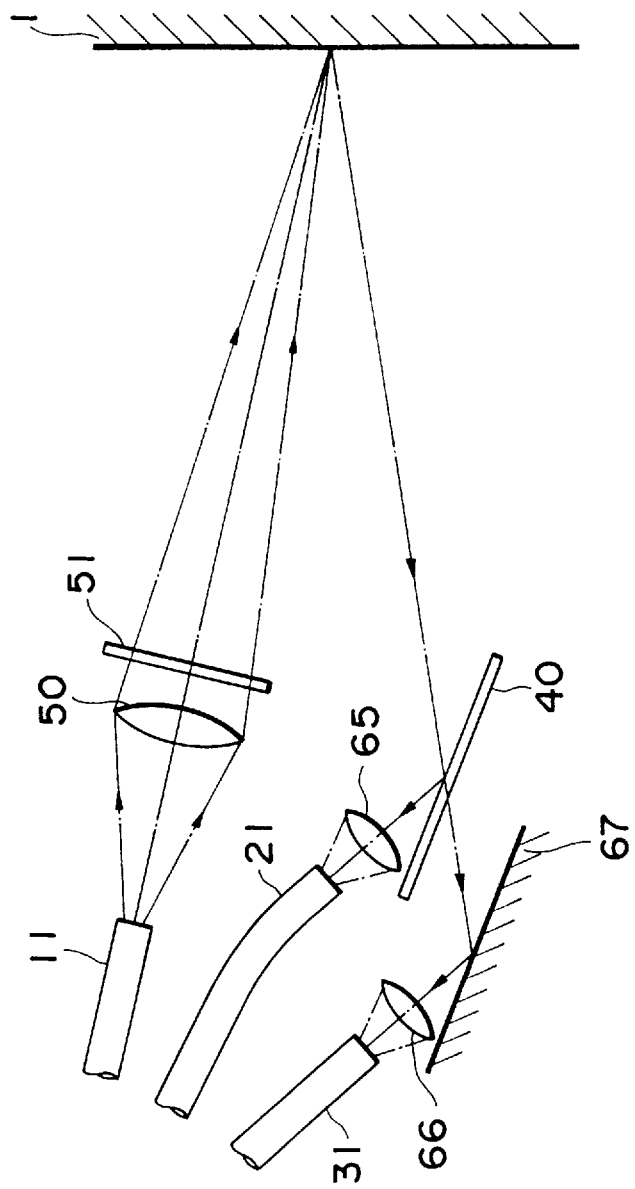
FIG. 77 shows an example of the arrangement of a reflective sensor head of vertical incidence type.

FIG. 77 illustrates an arrangement so adapted that transmitted light from the polarization beam splitter 40 is reflected by a mirror 67 and then introduced to the optical fiber 31 through the lens 66.

Figure 78:
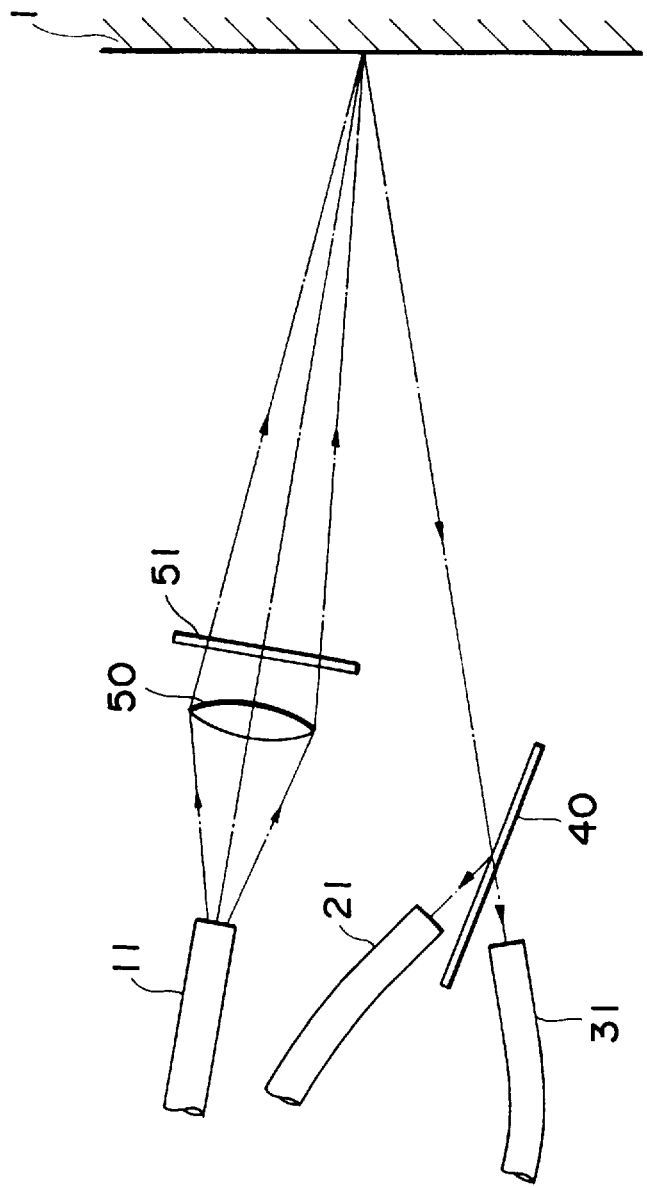
FIG. 78 shows an example of the arrangement of a reflective sensor head of vertical incidence type.

FIG. 78 illustrates a light-receiving optical system of optical fiber type in which no light-receiving lens is provided.

A transmissive sensor head will now be described.

Figure 79:
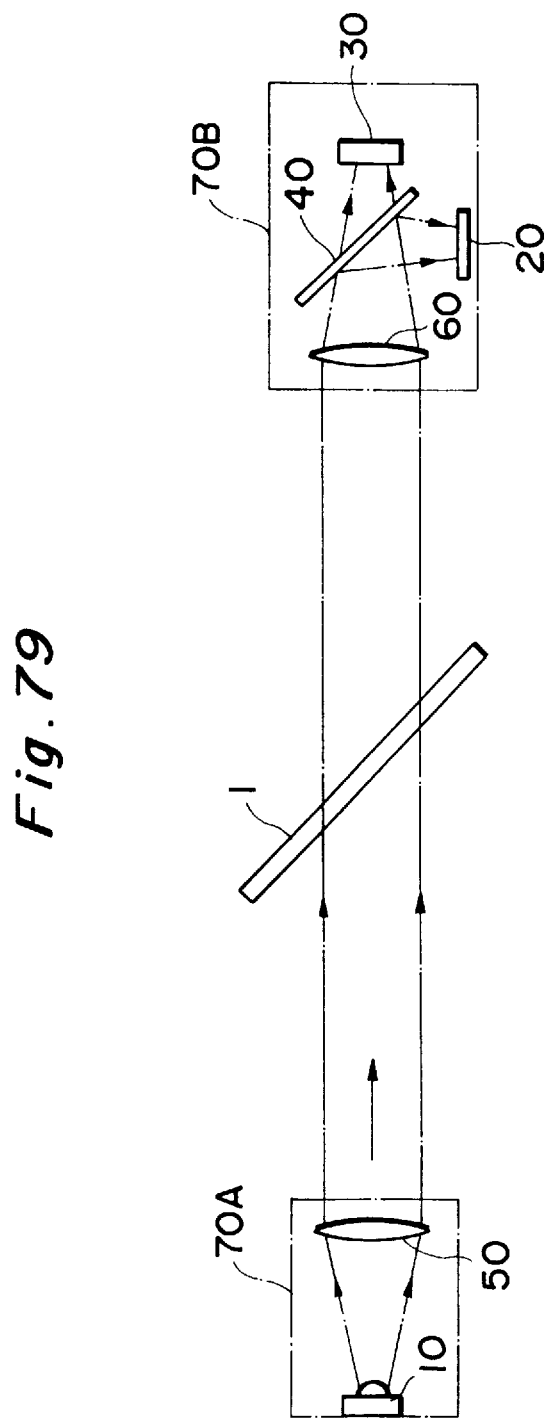
FIG. 79 shows an example of the arrangement of a transmissive sensor head.

As shown in FIG. 79, a transmissive sensor head is constituted by a light-projecting head 70A and a light-receiving 70B. The heads 70A, 70B are arranged so as to oppose each other across a certain distance. The object 1 situated between the heads 70A and 70B is sensed.

The light-projecting head 70A is provided with the light-emitting element 10 and projecting lens 50. Projected light is collimated by the projecting lens 50 and then projected toward the light-receiving head 70B. The projected light may be slightly diverged or converged by the projecting lens 50.

The light-receiving head 70B includes the light-receiving lens 60, the polarization beam splitter 40 and the two light-receiving elements 20, 30 and has a construction identical with that of the above-described light-receiving optical system.

In the arrangement shown in FIG. 79, a transparent body 1 present on the optic axis of the projected light and inclined with respect thereto is sensed. As mentioned above, the transparent body is such that transmittance of p-polarized light components is greater than transmittance of s-polarized light components with regard to light incident obliquely. Accordingly, the ratio S/P (or P/S or (P−S)/(P+S), P−kS., P−S, etc.) of the outputs of the light-receiving elements 20 and 30, is calculated and this ratio is compared with a threshold value, thereby determining whether the object is a transparent body or not.

Figure 80:
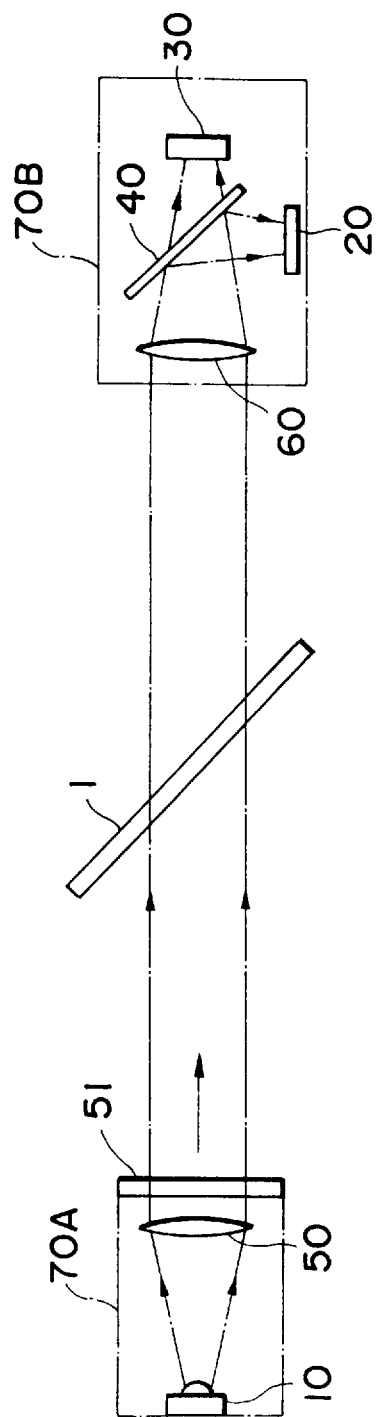
FIG. 80 shows an example of the arrangement of a transmissive sensor head.
Figure 81:
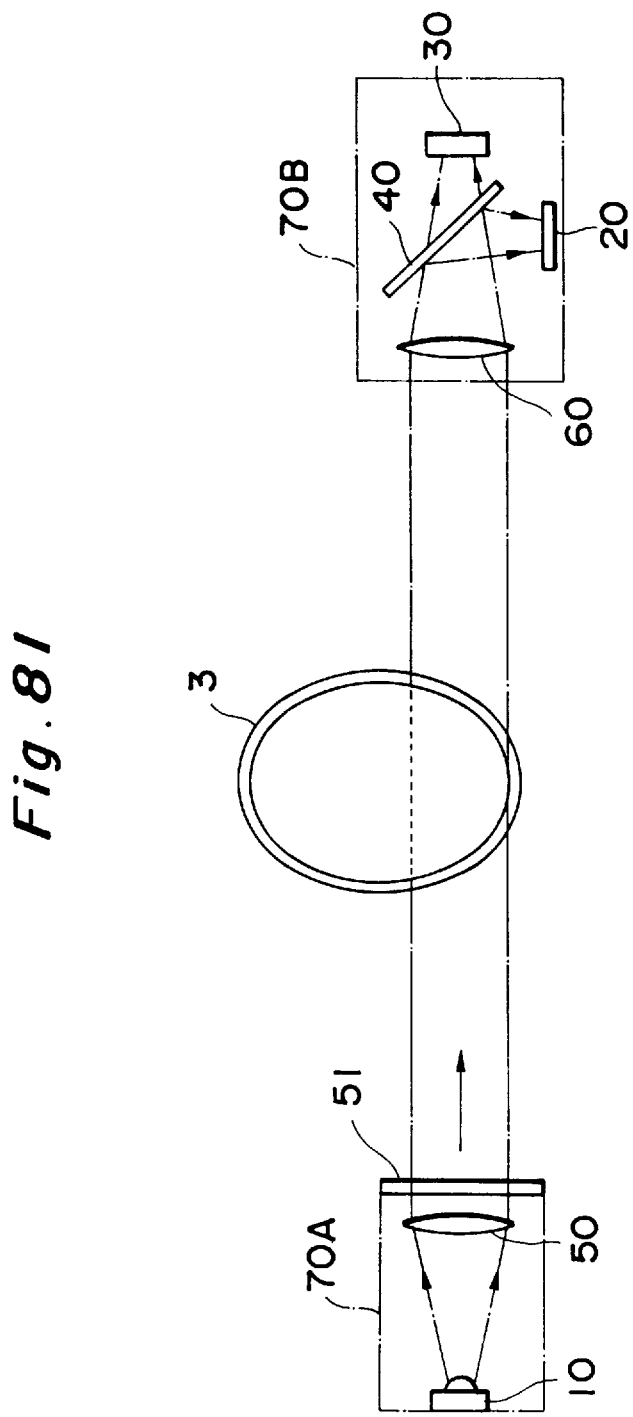
FIG. 81 shows an example of the arrangement of a transmissive sensor head.

In FIG. 80, the polarization filter 51 is provided in front of the light-projecting head 70A. The polarization filter 51 passes light composed of the p-polarized light component (or s-polarized light component) defined in the polarization beam splitter 40 of the light-receiving head 70B. When linearly polarized projected light is thus used, an object exhibiting birefringence can be sensed in the manner described, especially in a reflective-type sensor head. For example, a plastic bottle 3 having birefringence can be sensed, as shown in FIG. 81.

FIG. 82 illustrates a projecting head which generates linearly polarized light using the polarization beam splitter 52 instead of the polarization filter. Linearly polarized projected light is also used in order to sense an object which scatters light (such as rain, water, mist, snow and other particles, a transparent body having a rough surface, etc.). The projected light may be allowed to spread slightly, or this may be preferred, as shown in FIG. 82.

Scattered light from an object which scatters light is randomly polarized light. Accordingly, when s- or p-polarized projected light is used, a polarized-light component in a direction perpendicular to the polarized projected light will appear if a scattering object is present. Hence, by calculating the difference between the output signals of the two light-emitting elements 20, 30, or by taking the ratio between them or applying some other operation [the aforementioned operation (S−P)/(S+P), etc.] and then comparing the result of the operation with a threshold value, the presence of the scattering body can be sensed.

Figure 83:
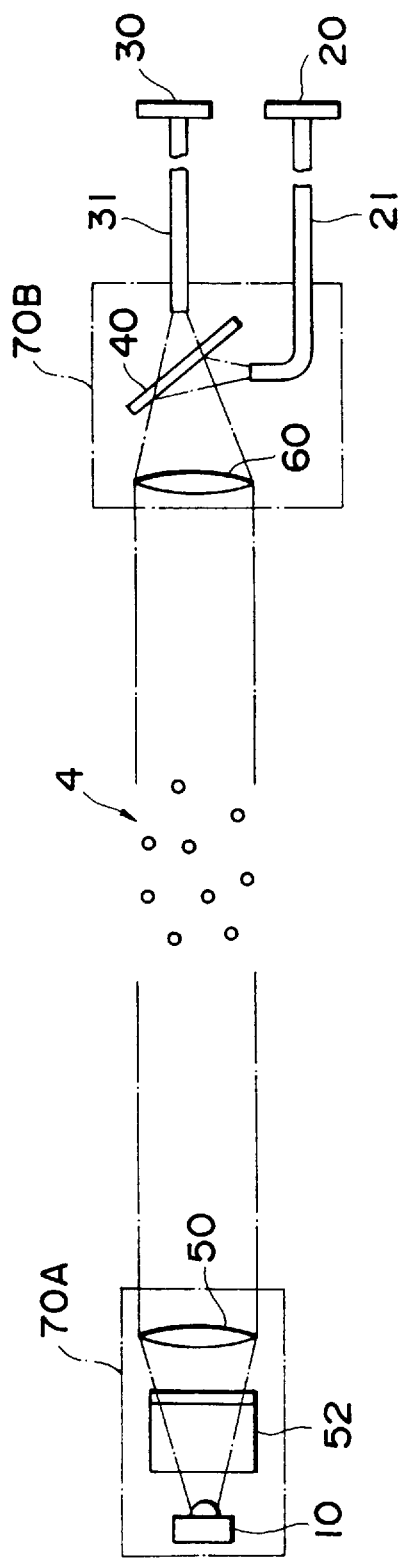
FIG. 83 shows an example of the arrangement of a transmissive sensor head.

FIG. 83 illustrates an arrangement in which the reflected light and transmitted light from the polarization beam splitter is introduced to the light-receiving elements 20, 30 using the optical fibers 21, 31, respectively, in the light-receiving head 70B.

Figure 84A:
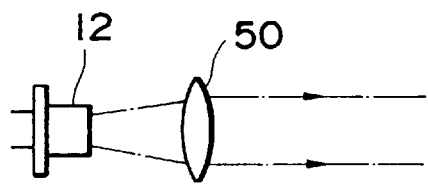
FIGS. 84a, 84b show further examples of light-projecting optical systems.
Figure 84B:
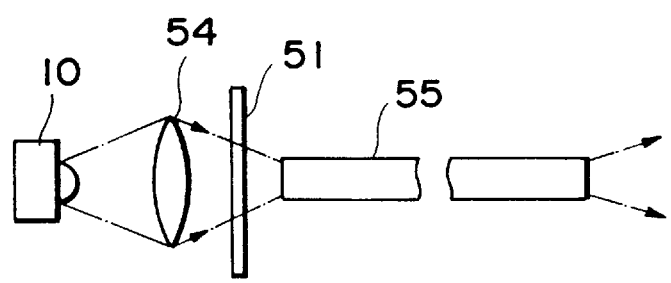

FIGS. 84a, 84b illustrate other examples of the light-projecting optical system.

In FIG. 84a, a laser diode (semiconductor laser) 12 is used as the light-emitting element. Since the light which exits from the laser diode is linearly polarized light, use of a polarization filter is unnecessary. In addition, since the light reaches far into the distance, this arrangement is effective for use performing detection over long distances.

In FIG. 84b, the arrangement is such that light emerging from the light-emitting diode 10 is converged by a lens 54, passes through the polarization filter 51, impinges upon one end of an optical fiber 55 that preserves the plane of polarization and emerges from the other end of the optical fiber 55 to be projected as linearly polarized light.

FIGS. 85a through 85e show further examples of light-receiving optical systems.

Figure 85A:
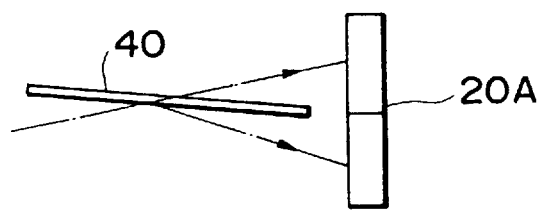
FIGS. 85a, 85b, 85c, 85d, 85e show further examples of light-receiving optical systems.

In FIG. 85a, a split photodiode 20A is used instead of the two light-receiving elements 20, 30.

Figure 85B:
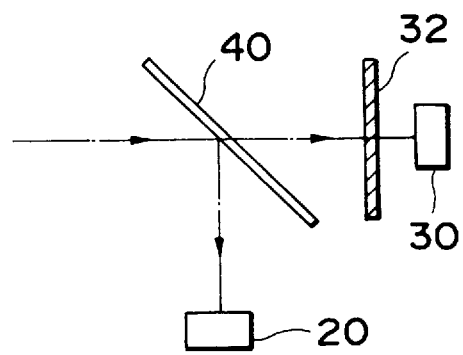

FIG. 85b illustrates an arrangement wherein a polarization filter 32 which passes the p-polarized light component is placed between the polarization beam splitter 40 and the light-receiving element 30. By eliminating the s-polarized light component in transmitted light from the polarization beam splitter 40 containing this component, the polarized light separating characteristic can be improved.

Figure 85C:
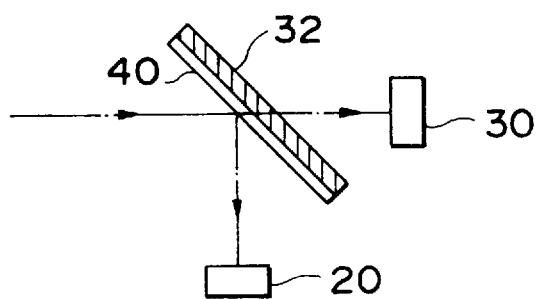

FIG. 85c illustrates an arrangement in which the polarization beam splitter 40 and polarization filter 32 are bonded together to integrate them.

Figure 85D:
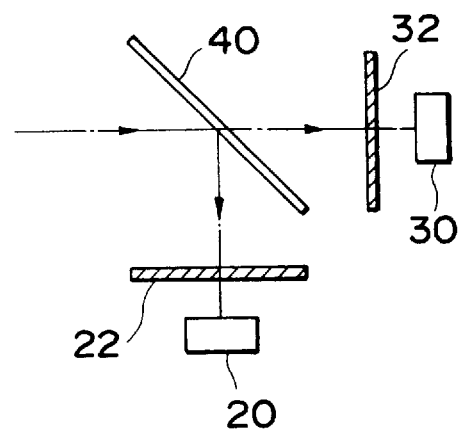

FIG. 85d depicts an arrangement wherein the polarization filter 22 which passes the s-polarized light component is arranged between the polarization beam splitter 40 and the light-receiving element 20. This arrangement is useful in a case where the reflected light from the polarization beam splitter 40 contains p-polarized light components.

Figure 85E:
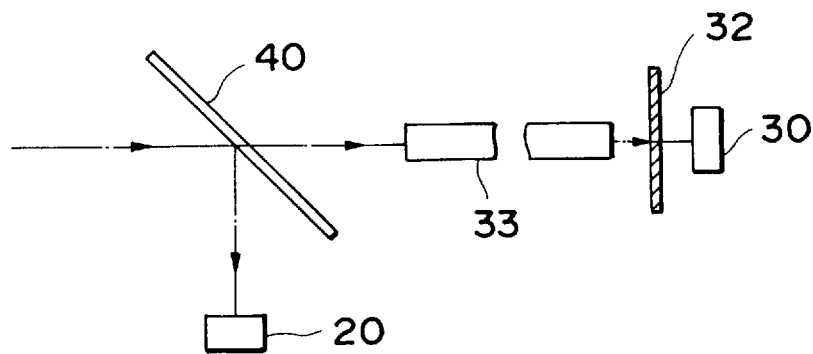

FIG. 85e depicts an arrangement wherein transmitted light from the polarization beam splitter 40 is introduced to the light-receiving element 30 by an optical fiber 33 which preserves the plane of polarization. If desired, the reflected light from the polarization beam splitter 40 may be introduced to the light-receiving element 20 by an optical fiber which preserves the plane of polarization.

Further examples of the light-receiving optical system will be described.

Figure 86:
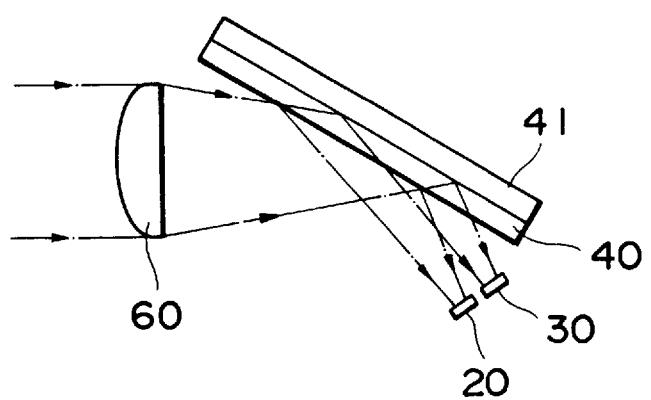
FIG. 86 illustrates a further example of a light-receiving optical system.

In FIG. 86, a reflector 41 is bonded to the back side of the polarization beam splitter 40. The reflector 41 is implemented by utilizing a mirror surface, multiple layers of films and total reflection.

Some of the light impinging upon the polarization beam splitter 40 while being converged by the light-receiving lens 60 is reflected so as to impinge upon the light-receiving element 20, and some of the light is transmitted so as to be reflected by the reflector 41 to impinge upon the light-receiving element 30. The two light-receiving elements 20, 30 can be placed at substantially identical positions in front of the polarization beam splitter 40.

Figure 87A:
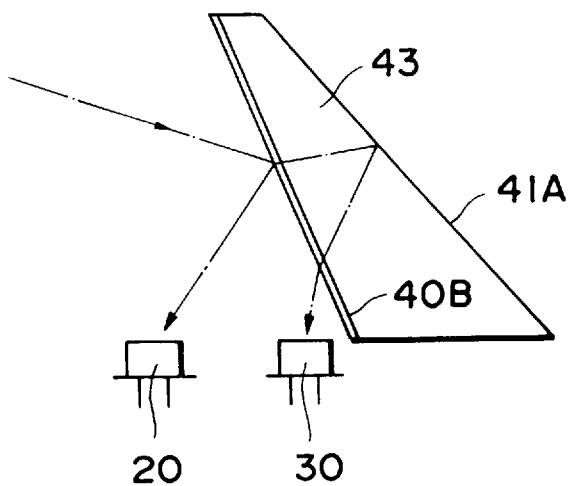
FIGS. 87a, 87b show further examples of light-receiving optical systems.
Figure 87B:
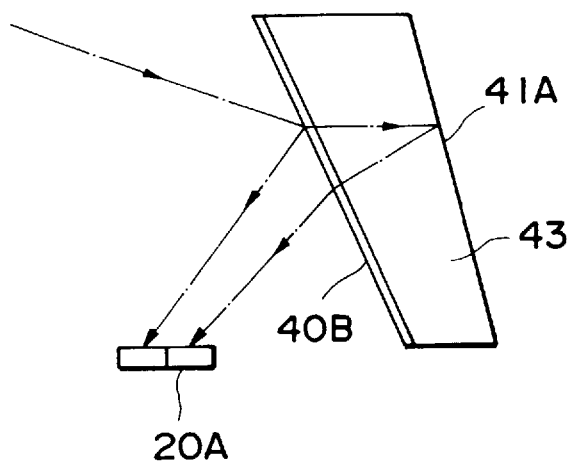

FIGS. 87a and 87b illustrate arrangements which utilize a wedge-shaped transparent substrate. Multilayered films 40B of a dielectric having a polarizing-light separating function are formed on one surface of the wedge-shaped substrate 43, and a reflecting surface 41A is formed on the other surface of the substrate. In FIG. 87a, the two light-receiving elements 20 and 30 can be spaced apart. In FIG. 87b, a split photodiode is used instead of the two light-receiving elements 20 and 30.

Figure 88A:
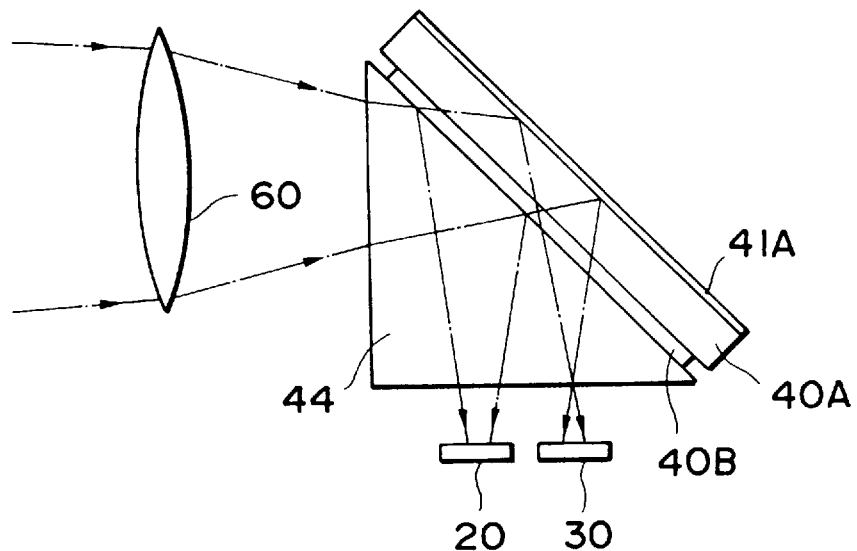
FIGS. 88a, 88b show further examples of light-receiving optical systems.
Figure 88B:
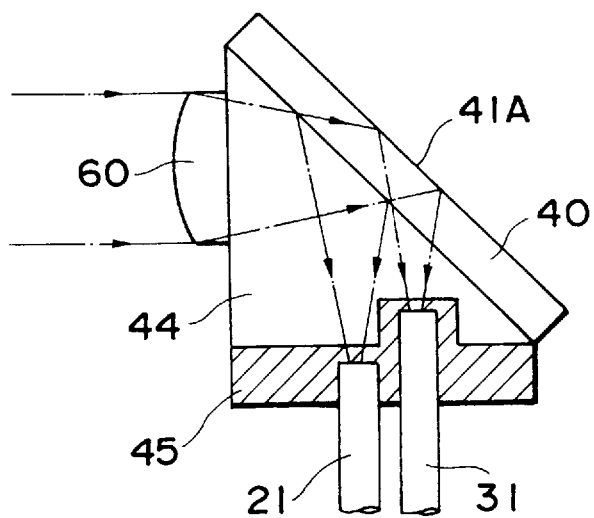

FIGS. 88a and 88b illustrate arrangements which utilize a prism. In FIG. 88a, a substrate 40A has multilayered films 40B of a dielectric exhibiting a polarizing-light separating function formed on one surface, and a reflecting film 41A formed on its other surface. The substrate 40A is bonded to an oblique surface of a prism 44. In FIG. 88b, the light-receiving lens 60 also bonded to the prism 44. Further, the arrangement is such that reflected light and transmitted light is led to the light-receiving elements using the optical fibers 21, 31.

In particular, in a sensor head of the oblique incidence type, projected light having a substantially circular cross section impinges obliquely upon the object to be sensed, the light is reflected obliquely and impinges upon the light-receiving optical system. In a case where the projected light is diverging or converging, the intensity of the light, which impinges upon the light-receiving element via the polarization beam splitter, per unit surface area fluctuates when the distance between the sensor head and the object varies. An arrangement will be described in which a correction is applied to a fluctuation in quantity of reflected light resulting from such a fluctuation in the distance to the object of interest.

In FIG. 89a, the angle of reflected light which impinges upon the light-receiving optical fiber 21 or 31 varies when the object 1 departs from or approaches the sensor head. (In FIG. 89a, as well as in FIGS. 89b and 89c explained next, the polarization beam splitter is deleted from the drawings for the sake of simplification). Here the optical fiber 21 or 31 is placed to conform to the angle of incidence of the reflected light in which the quantity of light is small, and it is so arranged that the reflected light which impinges upon the end face of the optical fiber 21 or 31 the most is the reflected light in which the quantity of light is small.

FIG. 89b shows a case in which the light-entrant end face of the light-receiving optical fiber 21 or 31 is cut off at an angle. In this case also the optical fibers 21, 31 are so arranged that the cut end face is directed toward the reflected light in which the quantity of light is small.

FIG. 89c illustrates an example in which a fiber bundle is used. The covering of the fiber bundle is deformed to obtain a shape in which the number of optical fibers is enlarged at a location where reflected light exhibiting a small quantity of light impinges.

Figure 90A:
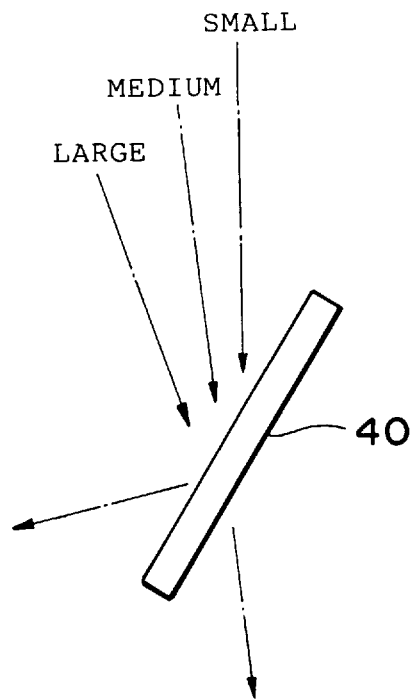
FIG. 90a illustrates an example of an arrangement in which the quantity of incident light is held constant irrespective of a fluctuation in the distance of an object to be sensed.
Figure 90B:
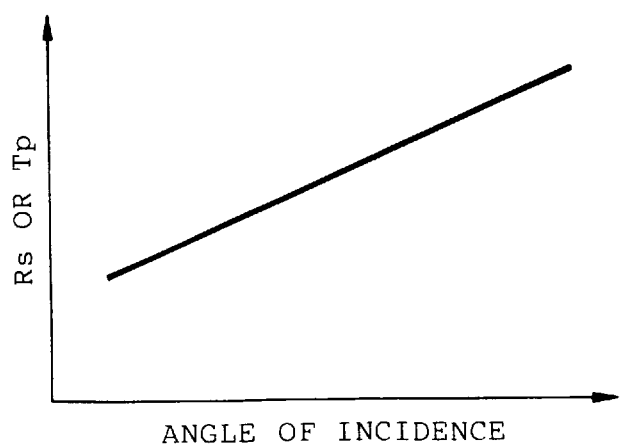
FIG. 90b is a graph showing a change in $R_s$ or $T_p$ with respect to a change in angle of incidence.

In FIG. 90a arrangement is such that the transmittance $T_p$ or reflectivity $R_s$ of the polarization beam splitter is varied in dependence upon the angle of incidence, as shown in FIG. 90b, with the transmittance $T_p$ or reflectivity $R_s$ being enlarged at the angle of incidence of the reflected light in which the quantity of light is small.

FIG. 91 illustrates an example in a transmissive-type optical sensing device. Here the projecting lens 50 is provided with aberration so that the distribution of light intensity will be rendered substantially uniform at the position of the light-receiving head.

Figure 92A:
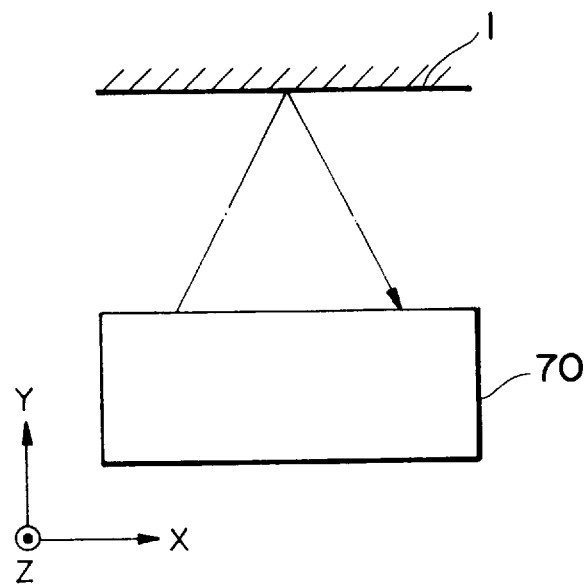
FIGS. 92a and 92b are front and plan views, respectively, showing an example of an arrangement in which the quantity of incident light is held constant irrespective of a fluctuation in the distance of an object to be sensed.
Figure 92B:
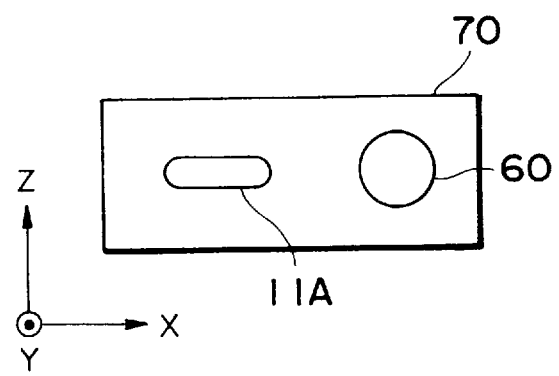
Figure 92C:
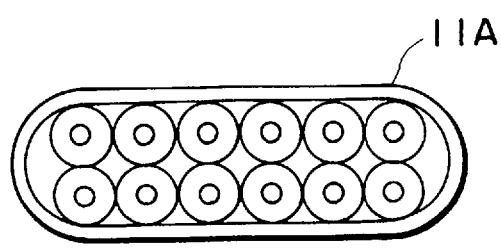
FIG. 92c is an enlarged view of a fiber bundle in this arrangement.

In FIGS. 92a, 92b and 92c, a fiber bundle 11A whose cross section is elongated in a direction in which projected light is obliquely incident is used as the light-projecting optical fibers.

FIG. 93 illustrates an example in which a light control film (LCF) 68 is placed at the front of the light-receiving optical system. The transmittance of the light control film 68 differs depending upon the angle of incidence. The light control film 68 used has a louver angle of 0°. The film 68 is so arranged that reflected light (in which the quantity of light is smallest) from the object (indicated by the phantom lines) 1 at a position of maximum detection distance will impinge upon the film 68 at angle of incidence of 0°.

(4) Applications of the optical sensor device

The above-described optical sensor devices are applicable in a wide variety of fields. Typical examples of apparatus utilizing optical sensor devices will be described.

FIGS. 94a through 95b illustrate arrangements in which the presence of plain paper is sensed or the type of paper (plain paper, coated paper, glossy paper, etc., mentioned above) is discriminated.

Figure 94A:
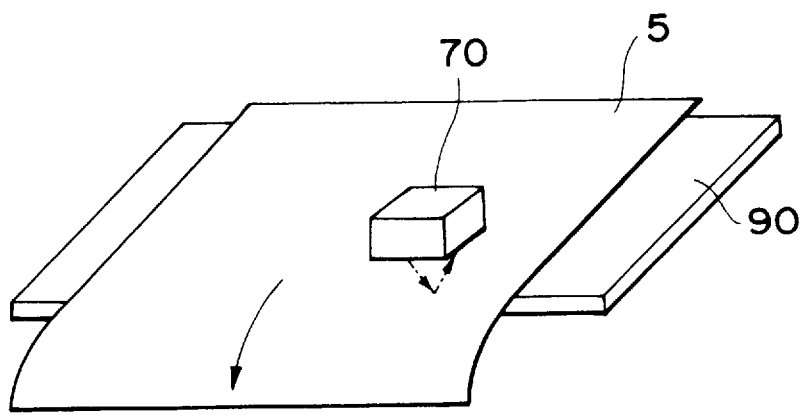
FIGS. 94a, 94b are perspective views showing examples of applications regarding discrimination of paper.

In FIG. 94a, paper 5 is fed on a base 90. The reflective sensor head 70 of oblique incidence type is situated above the base 90 and projects light downwardly.

The base 90 is a reflector (metal), by way of example. The projected light used in the sensor head 70 is linearly polarized light (e.g., s- or p-polarized light). Since a reflector preserves the plane of polarizing of light incident thereon, the light reflected by the reflector also possesses linearly polarized light identical with that of the projected light. If the paper 5 is plain paper, incident light is diffused and therefore reflected light approximates randomly polarized light. Further, scattered light is present if the paper 5 is coated paper or glossy paper. Accordingly, components whose directions of polarization perpendicularly intersect the direction of polarization of the projected light appear and the amount of these components vary depending upon the type of paper. This makes it possible to judge whether paper is present.

Figure 94B:
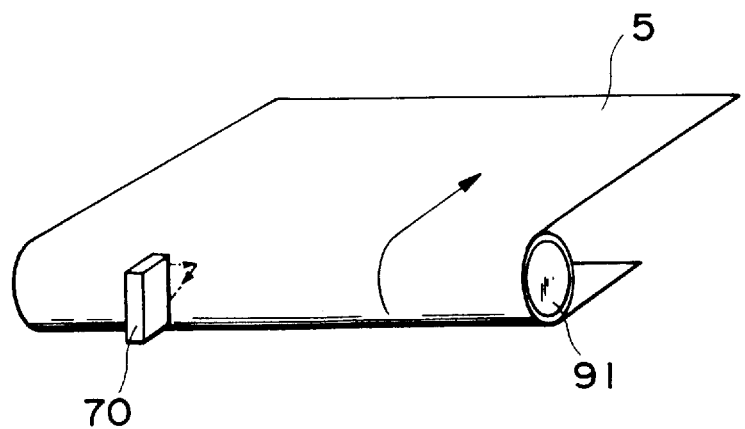

FIG. 94b illustrates an example in which the sensor head 70 is provided at a point along the return conveyance path of the paper 5. Here a cylindrical roller 91 for return conveyance also possesses a mirror surface.

Figure 95A:
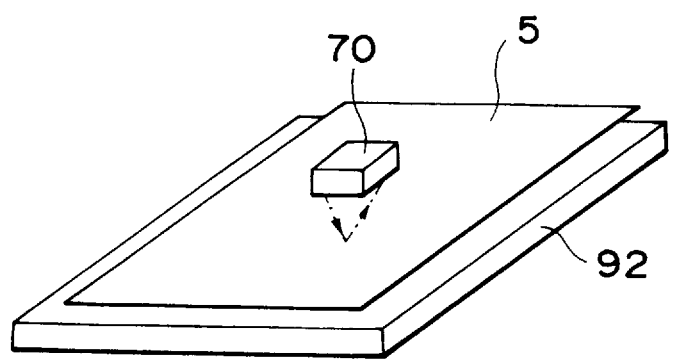
FIGS. 95a, 95b are perspective views showing examples of applications regarding discrimination of paper.

FIG. 95a illustrates a case in which the paper 5 is placed upon a base 92 comprising a dielectric. Projected light from the sensor head 70 possesses randomly polarized light. When randomly polarized light impinges upon a dielectric, the light reflected from the dielectric contains many s-polarized light components. On the other hand, in light reflected from the paper (plain paper) 5, the s- and p-polarized light components are approximately equal. Accordingly, it is possible to discriminate the presence of the paper 5 and, in some cases, the type thereof as well (which depends upon the proportion of s-polarized light components contained in the reflected light).

Figure 95B:
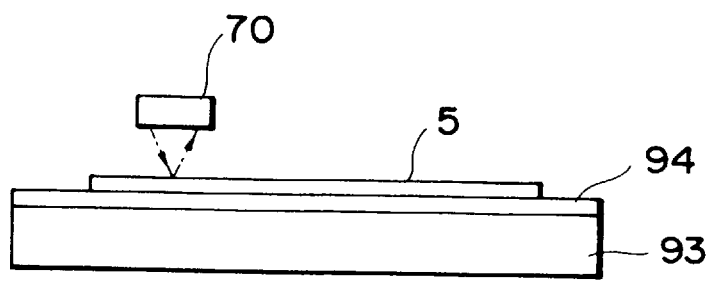

In FIG. 95b, a layer 94 of paint is applied to the surface of a base (of metal, for example) 93. The reflectivity of the s-polarized light component is higher than that of the p-polarized light component in the paint layer 94 as well.

Figure 96:
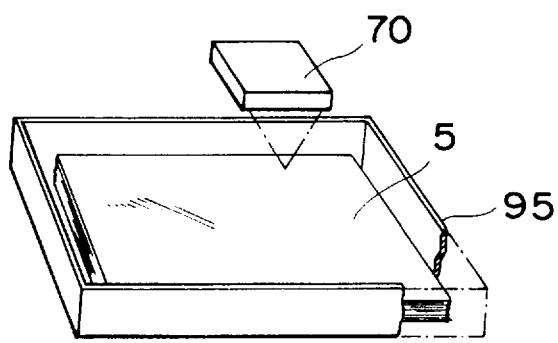
FIG. 96 is a perspective view showing an example of an application regarding discrimination of paper.

FIG. 96 shows an arrangement for sensing the presence and type of paper 5 contained in a tray 95. The detection principle is the same as that described above.

This arrangement is utilized in a printing machine of a printer or copier (or of a word processor, plotter, facsimile machine, recorder, etc.) to sense whether the printing medium 5 stored in the paper tray 95 is paper or OHP film (i.e., whether the printing medium is a transparent body or an opaque substance) or to sense the type of paper (plain paper, thermosensitive paper or coated paper).

The sensor head 70 is placed above the paper tray 95 to discriminate the printing medium and output the results of discrimination to a printing control unit (not shown). In dependence upon the results of discrimination, the printing control unit adjusts and sets mechanical parameters relating to the conveyance path and parameters such as the printing method and printing density when printing processing is executed.

It is possible to adopt a configuration in which the sensor head 70 is placed in a paper manual-feed section or in the conveyance path to discriminate the printing medium so that the adjustment and setting of the aforementioned parameters may be carried out.

Figure 97:
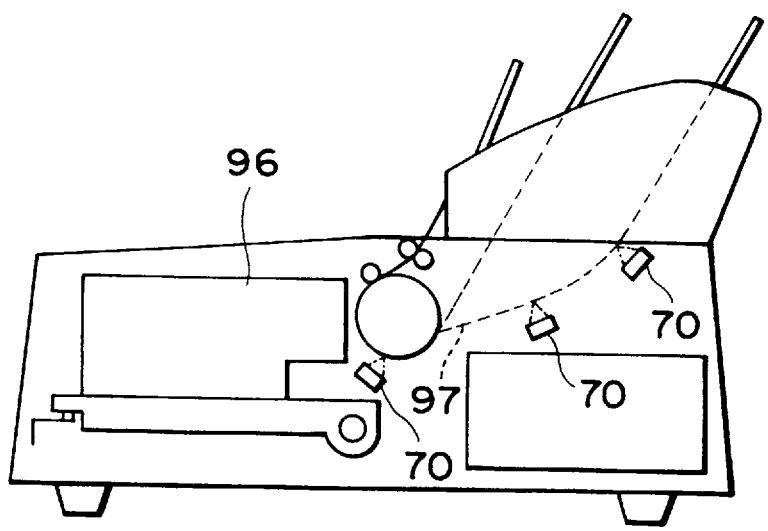
FIG. 97 is a structural view showing an example of application to a printing apparatus.

FIG. 97 shows the printing apparatus of a word processor having a printing head 96 of the dot-pin type. The sensor head 70 is provided in the paper-feed section or conveyance path, etc.

Figure 98:
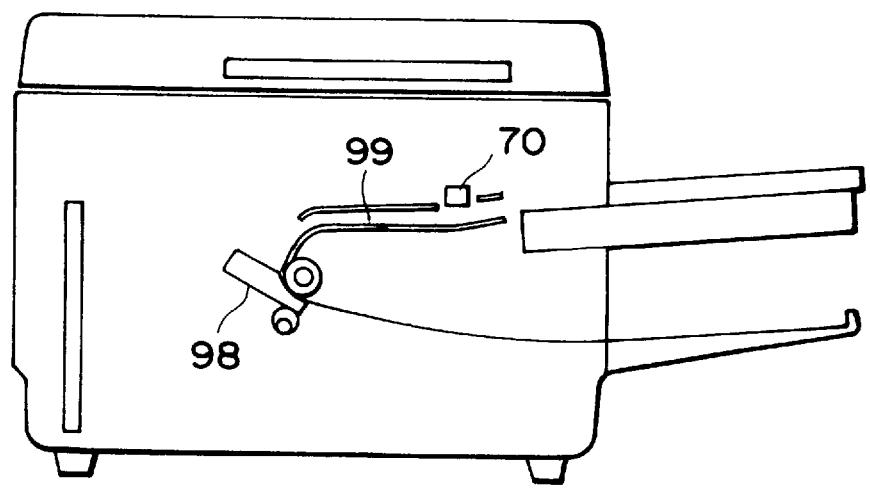
FIG. 98 is a structural view showing another example of application to a printing apparatus.

FIG. 98 shows a facsimile machine having a thermal head 98. Here the sensor head 70 is arranged so as to face a paper-feed conveyance path 99.

Figure 99:
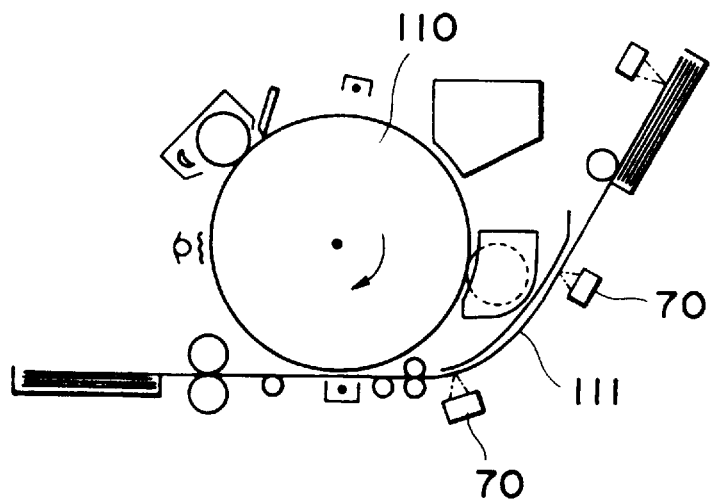
FIG. 99 is a structural view showing another example of application to a printing apparatus.

FIG. 99 depicts part of a copier having a photosensitive drum 100. Here the sensor head 70 is arranged so as to face a paper-feed conveyance path 111.

The output signal from the sensor head 70 in each of these apparatus is applied to a paper discriminating unit. The optimum amount of ink, the amount of charge of the photosensitive drum, etc., are adjusted in dependence upon the type of paper discriminated by the discriminating unit.

An example of control of amount of ink in a printing apparatus will be described with reference to FIGS. 100–102.

Figure 100:
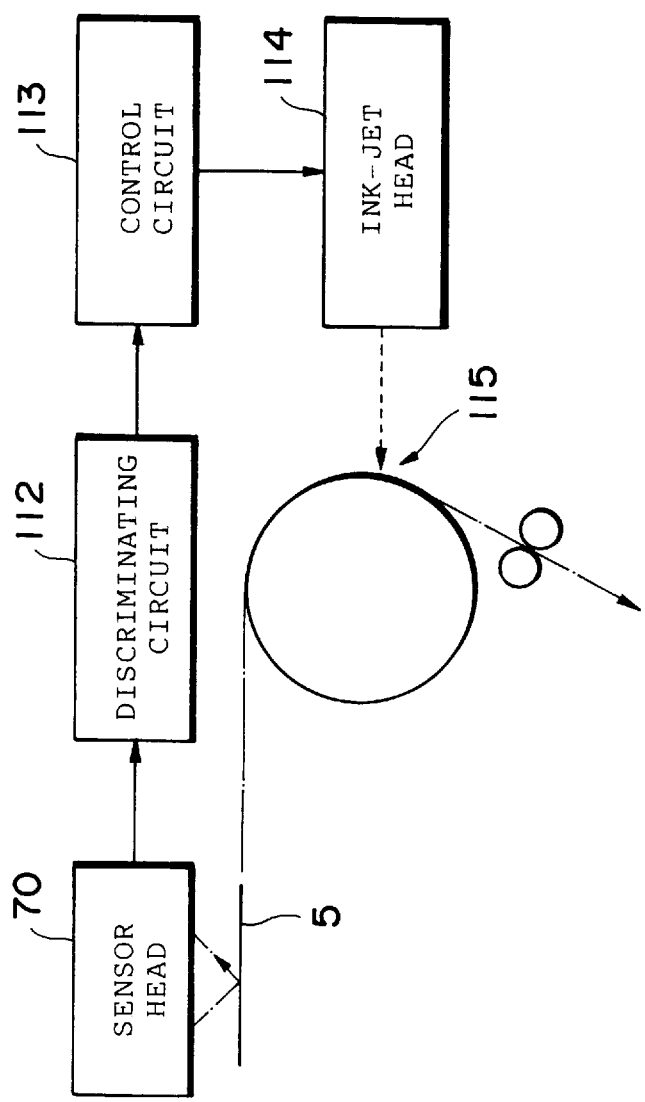
FIG. 100 is a block diagram showing application to an ink-jet printing apparatus and illustrating the construction of the printing apparatus.

FIG. 100 illustrates part of the construction of an ink-jet printing apparatus. Here the presence of the paper 5 and the type thereof are discriminated as the paper is being conveyed to a printing section 115. The types of paper are plain paper, coated paper and glossy paper described above.

The sensor head 70 is provided on the conveyance path of the paper 5. The light-reception signal from the sensor head 70 is sent to a discriminating circuit 112. (Though the construction of the discriminating circuit 112 will be described later, the circuit involves a concept broader than that of the discriminating circuit 104 in FIGS. 45–48). The result of discriminating the type of paper is applied to a control circuit 113, which includes a CPU, a memory, etc.. The amount of ink jetted in the ink-jet head 114 is controlled by the control circuit 113.

Figure 101:
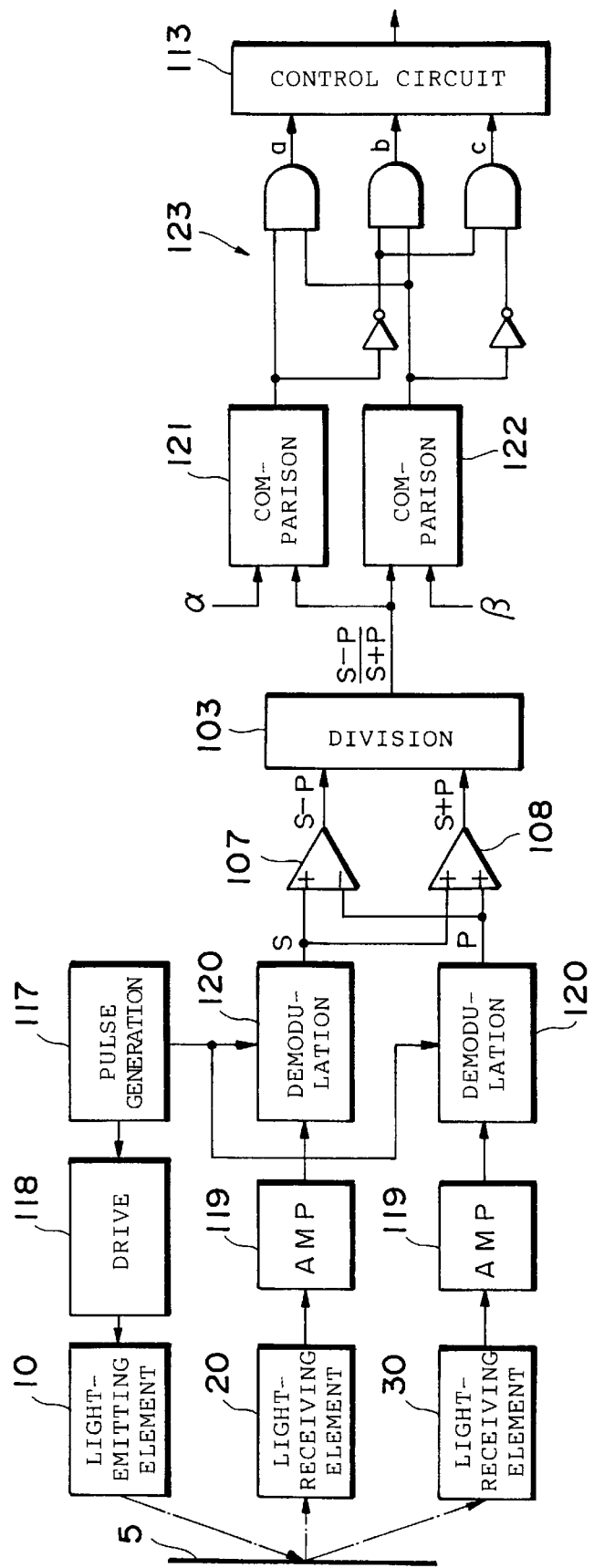
FIG. 101 is a block diagram illustrating the construction of a discriminating circuit in application to an ink-jet printing apparatus.

FIG. 101 illustrates an example of the construction of the discriminating circuit 112. Components identical with those shown in FIG. 46 are designated by like reference characters and need not be described again. Pulses having a fixed frequency are generated by a pulse generating circuit 117 and applied to a drive circuit 118, whereby the light-emitting element 10 is driven in pulsed fashion. After the pulsed output signals of the light-receiving elements 20, 30 are amplified by amplifiers 119, the amplified signals are each demodulated by demodulating circuits 120 so as to be converted to DC signals. The demodulating circuits 120 are sample-and-hold circuits.

The output of the dividing circuit 103 is applied to comparator circuits 121, 122, in which threshold values $\alpha$, $\beta$, respectively, have been set. The threshold values $\alpha$, $\beta$, correspond to the above-mentioned threshold values TH1, TH2. The comparator circuits 121, 122 output "1" signals when the level of the input signal is lower than the levels of the respective threshold values $\alpha$, $\beta$ ($0<\alpha<\beta<1$). The outputs of the comparator circuits 121, 122 are applied to a logic circuit 123. The latter corresponds to the discriminating circuit 104.

The logic circuit 123 is such that an output signal becomes "1" when the output of the dividing circuit 103 is less than the threshold-value level $\alpha$, and output b becomes "1" when the output signal is between $\alpha$ and $\beta$, and an output c becomes "1" when the output signal is greater than $\beta$. These discrimination signals a, b and c enter the control circuit 113.

Figure 102:
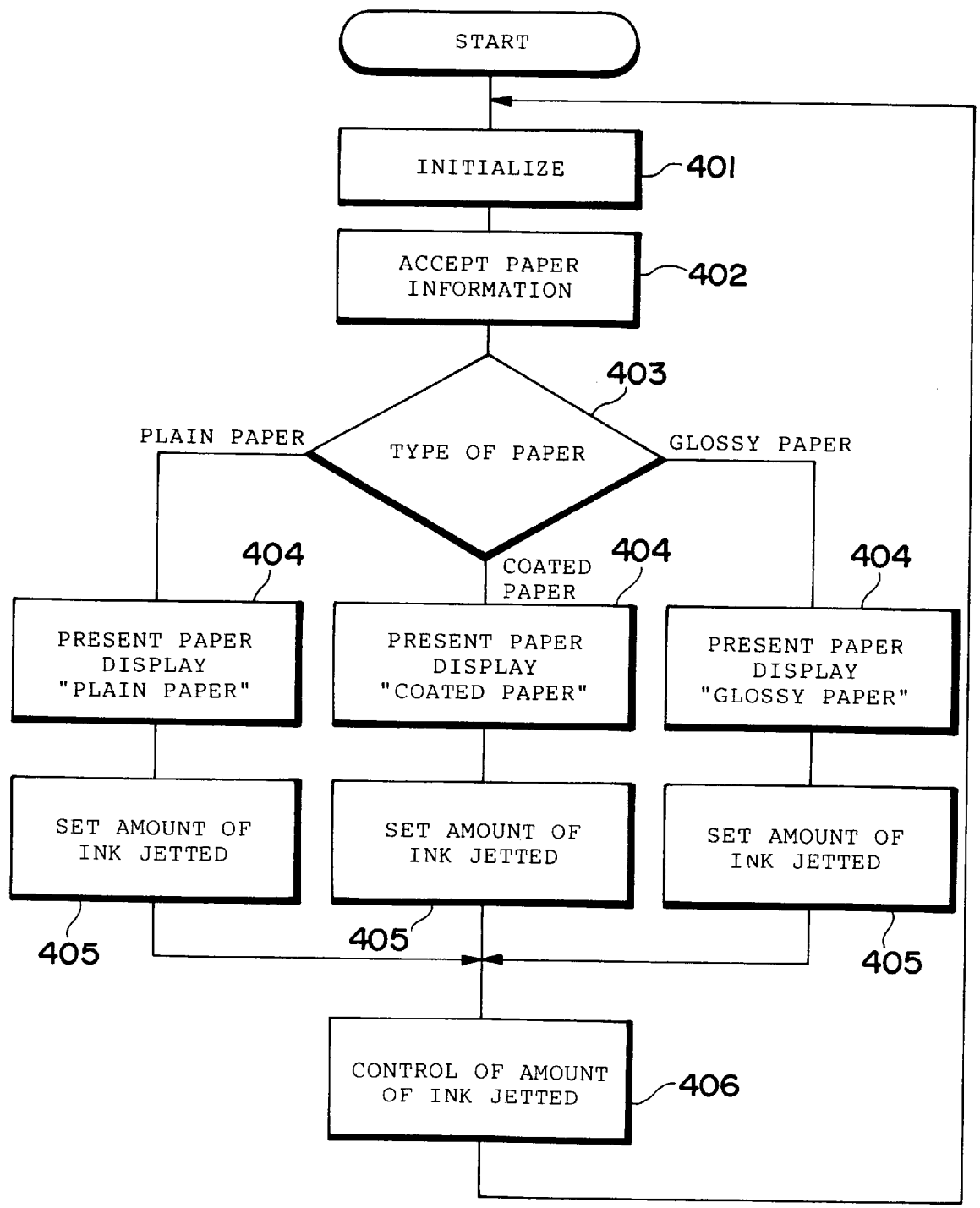
FIG. 102 is a flowchart illustrating a processing procedure for controlling the amount of jetting ink in application to an ink-jet printing apparatus.

The control circuit 113 performs the processing shown in FIG. 102 to control the amount of jetted ink in the ink-jet head 114. After initialization processing (step 401) is executed, the discrimination signal a, b or c is accepted (step 402). The signals a, b, and c indicate that the paper 5 is plain paper, coated paper and glossy paper, respectively. The results of discrimination are displayed on a display unit (not shown) (steps 403, 404) and the amount of ink jetted is set (step 405).

In general, the amount of ink jetted becomes progressively larger in the order of plain paper, coated paper and glossy paper. Ink jetting-quantity data conforming to the type of paper is stored in memory beforehand. The jetting quantity is read out of memory in conformity with the results of discrimination to control the amount of ink jetted in the ink-jet head 114 by a commensurate amount (as by controlling the voltage applied to piezoelectric element) (step 406).

Figure 103:
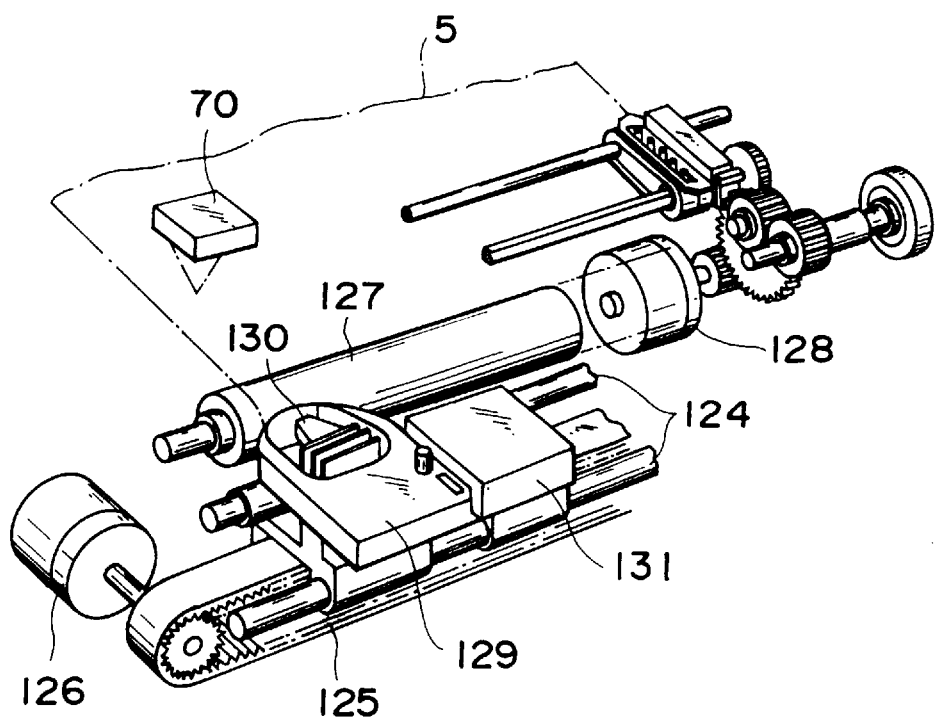
FIG. 103 is a perspective view showing an example of application to a printing apparatus.

FIG. 103 illustrates part of a printing apparatus in which the type of paper supplied is discriminated by the optical sensor device, whereby whichever one of a plurality of printing units is suited to the results of discrimination is selected and driven into operation.

A printing head 130 having an ink ribbon cartridge 129 and a ink-jet printing head 131 are provided on guide shafts 124 so as to be free to move. The printing heads 130, 131 are connected to a timing belt 125 driven by a motor 126 so that the heads can be moved to any position. The paper 5 is fed by being wound upon a platen roller 127 rotatively driven by a feed motor 128.

The paper 5 fed is sensed by the sensor head 70 and the type of paper is discriminated. Either of the printing heads 130, 131 is driven selectively in dependence upon the type of paper discriminated. A printing head of the type using a photosensitive drum, of the thermosensitive type or of some other type can be provided.

Figure 104:
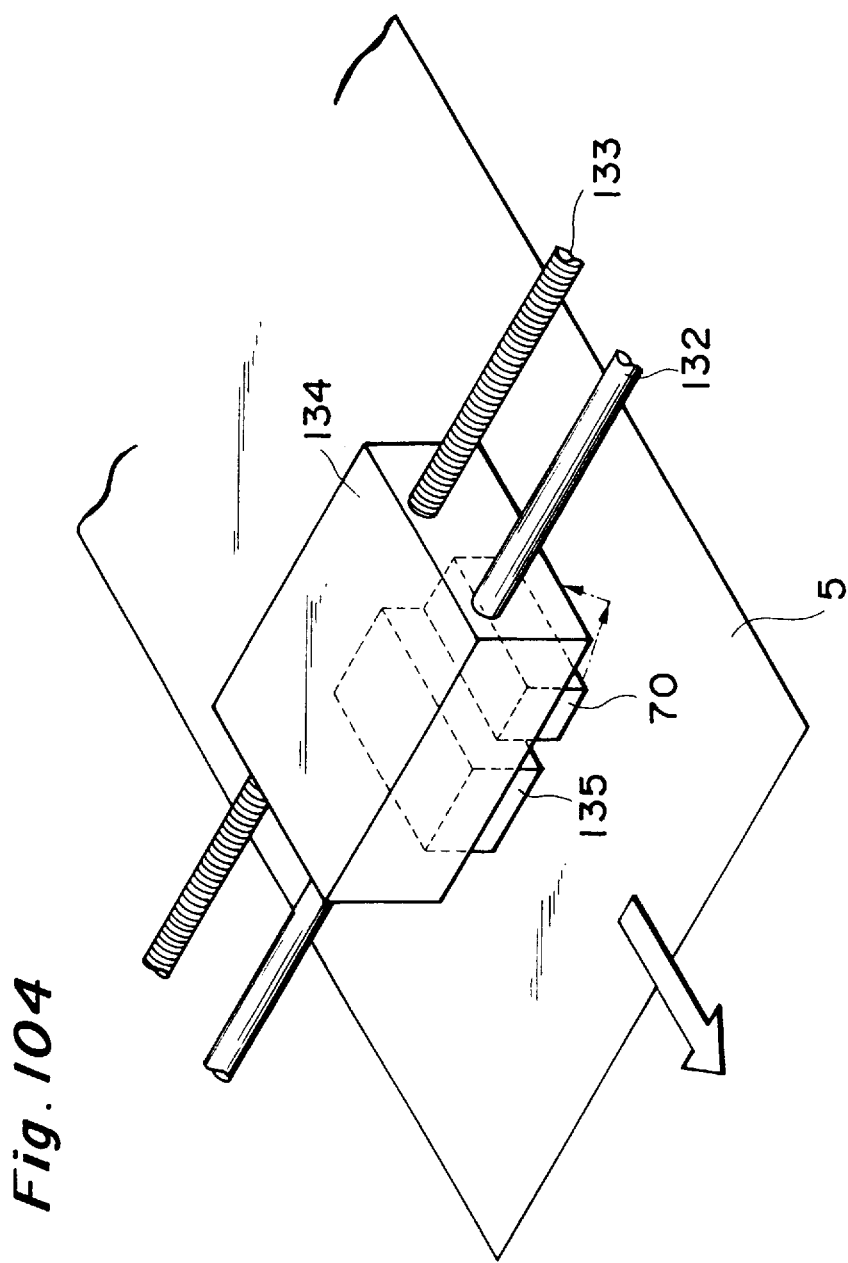
FIG. 104 is a perspective view showing another example of application to a printing apparatus.

As shown in FIG. 104, an arrangement can be adopted in which the sensor head 70 is moved together with the printing head 135.

A support block 134 is supported on a guide shaft 132 so as to be free to move and may be transported to any position by rotating a screw 133. The printing head 135 and the sensor head 70 are mounted on the support block 134.

When the sensor head 70 senses the side edge of the paper 5, printing is stopped and the paper is fed. Printing is performed again while the printing head 135 is being transported, printing is halted when the side edge of the paper is sensed by the sensor head 70, and then a transition is made to paper feed.

The type of paper may be discriminated on the basis of the output signal from the sensor head 70 and the above-mentioned control of the amount of jetted ink may be performed accordingly.

Figure 105:
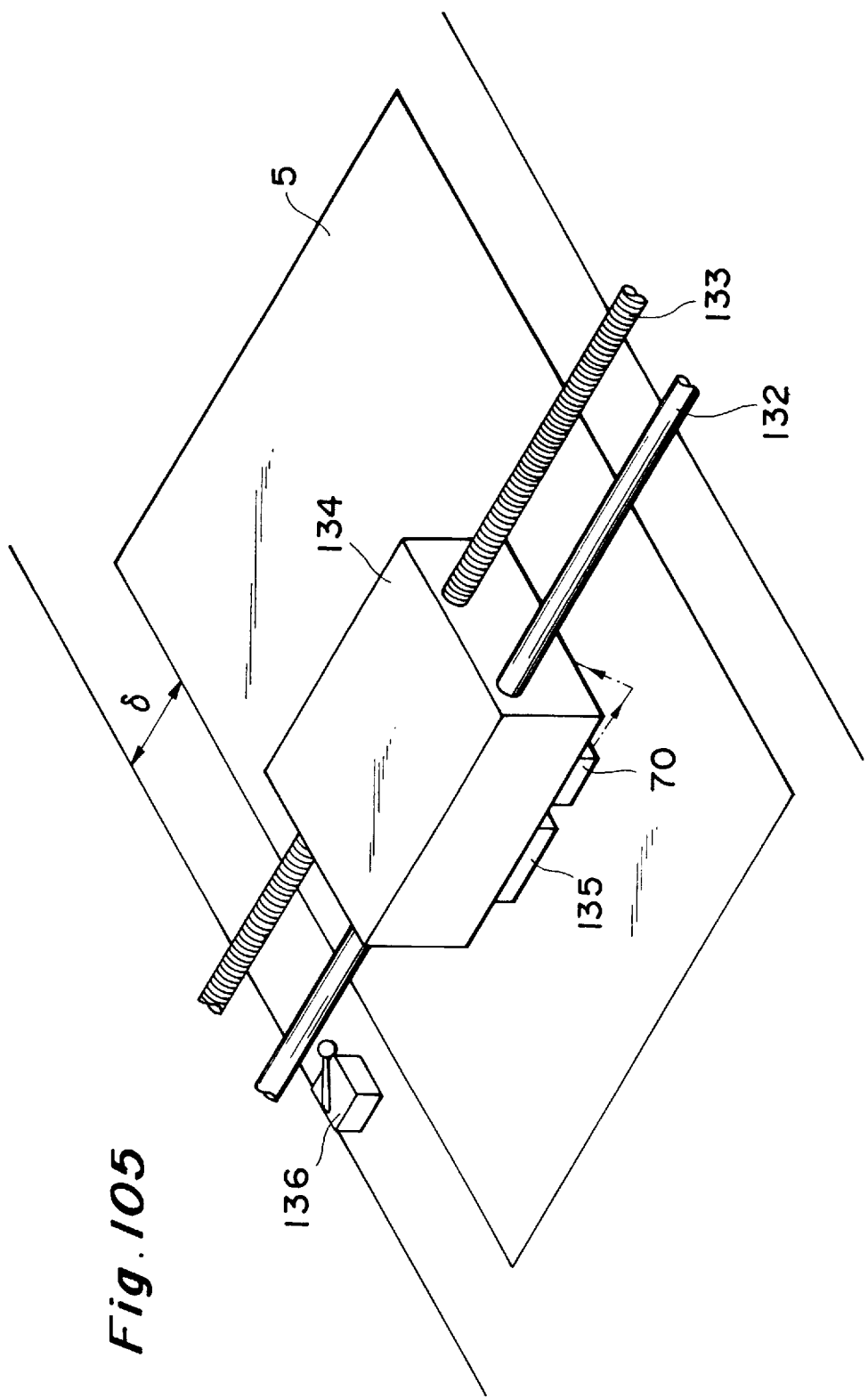
FIG. 105 is a perspective view showing yet another example of application to a printing apparatus.

FIG. 105 shows an arrangement in which an amount of offset $\delta$ of the paper 5 relative to a reference position is sensed. The reference position is decided by a microswitch 136. The offset quantity $\delta$ is measured on the basis of detection of the side edge of the paper 5 by the sensor 70 when the support block has moved a certain amount from a position sensed by the microswitch 136.

It can be so arranged that only the sensor head 70 is provided on the support block, with the leading edge trailing edge and both side edges of the paper being sensed by the sensor head 70.

Figure 106:
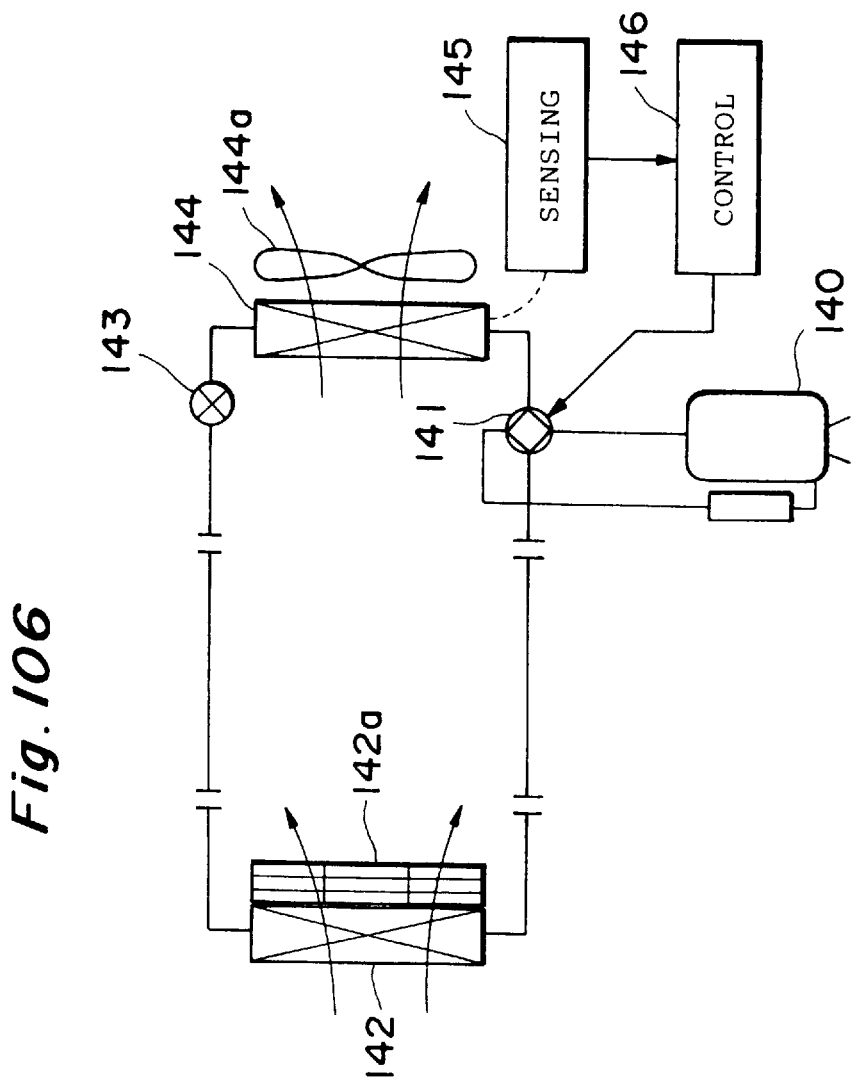
FIG. 106 illustrates an example of application to an air conditioner of heat pump type and shows the construction of the air conditioner.

FIG. 106 illustrates an example of application to an air conditioner of heat pump type. When the air conditioner operates as a heater, refrigerant flows through a path composed of a four-way valve 141, an indoor heat exchanger 142, a throttle mechanism 143 and an outdoor heat exchanger 144. When the air conditioner operates as a cooler, refrigerant flows through a path composed of the four-way valve 141, outdoor heat exchanger 144, throttle mechanism 143 and indoor heat exchanger 142. The refrigerant is compressed by a compressor 140.

The outdoor compressor 144 acts as a heat generator at the time of the heating operation. That is, outside air is drawn in by an outdoor fan 144a and heat is absorbed from the outside air. The heat is transmitted to the indoor heat exchanger 142 via the refrigerant, and the heat exchanger 142 discharges the heat into the room by an indoor fan 142a.

At the time of the cooling operation, heat drawn in by the indoor heat exchanger 142 utilizing the indoor fan 142a is supplied to the outdoor heat exchanger 144 via the refrigerant. The heat is discharged to the outside via the outdoor fan 144a.

A sensing unit 145 senses the state of icing (or condensation) on the outdoor heat exchanger 144 and outputs the result to a control circuit 146. The latter controls the four-way valve 141 to change over the direction of refrigerant flow in accordance with the output of the sensing unit 145.

Figure 107A:
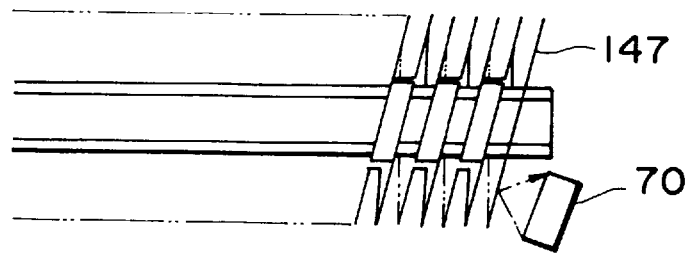
Figure 107B:
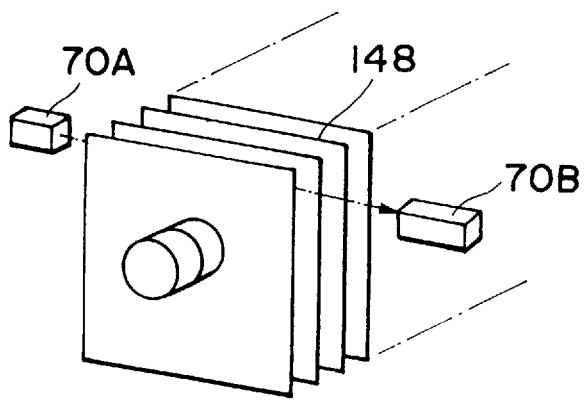
Figure 107C:
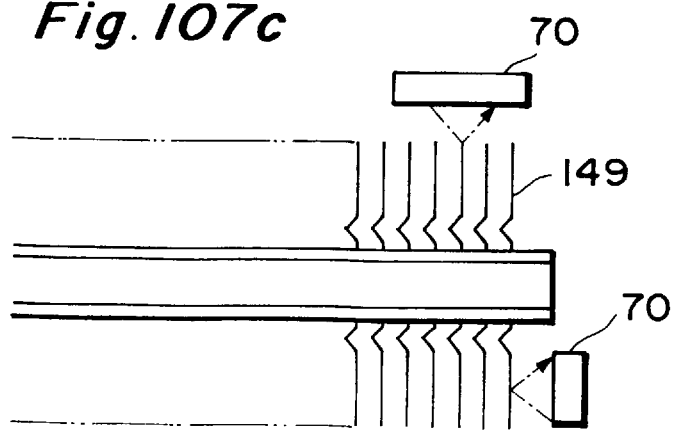

The sensing unit 145 includes an optical sensor device. As shown in FIG. 107a, the sensor head 70 irradiates a spiral fin 147 of the outdoor heat exchanger with light and receives light reflected from the fin. The accumulation of frost or condensation is thus sensed. Alternatively, as shown in FIG. 107b, the light-projecting head 70A and light-receiving head 70B are provided. In order to sense frost or condensation, the projected light from the projecting head 70A is received by the light-receiving head 70B through the spaces between plate fins 148 on the outdoor heat exchanger. Instead of this arrangement, the sensor head 70 may be arranged so as to sense the state of frost or condensation at an appropriate location on corrugated fins 149 of the outdoor heat exchanger, as depicted in FIG. 107c.

Figure 108:
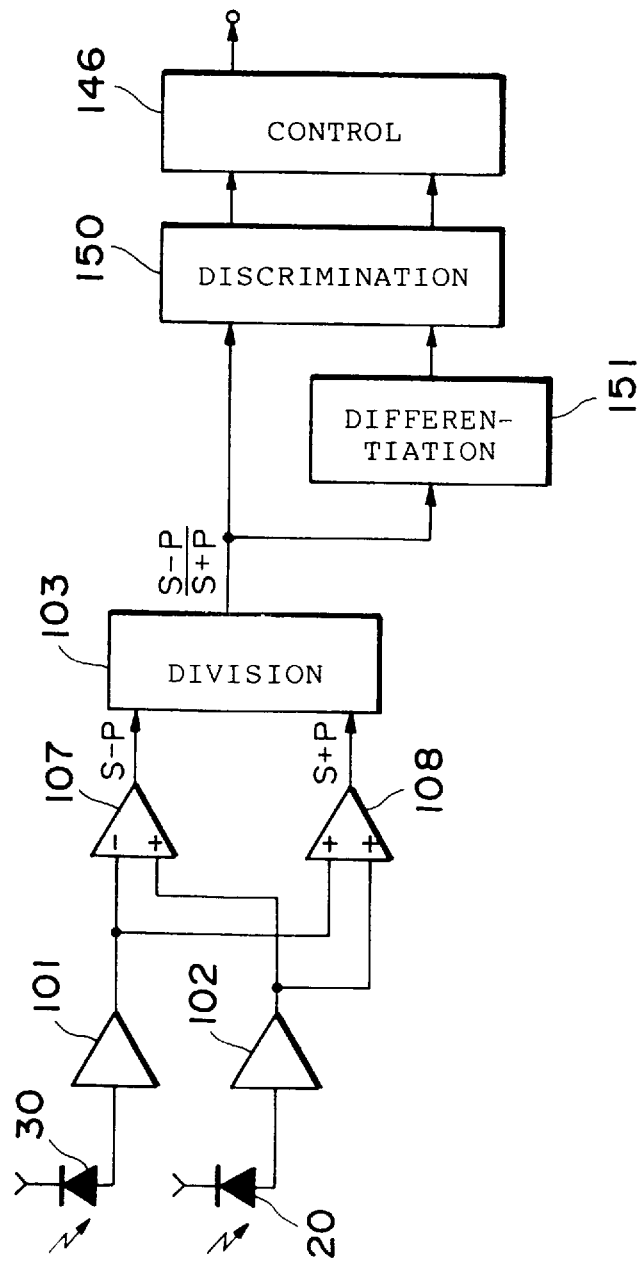
FIG. 108 is a block diagram showing the construction of a discriminating circuit.

FIG. 108 illustrates an example of the construction of the sensing circuit 145, in which components identical with those shown in FIG. 45 are designated by like reference characters and need not be described again. A differentiating circuit 151 detects a change in the output of the dividing circuit 103. As a result, a discriminating circuit 150 detects whether accumulation of frost or condensation has occurred or not as well as the rate at which it is taking place.

Figure 109:
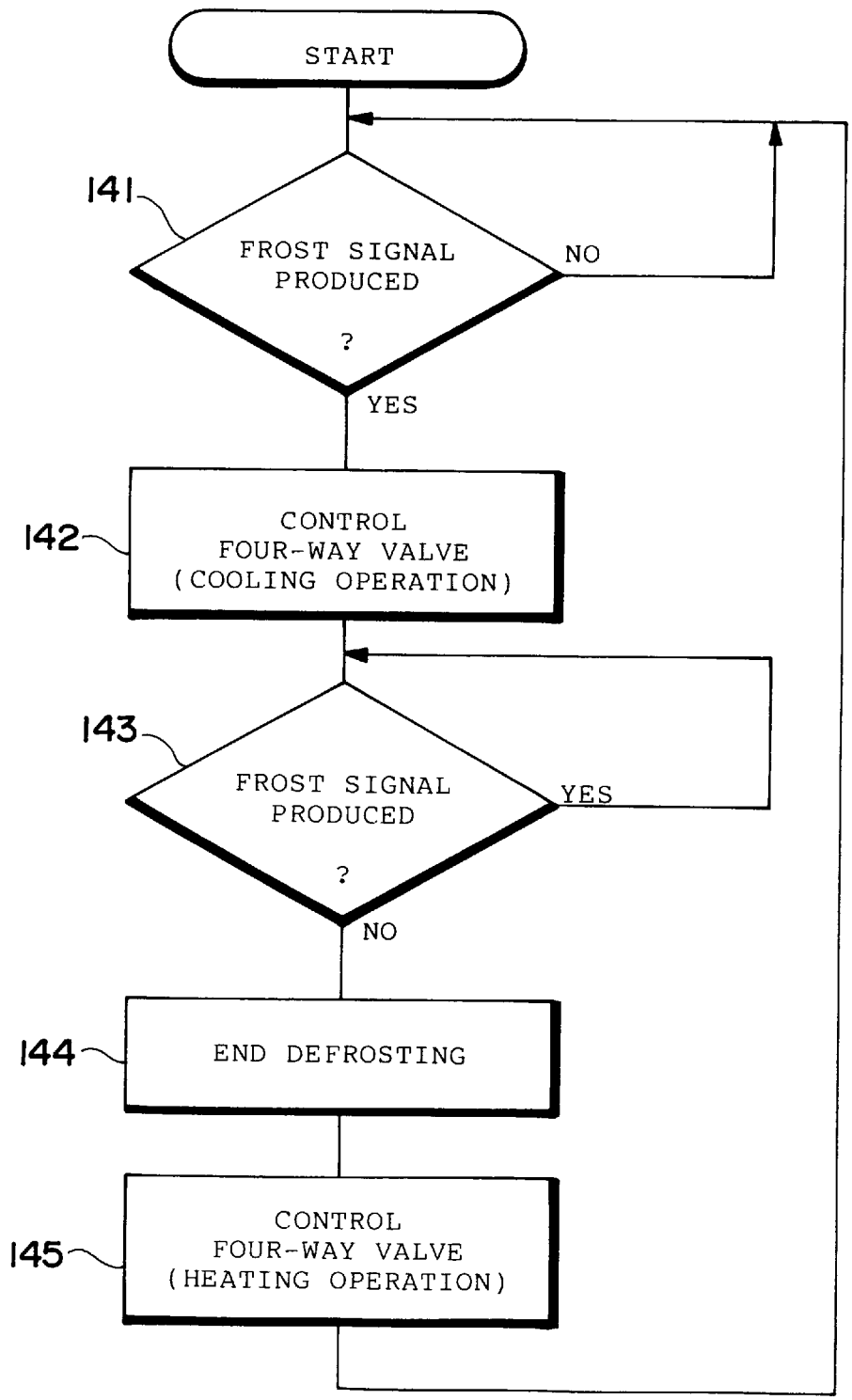
FIG. 109 is a flowchart illustrating a defrosting processing procedure.

The control circuit 146 includes a CPU, which executes defrosting processing shown in FIG. 109.

When the air conditioner is running in the heating mode, condensation (frost) is produced in the outdoor heat exchanger 144 with the passage of time. As the condensate or frost builds up, the surface state thereof is sensed by the sensor unit 145 (step 411). When built-up of frost is sensed, the control circuit 146 controls the four-way valve 141 to change over the direction of refrigerant flow to the direction for the cooling operation, thereby to start defrosting of the outdoor heat exchanger 144 (step 142).

The output of the sensing unit 145 is monitored and, when frost has been removed from the outdoor heat exchanger 144 (steps 143, 144), the control circuit 146 changes over the four-way valve 141 again to resume the heating operation (step 145).

The amount of air flow produced by the indoor fan 142a and the operation of the compressor 140 are controlled on the basis of sensed rate of frost built-up.

Figure 110:
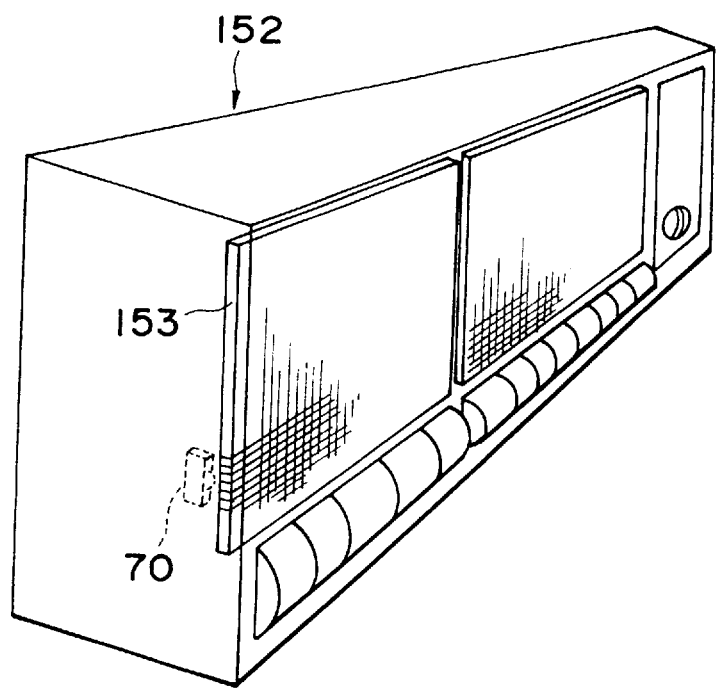
FIG. 110 is a perspective view of an air conditioner showing an example of application to detection of clogging of a filter in an air conditioner.

FIG. 110 shows an example of application to detection of clogging of a filter in an air conditioner. The sensor head 70 is provided in such a manner that light is projected upon a filter 153 in an air conditioner 152. The filter 153 is made of plastic and therefore the light reflected from the filter contains many s-polarized light components. When dust attaches itself to the filter 153, the reflected light approximates randomly polarized light and the s-polarized light components decrease as a result. It is on the basis of this phenomenon that attachment of dust to the filter 153 is sensed. A warning display or the like is presented in response to such a detection signal.

Figure 111:
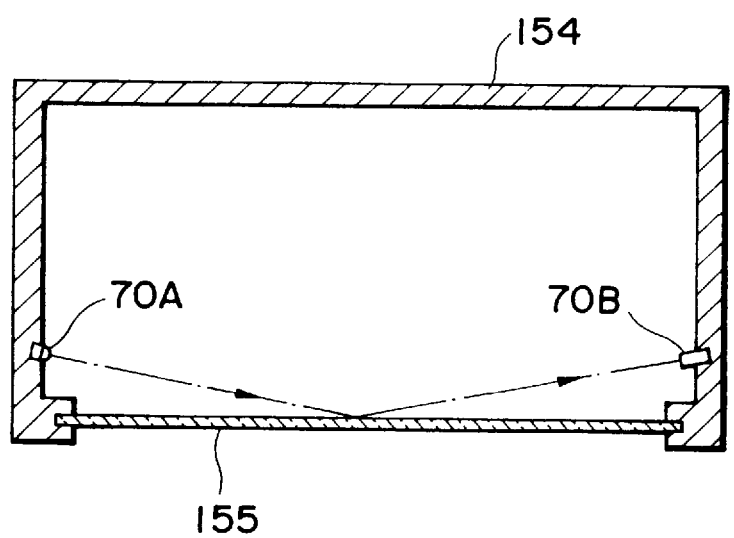
FIG. 111 is a sectional view of a showcase.

FIG. 111 shows an arrangement adapted to sense the fogging (or frosting) of glass 155 in a showcase 154. A transmissive-type sensor device is used, and the projecting head 70A and light-receiving head 70B are provided inside the case 154 at the front end thereof. The light which exits from the projecting head 70A impinges upon the glass 155, is reflected and impinges upon the light-receiving head 70B. The principle through which fogging is sensed is that same as that through which dust is sensed.

FIGS. 112 through 116 illustrate an example in which an optical sensor device is applied to an automobile air conditioner, especially an apparatus (defogger) for removing fog produced on the inner surface of the front windshield.

Figure 112:
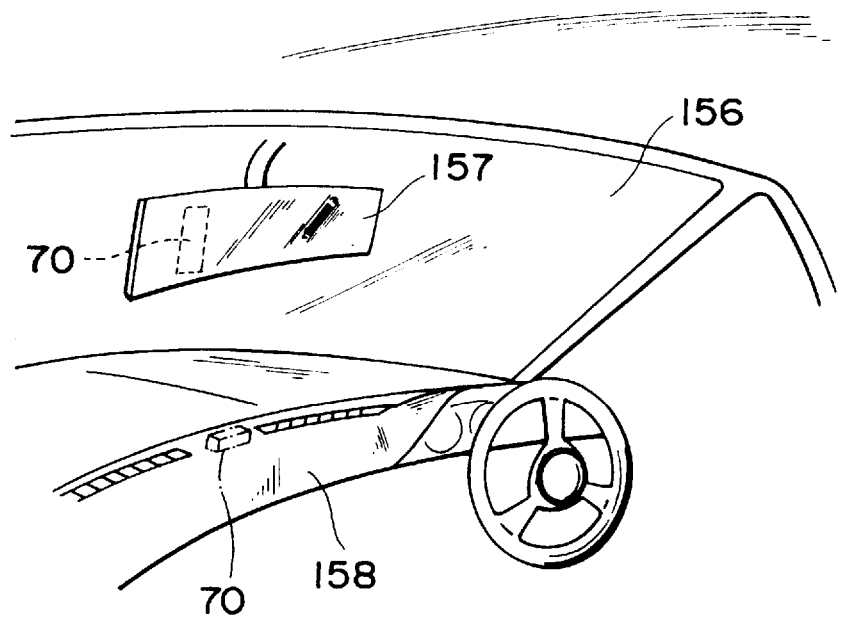
FIG. 112 is a perspective view showing application to a defogging apparatus and illustrating the front part of an automobile.

As shown in FIG. 112, the sensor head 70 is attached to the back side of a rearview mirror 157 provided on the upper portion of a front windshield 156 of an automotive vehicle. The sensor head 70 can also be placed on a dashboard 158.

Figure 113:
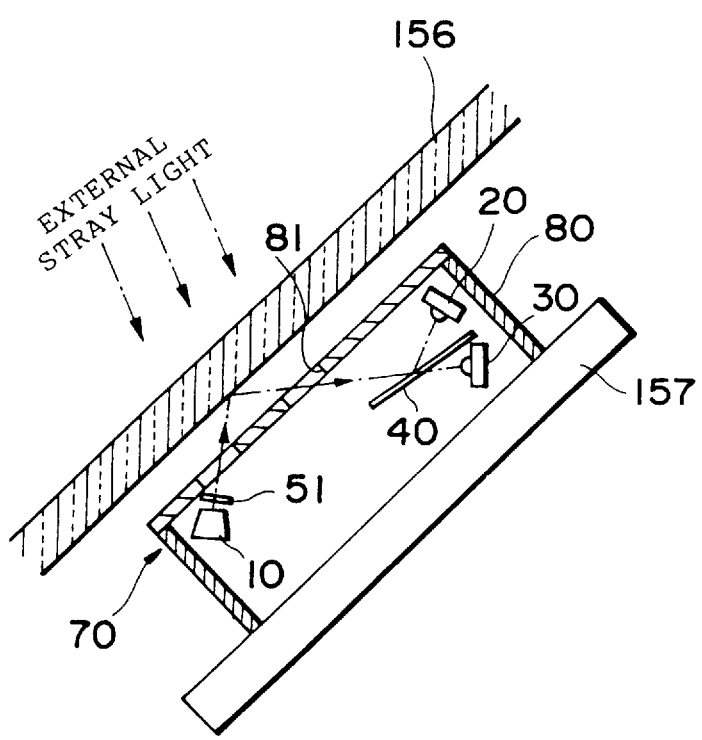
FIG. 113 shows the construction of a sensor head.

FIG. 113 illustrates the construction of the sensor head 70. This has already been described. The light-emitting element 10 is placed in the lower portion of the case 80, and the light-receiving elements 20, 30 are placed in the upper portion of the case. By thus arranging these elements, it is possible to eliminate erroneous detection caused by the impingement of natural light (especially sunlight) on the light-receiving elements 20, 30.

The opening 81 is provided in the case 80 at such a position that only the part of the projected light reflected at the inner surface of a the front windshield 156 will impinge upon the light-receiving optical system. If an infrared filter is provided at the opening and it is so arranged that only projected light (in the case of infrared light) impinges upon the light-receiving optical system, detection accuracy is greatly enhanced.

Figure 114:
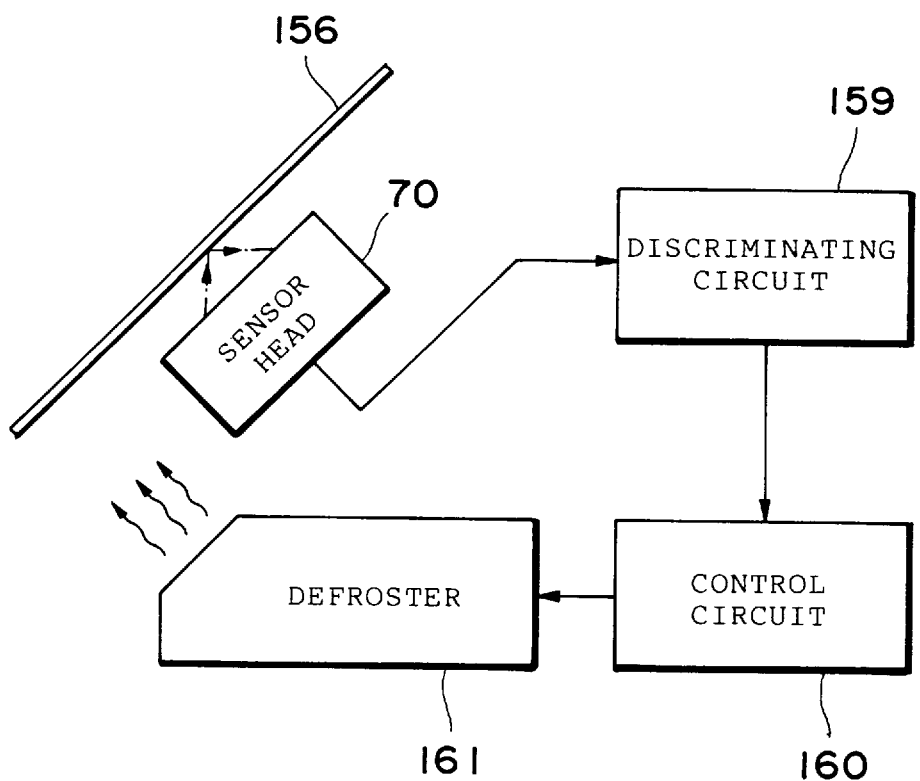
FIG. 114 is a perspective view showing application to a defogging apparatus and illustrating the construction of a control unit.

In FIG. 114, the light-reception signal from the sensor head 70 enters a discriminating circuit 159, which senses whether fogging has occurred and, if so, the extent thereof. A defroster 161 is controlled by a control circuit 160 on the basis of the results of detection.

Figure 115:
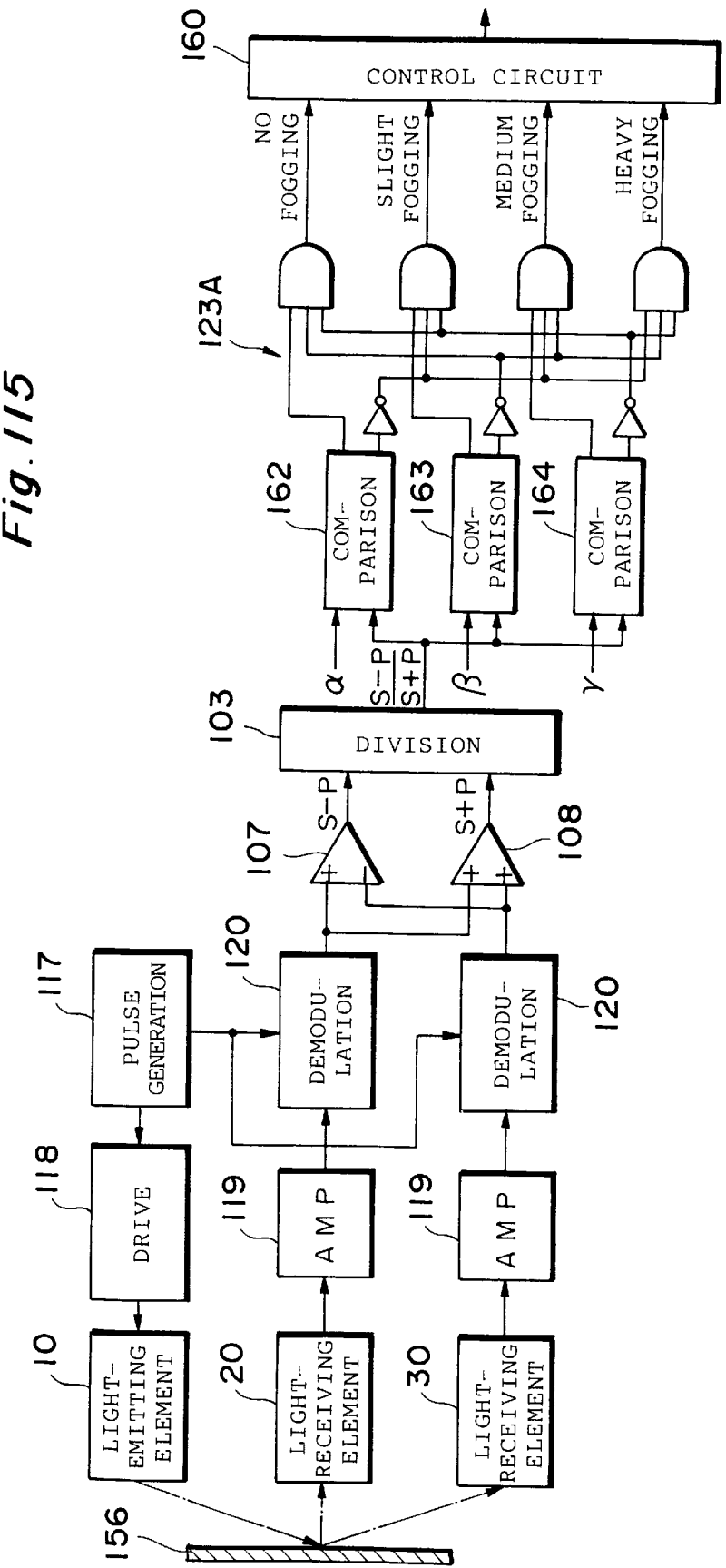
FIG. 115 is a block diagram showing the construction of a discriminating circuit.

FIG. 115 illustrates an example of the construction of the discriminating circuit 159. This is basically the same as the discriminating circuit depicted in FIG. 101. The circuit 159 differs from the circuit of FIG. 101 in that it is provided with three comparator circuits 162, 163, 164. This is accompanied also by a change in the construction of the logic circuit, which is shown at 123A.

Light of s-polarized light components is projected from the light-projecting optical system of the sensor head 70. When the inner surface of the front windshield 156 is free of fogging, the reflected light becomes s-polarized light. When fogging occurs, the reflected light approximates randomly polarized light and, hence, the p-polarized light components contained in the reflected light increases. Accordingly, the value of (S−P)/(S+P) indicates a maximum value when there is no fogging and becomes smaller as the degree of fogging increases.

The threshold value levels set in the comparators 162, 163, 164 are related by the expression ($\alpha > \beta > \gamma$). When the level of the input signal is greater than ($\alpha, \beta, \gamma$, the respective comparators 162, 163, 164 output logical "1". The logic circuit 123A outputs four discrimination signals indicative of no fogging, slight fogging, medium fogging and heavy fogging. These signals enter the control circuit 160.

Figure 116:
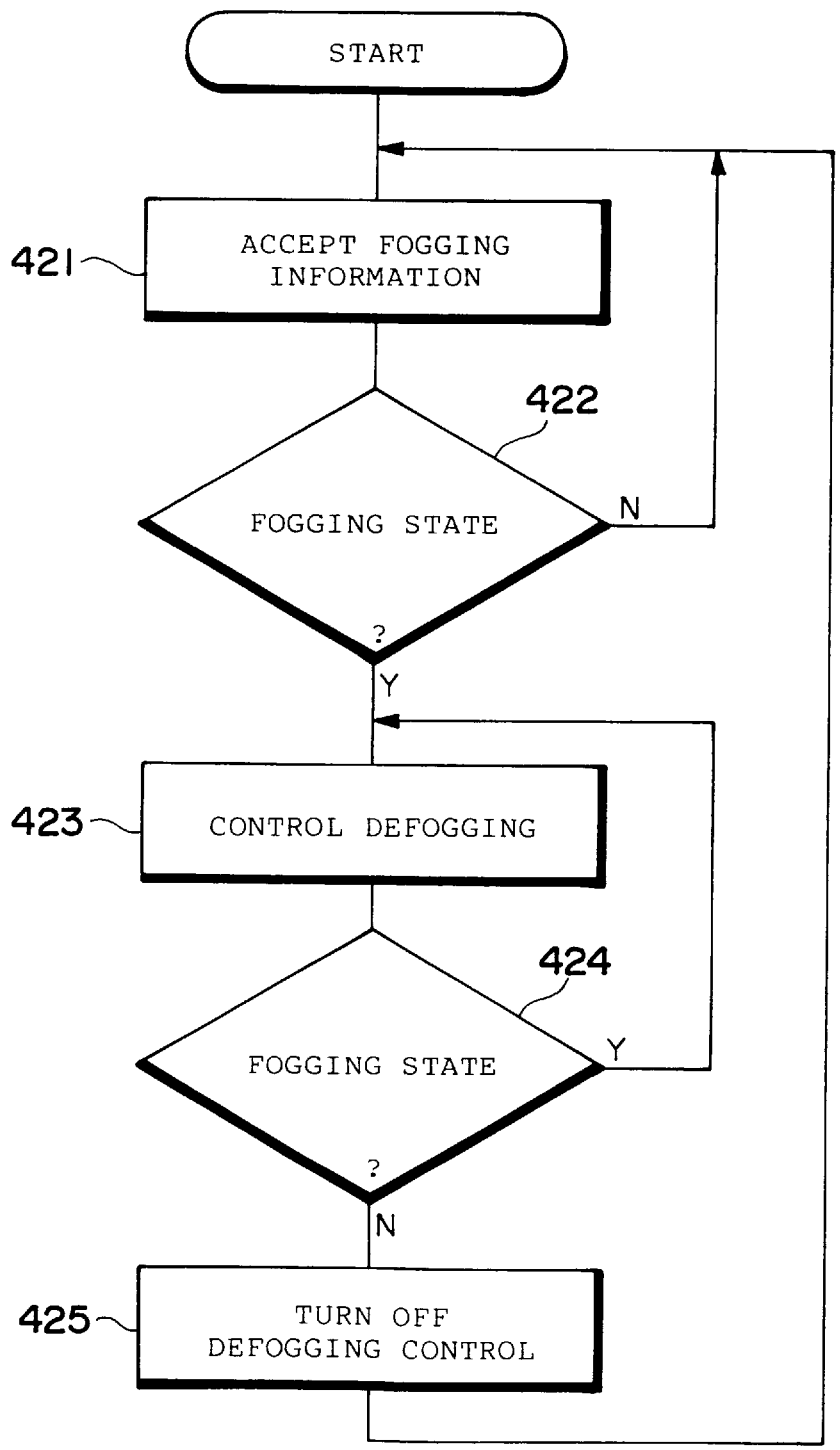
FIG. 116 is a flowchart showing a defogging processing procedure.

The control circuit 160 controls the defroster 161 in accordance with the procedure shown in FIG. 116. Specifically, when fogging is sensed (steps 421, 422), the defroster 161 is driven in dependence upon the extent of fogging to remove the fog (step 423). If fogging is eliminated, the defogging operation ends (steps 424, 425). The temperature of the hot air expelled from the defroster 161 and the strength of the wind would be controlled in accordance with the degree of fogging.

Figure 117:
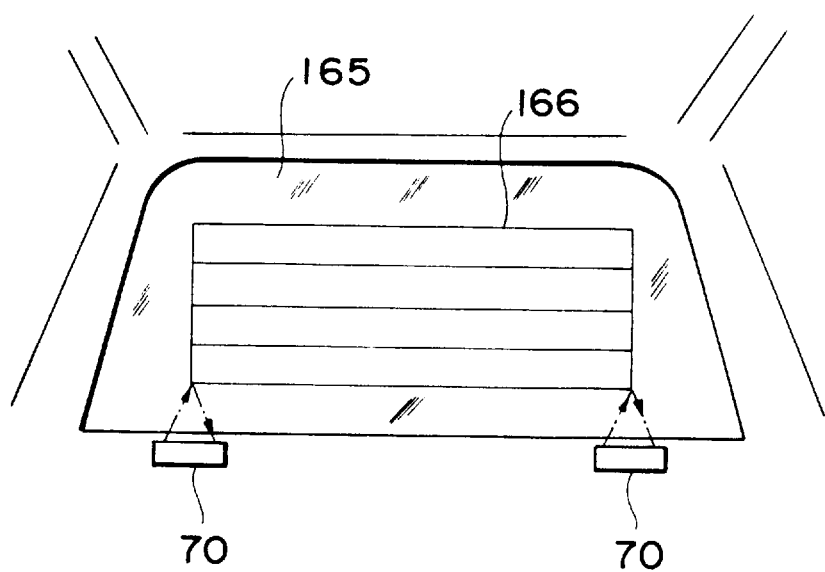
FIG. 117 is a perspective view showing application to a defogging apparatus and illustrating the rear part of an automobile.

As shown in FIG. 117, the sensor heads 70 can also be placed on the left and right sides of a rear window 165 near the bottom thereof. The positions on the left and right sides of the rear window 165 near the bottom thereof are locations where fog lasts longest even when the window 165 is heated by heating wires 166. By sensing the fog at these positions, the state of fogging of the rear window 165 can be sensed in reliable fashion.

Figure 118:
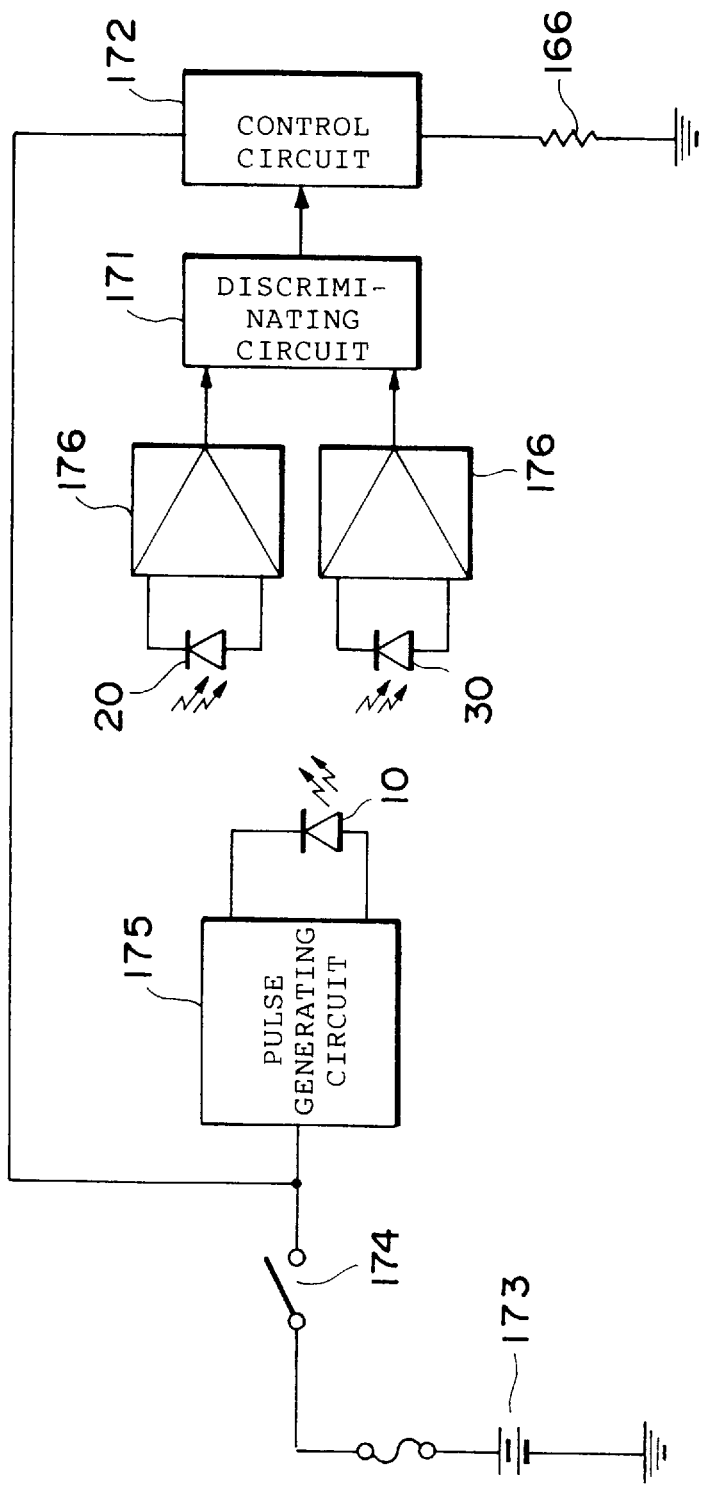
FIG. 118 is a block diagram showing the construction of a control unit in an application to a defogging apparatus.

FIG. 118 illustrates an arrangement for controlling the heating wires 166. When an ignition switch (or prescribed manual switch) 174 is turned on, power from a battery (power supply) 173 is supplied to a pulse generating circuit 175 and a control circuit 172. The pulse generating circuit 175 generates pulses to drive the light-emitting diode 10 and cause it to flash when the ignition switch 174 has been turned on.

Light projected from the light-emitting diode 10 is reflected at the inner surface of the rear window 165 and received by the light-receiving elements 20, 30 via the polarization beam splitter. A discriminating circuit 171 is the same as that shown in FIG. 115. The control circuit 172 passes a current, which is commensurate with the degree of fogging discriminated, through the heating wire 166.

By driving the light-emitting element 10 in pulsed fashion, it can be so arranged that operation is performed by the discriminating circuit 171 only at the timing at which the light-emitting element is driven. This makes it possible to suppress the effects of stray external light.

Figure 119:
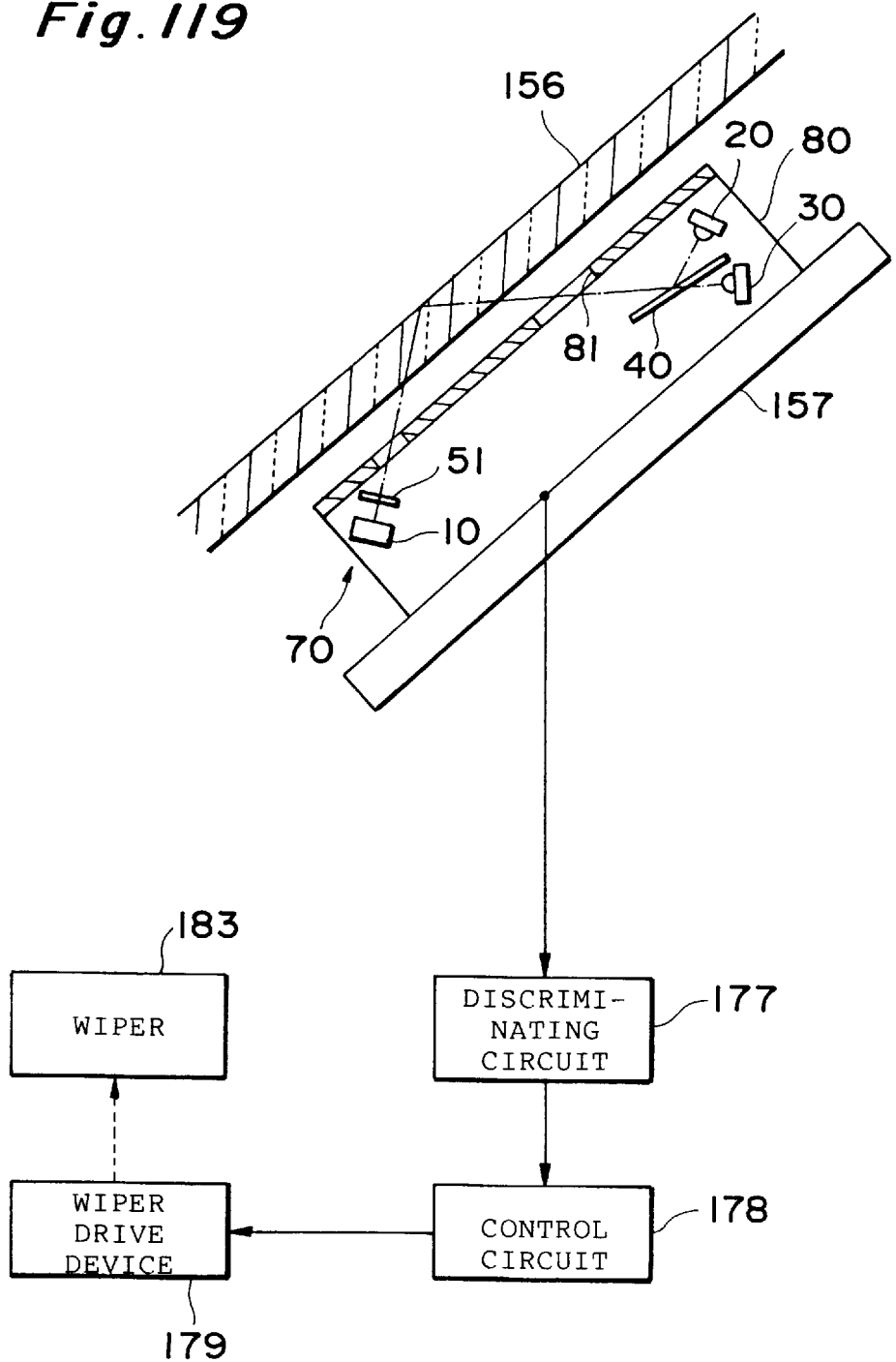
FIG. 119 is a structural view showing application windshield wiper control.

FIG. 119 is an example of an application in which a window wiper is controlled upon sensing raindrops upon the outer surface of the glass constituting the front windshield of an automotive vehicle.

The sensor head 70 is attached to the back side of the rearview mirror 157. In order to sense raindrops on the front side (outer surface) of the front windshield 156, the opening 81 is provided in the case 80 of the sensor head 70 so as to receive reflected light from the outer surface of the windshield 156. The sensor head 70 may be secured to the inner surface of the windshield 156.

The discriminating circuit 177 and the principle through which raindrops are sensed are the same as in the above-described case in which fogging is sensed (see FIG. 115).

Figure 120:
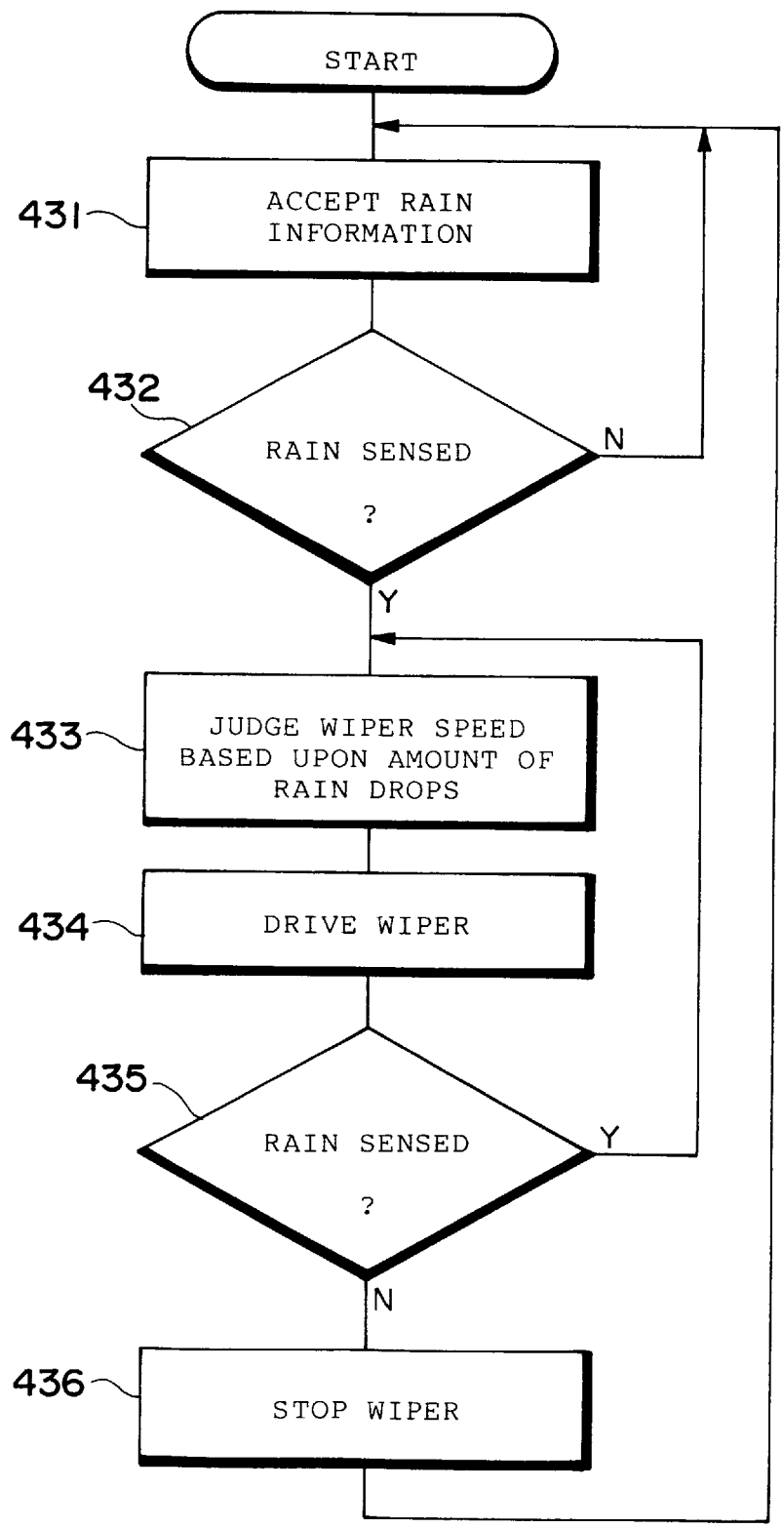
FIG. 120 is a flowchart showing a processing procedure for wiper control.

The control circuit 178 drives a wiper 183 by controlling a wiper drive device 179, in dependence upon the results of discrimination, through the procedure illustrated in FIG. 120.

Specifically, when raindrops on the front windshield 156 are sensed (steps 431, 432), a wiper speed commensurate with the amount of raindrops sensed is set and the wiper 183 is driven into operation (steps 433, 434). In general, the larger the amount of raindrops, the higher the wiper speed is made. The above operation is repeated (step 435) until raindrops are no longer sensed. When raindrops are no longer sensed, the wiper 183 is stopped (step 436).

Figure 121:
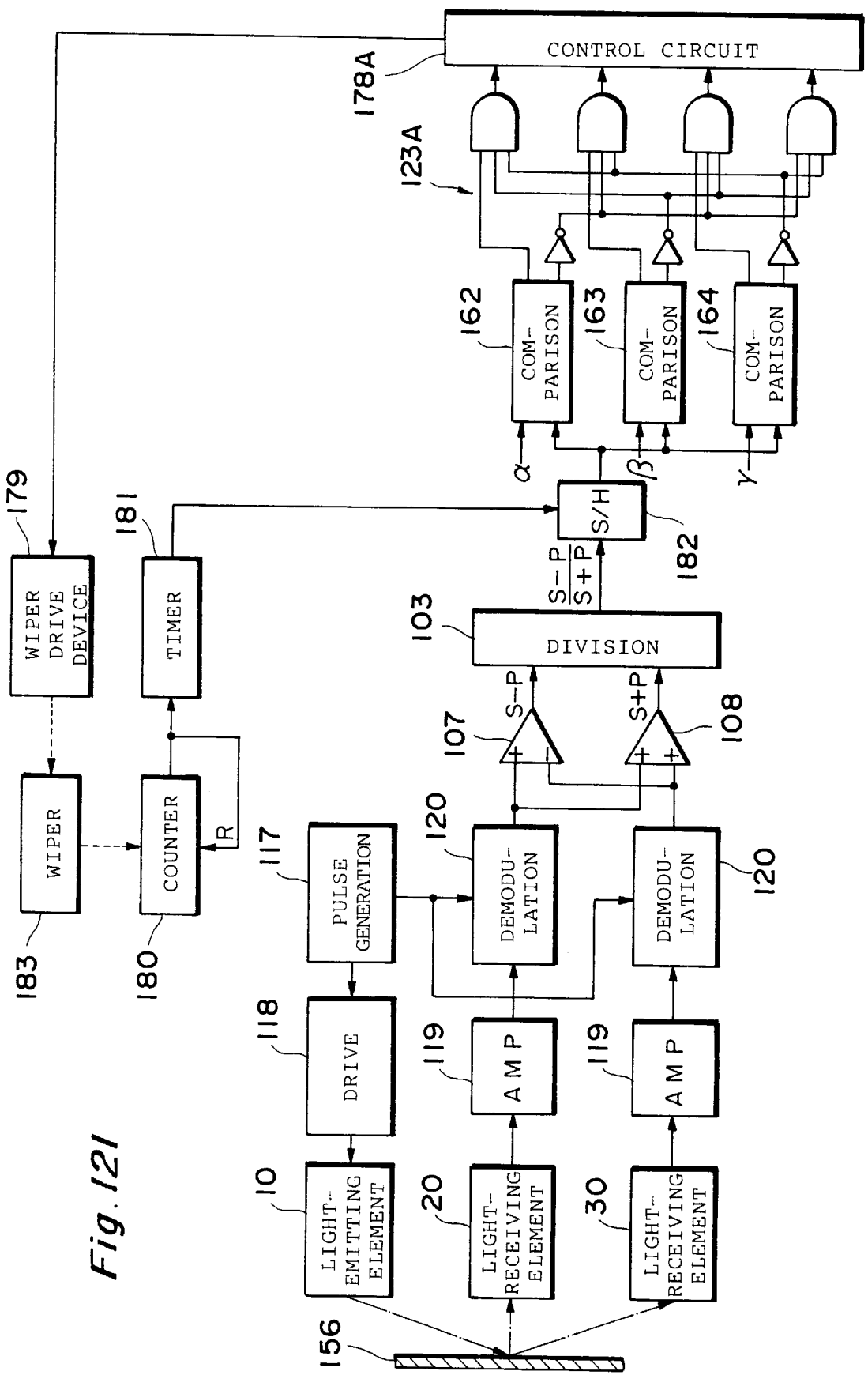

FIG. 121 illustrates hardware circuitry for executing the wiper control described above. Components identical with those shown in FIG. 115 are designated by like reference characters and need not be described again.

A counter 180 counts the number of times the wiper moves. Following a short delay after the value counted by the counter 180 attains a prescribed value, a timer generates a sampling pulse and is reset. A sample-and-hold circuit 182 samples the output of the dividing circuit 103 at the moment the sampling pulse is applied thereto and holds this output until the arrival of the next sampling pulse. The output of the sample-and-hold circuit 182 is sent to the comparators 162~164. The wiper 183 is driven by the wiper drive device 179 in accordance with the latest results of discrimination. A control circuit 178A decides the wiper speed in accordance with the results of discrimination and applies a signal indicative of the decided wiper speed to the wiper drive device 179.

Thus, the wiper 183 is driven at the same speed during the time that it is sweeping and back and forth the prescribed number of times. As a result, the individual driving the vehicle does not experience an annoying sensation (caused by a frequent changeover in wiper speed).

Figure 122:
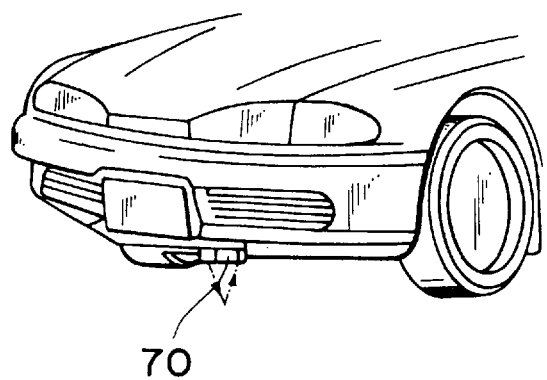
Figure 123:
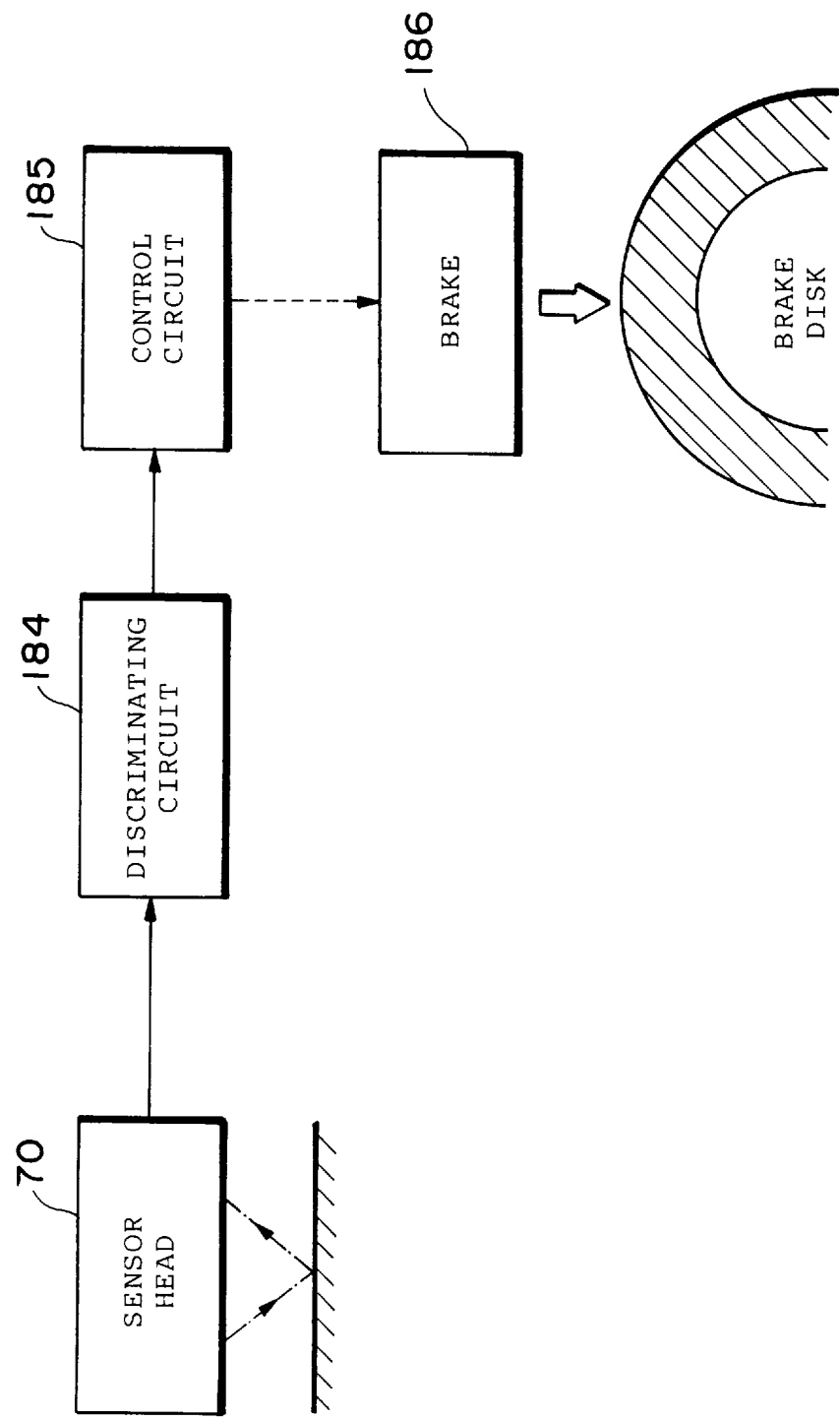
Figure 124:
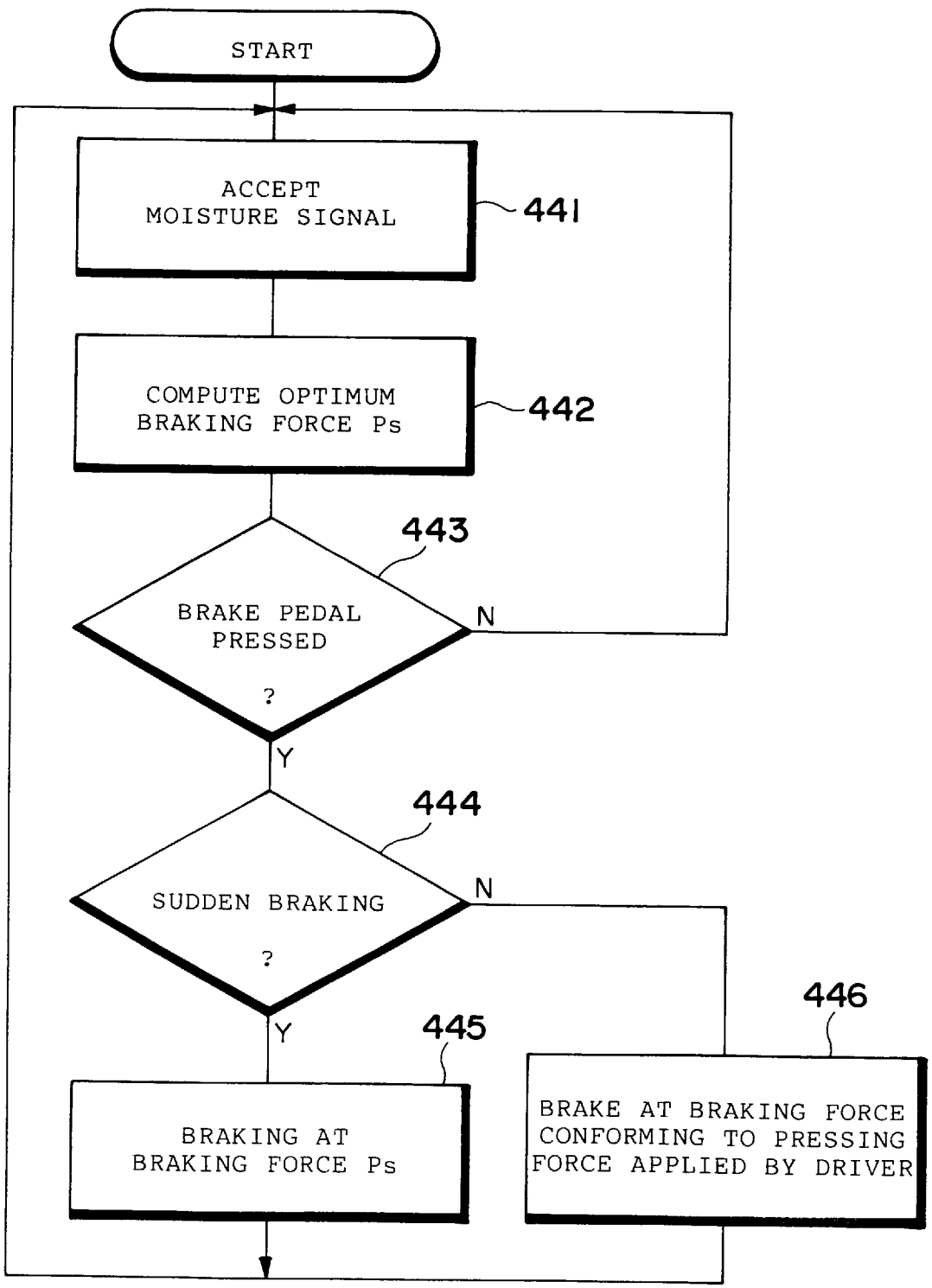

FIGS. 122~124 illustrate an example in which the optical sensor device is applied to a vehicular antilock brake system.

As shown in FIG. 122, the sensor head 70 is attached to the underside of the vehicle body and is directed downward.

In FIG. 123, s-polarized light is projected from the sensor head 70 toward the road surface. When the road surface is dry, the light reflected from it is randomly polarized light or nearly randomly polarized since the road surface is rough. When the road surface is wet or when puddles are encountered, regular braking, the brake is controlled (step 446) in conformity with the force being applied by the driver's foot. As a result, slipping and skidding caused under moist road conditions when there is a sudden increase in foot pressure upon the brake can be alleviated.

Even if projected light from the sensor head 70 is randomly polarized light, degree of moisture can be obtained based upon S/P.

Figure 125:
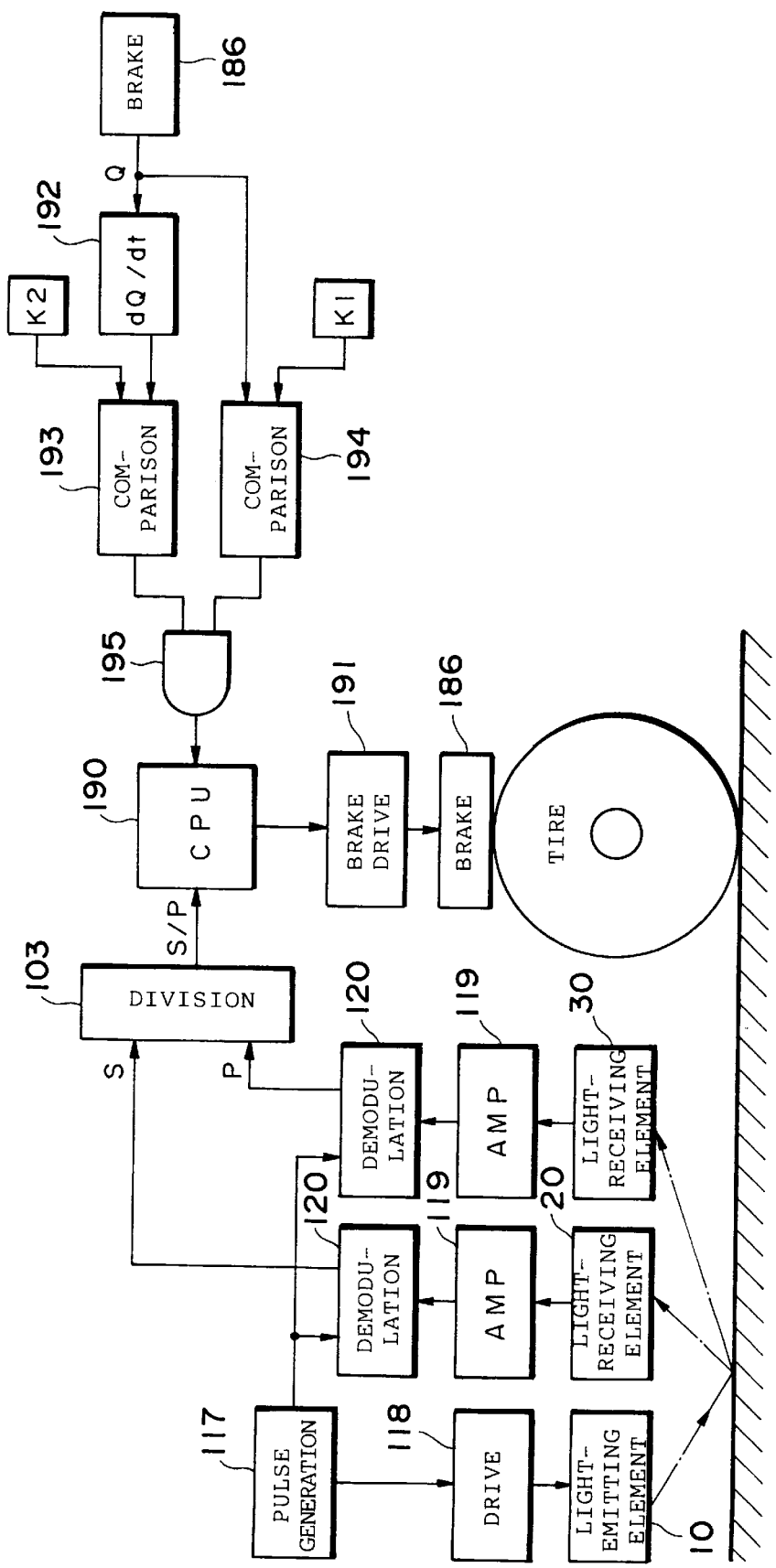

FIG. 125 illustrates a hardware circuit for performing the processing shown in FIG. 124. Components already described above will not be described again to avoid redundancy.

The dividing circuit 103 calculates S/P and applies the result to a CPU 190. The latter converts S/P to degree of moisture.

Force Q applied to the brake 186 by stepping down on it is sensed by a sensor. The force Q is compared with a prescribed threshold value K1 in a comparator circuit 194. A differentiating circuit 192 calculates the differentiated value dQ/dt of the force Q, and a comparator circuit 193 compares the differentiated value with a prescribed threshold value K2.

Sudden braking is judged to have occurred when the force Q is greater than K1 and the differentiated value dQ/dt is greater than K2. In such case an AND gate 195 applies sudden-braking signal to the CPU 190.

The CPU 190 controls a brake drive device 191 in such a manner that a braking force commensurate with the reflected light components increase and, hence, the reflected light contains more s-polarized light components.

The discriminating circuit 184 calculates S/P. When the value of S/P becomes larger than 1, this means that the road surface is wet. The degree of moisture rises as S/P increases. The discriminating circuit 184 converts the value of S/P to degree of moisture and applies the latter to a control circuit 185.

The control circuit 185 executes the brake control processing illustrated in FIG. 124. Specifically, the control circuit 185 accepts the moisture signal from the discriminating circuit 184 and calculates a braking force $P_s$ conforming to the degree of moisture (steps 441, 442). If desired a table indicating the correspondence between degree of moisture and optimum braking force may be stored in memory and the optimum braking force may be obtained from the memory subsequently.

When a signal representing the fact that the driver of the vehicle has stepped down on the brake pedal is provided by a brake 186 (step 443), whether sudden braking has been applied is judged on the basis of whether there has been a sudden increase in the stepping force upon the brake (step 444). In case of sudden braking, the brake 186 is controlled (step 445) in such a manner that braking is applied at the braking force $P_s$ determined earlier. If the braking is not sudden degree of moisture is applied to the tires of the vehicle at the time of sudden braking.

Figure 126:
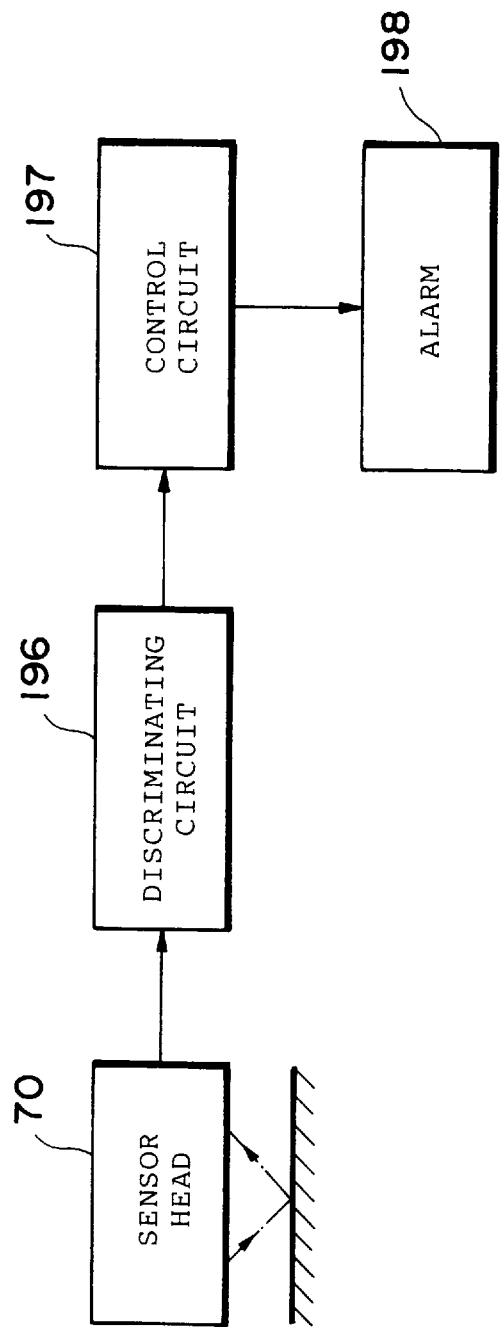
Figure 127:
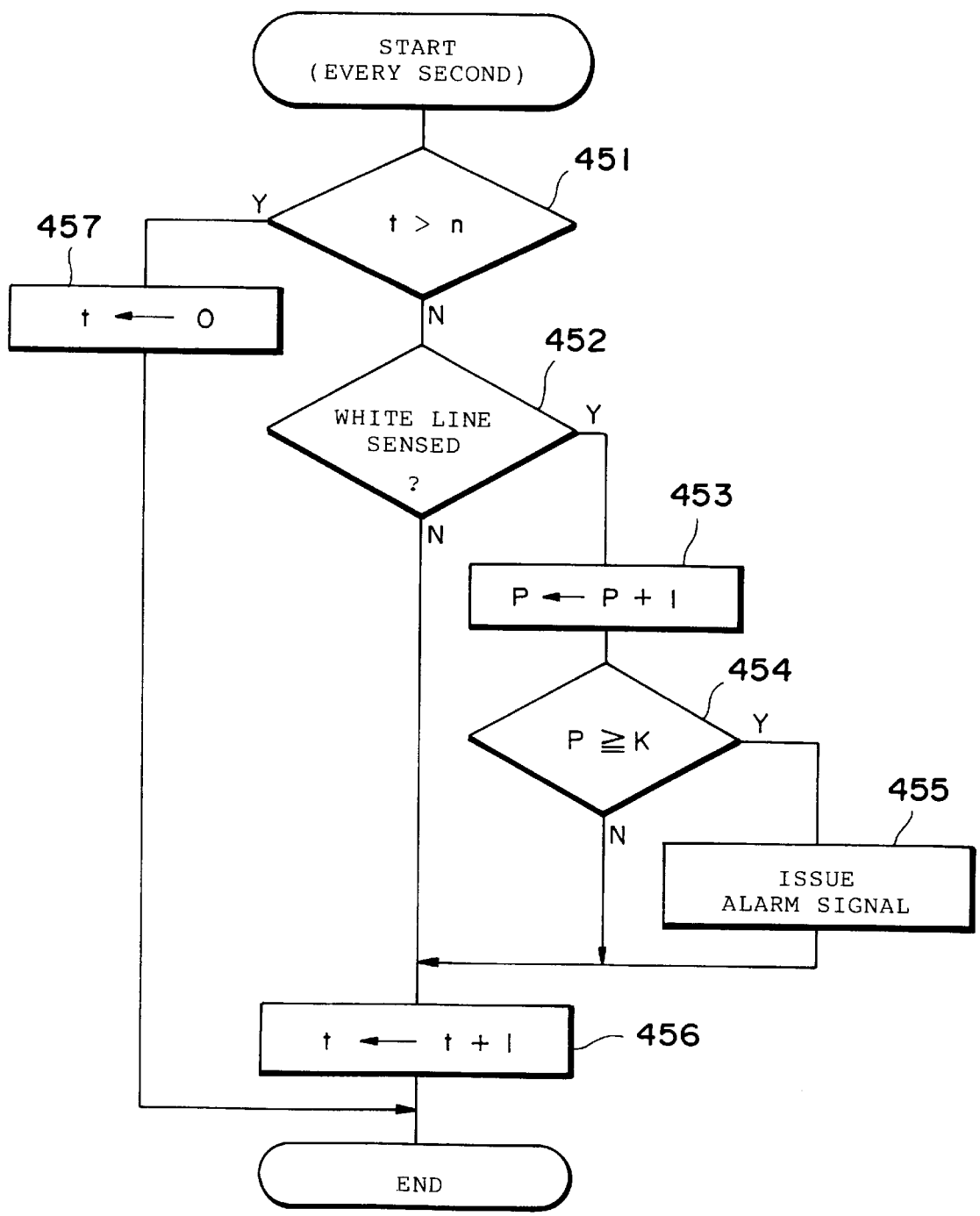

FIGS. 126 and 127 illustrate an example in which the optical sensor device is applied to sense that the driver is dozing at the wheel.

The surface of a road often has a white or yellow line paralleling the roadway in order to divide the roadway into lanes. When the apparatus of this application senses the white or yellow line in excess of a prescribed number of times within a fixed period of time, the apparatus construes this as indicating that the driver is dozing at the wheel and responds by issuing an alarm.

Light reflected from a white or yellow line contains many s-polarized light components. On the basis of the light-reception signal from the sensor head 70, a discriminating circuit 196 in FIG. 126 judges that the white or yellow line has been sensed when the value of S/P is greater than a prescribed value. The circuit 196 applies the result to a control circuit 197.

The control circuit 197, which includes a CPU, executes processing in accordance with FIG. 127 at regular time intervals (e.g., every second).

Let t represent a counter which measures time, n the above-mentioned regular time interval and P a counter which counts the number of times the white or yellow line is sensed. Let K represent a threshold value for the count value P.

When the white or yellow line is sensed (step 452), the counter P is incremented (step 453) and it is determined whether the new value in counter P has reached the threshold value K (step 454).

If the value in counter P has not reached the threshold value K, the counter t is incremented (step 456).

When the value in counter P reaches the threshold value K, an alarm device 198 generates an alarm. The alarm is implemented by a warning produced by a buzzer or synthesized voice track or by the flashing of an indicator lamp.

When the fixed time n is attained, the counter t is cleared (step 457).

Figure 128:
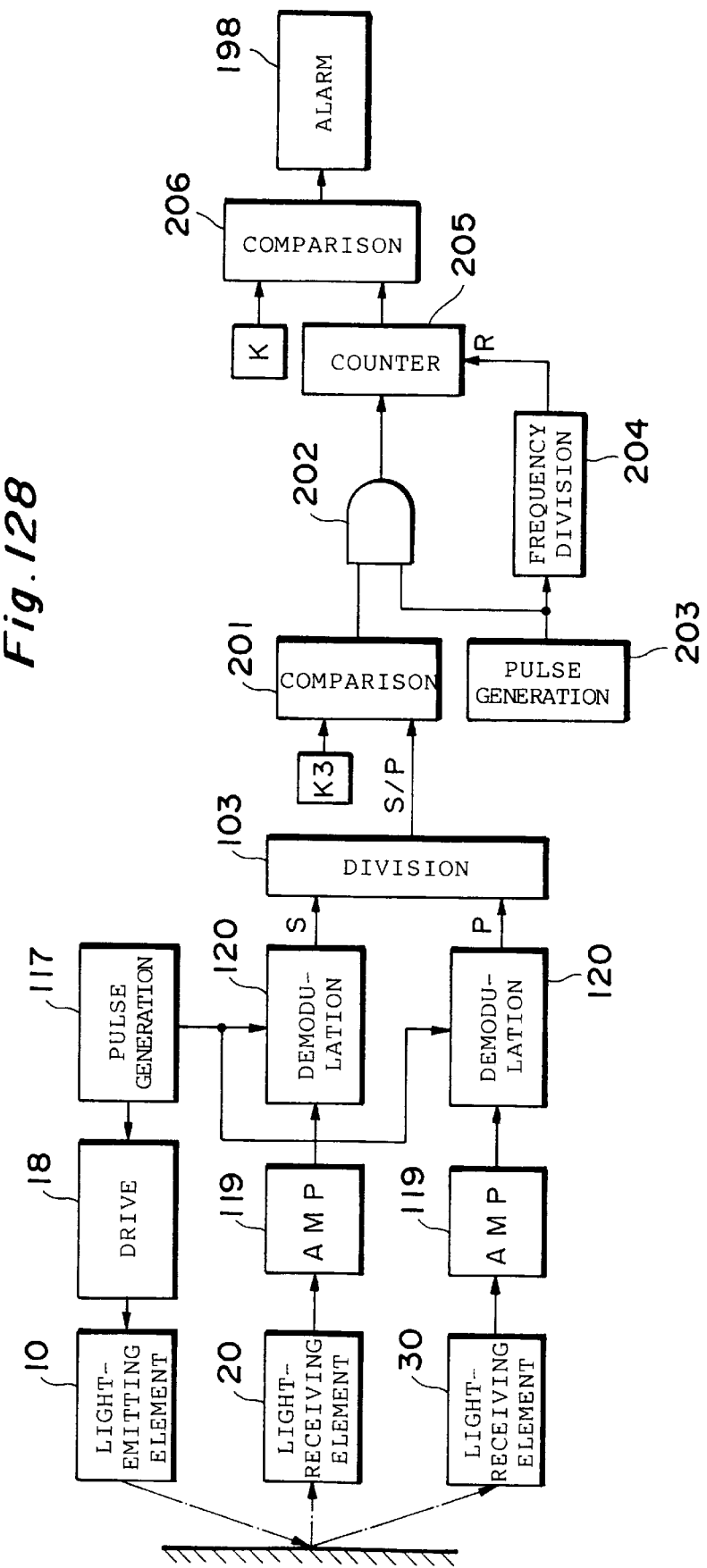

FIG. 128 illustrates a hardware circuit which executes the processing of FIG. 127.

The output S/P of the dividing circuit 103 is compared with a threshold value K3 in a comparator circuit 201. The latter generates an output if the threshold value K3 is exceeded.

A pulse generating circuit 203 generates one pulse every second, by way of example. When the pulse is generated, the output of the comparator circuit 201 is applied to the counter 205 through an AND gate 202. The value of the count in the counter 205 is compared with the alarm threshold value K in a comparator circuit 206. An alarm device 198 generates alarm information if the value of the count exceeds K.

A frequency divider circuit 204, which measures the fixed time n, frequency-divides the input pulses by n. The counter 205 is reset by the output of the frequency divider circuit 204.

Figure 129:
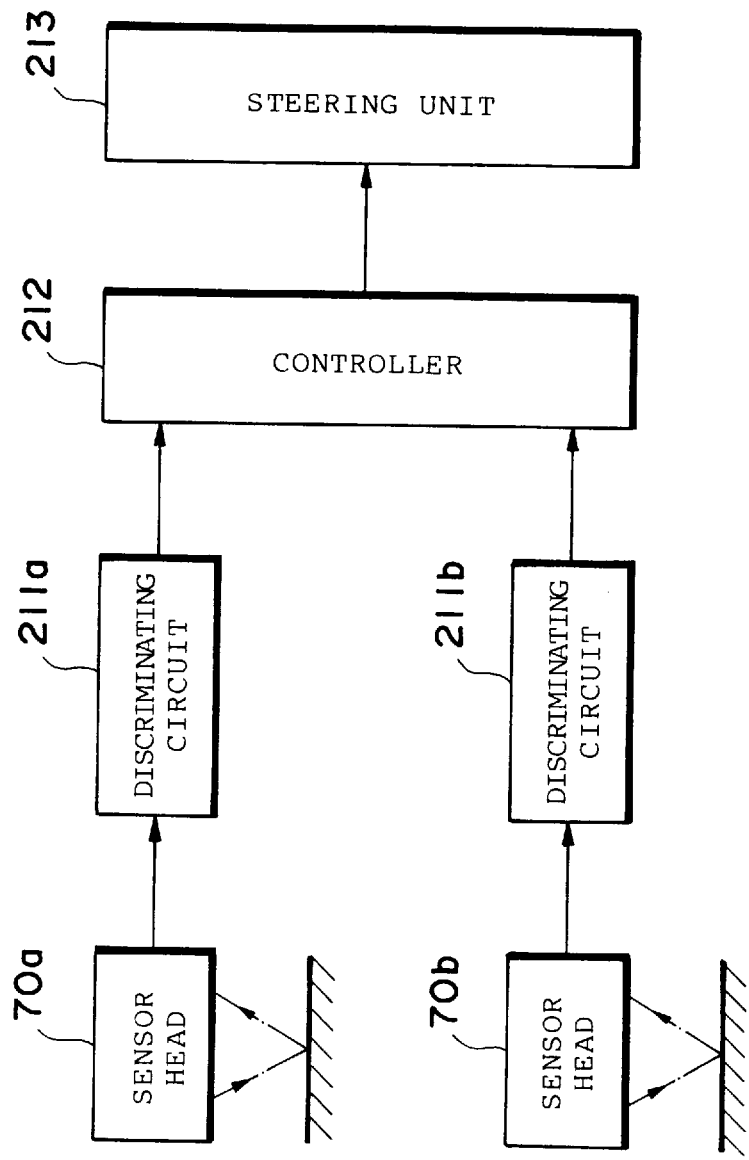
Figure 130:
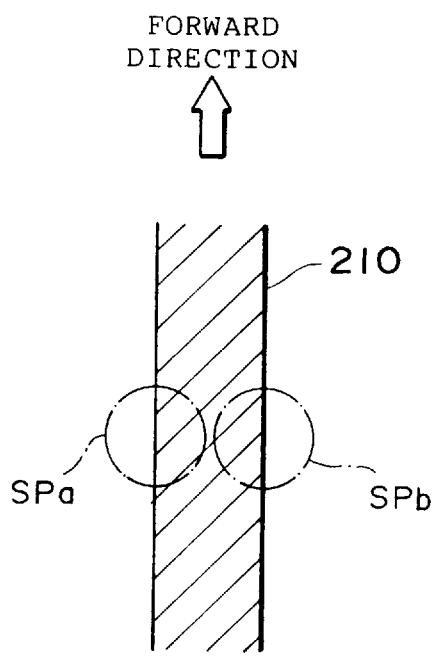
Figure 131:
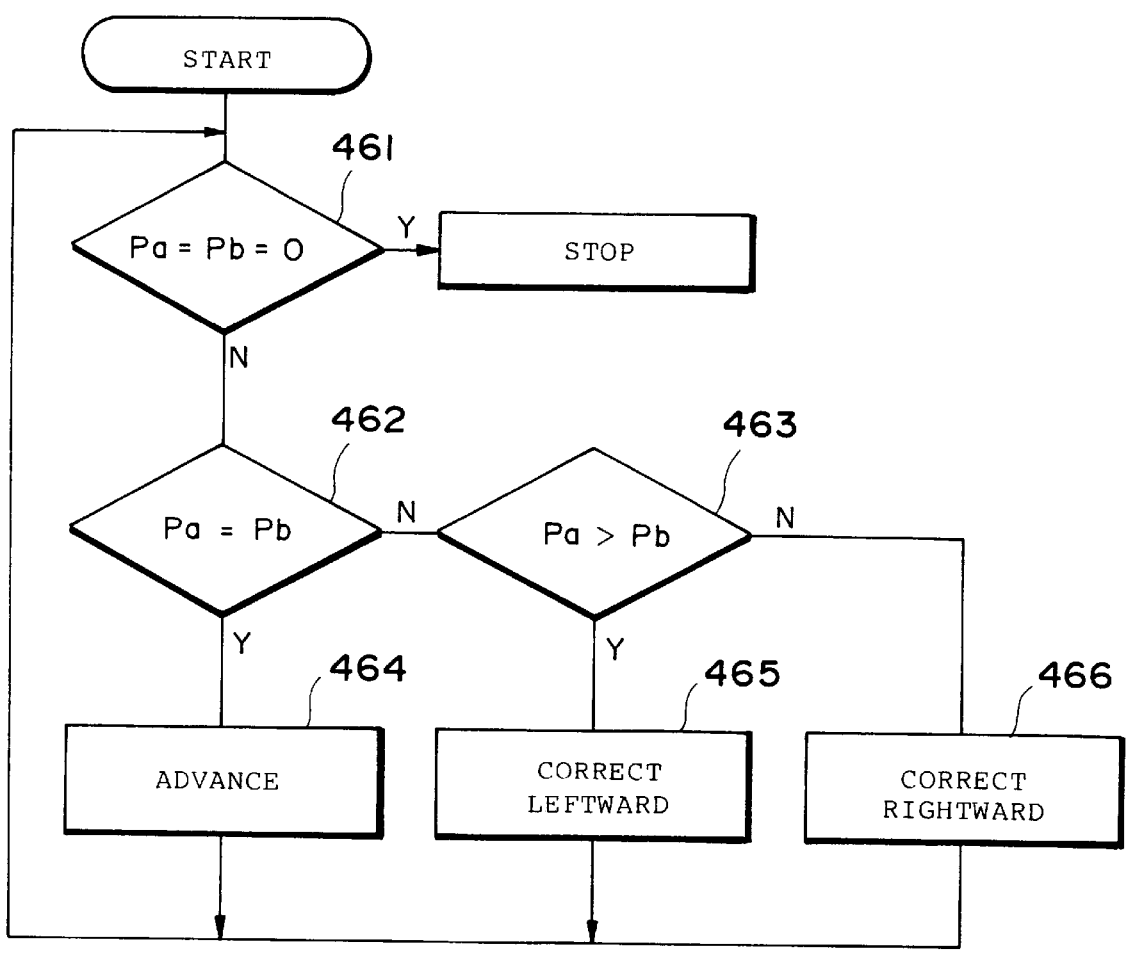

FIGS. 129~131 show an example of application to steering control of an unmanned transport vehicle (traveling body).

A white line (glossy paint or a metal wire) for guiding purposes is drawn along the traveling path of an unmanned vehicle. Two sensors 70a, 70b are attached to the underside of the unmanned vehicle body. When the unmanned vehicle is traveling correctly, projected beam spots SPa, SPb from these sensor heads irradiate equal areas on the white line 210 (see FIG. 130).

On the basis of light-reception signals from the sensor heads 70a, 70b, discriminating circuits 211a, 211b output signals Pa, Pb representing S/P, etc. The signals Pa, Pb are applied to a controller 212.

The controller 212, which includes a CPU, subjects a steering unit 213 to steering control shown in FIG. 131.

When Pa=Pb=0 holds, this means that the vehicle has left the guide or is traveling abnormally. The vehicle is stopped as a result (step 161).

When Pa=Pb holds, the vehicle is traveling correctly and, hence, the vehicle is allowed proceed (steps 462, 464). When Pa>Pb holds, this means that the vehicle has deviated toward the right side; hence, the vehicle is steered to the left. When the converse holds, the vehicle is steered to the right (steps 463, 465, 466).

FIGS. 132~134 illustrate an application in which tape adhered to a bank note is sensed. By way of example, this device is provided inside a bank note handling apparatus such as an automated teller machine.

A prescribed location along a bank note conveyance path is adopted as a sensing point, and sensor heads 70a , 70b are provided on both sides of the conveyance path. Since the orientation of the bank note conveyed is indeterminate and it is not known on which side of the bank note the adhesive tape is present, the sensor heads 70a, 70b are provided on both sides of the conveyance path. Light projected from the sensor heads 70a, 70b irradiates the surfaces of the conveyed bank note.

On the basis of light-reception signals from the sensor heads 70a, 70b, discriminating circuits 215a, 215b, respectively, calculate S–P, S/P or (S–P)/(S+P). When tape 6a is affixed to a bank note 6, as shown in FIG. 133, these values become high. When these values exceed a threshold value, the discriminating circuits 215a, 215b output tape detection signals.

The tape detection signals are applied to a control circuit 217, which includes a CPU, via an OR gate 216. The control circuit 217 executes processing illustrated in FIG. 134.

If bank notes are present in a bank note introduction slot, the bank notes are sent to the sensing point one at a time (steps 471, 472). When a tape detection signal enters from the discriminating circuit 215a or 215b (steps 473, 474), the bank note having this tape is sent back to the introduction slot or to a refund port by a conveyance controller 219 or is delivered to a bank note collection box (step 475) and a display to this effect is presented on a display unit 218.

FIG. 135 illustrates part of an offset printing apparatus.

In an offset printing apparatus, the balance between wetting water and amount of ink supplied is a major effect upon the quality of offset printing. In order to maintain an excellent printing state, it is required that the amount of wetting water be varied in dependence upon the condition of the printed matter, the type of paper, the type of ink, etc. In order to adjust the amount of wetting water, it is necessary to measure the thickness of the water film on the printing surface of the printing roller.

The thickness of the water film on the printing surface of a printing roller 225 is sensed by the sensor head 70. The light projected from the sensor head 70 is projected upon the printing surface. A discriminating circuit 221 calculates S/P or (S−P)/(S+P). If these values are large, this means the thickness of the water film is large.

The calculated value of S/P or the like is applied to a control unit 222, which includes a CPU. While taking into consideration the prevailing printing conditions, the control unit 222 controls the rotating speed of a water supply roller 224 via a drive unit 223 for the water supply roller on the basis of the value of S/P or the like in such a manner that the appropriate water film thickness is obtained.

FIGS. 136~138 illustrate an inspection apparatus is a manufacturing line. The apparatus of this example is for performing an inspection to determine whether paint has been applied to the surface of a manufactured article 7 properly. The optical sensor device can be applied also to a line in which an inspection is performed to determine whether a wrapping film is present, as described above.

Manufactured articles 7 are delivered successively to a manufacturing line 230. The sensor head 70 is placed at the inspection position in such a manner that the light is projected toward the surface of each manufactured article conveyed.

The light-reception signal from the sensor head 70 is sent to a discriminating circuit 234, which calculates the value of, say, S/P. If paint has been applied to the surface of the manufactured article correctly, the calculated value will be larger than a threshold value; otherwise, the calculated value will be smaller than threshold value.

The controller 235 includes a CPU, which executes the processing shown in FIG. 138.

Counters for counting the total number T of manufactured articles, the number R of acceptable articles and the number F of defective articles are initialized (step 481).

When the article arrives at the inspection location (step 482), the quality (acceptable or defective) is judged based upon the signal from the discriminating circuit 234. If the article is acceptable, the counter R is incremented (step 484). In case of a defective article, a pusher 232 is driven to send the defective article to a defective-article conveyance path (step 486). In addition, the counter F is incremented (step 487). The counter T is incremented after the R counter or F counter is incremented (step 485).

An arrangement may be adopted in which, rather than changing over the conveyance direction of the article based upon the results of discrimination, control of painting in the next step of the process is carried out on the basis of the value of S/P.

As shown in FIG. 139, the absence or presence of a transparent film (sheet) 8 delivered on a manufacturing line 240 can also be sensed on the basis of an output signal from the sensor head 70.

As many apparently widely different embodiments of the present invention can be made without departing from the spirit and scope thereof, it is to be understood that the invention is not limited to the specific embodiments thereof except as defined in the appended claims.

What is claimed is:

1. An optical sensor device comprising:
   a light-projecting optical system for projecting light toward an object to be sensed, said projected light having the characteristic that it is not separated into a plurality of polarized light beams by said light-projecting optical system; and
   a light-receiving optical system upon which reflected light, transmitted light or scattered light from the object to be sensed impinges;
   said light-projecting optical system including at least a light-emitting element for outputting projected light; and
   said light-receiving optical system including:
      a polarization beam splitter for separating the reflected light, transmitted light or scattered light from the object into a first luminous flux which is mainly an s-polarized component with regard to the plane of incidence and a second luminous flux which is mainly a p-polarized component with regard to the plane of incidence, said polarization beam splitter having a light separating characteristic that is substantially constant within a range of angles of incidence used;
      a first light-receiving element for receiving the first luminous flux; and
      a second light-receiving element for receiving the second luminous flux.

2. The device according to claim 1, wherein said polarization beam splitter maintains said light separating characteristic, which is substantially constant within the range of angles of incidence used, within a range of wavelength spread exhibited by the projected light from said light-emitting element.

3. The device according to claim 1, further comprising discriminating means for outputting a signal relating to absence/presence of the object, surface property of the object or material constituting the object on the basis of outputs from said first and second light-receiving elements.

4. The device according to claim 1, wherein said light-projecting optical system is so arranged that the projected light is projected upon the surface of the object obliquely or substantially perpendicularly, and said light-receiving optical system is so arranged that the reflected light or scattered light from the surface of the object impinges upon it obliquely or substantially perpendicularly.

5. The device according to claim 1, wherein said light-projecting optical system and said light-receiving optical system are arranged to oppose each other in spaced-apart relation.

6. The device according to claim 1, wherein said light separating characteristic is represented by:
   a first proportion expressed by a ratio of the quantity of light of the s-polarized component contained in the first luminous flux to the quantity of light of the s-polarized component incident upon said polarization beam splitter,
   a second proportion expressed by a ratio of the quantity of light of the p-polarized component contained in the second luminous flux to the quantity of light of the p-polarized component incident upon said polarization beam splitter, or
   the ratio of said first proportion to said second proportion;
   at least one of said first proportion and said second proportion or said ratio between them being held substantially constant.

7. The device according to claim 6, wherein said first proportion, said second proportion and said ratio between them are represented by values obtained by multiplying a light-emission spectrum of said light-emitting element and a spectral sensitivity characteristic of said light-receiving element and by integrating the result with regard to wavelength.

8. The device according to claim 1, further comprising a projecting lens, wherein the projected light is projected upon being converged, diverged or collimated by said projecting lens.

9. The device according to claim 1, further comprising polarizing means for converting projected light composed of randomly polarized light to projected light composed of linearly polarized light.

10. The device according to claim 1, wherein light which has emerged from said light-emitting element is introduced to a projecting optical fiber and light which has emerged from an end face of said projecting optical fiber is projected.

11. The device according to claim 1, further comprising a light-receiving lens for converging light incident upon said light-receiving optical system.

12. The device according to claim 11, wherein said polarization beam splitter is placed in the optical path of the light converged by said light-receiving lens.

13. The device according to claim 1, wherein the first and second luminous fluxes are introduced to said first and second light-receiving elements, respectively, by respective light-receiving optical fibers.

14. The device according to claim 1, further comprising at least one of first analyzing means provided in front of said first light-receiving element for allowing transmission of s-polarized light and second analyzing means provided in front of said second light-receiving element for allowing transmission of p-polarized light.

15. The device according to claim 1, further comprising a reflector provided to face said polarization beam splitter on a side from which the first or second luminous flux emerges, wherein the first or second luminous flux is reflected from said reflector.

16. The device according to claim 1, wherein an opening for limiting incident light is formed in front of said light-receiving optical system.

17. An optical sensor device comprising:
a light-projecting optical system for projecting light toward an object to be sensed, said projected light having the characteristic that it is not separated into a plurality of polarized light beams by said light-projecting optical system; and
a light-receiving optical system upon which reflected light, transmitted light or scattered light from the object to be sensed impinges;
said light-projecting optical system including at least a light-emitting element for outputting projected light; and
said light-receiving optical system including:
a polarization beam splitter for separating the reflected light, transmitted light or scattered light from the object into a first luminous flux which is mainly an s-polarized component with regard to the plane of incidence and a second luminous flux which is mainly a p-polarized component with regard to the plane of incidence, said polarization beam splitter having a light separating characteristic that is substantially constant within a range of wavelength spread exhibited by the projected light from said light-emitting element;
a first light-receiving element for receiving the first luminous flux; and
a second light-receiving element for receiving the second luminous flux.

18. The device according to claim 17, further comprising discriminating means for outputting a signal relating to absence/presence of the object, surface property of the object or material constituting the object on the basis of outputs from said first and second light-receiving elements.

19. The device according to claim 17, wherein said light-projecting optical system is so arranged that the projected light is projected upon the surface of the object obliquely or substantially perpendicularly, and said light-receiving optical system is so arranged that the reflected light or scattered light from the surface of the object impinges upon it obliquely or substantially perpendicularly.

20. The device according to claim 17, wherein said light-projecting optical system and said light-receiving optical system are arranged to oppose each other in spaced-apart relation.

21. The device according to claim 17, wherein said light separating characteristic is represented by:
a first proportion expressed by a ratio of the quantity of light of the s-polarized component contained in the first luminous flux to the quantity of light of the s-polarized component incident upon said polarization beam splitter,
a second proportion expressed by a ratio of the quantity of light of the p-polarized component contained in the second luminous flux to the quantity of light of the p-polarized component incident upon said polarization beam splitter, or
the ratio of said first proportion to said second proportion;
at least one of said first proportion and said second proportion or said ratio between them being held substantially constant.

22. The device according to claim 21, wherein said first proportion, said second proportion and said ratio between them are represented by values obtained by multiplying a light-emission spectrum of said light-emitting element and a spectral sensitivity characteristic of said light-receiving element and by integrating the result with regard to wavelength.

23. The device according to claim 17, further comprising a projecting lens, wherein the projected light is projected upon being converged, diverged or collimated by said projecting lens.

24. The device according to claim 17, further comprising polarizing means for converting projected light composed of randomly polarized light to projected light composed of linearly polarized light.

25. The device according to claim 17, wherein light which has emerged from said light-emitting element is introduced to a projecting optical fiber and light which has emerged from an end face of said projecting optical fiber is projected.

26. The device according to claim 17, further comprising a light-receiving lens for converging light incident upon said light-receiving optical system.

27. The device according to claim 26, wherein said polarization beam splitter is placed in the optical path of the light converged by said light-receiving lens.

28. The device according to claim 17, wherein the first and second luminous fluxes are introduced to said first and second light-receiving elements, respectively, by respective light-receiving optical fibers.

29. The device according to claim 17, further comprising at least one of first analyzing means provided in front of said first light-receiving element for allowing transmission of s-polarized light and second analyzing means provided in front of said second light-receiving element for allowing transmission of p-polarized light.

30. The device according to claim 17, further comprising a reflector provided to face said polarization beam splitter on a side from which the first or second luminous flux emerges, wherein the first or second luminous flux is reflected from said reflector.

31. The device according to claims 17, wherein an opening for limiting incident light is formed in front of said light-receiving optical system.

32. An optical sensor device comprising:
a light-projecting optical system for projecting light toward an object to be sensed, said projected light having the characteristic that it is not separated into a plurality of polarized light beams by said light-projecting optical system; and
a light-receiving optical system upon which reflected light, transmitted light or scattered light from the object to be sensed impinges;
said light-projecting optical system including at least a light-emitting element for outputting projected light; and
said light-receiving optical system including:
a polarization beam splitter for separating the reflected light, transmitted light or scattered light from the object into a first luminous flux which is mainly an s-polarized component with regard to the plane of incidence and a second luminous flux which is mainly a p-polarized component with regard to the plane of incidence;
a first light-receiving element for receiving the first luminous flux; and
a second light-receiving element for receiving the second luminous flux.

33. The device according to claim 32, further comprising discriminating means for outputting a signal relating to absence/presence of the object, surface property of the object or material constituting the object on the basis of outputs from said first and second light-receiving elements.

34. A sensing method comprising the steps of:
projecting projected light toward an object to be sensed, said projected light having the characteristic that it is not separated into a plurality of polarized light beams by said light-projecting optical system;
using a polarization beam splitter having a light separating characteristic that is substantially constant within a range of angles of incidence used;
separating reflected light, transmitted light or scattered light from the object into a first luminous flux which is mainly an s-polarized component with regard to the plane of incidence of said polarization beam splitter and a second luminous flux which is mainly a p-polarized component with regard to the plane of incidence of said polarization beam splitter; and
outputting a signal relating to absence/presence of the object, surface property of the object or material constituting the object on the basis of quantity of light of the first luminous flux and quantity of light of the second luminous flux.

35. The method according to claim 32, wherein said polarization beam splitter maintains said light separating characteristic, which is substantially constant within the range of angles of incidence used, within a range of wavelength spread exhibited by the projected light.

36. A sensing method comprising the steps of:
projecting projected light toward an object to be sensed, said projected light having the characteristic that it is not separated into a plurality of polarized light beams by said light-projecting optical system;
using a polarization beam splitter having a light separating characteristic that is substantially constant within a range of wavelength spread exhibited by the projected light;
separating reflected light, transmitted light or scattered light from the object into a first luminous flux which is mainly an s-polarized component with regard to the plane of incidence of said polarization beam splitter and a second luminous flux which is mainly a p-polarized component with regard to the plane of incidence of said polarization beam splitter; and
outputting a signal relating to absence/presence of the object, surface property of the object or material constituting the object on the basis of quantity of light of the first luminous flux and quantity of light of the second luminous flux.

37. A sensing method comprising the steps of:
projecting projected light toward an object to be sensed, said projected light having the characteristic that it is not separated into a plurality of polarized light beams by said light-projecting optical system;
separating, by using a polarization beam splitter, reflected light, transmitted light or scattered light from the object into a first luminous flux which is mainly an s-polarized component with regard to the plane of incidence of said polarization beam splitter and a second luminous flux which is mainly a p-polarized component with regard to the plane of incidence of said polarization beam splitter; and
outputting a signal relating to absence/presence of the object, surface property of the object or material constituting the object on the basis of quantity of light of the first luminous flux and quantity of light of the second luminous flux.

38. An object identification apparatus in which the optical sensor device described in claim 32 is placed on an object conveyance path and objects conveyed on said conveyance path are identified on the basis of an output signal from said optical sensor device.

39. A printing apparatus in which the optical sensor device described in claim 32 is placed on a conveyance path of a printing medium and an edge or positional offset of the printing medium is sensed on the basis of an output signal from said optical sensor device.

40. The printing apparatus according to claim 39, wherein said optical sensing device is held so as to move together with a printing head.

41. A printing apparatus comprising:
the optical sensor device described in claim 32;
discriminating means for discriminating the type of a printing medium on the basis of an output signal from said optical sensor device; and
control means for controlling printing conditions on the basis of results of discrimination performed by said discriminating means.

42. An air conditioner comprising:
the optical sensor device, which is described in claim 32, arranged so as to discriminate the surface state of a condensation medium or frost medium; and
control means for controlling air-conditioning running conditions on the basis of an output signal from said optical sensor device.

43. A humidity control apparatus comprising:
a heat exchanger;
the optical sensor device, which is described in claim 32, for discriminating the surface state of said heat exchanger; and a control unit for controlling running conditions on the basis of an output signal from said optical sensor device.

44. A vehicle comprising:
the optical sensor device, which is described in claim 32, so arranged as to discriminate the surface state on the inner side of a window glass of the vehicle;
defogging means for eliminating fogging of said window glass; and
control means for controlling said defogging means on the basis of an output signal from said optical sensor device.

45. A vehicle comprising:
the optical sensor device, which is described in claim 32, so arranged as to discriminate the surface state on the outer side of a window glass of the vehicle;
a window wiper device for cleaning the surface on the outer side of said window glass; and
control means for controlling the operation of said window wiper device on the basis of an output signal from said optical sensor device.

46. A vehicle comprising:
the optical sensor device, which is described in claim 32, so arranged as to discriminate the state of a road surface;
operating-state detecting means for detecting the state in which the vehicle is being operated; and
control means for controlling drive of an actuator, which is related to a driving operation of the vehicle, on the basis of results of discriminating the road surface by said optical sensor device and results of detecting the operating state by said operating-state detecting means.

47. A vehicle comprising:
the optical sensor device, which is described in claim 32, so arranged and constructed as to sense a mark or the like represented on a road surface;
warning means for warning an individual driving the vehicle; and
control means for controlling said warning means on the basis of an output signal from said optical sensor device.

48. A vehicle comprising:
the optical sensor device, which is described in claim 32, for sensing deviation from a guide provided along a path of travel; and
means for performing steering on the basis of a detection signal from said optical sensor device.

49. A bank note handling apparatus comprising:
the optical sensor device, which is described in claim 32, for sensing the surface of a bank note; and
control means for controlling operation of the apparatus on the basis of an output from said sensor device.

50. An offset printing apparatus comprising:
a printing roller for fixing a printing original sheet;
wetting-water supply means for supplying the printing original sheet with wetting water;
the optical sensor device, which is described in claim 32, for sensing the surface of the printing original sheet; and
control means for controlling said wetting-water supply means on the basis of an output from said optical sensor device.

51. An inspection apparatus comprising:
the optical sensor device, which is described in claim 32, so arranged as to discriminate the surface state of an article conveyed on a conveyance path;
direction changing means for changing conveyance direction of the conveyed article; and
means for controlling said direction changing means on the basis of results of discrimination by said optical sensor device.

52. An inspection method comprising the steps of:
discriminating the surface state of an article, conveyed on a conveyance path, by the optical sensor device described in claim 1; and
controlling the conveyance direction of the article on the basis of the results of discrimination.

53. An inspection method comprising the steps of:
discriminating the surface state of an article, conveyed on a conveyance path, by the optical sensor device described in claim 2; and
controlling the conveyance direction of the article on the basis of the results of discrimination.

54. An inspection method comprising the steps of:
discriminating the surface state of an article, conveyed on a conveyance path, by the optical sensor device described in claim 3; and
controlling the conveyance direction of the article on the basis of the results of discrimination.

55. An inspection method comprising the steps of:
discriminating the surface state of an article, conveyed on a conveyance path, by the optical sensor device described in claim 4; and
controlling the conveyance direction of the article on the basis of the results of discrimination.

56. An inspection method comprising the steps of:
discriminating the surface state of an article, conveyed on a conveyance path, by the optical sensor device described in claim 5; and
controlling the conveyance direction of the article on the basis of the results of discrimination.

57. An inspection method comprising the steps of:
discriminating the surface state of an article, conveyed on a conveyance path, by the optical sensor device described in claim 6; and
controlling the conveyance direction of the article on the basis of the results of discrimination.

58. An inspection method comprising the steps of:
discriminating the surface state of an article, conveyed on a conveyance path, by the optical sensor device described in claim 7; and
controlling the conveyance direction of the article on the basis of the results of discrimination.

59. An inspection method comprising the steps of:
discriminating the surface state of an article, conveyed on a conveyance path, by the optical sensor device described in claim 8; and
controlling the conveyance direction of the article on the basis of the results of discrimination.

60. An inspection method comprising the steps of:
discriminating the surface state of an article, conveyed on a conveyance path, by the optical sensor device described in claim 9; and
controlling the conveyance direction of the article on the basis of the results of discrimination.

61. An inspection method comprising the steps of:
discriminating the surface state of an article, conveyed on a conveyance path, by the optical sensor device described in claim 10; and
controlling the conveyance direction of the article on the basis of the results of discrimination.

62. An inspection method comprising the steps of:
discriminating the surface state of an article, conveyed on a conveyance path, by the optical sensor device described in claim 11; and
controlling the conveyance direction of the article on the basis of the results of discrimination.

63. An inspection method comprising the steps of:
discriminating the surface state of an article, conveyed on a conveyance path, by the optical sensor device described in claim 12; and
controlling the conveyance direction of the article on the basis of the results of discrimination.

64. An inspection method comprising the steps of:
discriminating the surface state of an article, conveyed on a conveyance path, by the optical sensor device described in claim 13; and
controlling the conveyance direction of the article on the basis of the results of discrimination.

65. An inspection method comprising the steps of:
discriminating the surface state of an article, conveyed on a conveyance path, by the optical sensor device described in claim 14; and
controlling the conveyance direction of the article on the basis of the results of discrimination.

66. An inspection method comprising the steps of:
discriminating the surface state of an article, conveyed on a conveyance path, by the optical sensor device described in claim 15; and
controlling the conveyance direction of the article on the basis of the results of discrimination.

67. An inspection method comprising the steps of:
discriminating the surface state of an article, conveyed on a conveyance path, by the optical sensor device described in claim 16; and
controlling the conveyance direction of the article on the basis of the results of discrimination.

68. An inspection method comprising the steps of:
discriminating the surface state of an article, conveyed on a conveyance path, by the optical sensor device described in claim 17; and
controlling the conveyance direction of the article on the basis of the results of discrimination.

69. An inspection method comprising the steps of:
discriminating the surface state of an article, conveyed on a conveyance path, by the optical sensor device described in claim 18; and
controlling the conveyance direction of the article on the basis of the results of discrimination.

70. An inspection method comprising the steps of:
discriminating the surface state of an article, conveyed on a conveyance path, by the optical sensor device described in claim 19; and
controlling the conveyance direction of the article on the basis of the results of discrimination.

71. An optical sensor device comprising:
a light-projecting optical system for projecting light toward an object to be sensed; and
a light-receiving optical system upon which reflected light, transmitted light or scattered light from the object to be sensed impinges;
said light-projecting optical system including at least a light-emitting element for outputting projected light; and
said light-receiving optical system including:
  a polarization beam splitter for separating the reflected light, transmitted light or scattered light from the object into a first luminous flux which is mainly an s-polarized component with regard to the plane of incidence and a second luminous flux which is mainly a p-polarized component with regard to the plane of incidence, said polarization beam splitter having a light separating characteristic that is substantially constant within a range of angles of incidence used, and wherein said light separating characteristic is represented by:
    a first proportion expressed by a ratio of the quantity of light of the s-polarized component contained in the first luminous flux to the quantity of light of the s-polarized component incident upon said polarization beam splitter,
    a second proportion expressed by a ratio of the quantity of light of the p-polarized component contained in the second luminous flux to the quantity of light of the p-polarized component incident upon said polarization beam splitter, or
    the ratio of said first proportion to said second proportion;
    at least one of said first proportion and said second proportion or said ratio between them being held substantially constant;
  a first light-receiving element for receiving the first luminous flux; and
  a second light-receiving element for receiving the second luminous flux.

72. The device according to claim 71, wherein said first proportion, said second proportion and said ratio between them are represented by values obtained by multiplying a light-emission spectrum of said light-emitting element and a spectral sensitivity characteristic of said light-receiving element and by integrating the result with regard to wavelength.

73. An optical sensor device comprising:
a light-projecting optical system for projecting light toward an object to be sensed; and
a light-receiving optical system upon which reflected light, transmitted light or scattered light from the object to be sensed impinges:
  a light-receiving lens for converging light incident upon said light-receiving optical system;
  said light-projecting optical system including at least a light-emitting element for outputting projected light; and
  said light-receiving optical system including:
    a polarization beam splitter for separating the reflected light, transmitted light or scattered light from the object into a first luminous flux which is mainly an s-polarized component with regard to the plane of incidence and a second luminous flux which is mainly a p-polarized component with regard to the plane of incidence, said polarization beam splitter having a light separating characteristic that is substantially constant within a range of angles of incidence used;
    a first light-receiving element for receiving the first luminous flux; and
    a second light-receiving element for receiving the second luminous flux.

74. An optical sensor device comprising:
a light-projecting optical system for projecting light toward an object to be sensed; and
a light-receiving optical system upon which reflected light, transmitted light or scattered light from the object to be sensed impinges;

said light-projecting optical system including at least a light-emitting element for outputting projected light; and said light-receiving optical system including:
  a polarization beam splitter for separating the reflected light, transmitted light or scattered light from the object into a first luminous flux which is mainly a p-polarized component with regard to the plane of incidence, said polarization beam splitter having a light separating characteristic that is substantially constant within a range of angles of incidence used;

a first light-receiving element for receiving the first luminous flux;

a second light-receiving element for receiving the second luminous flux; and, a reflector provided to face said polarization beam splitter on a side from which the first or second luminous flux emerges, wherein the first or second luminous flux is reflected from said reflector.

* * * * *